(12) United States Patent
Duan et al.

(10) Patent No.: US 7,892,824 B2
(45) Date of Patent: Feb. 22, 2011

(54) SYNTHETIC MINI/MICRO-DYSTROPHIN GENES TO RESTORE NNOS TO THE SARCOLEMMA

(75) Inventors: Dongsheng Duan, Columbia, MO (US); Yi Lai, Columbia, MO (US); Yongping Yue, Columbia, MO (US)

(73) Assignee: University of Missouri-Columbia, Columbia, MO (US)

( * ) Notice: Subject to any disclaimer, the term of this patent is extended or adjusted under 35 U.S.C. 154(b) by 0 days.

(21) Appl. No.: 12/009,537

(22) Filed: Jan. 18, 2008

(65) Prior Publication Data

US 2008/0249052 A1    Oct. 9, 2008

Related U.S. Application Data

(60) Provisional application No. 60/881,129, filed on Jan. 18, 2007, provisional application No. 60/999,321, filed on Oct. 16, 2007.

(51) Int. Cl.
*C12N 15/00* (2006.01)
*C12N 15/09* (2006.01)
*C07H 21/04* (2006.01)

(52) U.S. Cl. .................. 435/320.1; 536/23.5; 536/24.1

(58) Field of Classification Search ................ 536/23.5, 536/24.1; 435/320.1
See application file for complete search history.

(56) References Cited

U.S. PATENT DOCUMENTS

2005/0049219 A1 * 3/2005 Chamberlain et al.

OTHER PUBLICATIONS

D'Souza et al., 1995, Human Molecular Genetics, vol. 4, No. 5, p. 837-842.*
Gorecki D. C. et al., "Prospects and problems of gene therapy: an update", *Expert Opin. Emerging Drugs* 6(*2*): 187-198 (2001).
Skolnick J. et al., "From genes to protein structure and function: novel applications of computational approaches in the genomic era", *TIBTECH 18*: 34-39 (2000).
Eck S. L. et al., "Chapter 5: Gene Based Therapy", *Goodman & Gilman's The Pharmacological Basis of Therapeutics, Ninth Edition*, McGraw-Hill, pp. 77-101 (especially pp. 81 and 82) (1996).

* cited by examiner

*Primary Examiner*—Shin-Lin Chen
(74) *Attorney, Agent, or Firm*—Perkins Coie LLP

(57) ABSTRACT

The present invention provides novel dystrophin mini/micro-genes that retain the essential biological functions of a full-length dystrophin gene. More particularly, the present invention provides to a series of synthetic mini/micro-dystrophin genes capable of restoring neuronal nitric oxide synthase (nNOS) to the sarcolemma. A method as well as a pharmaceutical composition for treatment of Duchenne Muscular Dystrophy (DMD), Becker Muscular Dystrophy (BMD), and X-linked Dilated Cardiomyopathy (XLDC) are also provided.

8 Claims, 29 Drawing Sheets
(2 of 29 Drawing Sheet(s) Filed in Color)

```
I  H  T  V  R  E  E  T  M  M  V  M  T  E  D  M  P  L  E  I
ATTCACACTGTCCGTGAAGAAACGATGATGGTGATGACTGAAGACATGCCTTTGGAAATT

S  Y  V  P  S  T  Y  L  T  E  I  T  H  V  S  Q  A  L  L  E
TCTTATGTGCCTTCTACTTATTTGACTGAAATCACTCATGTCTCACAAGCCCTATTAGAA

V  E  Q  L  L  N  A  P  D  L  C  A  K  D  F  E  D  L  F  K
GTGGAACAACTTCTCAATGCTCCTGACCTCTGTGCTAAGGACTTTGAAGATCTCTTTAAG

Q  E  E  S  L  K  N  I  K  D  S  L  Q  Q  S  S  G  R  I  D
CAAGAGGAGTCTCTGAAGAATATAAAAGATAGTCTACAACAAAGCTCAGGTCGGATTGAC

I  I  H  S  K  K  T  A  A  L  Q  S  A  T  P  V  E  R  V  K
ATTATTCATAGCAAGAAGACAGCAGCATTGCAAAGTGCAACGCCTGTGGAAAGGGTGAAG

L  Q  E  A  L  S  Q  L  D  F  Q  W  E  K  V  N  K  M  Y  K
CTACAGGAAGCTCTCTCCCAGCTTGATTTCCAATGGGAAAAAGTTAACAAAATGTACAAG

D  R  Q  G  R  F  D  R  S  V  E  K  W  R  R  F  H  Y  D  I
GACCGACAAGGGCGATTTGACAGA|CTGTTGAGAAATGGCGGCGTTTTCATTATGATATA

K  I  F  N  Q  W  L  T  E  A  E  Q  F  L  R  K  T  Q  I  P
AAGATATTTAATCAGTGGCTAACAGAAGCTGAACAGTTTCTCAGAAAGACACAAATTCCT

E  N  W  E  H  A  K  Y  K  W  Y  L  K  E  L  Q  D  G  I  G
GAGAATTGGGAACATGCTAAATACAAATGGTATCTTAAGGAACTCCAGGATGGCATTGGG

Q  R  Q  T  V  V  R  T  L  N  A  T  G  E  E  I  I  Q  Q  S
CAGCGGCAAACTGTTGTCAGAACATTGAATGCAACTGGGGAAGAAATAATTCAGCAATCC

S  K  T  D  A  S  I  L  Q  E  K  L  G  S  L  N  L  R  W  Q
TCAAAAACAGATGCCAGTATTCTACAGGAAAAATTGGGAAGCCTGAATCTGCGGTGGCAG

E  V  C  K  Q  L  S  D  R  K  K  R  L  E  E
GAGGTCTGCAAACAGCTGTCAGACAGAAAAAAGAGGCTAGAAGAA
```

Fig. 1B

```
         Human EISYVPSTYLTEITHVSQALLEVEQLLNAPDLCAKDFEDLFKQEESLKNIKDSLQQSSGR  60
Macaca mulatta EISYVPSTYLTEITHVSQALSEVEQLLNAPDLCAKDFEDLFKQEESLKNIKDILQQSSGR  60
    Sus scrofa EISYVPSAYLTEITHVSQALSEVEQLLNAPDLCAKDFEDLFKQEESLKNIKDSLQQISGR  60
Canis familliaris EISYVPSTYLTEITHVSQALSEVEELLNAPDLCAQDFEDLFKQEESLKNIKDSLQQISGR  60
  Mus musculus DVSYVPSTYLTEISHILQALSEVDHLLNTPELCAKDFEDLFKQEESLKNIKDNLQQISGR  60
  Gallus gallus ETTYVPSTYLAEILQLIQALSEVEERLNSPVLQAKDCEDLLKQEECLKNIKDCLGRLQGH  60
               : :****:**:** :: *** **:. **:* * *;* ***;****.****** * ; .*:

Human IDIIHSKKTAALQSATPVERVKLQEALSQLDFQWEKVNKMYKDRQGRFDR 110
Macaca mulatta IDIIHSKKTAALQSATPVERVKLQEALSQIDFQWEKVNKMYKDRQGRFDR 110
    Sus scrofa VDIIHNKKTAGLQSATPVERTRLQEALSQLDFQWERVNKMYKDRQGKFDR 110
Canis familliaris IDIIHNKKTAALHSATPAERAKLQEALSRLDFQWERVNNMYKDRQGRFDR 110
  Mus musculus IDIIHKKKTAALQSATSMEKVKVQEAVAQMDFQGEKLHRMYKERQGRFDR 110
  Gallus gallus IDIIHSKKTPALQSATPRETANIQDKLTQLNSQWEKVNKMYRDRQARFDK 110
               :****.***..*.:***.  *  ..:*:  :::::  *  *:::.**::**.:**:
```
} R16

```
         Human SVEKWRRFHYDIKIFNQWLTEAEQFLRKTQIPE-NWEHAKYKWYLKELQDGIGQRQTVVR 59
Macaca mulatta SVEKWRRFHYDIKIFNQWLTEAEQFLRKTQIPE-NWEHAKYKWYLKELQDGIGQRQTVVR 59
    Sus scrofa SVEKWRRFHYDMKIFNQWLTEAEHFLKKTQIPE-NWEHAKYKWYLKELQDGIGQRQTIVR 59
Canis familliaris SVEKWRRFHYDMKILNQWLTEAEQFLKKTQIPE-NWEHAKYKWYLKELQDGIGQRQSVVR 59
  Mus musculus SVEKWRHFHYDMKVFNQWLNEVEQFFKKTQNPE-NWEHAKYKWYLKELQDGIGQRQAVVR 59
  Gallus gallus --EKWRLFHCEMKSFNEWLTETEEKLSRAQIEAGDVGHVRTKQFLQELQDGIGRQQTVVK 58
                 **** **  ::* :*:**.*.*. :  : :*    ;   *.* *  :*:********::*::*:

Human TLNATGEEIIQQSSKTDASILQEKLGSLNLRWQEVCKQLSDRKKRLEE 107
Macaca mulatta TLNATGEEIIQQSSKTDASILQEKLGSLNLRWQEVCKQLSERKKRLEE 107
    Sus scrofa VLNATGEEVIQQSSKTDASILQEKLGSLNLRWQEVCKQLAERKKRLEE 107
Canis familliaris VLNATGEEIIQQSSKTDASILQEKLGSLNLRWQEVCKQLAERKKRLEE 107
  Mus musculus TLNATGEEIIQQSSKTDVNILQEKLGSLSLRWHDICKELAERRKRIEE 107
  Gallus gallus TLNVTGEEIIEQSSAADANVLKEQLGNLNTRWQEICRQLVEKRKRIEE 106
               .**.****:*;*** :*...:*;*:**.*.  **:::*:: ::*;****:
```
} R17

Fig. 1C

SEQUENCE LISTING

<160> NUMBER OF SEQ IDS: 61

<210> SEQ ID NO 1
<211> LENGTH: 3685
<212> TYPE: PRT
<213> ORGANISM: Homo sapiens

<400> SEQUENCE: 1

Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe

```
                    20                  25                  30
Gly Lys Gln His Ile Glu Asn Leu Phe Ser Asp Leu Gln Asp Gly Arg
            35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Val Asp Leu Val Asn Ile Gly Ser
                85                  90                  95

Thr Asp Ile Val Asp Gly Asn His Lys Leu Thr Leu Gly Leu Ile Trp
                100                 105                 110

Asn Ile Ile Leu His Trp Gln Val Lys Asn Val Met Lys Asn Ile Met
            115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
                180                 185                 190

Thr Gln Arg Leu Glu His Ala Phe Asn Ile Ala Arg Tyr Gln Leu Gly
            195                 200                 205

Ile Glu Lys Leu Leu Asp Pro Glu Asp Val Asp Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
                260                 265                 270

His Tyr Ser Gln Gln Ile Thr Val Ser Leu Ala Gln Gly Tyr Glu Arg
            275                 280                 285

Thr Ser Ser Pro Lys Pro Arg Phe Lys Ser Tyr Ala Tyr Thr Gln Ala
    290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
                340                 345                 350

Ser Trp Leu Leu Ser Ala Glu Asp Thr Leu Gln Ala Gln Gly Glu Ile
            355                 360                 365

Ser Asn Asp Val Glu Val Val Lys Asp Gln Phe His Thr His Glu Gly
    370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415

Glu Thr Glu Val Gln Glu Gln Met Asn Leu Leu Asn Ser Arg Trp Glu
                420                 425                 430

Cys Leu Arg Val Ala Ser Met Glu Lys Gln Ser Asn Leu His Arg Val
            435                 440                 445
```

```
Leu Met Asp Leu Gln Asn Gln Lys Leu Lys Glu Leu Asn Asp Trp Leu
    450                 455                 460
Thr Lys Thr Glu Glu Arg Thr Arg Lys Met Glu Glu Pro Leu Gly
465                 470                 475                 480
Pro Asp Leu Glu Asp Leu Lys Arg Gln Val Gln Gln His Lys Val Leu
                    485                 490                 495
Gln Glu Asp Leu Glu Gln Glu Val Arg Val Asn Ser Leu Thr His
                500                 505                 510
Met Val Val Val Asp Glu Ser Ser Gly Asp His Ala Thr Ala Ala
            515                 520                 525
Leu Glu Glu Gln Leu Lys Val Leu Gly Asp Arg Trp Ala Asn Ile Cys
    530                 535                 540
Arg Trp Thr Glu Asp Arg Trp Val Leu Leu Gln Asp Ile Leu Leu Lys
545                 550                 555                 560
Trp Gln Arg Leu Thr Glu Glu Gln Cys Leu Phe Ser Ala Trp Leu Ser
                565                 570                 575
Glu Lys Glu Asp Ala Val Asn Lys Ile His Thr Thr Gly Phe Lys Asp
                580                 585                 590
Gln Asn Glu Met Leu Ser Ser Leu Gln Lys Leu Ala Val Leu Lys Ala
            595                 600                 605
Asp Leu Glu Lys Lys Lys Gln Ser Met Gly Lys Leu Tyr Ser Leu Lys
    610                 615                 620
Gln Asp Leu Leu Ser Thr Leu Lys Asn Lys Ser Val Thr Gln Lys Thr
625                 630                 635                 640
Glu Ala Trp Leu Asp Asn Phe Ala Arg Cys Trp Asp Asn Leu Val Gln
                645                 650                 655
Lys Leu Glu Lys Ser Thr Ala Gln Ile Ser Gln Ala Val Thr Thr Thr
                660                 665                 670
Gln Pro Ser Leu Thr Gln Thr Thr Val Met Glu Thr Val Thr Thr Val
            675                 680                 685
Thr Thr Arg Glu Gln Ile Leu Val Lys His Ala Gln Glu Glu Leu Pro
    690                 695                 700
Pro Pro Pro Pro Gln Lys Lys Arg Gln Ile Thr Val Asp Ser Glu Ile
705                 710                 715                 720
Arg Lys Arg Leu Asp Val Asp Ile Thr Glu Leu His Ser Trp Ile Thr
                725                 730                 735
Arg Ser Glu Ala Val Leu Gln Ser Pro Glu Phe Ala Ile Phe Arg Lys
                740                 745                 750
Glu Gly Asn Phe Ser Asp Leu Lys Glu Lys Val Asn Ala Ile Glu Arg
            755                 760                 765
Glu Lys Ala Glu Lys Phe Arg Lys Leu Gln Asp Ala Ser Arg Ser Ala
    770                 775                 780
Gln Ala Leu Val Glu Gln Met Val Asn Glu Gly Val Asn Ala Asp Ser
785                 790                 795                 800
Ile Lys Gln Ala Ser Glu Gln Leu Asn Ser Arg Trp Ile Glu Phe Cys
                805                 810                 815
Gln Leu Leu Ser Glu Arg Leu Asn Trp Leu Glu Tyr Gln Asn Asn Ile
                820                 825                 830
Ile Ala Phe Tyr Asn Gln Leu Gln Gln Leu Glu Gln Met Thr Thr Thr
            835                 840                 845
Ala Glu Asn Trp Leu Lys Ile Gln Pro Thr Thr Pro Ser Glu Pro Thr
    850                 855                 860
```

-continued

```
Ala Ile Lys Ser Gln Leu Lys Ile Cys Lys Asp Glu Val Asn Arg Leu
865                 870                 875                 880

Ser Gly Leu Gln Pro Gln Ile Glu Arg Leu Lys Ile Gln Ser Ile Ala
                885                 890                 895

Leu Lys Glu Lys Gly Gln Gly Pro Met Phe Leu Asp Ala Asp Phe Val
            900                 905                 910

Ala Phe Thr Asn His Phe Lys Gln Val Phe Ser Asp Val Gln Ala Arg
        915                 920                 925

Glu Lys Glu Leu Gln Thr Ile Phe Asp Thr Leu Pro Pro Met Arg Tyr
    930                 935                 940

Gln Glu Thr Met Ser Ala Ile Arg Thr Trp Val Gln Gln Ser Glu Thr
945                 950                 955                 960

Lys Leu Ser Ile Pro Gln Leu Ser Val Thr Asp Tyr Glu Ile Met Glu
                965                 970                 975

Gln Arg Leu Gly Glu Leu Gln Ala Leu Gln Ser Ser Leu Gln Glu Gln
            980                 985                 990

Gln Ser Gly Leu Tyr Tyr Leu Ser Thr Thr Val Lys Glu Met Ser Lys
        995                 1000                1005

Lys Ala Pro Ser Glu Ile Ser Arg Lys Tyr Gln Ser Glu Phe Glu
    1010                1015                1020

Glu Ile Glu Gly Arg Trp Lys Lys Leu Ser Ser Gln Leu Val Glu
    1025                1030                1035

His Cys Gln Lys Leu Glu Glu Gln Met Asn Lys Leu Arg Lys Ile
    1040                1045                1050

Gln Asn His Ile Gln Thr Leu Lys Lys Trp Met Ala Glu Val Asp
    1055                1060                1065

Val Phe Leu Lys Glu Glu Trp Pro Ala Leu Gly Asp Ser Glu Ile
    1070                1075                1080

Leu Lys Lys Gln Leu Lys Gln Cys Arg Leu Leu Val Ser Asp Ile
    1085                1090                1095

Gln Thr Ile Gln Pro Ser Leu Asn Ser Val Asn Glu Gly Gly Gln
    1100                1105                1110

Lys Ile Lys Asn Glu Ala Glu Pro Glu Phe Ala Ser Arg Leu Glu
    1115                1120                1125

Thr Glu Leu Lys Glu Leu Asn Thr Gln Trp Asp His Met Cys Gln
    1130                1135                1140

Gln Val Tyr Ala Arg Lys Glu Ala Leu Lys Gly Gly Leu Glu Lys
    1145                1150                1155

Thr Val Ser Leu Gln Lys Asp Leu Ser Glu Met His Glu Trp Met
    1160                1165                1170

Thr Gln Ala Glu Glu Glu Tyr Leu Glu Arg Asp Phe Glu Tyr Lys
    1175                1180                1185

Thr Pro Asp Glu Leu Gln Lys Ala Val Glu Glu Met Lys Arg Ala
    1190                1195                1200

Lys Glu Glu Ala Gln Gln Lys Glu Ala Lys Val Lys Leu Leu Thr
    1205                1210                1215

Glu Ser Val Asn Ser Val Ile Ala Gln Ala Pro Pro Val Ala Gln
    1220                1225                1230

Glu Ala Leu Lys Lys Glu Leu Glu Thr Leu Thr Thr Asn Tyr Gln
    1235                1240                1245

Trp Leu Cys Thr Arg Leu Asn Gly Lys Cys Lys Thr Leu Glu Glu
    1250                1255                1260

Val Trp Ala Cys Trp His Glu Leu Leu Ser Tyr Leu Glu Lys Ala
```

-continued

```
                1265                1270                1275
Asn Lys Trp Leu Asn Glu Val Glu Phe Lys Leu Lys Thr Thr Glu
    1280                1285                1290
Asn Ile Pro Gly Gly Ala Glu Glu Ile Ser Glu Val Leu Asp Ser
    1295                1300                1305
Leu Glu Asn Leu Met Arg His Ser Glu Asp Asn Pro Asn Gln Ile
    1310                1315                1320
Arg Ile Leu Ala Gln Thr Leu Thr Asp Gly Gly Val Met Asp Glu
    1325                1330                1335
Leu Ile Asn Glu Glu Leu Glu Thr Phe Asn Ser Arg Trp Arg Glu
    1340                1345                1350
Leu His Glu Glu Ala Val Arg Arg Gln Lys Leu Leu Glu Gln Ser
    1355                1360                1365
Ile Gln Ser Ala Gln Glu Thr Glu Lys Ser Leu His Leu Ile Gln
    1370                1375                1380
Glu Ser Leu Thr Phe Ile Asp Lys Gln Leu Ala Ala Tyr Ile Ala
    1385                1390                1395
Asp Lys Val Asp Ala Ala Gln Met Pro Gln Glu Ala Gln Lys Ile
    1400                1405                1410
Gln Ser Asp Leu Thr Ser His Glu Ile Ser Leu Glu Glu Met Lys
    1415                1420                1425
Lys His Asn Gln Gly Lys Glu Ala Ala Gln Arg Val Leu Ser Gln
    1430                1435                1440
Ile Asp Val Ala Gln Lys Lys Leu Gln Asp Val Ser Met Lys Phe
    1445                1450                1455
Arg Leu Phe Gln Lys Pro Ala Asn Phe Glu Leu Arg Leu Gln Glu
    1460                1465                1470
Ser Lys Met Ile Leu Asp Glu Val Lys Met His Leu Pro Ala Leu
    1475                1480                1485
Glu Thr Lys Ser Val Glu Gln Glu Val Val Gln Ser Gln Leu Asn
    1490                1495                1500
His Cys Val Asn Leu Tyr Lys Ser Leu Ser Glu Val Lys Ser Glu
    1505                1510                1515
Val Glu Met Val Ile Lys Thr Gly Arg Gln Ile Val Gln Lys Lys
    1520                1525                1530
Gln Thr Glu Asn Pro Lys Glu Leu Asp Glu Arg Val Thr Ala Leu
    1535                1540                1545
Lys Leu His Tyr Asn Glu Leu Gly Ala Lys Val Thr Glu Arg Lys
    1550                1555                1560
Gln Gln Leu Glu Lys Cys Leu Lys Leu Ser Arg Lys Met Arg Lys
    1565                1570                1575
Glu Met Asn Val Leu Thr Glu Trp Leu Ala Ala Thr Asp Met Glu
    1580                1585                1590
Leu Thr Lys Arg Ser Ala Val Glu Gly Met Pro Ser Asn Leu Asp
    1595                1600                1605
Ser Glu Val Ala Trp Gly Lys Ala Thr Gln Lys Glu Ile Glu Lys
    1610                1615                1620
Gln Lys Val His Leu Lys Ser Ile Thr Glu Val Gly Glu Ala Leu
    1625                1630                1635
Lys Thr Val Leu Gly Lys Lys Glu Thr Leu Val Glu Asp Lys Leu
    1640                1645                1650
Ser Leu Leu Asn Ser Asn Trp Ile Ala Val Thr Ser Arg Ala Glu
    1655                1660                1665
```

```
Glu Trp Leu Asn Leu Leu Leu Glu Tyr Gln Lys His Met Glu Thr
    1670                1675                1680

Phe Asp Gln Asn Val Asp His Ile Thr Lys Trp Ile Ile Gln Ala
    1685                1690                1695

Asp Thr Leu Leu Asp Glu Ser Glu Lys Lys Lys Pro Gln Gln Lys
    1700                1705                1710

Glu Asp Val Leu Lys Arg Leu Lys Ala Glu Leu Asn Asp Ile Arg
    1715                1720                1725

Pro Lys Val Asp Ser Thr Arg Asp Gln Ala Ala Asn Leu Met Ala
    1730                1735                1740

Asn Arg Gly Asp His Cys Arg Lys Leu Val Glu Pro Gln Ile Ser
    1745                1750                1755

Glu Leu Asn His Arg Phe Ala Ala Ile Ser His Arg Ile Lys Thr
    1760                1765                1770

Gly Lys Ala Ser Ile Pro Leu Lys Glu Leu Glu Gln Phe Asn Ser
    1775                1780                1785

Asp Ile Gln Lys Leu Leu Glu Pro Leu Glu Ala Glu Ile Gln Gln
    1790                1795                1800

Gly Val Asn Leu Lys Glu Glu Asp Phe Asn Lys Asp Met Asn Glu
    1805                1810                1815

Asp Asn Glu Gly Thr Val Lys Glu Leu Leu Gln Arg Gly Asp Asn
    1820                1825                1830

Leu Gln Gln Arg Ile Thr Asp Glu Arg Lys Arg Glu Glu Ile Lys
    1835                1840                1845

Ile Lys Gln Gln Leu Leu Gln Thr Lys His Asn Ala Leu Lys Asp
    1850                1855                1860

Leu Arg Ser Gln Arg Arg Lys Lys Ala Leu Glu Ile Ser His Gln
    1865                1870                1875

Trp Tyr Gln Tyr Lys Arg Gln Ala Asp Asp Leu Leu Lys Cys Leu
    1880                1885                1890

Asp Asp Ile Glu Lys Lys Leu Ala Ser Leu Pro Glu Pro Arg Asp
    1895                1900                1905

Glu Arg Lys Ile Lys Glu Ile Asp Arg Glu Leu Gln Lys Lys Lys
    1910                1915                1920

Glu Glu Leu Asn Ala Val Arg Arg Gln Ala Glu Gly Leu Ser Glu
    1925                1930                1935

Asp Gly Ala Ala Met Ala Val Glu Pro Thr Gln Ile Gln Leu Ser
    1940                1945                1950

Lys Arg Trp Arg Glu Ile Glu Ser Lys Phe Ala Gln Phe Arg Arg
    1955                1960                1965

Leu Asn Phe Ala Gln Ile His Thr Val Arg Glu Glu Thr Met Met
    1970                1975                1980

Val Met Thr Glu Asp Met Pro Leu Glu Ile Ser Tyr Val Pro Ser
    1985                1990                1995

Thr Tyr Leu Thr Glu Ile Thr His Val Ser Gln Ala Leu Leu Glu
    2000                2005                2010

Val Glu Gln Leu Leu Asn Ala Pro Asp Leu Cys Ala Lys Asp Phe
    2015                2020                2025

Glu Asp Leu Phe Lys Gln Glu Ser Leu Lys Asn Ile Lys Asp
    2030                2035                2040

Ser Leu Gln Gln Ser Ser Gly Arg Ile Asp Ile Ile His Ser Lys
    2045                2050                2055
```

-continued

```
Lys Thr Ala Ala Leu Gln Ser Ala Thr Pro Val Glu Arg Val Lys
    2060                2065                2070

Leu Gln Glu Ala Leu Ser Gln Leu Asp Phe Gln Trp Glu Lys Val
    2075                2080                2085

Asn Lys Met Tyr Lys Asp Arg Gln Gly Arg Phe Asp Arg Ser Val
    2090                2095                2100

Glu Lys Trp Arg Arg Phe His Tyr Asp Ile Lys Ile Phe Asn Gln
    2105                2110                2115

Trp Leu Thr Glu Ala Glu Gln Phe Leu Arg Lys Thr Gln Ile Pro
    2120                2125                2130

Glu Asn Trp Glu His Ala Lys Tyr Lys Trp Tyr Leu Lys Glu Leu
    2135                2140                2145

Gln Asp Gly Ile Gly Gln Arg Gln Thr Val Val Arg Thr Leu Asn
    2150                2155                2160

Ala Thr Gly Glu Glu Ile Ile Gln Gln Ser Ser Lys Thr Asp Ala
    2165                2170                2175

Ser Ile Leu Gln Glu Lys Leu Gly Ser Leu Asn Leu Arg Trp Gln
    2180                2185                2190

Glu Val Cys Lys Gln Leu Ser Asp Arg Lys Lys Arg Leu Glu Glu
    2195                2200                2205

Gln Lys Asn Ile Leu Ser Glu Phe Gln Arg Asp Leu Asn Glu Phe
    2210                2215                2220

Val Leu Trp Leu Glu Glu Ala Asp Asn Ile Ala Ser Ile Pro Leu
    2225                2230                2235

Glu Pro Gly Lys Glu Gln Gln Leu Lys Glu Lys Leu Glu Gln Val
    2240                2245                2250

Lys Leu Leu Val Glu Glu Leu Pro Leu Arg Gln Gly Ile Leu Lys
    2255                2260                2265

Gln Leu Asn Glu Thr Gly Gly Pro Val Leu Val Ser Ala Pro Ile
    2270                2275                2280

Ser Pro Glu Glu Gln Asp Lys Leu Glu Asn Lys Leu Lys Gln Thr
    2285                2290                2295

Asn Leu Gln Trp Ile Lys Val Ser Arg Ala Leu Pro Glu Lys Gln
    2300                2305                2310

Gly Glu Ile Glu Ala Gln Ile Lys Asp Leu Gly Gln Leu Glu Lys
    2315                2320                2325

Lys Leu Glu Asp Leu Glu Glu Gln Leu Asn His Leu Leu Leu Trp
    2330                2335                2340

Leu Ser Pro Ile Arg Asn Gln Leu Glu Ile Tyr Asn Gln Pro Asn
    2345                2350                2355

Gln Glu Gly Pro Phe Asp Val Gln Glu Thr Glu Ile Ala Val Gln
    2360                2365                2370

Ala Lys Gln Pro Asp Val Glu Glu Ile Leu Ser Lys Gly Gln His
    2375                2380                2385

Leu Tyr Lys Glu Lys Pro Ala Thr Gln Pro Val Lys Arg Lys Leu
    2390                2395                2400

Glu Asp Leu Ser Ser Glu Trp Lys Ala Val Asn Arg Leu Leu Gln
    2405                2410                2415

Glu Leu Arg Ala Lys Gln Pro Asp Leu Ala Pro Gly Leu Thr Thr
    2420                2425                2430

Ile Gly Ala Ser Pro Thr Gln Thr Val Thr Leu Val Thr Gln Pro
    2435                2440                2445

Val Val Thr Lys Glu Thr Ala Ile Ser Lys Leu Glu Met Pro Ser
```

```
                2450                2455                2460

Ser Leu Met Leu Glu Val Pro Ala Leu Ala Asp Phe Asn Arg Ala
    2465                2470                2475

Trp Thr Glu Leu Thr Asp Trp Leu Ser Leu Leu Asp Gln Val Ile
    2480                2485                2490

Lys Ser Gln Arg Val Met Val Gly Asp Leu Glu Asp Ile Asn Glu
    2495                2500                2505

Met Ile Ile Lys Gln Lys Ala Thr Met Gln Asp Leu Glu Gln Arg
    2510                2515                2520

Arg Pro Gln Leu Glu Glu Leu Ile Thr Ala Ala Gln Asn Leu Lys
    2525                2530                2535

Asn Lys Thr Ser Asn Gln Glu Ala Arg Thr Ile Ile Thr Asp Arg
    2540                2545                2550

Ile Glu Arg Ile Gln Asn Gln Trp Asp Glu Val Gln Glu His Leu
    2555                2560                2565

Gln Asn Arg Arg Gln Gln Leu Asn Glu Met Leu Lys Asp Ser Thr
    2570                2575                2580

Gln Trp Leu Glu Ala Lys Glu Glu Ala Glu Gln Val Leu Gly Gln
    2585                2590                2595

Ala Arg Ala Lys Leu Glu Ser Trp Lys Glu Gly Pro Tyr Thr Val
    2600                2605                2610

Asp Ala Ile Gln Lys Lys Ile Thr Glu Thr Lys Gln Leu Ala Lys
    2615                2620                2625

Asp Leu Arg Gln Trp Gln Thr Asn Val Asp Val Ala Asn Asp Leu
    2630                2635                2640

Ala Leu Lys Leu Leu Arg Asp Tyr Ser Ala Asp Asp Thr Arg Lys
    2645                2650                2655

Val His Met Ile Thr Glu Asn Ile Asn Ala Ser Trp Arg Ser Ile
    2660                2665                2670

His Lys Arg Val Ser Glu Arg Glu Ala Ala Leu Glu Glu Thr His
    2675                2680                2685

Arg Leu Leu Gln Gln Phe Pro Leu Asp Leu Glu Lys Phe Leu Ala
    2690                2695                2700

Trp Leu Thr Glu Ala Glu Thr Thr Ala Asn Val Leu Gln Asp Ala
    2705                2710                2715

Thr Arg Lys Glu Arg Leu Leu Glu Asp Ser Lys Gly Val Lys Glu
    2720                2725                2730

Leu Met Lys Gln Trp Gln Asp Leu Gln Gly Glu Ile Glu Ala His
    2735                2740                2745

Thr Asp Val Tyr His Asn Leu Asp Glu Asn Ser Gln Lys Ile Leu
    2750                2755                2760

Arg Ser Leu Glu Gly Ser Asp Asp Ala Val Leu Leu Gln Arg Arg
    2765                2770                2775

Leu Asp Asn Met Asn Phe Lys Trp Ser Glu Leu Arg Lys Lys Ser
    2780                2785                2790

Leu Asn Ile Arg Ser His Leu Glu Ala Ser Ser Asp Gln Trp Lys
    2795                2800                2805

Arg Leu His Leu Ser Leu Gln Glu Leu Leu Val Trp Leu Gln Leu
    2810                2815                2820

Lys Asp Asp Glu Leu Ser Arg Gln Ala Pro Ile Gly Gly Asp Phe
    2825                2830                2835

Pro Ala Val Gln Lys Gln Asn Asp Val His Arg Ala Phe Lys Arg
    2840                2845                2850
```

```
Glu Leu Lys Thr Lys Glu Pro Val Ile Met Ser Thr Leu Glu Thr
2855                2860                2865

Val Arg Ile Phe Leu Thr Glu Gln Pro Leu Glu Gly Leu Glu Lys
2870                2875                2880

Leu Tyr Gln Glu Pro Arg Glu Leu Pro Pro Glu Glu Arg Ala Gln
2885                2890                2895

Asn Val Thr Arg Leu Leu Arg Lys Gln Ala Glu Glu Val Asn Thr
2900                2905                2910

Glu Trp Glu Lys Leu Asn Leu His Ser Ala Asp Trp Gln Arg Lys
2915                2920                2925

Ile Asp Glu Thr Leu Glu Arg Leu Gln Glu Leu Gln Glu Ala Thr
2930                2935                2940

Asp Glu Leu Asp Leu Lys Leu Arg Gln Ala Glu Val Ile Lys Gly
2945                2950                2955

Ser Trp Gln Pro Val Gly Asp Leu Leu Ile Asp Ser Leu Gln Asp
2960                2965                2970

His Leu Glu Lys Val Lys Ala Leu Arg Gly Glu Ile Ala Pro Leu
2975                2980                2985

Lys Glu Asn Val Ser His Val Asn Asp Leu Ala Arg Gln Leu Thr
2990                2995                3000

Thr Leu Gly Ile Gln Leu Ser Pro Tyr Asn Leu Ser Thr Leu Glu
3005                3010                3015

Asp Leu Asn Thr Arg Trp Lys Leu Leu Gln Val Ala Val Glu Asp
3020                3025                3030

Arg Val Arg Gln Leu His Glu Ala His Arg Asp Phe Gly Pro Ala
3035                3040                3045

Ser Gln His Phe Leu Ser Thr Ser Val Gln Gly Pro Trp Glu Arg
3050                3055                3060

Ala Ile Ser Pro Asn Lys Val Pro Tyr Tyr Ile Asn His Glu Thr
3065                3070                3075

Gln Thr Thr Cys Trp Asp His Pro Lys Met Thr Glu Leu Tyr Gln
3080                3085                3090

Ser Leu Ala Asp Leu Asn Asn Val Arg Phe Ser Ala Tyr Arg Thr
3095                3100                3105

Ala Met Lys Leu Arg Arg Leu Gln Lys Ala Leu Cys Leu Asp Leu
3110                3115                3120

Leu Ser Leu Ser Ala Ala Cys Asp Ala Leu Asp Gln His Asn Leu
3125                3130                3135

Lys Gln Asn Asp Gln Pro Met Asp Ile Leu Gln Ile Ile Asn Cys
3140                3145                3150

Leu Thr Thr Ile Tyr Asp Arg Leu Glu Gln Glu His Asn Asn Leu
3155                3160                3165

Val Asn Val Pro Leu Cys Val Asp Met Cys Leu Asn Trp Leu Leu
3170                3175                3180

Asn Val Tyr Asp Thr Gly Arg Thr Gly Arg Ile Arg Val Leu Ser
3185                3190                3195

Phe Lys Thr Gly Ile Ile Ser Leu Cys Lys Ala His Leu Glu Asp
3200                3205                3210

Lys Tyr Arg Tyr Leu Phe Lys Gln Val Ala Ser Ser Thr Gly Phe
3215                3220                3225

Cys Asp Gln Arg Arg Leu Gly Leu Leu Leu His Asp Ser Ile Gln
3230                3235                3240
```

-continued

| | | | | | | | | | | |
|---|---|---|---|---|---|---|---|---|---|---|
| Ile | Pro | Arg | Gln | Leu | Gly | Glu | Val | Ala | Ser | Phe | Gly | Gly | Ser | Asn |
| 3245 | | | | 3250 | | | | 3255 | | |
| Ile | Glu | Pro | Ser | Val | Arg | Ser | Cys | Phe | Gln | Phe | Ala | Asn | Asn | Lys |
| 3260 | | | | 3265 | | | | 3270 | | |
| Pro | Glu | Ile | Glu | Ala | Ala | Leu | Phe | Leu | Asp | Trp | Met | Arg | Leu | Glu |
| 3275 | | | | 3280 | | | | 3285 | | |
| Pro | Gln | Ser | Met | Val | Trp | Leu | Pro | Val | Leu | His | Arg | Val | Ala | Ala |
| 3290 | | | | 3295 | | | | 3300 | | |
| Ala | Glu | Thr | Ala | Lys | His | Gln | Ala | Lys | Cys | Asn | Ile | Cys | Lys | Glu |
| 3305 | | | | 3310 | | | | 3315 | | |
| Cys | Pro | Ile | Ile | Gly | Phe | Arg | Tyr | Arg | Ser | Leu | Lys | His | Phe | Asn |
| 3320 | | | | 3325 | | | | 3330 | | |
| Tyr | Asp | Ile | Cys | Gln | Ser | Cys | Phe | Phe | Ser | Gly | Arg | Val | Ala | Lys |
| 3335 | | | | 3340 | | | | 3345 | | |
| Gly | His | Lys | Met | His | Tyr | Pro | Met | Val | Glu | Tyr | Cys | Thr | Pro | Thr |
| 3350 | | | | 3355 | | | | 3360 | | |
| Thr | Ser | Gly | Glu | Asp | Val | Arg | Asp | Phe | Ala | Lys | Val | Leu | Lys | Asn |
| 3365 | | | | 3370 | | | | 3375 | | |
| Lys | Phe | Arg | Thr | Lys | Arg | Tyr | Phe | Ala | Lys | His | Pro | Arg | Met | Gly |
| 3380 | | | | 3385 | | | | 3390 | | |
| Tyr | Leu | Pro | Val | Gln | Thr | Val | Leu | Glu | Gly | Asp | Asn | Met | Glu | Thr |
| 3395 | | | | 3400 | | | | 3405 | | |
| Pro | Val | Thr | Leu | Ile | Asn | Phe | Trp | Pro | Val | Asp | Ser | Ala | Pro | Ala |
| 3410 | | | | 3415 | | | | 3420 | | |
| Ser | Ser | Pro | Gln | Leu | Ser | His | Asp | Asp | Thr | His | Ser | Arg | Ile | Glu |
| 3425 | | | | 3430 | | | | 3435 | | |
| His | Tyr | Ala | Ser | Arg | Leu | Ala | Glu | Met | Glu | Asn | Ser | Asn | Gly | Ser |
| 3440 | | | | 3445 | | | | 3450 | | |
| Tyr | Leu | Asn | Asp | Ser | Ile | Ser | Pro | Asn | Glu | Ser | Ile | Asp | Asp | Glu |
| 3455 | | | | 3460 | | | | 3465 | | |
| His | Leu | Leu | Ile | Gln | His | Tyr | Cys | Gln | Ser | Leu | Asn | Gln | Asp | Ser |
| 3470 | | | | 3475 | | | | 3480 | | |
| Pro | Leu | Ser | Gln | Pro | Arg | Ser | Pro | Ala | Gln | Ile | Leu | Ile | Ser | Leu |
| 3485 | | | | 3490 | | | | 3495 | | |
| Glu | Ser | Glu | Glu | Arg | Gly | Glu | Leu | Glu | Arg | Ile | Leu | Ala | Asp | Leu |
| 3500 | | | | 3505 | | | | 3510 | | |
| Glu | Glu | Glu | Asn | Arg | Asn | Leu | Gln | Ala | Glu | Tyr | Asp | Arg | Leu | Lys |
| 3515 | | | | 3520 | | | | 3525 | | |
| Gln | Gln | His | Glu | His | Lys | Gly | Leu | Ser | Pro | Leu | Pro | Ser | Pro | Pro |
| 3530 | | | | 3535 | | | | 3540 | | |
| Glu | Met | Met | Pro | Thr | Ser | Pro | Gln | Ser | Pro | Arg | Asp | Ala | Glu | Leu |
| 3545 | | | | 3550 | | | | 3555 | | |
| Ile | Ala | Glu | Ala | Lys | Leu | Leu | Arg | Gln | His | Lys | Gly | Arg | Leu | Glu |
| 3560 | | | | 3565 | | | | 3570 | | |
| Ala | Arg | Met | Gln | Ile | Leu | Glu | Asp | His | Asn | Lys | Gln | Leu | Glu | Ser |
| 3575 | | | | 3580 | | | | 3585 | | |
| Gln | Leu | His | Arg | Leu | Arg | Gln | Leu | Leu | Glu | Gln | Pro | Gln | Ala | Glu |
| 3590 | | | | 3595 | | | | 3600 | | |
| Ala | Lys | Val | Asn | Gly | Thr | Thr | Val | Ser | Ser | Pro | Ser | Thr | Ser | Leu |
| 3605 | | | | 3610 | | | | 3615 | | |
| Gln | Arg | Ser | Asp | Ser | Ser | Gln | Pro | Met | Leu | Leu | Arg | Val | Val | Gly |
| 3620 | | | | 3625 | | | | 3630 | | |
| Ser | Gln | Thr | Ser | Asp | Ser | Met | Gly | Glu | Glu | Asp | Leu | Leu | Ser | Pro |

-continued

```
                3635                3640                3645
Pro Gln Asp Thr Ser Thr Gly Leu Glu Glu Val Met Glu Gln Leu
        3650                3655                3660

Asn Asn Ser Phe Pro Ser Ser Arg Gly Arg Asn Thr Pro Gly Lys
    3665                3670                3675

Pro Met Arg Glu Asp Thr Met
        3680                3685

<210> SEQ ID NO 2
<211> LENGTH: 11058
<212> TYPE: DNA
<213> ORGANISM: Homo sapiens

<400> SEQUENCE: 2
atgctttggt gggaagaagt agaggactgt tatgaaagag aagatgttca aaagaaaaca      60
ttcacaaaat gggtaaatgc acaatttct aagtttggga agcagcatat tgagaacctc     120
ttcagtgacc tacaggatgg gaggcgcctc ctagacctcc tcgaaggcct gacagggcaa     180
aaactgccaa agaaaaagg atccacaaga gttcatgccc tgaacaatgt caacaaggca     240
ctgcgggttt tgcagaacaa taatgttgat ttagtgaata ttggaagtac tgacatcgta     300 gatgaaatc ataaactgac tcttggtttg atttggaata taatcctcca ctggcaggtc     360
aaaaatgtaa tgaaaatat catggctgga ttgcaacaaa ccaacagtga aaagattctc     420
ctgagctggg tccgacaatc aactcgtaat tatccacagg ttaatgtaat caacttcacc     480
accagctggt ctgatggcct ggctttgaat gctctcatcc atagtcatag gccagaccta     540
tttgactgga atagtgtggt ttgccagcag tcagccacac aacgactgga acatgcattc     600
aacatcgcca gatatcaatt aggcatagag aaactactcg atcctgaaga tgttgatacc     660
acctatccag ataagaagtc catcttaatg tacatcacat cactcttcca gttttgcct      720 caacaagtga gcattgaagc catccaggaa gtggaaatgt tgccaaggcc acctaaagtg     780 actaagaag aacatttca gttacatcat caaatgcact attctcaaca gatcacggtc     840
agtctagcac agggatatga gagaacttct tcccctaagc ctcgattcaa gagctatgcc     900
tacacacagg ctgcttatgt caccacctct gaccctacac ggagcccatt tccttcacag     960
catttggaag ctcctgaaga caagtcattt ggcagttcat tgatggagag tgaagtaaac    1020
ctggaccgtt atcaaacagc tttagaagaa gtattatcgt ggcttctttc tgctgaggac    1080
acattgcaag cacaaggaga gatttctaat gatgtggaag tggtgaaaga ccagttctca    1140
actcatgagg ggtacatgat ggatttgaca gcccatcagg gccgggttgg taatattcta    1200
caattgggaa gtaagctgat tggaacagga aaattatcag aagatgaaga aactgaagta    1260
caagagcaga tgaatctcct aaattcaaga tgggaatgcc tcagggtagc tagcatggaa    1320
aaacaaagca atttacatag agttttaatg gatctccaga atcagaaact gaaagagttg    1380
aatgactggc taacaaaaac agaagaaaga acaaggaaaa tggaggaaga gcctcttgga    1440
cctgatcttg aagacctaaa acgccaagta caacaacata aggtgcttca agaagatcta    1500
gaacaagaac aagtcagggt caattctctc actcacatgg tggtggtagt tgatgaatct    1560
agtggagatc acgcaactgc tgctttggaa gaacaactta aggtattggg agatcgatgg    1620
gcaaacatct gtagatggac agaagaccgc tgggttcttt tacaagacat ccttctcaaa    1680
tggcaacgtc ttactgaaga acagtgcctt tttagtgcat ggcttcaga aaaagaagat    1740 gcagtgaaca agattcacac aactggcttt aaagatcaaa atgaaatgtt atcaagtctt    1800
```

```
caaaaactgg ccgttttaaa agcggatcta gaaaagaaaa agcaatccat gggcaaactg    1860
tattcactca aacaagatct tctttcaaca ctgaagaata agtcagtgac ccagaagacg    1920
gaagcatggc tggataactt tgcccggtgt tgggataatt tagtccaaaa acttgaaaag    1980
agtacagcac agatttcaca ggctgtcacc accactcagc catcactaac acagacaact    2040
gtaatggaaa cagtaactac ggtgaccaca agggaacaga tcctggtaaa gcatgctcaa    2100
gaggaacttc caccaccacc tccccaaaag aagaggcaga ttactgtgga ttctgaaatt    2160
aggaaaaggt tggatgttga tataactgaa cttcacagct ggattactcg ctcagaagct    2220
gtgttgcaga gtcctgaatt tgcaatcttt cggaaggaag caacttctc agacttaaaa    2280 gaaaaagtca atgccataga gcgagaaaaa gctgagaagt tcagaaaact gcaagatgcc    2340
agcagatcag ctcaggccct ggtggaacag atggtgaatg agggtgttaa tgcagatagc    2400
atcaaacaag cctcagaaca actgaacagc cggtggatcg aattctgcca gttgctaagt    2460
gagagactta actggctgga gtatcagaac aacatcatcg ctttctataa tcagctacaa    2520
caattggagc agatgacaac tactgctgaa aactggttga aaatccaacc caccaccca    2580 tcagagccaa cagcaattaa aagtcagtta aaaatttgta aggatgaagt caaccggcta    2640
tcaggtcttc aacctcaaat tgaacgatta aaaattcaaa gcatagccct gaaagagaaa    2700
ggacaaggac ccatgttcct ggatgcagac tttgtggcct ttacaaatca ttttaagcaa    2760
gtcttttctg atgtgcaggc cagagagaaa gagctacaga caattttga cactttgcca    2820 ccaatgcgct atcaggagac catgagtgcc atcaggacat gggtccagca gtcagaaacc    2880
aaactctcca tacctcaact tagtgtcacc gactatgaaa tcatggagca gagactcggg    2940
gaattgcagg ctttacaaag ttctctgcaa gagcaacaaa gtggcctata ctatctcagc    3000
accactgtga agagatgtc gaagaaagcg ccctctgaaa ttagccggaa atatcaatca    3060
gaatttgaag aaattgaggg acgctggaag aagctctcct cccagctggt tgagcattgt    3120
caaaagctag aggagcaaat gaataaactc cgaaaaattc agaatcacat acaaacctg    3180 aagaaatgga tggctgaagt tgatgttttt ctgaaggagg aatggcctgc ccttgggat    3240 tcagaaattc taaaaagca gctgaaacag tgcagacttt tagtcagtga tattcagaca    3300
attcagccca gtctaaacag tgtcaatgaa ggtgggcaga agataaagaa tgaagcagag    3360
ccagagtttg cttcgagact tgagacagaa ctcaaagaac ttaacactca gtgggatcac    3420
atgtgccaac aggtctatgc cagaaaggag gccttgaagg gaggtttgga gaaaactgta    3480
agcctccaga aagatctatc agagatgcac gaatggatga cacaagctga agaagagtat    3540
cttgagagag attttgaata taaaactcca gatgaattac agaaagcagt tgaagagatg    3600
aagagagcta agaagaggc ccaacaaaaa gaagcgaaag tgaaactcct tactgagtct    3660
gtaaatagtg tcatagctca agctccacct gtagcacaag aggccttaaa aaaggaactt    3720
gaaactctaa ccaccaacta ccagtggctc tgcactaggc tgaatgggaa atgcaagact    3780
ttggaagaag tttgggcatg ttggcatgag ttattgtcat acttggagaa agcaaacaag    3840
tggctaaatg aagtagaatt taaacttaaa accactgaaa acattcctgg cggagctgag    3900
gaaatctctg aggtgctaga ttcacttgaa aatttgatgc acattcaga ggataaccca    3960 aatcagattc gcatattggc acagaccta acagatggcg gagtcatgga tgagctaatc    4020
aatgaggaac ttgagacatt taattctcgt tggagggaac tacatgaaga ggctgtaagg    4080
aggcaaaagt tgcttgaaca gagcatccag tctgcccagg agactgaaaa atccttacac    4140
ttaatccagg agtccctcac attcattgac aagcagttgg cagcttatat tgcagacaag    4200
```

-continued

```
gtggacgcag ctcaaatgcc tcaggaagcc cagaaaatcc aatctgattt gacaagtcat    4260
gagatcagtt tagaagaaat gaagaaacat aatcagggga aggaggctgc ccaaagagtc    4320
ctgtctcaga ttgatgttgc acagaaaaaa ttacaagatg tctccatgaa gtttcgatta    4380
ttccagaaac cagccaattt tgagctgcgt ctacaagaaa gtaagatgat tttagatgaa    4440
gtgaagatga acttgcctgc attggaaaca aagagtgtgg aacaggaagt agtacagtca    4500
cagctaaatc attgtgtgaa cttgtataaa agtctgagtg aagtgaagtc tgaagtggaa    4560
atggtgataa agactggacg tcagattgta cagaaaaagc agacggaaaa tcccaaagaa    4620
cttgatgaaa gagtaacagc tttgaaattg cattataatg agctgggagc aaaggtaaca    4680
gaaagaaagc aacagttgga gaaatgcttg aaattgtccc gtaagatgcg aaaggaaatg    4740
aatgtcttga cagaatggct ggcagctaca gatatggaat tgacaaagag atcagcagtt    4800
gaaggaatgc ctagtaattt ggattctgaa gttgcctggg aaaggctac tcaaaaagag    4860
attgagaaac agaaggtgca cctgaagagt atcacagagg taggagaggc cttgaaaaca    4920
gttttgggca agaaggagac gttggtggaa gataaactca gtcttctgaa tagtaactgg    4980
atagctgtca cctcccgagc agaagagtgg ttaaatcttt tgttggaata ccagaaacac    5040
atggaaactt tgaccagaa tgtggaccac atcacaaagt ggatcattca ggctgacaca    5100
cttttggatg aatcagagaa aaagaaaccc cagcaaaaag aagacgtgct taagcgttta    5160
aaggcagaac tgaatgacat acgcccaaag gtggactcta cacgtgacca agcagcaaac    5220
ttgatggcaa accgcggtga ccactgcagg aaattagtag agcccaaat ctcagagctc    5280
aaccatcgat ttgcagccat ttcacacaga attaagactg gaaaggcctc cattcctttg    5340
aaggaattgg agcagtttaa ctcagatata caaaaattgc ttgaaccact ggaggctgaa    5400
attcagcagg gggtgaatct gaaagaggaa gacttcaata agatatgaa tgaagacaat    5460
gagggtactg taaagaatt gttgcaaaga ggagacaact acaacaaag aatcacagat    5520
gagagaaaga gagaggaaat aaagataaaa cagcagctgt tacagacaaa acataatgct    5580
ctcaaggatt tgaggtctca aagaagaaaa aaggctctag aaatttctca tcagtggtat    5640
cagtacaaga ggcaggctga tgatctcctg aaatgcttgg atgacattga aaaaaaatta    5700
gccagcctac ctgagcccag agatgaaagg aaaataaagg aaattgatcg ggaattgcag    5760
aagaagaaag aggagctgaa tgcagtgcgt aggcaagctg agggcttgtc tgaggatggg    5820
gccgcaatgg cagtggagcc aactcagatc cagctcagca agcgctggcg ggaaattgag    5880
agcaaatttg ctcagtttcg aagactcaac tttgcacaaa ttcacactgt ccgtgaagaa    5940
acgatgatgt tgatgactga agacatgcct ttggaaattt cttatgtgcc ttctacttat    6000
ttgactgaaa tcactcatgt ctcacaagcc ctattagaag tggaacaact tctcaatgct    6060
cctgacctct gtgctaagga ctttgaagat ctctttaagc aagaggagtc tctgaagaat    6120
ataaaagata gtctacaaca aagctcaggt cggattgaca ttattcatag caagaagaca    6180
gcagcattgc aaagtgcaac gcctgtggaa agggtgaagc tacaggaagc tctctcccag    6240
cttgatttcc aatgggaaaa agttaacaaa atgtacaagg accgacaagg gcgatttgac    6300
agatctgttg agaaatggcg gcgttttcat tatgatataa agatatttaa tcagtggcta    6360
acagaagctg aacagtttct cagaaagaca caaattcctg agaattggga acatgctaaa    6420
tacaaatggt atcttaagga actccaggat ggcattgggc agcggcaaac tgttgtcaga    6480
acattgaatg caactgggga agaaataatt cagcaatcct caaaaacaga tgccagtatt    6540
```

```
ctacaggaaa aattgggaag cctgaatctg cggtggcagg aggtctgcaa acagctgtca   6600
gacagaaaaa agaggctaga agaacaaaag aatatcttgt cagaatttca aagagattta   6660
aatgaatttg ttttatggtt ggaggaagca gataacattg ctagtatccc acttgaacct   6720
ggaaaagagc agcaactaaa agaaaagctt gagcaagtca agttactggt ggaagagttg   6780
cccctgcgcc agggaattct caaacaatta aatgaaactg gaggacccgt gcttgtaagt   6840
gctcccataa gcccagaaga gcaagataaa cttgaaaata agctcaagca gacaaatctc   6900
cagtggataa aggtttccag agctttacct gagaaacaag gagaaattga agctcaaata   6960
aaagaccttg ggcagcttga aaaaaagctt gaagaccttg aagagcagtt aaatcatctg   7020
ctgctgtggt tatctcctat taggaatcag ttggaaattt ataaccaacc aaaccaagaa   7080
ggaccatttg acgttcagga aactgaaata gcagttcaag ctaaacaacc ggatgtggaa   7140 gagatttttgt ctaaagggca gcatttgtac aaggaaaaac cagccactca gccagtgaag   7200
aggaagttag aagatctgag ctctgagtgg aaggcggtaa accgtttact tcaagagctg   7260
agggcaaagc agcctgacct agctcctgga ctgaccacta ttggagcctc tcctactcag   7320
actgttactg tggtgacaca acctgtggtt actaaggaaa ctgccatctc caaactagaa   7380
atgccatctt ccttgatgtt ggaggtacct gctctggcag atttcaaccg ggcttggaca   7440
gaacttaccg actggctttc tctgcttgat caagttataa atcacagag ggtgatggtg   7500 ggtgaccttg aggatatcaa cgagatgatc atcaagcaga aggcaacaat gcaggatttg   7560
gaacagaggc gtccccagtt ggaagaactc attaccgctg cccaaaattt gaaaaacaag   7620
accagcaatc aagaggctag aacaatcatt acggatcgaa ttgaaagaat tcagaatcag   7680
tgggatgaag tacaagaaca ccttcagaac cggaggcaac agttgaatga aatgttaaag   7740
gattcaacac aatggctgga agctaaggaa gaagctgagc aggtcttagg acaggccaga   7800
gccaagcttg agtcatggaa ggagggtccc tatacagtag atgcaatcca aaagaaaatc   7860
acagaaacca agcagttggc caaagacctc cgccagtggc agacaaatgt agatgtggca   7920
aatgacttgg ccctgaaact tctccgggat tattctgcag atgataccag aaaagtccac   7980
atgataacag agaatatcaa tgcctcttgg agaagcattc ataaagggt gagtgagcga   8040 gaggctgctt tggaagaaac tcatagatta ctgcaacagt tcccccctgga cctgaaaaag   8100 tttcttgcct ggcttacaga agctgaaaca actgccaatg tcctacagga tgctacccgt   8160
aaggaaaggc tcctagaaga ctccaaggga gtaaaagagc tgatgaaaca atggcaagac   8220
ctccaaggtg aaattgaagc tcacacagat gtttatcaca acctggatga aaacagccaa   8280
aaaatcctga tcccctggaa ggttccgat gatgcagtcc tgttacaaag acgtttggat   8340
aacatgaact tcaagtggag tgaacttcgg aaaaagtctc tcaacattag gtcccatttg   8400
gaagccagtt ctgaccagtg gaagcgtctg cacctttctc tgcaggaact tctggtgtgg   8460
ctacagctga aagatgatga attaagccgg caggcaccta ttggaggcga ctttccagca   8520
gttcagaagc agaacgatgt acatagggcc ttcaagaggg aattgaaaac taagaacct   8580 gtaatcatga gtactcttga gactgtacga atatttctga cagagcagcc tttggaagga   8640
ctagagaaac tctaccagga gcccagagag ctgcctcctg aggagagagc ccagaatgtc   8700
actcggcttc tacgaaagca ggctgaggag gtcaatactg agtgggaaaa attgaacctg   8760
cactccgctg actggcagag aaaaatagat gagaccttg aaagactcca ggaacttcaa   8820
gaggccacgg atgagctgga cctcaagctg cgccaagctg aggtgatcaa gggatcctgg   8880
cagcccgtgg gcgatctcct cattgactct ctccaagatc acctcgagaa agtcaaggca   8940
```

```
cttcgaggag aaattgcgcc tctgaaagag aacgtgagcc acgtcaatga ccttgctcgc    9000
cagcttacca ctttgggcat tcagctctca ccgtataacc tcagcactct ggaagacctg    9060
aacaccagat ggaagcttct gcaggtggcc gtcgaggacc gagtcaggca gctgcatgaa    9120
gcccacaggg actttggtcc agcatctcag cactttcttt ccacgtctgt ccagggtccc    9180
tgggagagag ccatctcgcc aaacaaagtg ccctactata tcaaccacga gactcaaaca    9240
acttgctggg accatcccaa aatgacagag ctctaccagt ctttagctga cctgaataat    9300
gtcagattct cagcttatag gactgccatg aaactccgaa gactgcagaa ggcccttttgc   9360 ttggatctct tgagcctgtc agctgcatgt gatgccttgg accagcacaa cctcaagcaa    9420
aatgaccagc ccatggatat cctgcagatt attaattgtt tgaccactat ttatgaccgc    9480
ctggagcaag agcacaacaa tttggtcaac gtccctctct gcgtggatat gtgtctgaac    9540
tggctgctga atgtttatga tacgggacga acagggagga tccgtgtcct gtcttttaaa    9600
actggcatca tttccctgtg taaagcacat ttggaagaca agtacagata ccttttcaag    9660
caagtggcaa gttcaacagg attttgtgac cagcgcaggc tgggcctcct tctgcatgat    9720
tctatccaaa ttccaagaca gttgggtgaa gttgcatcct ttgggggcag taacattgag    9780
ccaagtgtcc ggagctgctt ccaatttgct aataataagc cagagatcga agcggccctc    9840
ttcctagact ggatgagact ggaacccag tccatggtgt ggctgcccgt cctgcacaga     9900
gtggctgctg cagaaactgc caagcatcag gccaaatgta acatctgcaa agagtgtcca    9960
atcattggat tcaggtacag gagtctaaag cactttaatt atgacatctg ccaaagctgc    10020
tttttttctg gtcgagttgc aaaaggccat aaaatgcact atcccatggt ggaatattgc    10080
actccgacta catcaggaga agatgttcga gactttgcca aggtactaaa aaacaaattt    10140
cgaaccaaaa ggtattttgc gaagcatccc cgaatgggct acctgccagt gcagactgtc    10200 ttagagggg acaacatgga aactcccgtt actctgatca acttctggcc agtagattct     10260
gcgcctgcct cgtcccctca gctttcacac gatgatactc attcacgcat tgaacattat    10320
gctagcaggg tagcagaaat ggaaaacagc aatggatctt atctaaatga tagcatctct    10380
cctaatgaga gcatagatga tgaacatttg ttaatccagc attactgcca aagtttgaac    10440
caggactccc ccctgagcca gcctcgtagt cctgcccaga tcttgatttc cttagagagt    10500
gaggaaagag gggagctaga gagaatccta gcagatcttg aggaagaaaa caggaatctg    10560
caagcagaat atgaccgtct aaagcagcag cacgaacata aaggcctgtc cccactgccg    10620 tccccctcctg aaatgatgcc cacctctccc cagagtcccc gggatgctga gctcattgct    10680
gaggccaagc tactgcgtca acacaaaggc cgcctggaag ccaggatgca aatcctggaa    10740
gaccacaata aacagctgga gtcacagtta cacaggctaa ggcagctgct ggagcaaccc    10800
caggcagagg ccaaagtgaa tggcacaacg gtgtcctctc cttctacctc tctacagagg    10860
tccgacagca gtcagcctat gctgctccga gtggttggca gtcaaacttc ggactccatg    10920
ggtgaggaag atcttctcag tcctccccag gacacaagca cagggttaga ggaggtgatg    10980
gagcaactca acaactcctt ccctagttca agaggaagaa ataccctggg aaagccaatg    11040
agagaggaca caatgtag                                                   11058
```

<210> SEQ ID NO 3
<211> LENGTH: 5952
<212> TYPE: DNA
<213> ORGANISM: Artificial Sequence
<220> FEATURE:

<223> OTHER INFORMATION: Synthetic oligonucleotide

<400> SEQUENCE: 3

```
atgctttggt gggaagaagt agaggactgt tatgaaagag aagatgttca aaagaaaaca    60
ttcacaaaat gggtaaatgc acaatttct aagtttggga agcagcatat tgagaacctc   120
ttcagtgacc tacaggatgg gaggcgcctc ctagacctcc tcgaaggcct gacagggcaa   180
aaactgccaa agaaaaagg atccacaaga gttcatgccc tgaacaatgt caacaaggca   240
ctgcgggttt tgcagaacaa taatgttgat ttagtgaata ttggaagtac tgacatcgta   300
gatggaaatc ataaactgac tcttggtttg atttggaata taatcctcca ctggcaggtc   360
aaaaatgtaa tgaaaatat catggctgga ttgcaacaaa ccaacagtga aagattctc    420
ctgagctggg tccgacaatc aactcgtaat tatccacagg ttaatgtaat caacttcacc   480
accagctggt ctgatggcct ggctttgaat gctctcatcc atagtcatag gccagaccta   540
tttgactgga atagtgtggt ttgccagcag tcagccacac aacgactgga acatgcattc   600
aacatcgcca gatatcaatt aggcatagag aaactactcg atcctgaaga tgttgatacc   660
acctatccag ataagaagtc catcttaatg tacatcacat cactcttcca gttttgcct   720
caacaagtga gcattgaagc catccaggaa gtggaaatgt tgccaaggcc acctaaagtg   780
actaaagaag aacattttca gttacatcat caaatgcact attctcaaca gatcacggtc   840
agtctagcac agggatatga gagaacttct tcccctaagc ctcgattcaa gagctatgcc   900
tacacacagg ctgcttatgt caccacctct gaccctacac ggagcccatt tccttcacag   960
catttggaag ctcctgaaga caagtcattt ggcagttcat tgatggagag tgaagtaaac  1020
ctggaccgtt atcaaacagc tttagaagaa gtattatcgt ggcttctttc tgctgaggac  1080
acattgcaag cacaaggaga gatttctaat gatgtggaag tggtgaaaga ccagtttcat  1140
actcatgagg ggtacatgat ggatttgaca gcccatcagg gccgggttgg taatattcta  1200
caattgggaa gtaagctgat tggaacagga aaattatcag aagatgaaga aactgaagta  1260
caagagcaga tgaatctcct aaattcaaga tgggaatgcc tcagggtagc tagcatggaa  1320
aaacaaagca atttacatag agtttaatg gatctccaga atcagaaact gaaagagttg  1380
aatgactggc taacaaaaac agaagaaaga acaggaaaa tggaggaaga gcctcttgga  1440
cctgatcttg aagacctaaa acgccaagta caacaacata aggtgcttca agaagatcta  1500
gaacaagaac aagtcagggt caattctctc actcacatgg tggtggtagt tgatgaatct  1560
agtggagatc acgcaactgc tgctttggaa gaacaactta aggtattggg agatcgatgg  1620
gcaaacatct gtagatggac agaagaccgc tgggttcttt tacaagacat ccttctcaaa  1680
tggcaacgtc ttactgaaga acagtgcctt tttagtgcat ggctttcaga aaagaagat   1740
gcagtgaaca agattcacac aactggcttt aaagatcaaa atgaaatgtt atcaagtctt  1800
caaaaactgg ccgttttaaa agcggatcta gaaagaaaa agcaatccat gggcaaactg  1860
tattcactca acaagatct tctttcaaca ctgaagaata agtcagtgac ccagaagacg  1920
gaagcatggc tggataactt tgcccggtgt gggataatt tagtccaaaa acttgaaaag  1980
agtacagcac aggaaactga aatagcagtt caagctaaac aaccggatgt ggaagagatt  2040
ttgtctaaag gcagcattt gtacaaggaa aaaccagcca ctcagccagt gaagaggaag  2100
ttagaagatc tgagctctga gtggaaggcg gtaaaccgtt tacttcaaga gctgagggca  2160
aagcagcctg acctagctcc tggactgacc actattggag cctctcctac tcagactgtt  2220
actctggtga cacaacctgt ggttactaag gaaactgcca tctccaaact agaaatgcca  2280
```

-continued

```
tcttccttga tgttggaggt acctgctctg gcagatttca accgggcttg gacagaactt     2340
accgactggc tttctctgct tgatcaagtt ataaaatcac agagggtgat ggtgggtgac     2400
cttgaggata tcaacgagat gatcatcaag cagaaggcaa caatgcagga tttggaacag     2460
aggcgtcccc agttggaaga actcattacc gctgcccaaa atttgaaaaa caagaccagc     2520
aatcaagagg ctagaacaat cattacggat cgaattgaaa gaattcagaa tcagtgggat     2580
gaagtacaag aacaccttca gaaccggagg caacagttga atgaaatgtt aaaggattca     2640
acacaatggc tggaagctaa ggaagaagct gagcaggtct taggacaggc cagagccaag     2700
cttgagtcat ggaaggaggg tccctataca gtagatgcaa tccaaaagaa aatcacagaa     2760
accaagcagt tggccaaaga cctccgccag tggcagacaa atgtagatgt ggcaaatgac     2820
ttggccctga aacttctccg ggattattct gcagatgata ccagaaaagt ccacatgata     2880
acagagaata tcaatgcctc ttggagaagc attcataaaa gggtgagtga gcagagggct     2940
gctttggaag aaactcatag attactgcaa cagttccccc tggacctgga aaagtttctt     3000
gcctggctta cagaagctga aacaactgcc aatgtcctac aggatgctac ccgtaaggaa     3060
aggctcctag aagactccaa gggagtaaaa gagctgatga acaatggca agacctccaa     3120 ggtgaaattg aagctcacac agatgtttat cacaacctgg atgaaaacag ccaaaaaatc     3180
ctgagatccc tggaaggttc cgatgatgca gtcctgttac aaagacgttt ggataacatg     3240
aacttcaagt ggagtgaact tcggaaaaag tctctcaaca ttaggtccca tttggaagcc     3300
agttctgacc agtggaagcg tctgcacctt tctctgcagg aacttctggt gtggctacag     3360
ctgaaagatg atgaattaag ccggcaggca cctattggag gcgactttcc agcagttcag     3420
aagcagaacg atgtacatag ggccttcaag agggaattga aaactaaaga acctgtaatc     3480
atgagtactc ttgagactgt acgaatattt ctgacagagc agcctttgga aggactagag     3540
aaactctacc aggagcccag agagctgcct cctgaggaga gagcccagaa tgtcactcgg     3600
cttctacgaa agcaggctga ggaggtcaat actgagtggg aaaaattgaa cctgcactcc     3660
gctgactggc agagaaaaat agatgagacc cttgaaagac tccaggaact tcaagaggcc     3720
acggatgagc tggacctcaa gctgcgccaa gctgaggtga tcaagggatc ctggcagccc     3780
gtgggcgatc tcctcattga ctctctccaa gatcacctcg agaaagtcaa ggcacttcga     3840
ggagaaattg cgcctctgaa agagaacgtg agccacgtca atgaccttgc tcgccagctt     3900
accactttgg gcattcagct ctcaccgtat aacctcagca ctctggaaga cctgaacacc     3960
agatggaagc ttctgcaggt ggccgtcgag gaccgagtca ggcagctgca tgaagcccac     4020
agggactttg gtccagcatc tcagcacttt cttccacgt ctgtccaggg tccctgggag     4080
agagccatct cgccaaacaa agtgccctac tatatcaacc acgagactca aacaacttgc     4140
tgggaccatc ccaaaatgac agagctctac cagtctttag ctgacctgaa taatgtcaga     4200
ttctcagctt ataggactgc catgaaactc cgaagactgc agaaggccct ttgcttggat     4260
ctcttgagcc tgtcagctgc atgtgatgcc ttggaccagc acaacctcaa gcaaaatgac     4320
cagcccatgg atatcctgca gattattaat tgtttgacca ctatttatga ccgcctggag     4380
caagagcaca caatttggt caacgtccct ctctgcgtgg atatgtgtct gaactggctg     4440
ctgaatgttt atgatacggg acgaacaggg aggatccgtg tcctgtcttt taaaactggc     4500
atcatttccc tgtgtaaagc acatttggaa gacaagtaca gataccttt caagcaagtg     4560 gcaagttcaa caggattttg tgaccagcgc aggctgggcc tccttctgca tgattctatc     4620
```

-continued

```
caaattccaa gacagttggg tgaagttgca tcctttgggg gcagtaacat tgagccaagt    4680
gtccggagct gcttccaatt tgctaataat aagccagaga tcgaagcggc cctcttccta    4740
gactggatga gactggaacc ccagtccatg gtgtggctgc ccgtcctgca cagagtggct    4800
gctgcagaaa ctgccaagca tcaggccaaa tgtaacatct gcaaagagtg tccaatcatt    4860
ggattcaggt acaggagtct aaagcacttt aattatgaca tctgccaaag ctgcttttt    4920
tctggtcgag ttgcaaaagg ccataaaatg cactatccca tggtgaata ttgcactccg      4980
actacatcag gagaagatgt tcgagacttt gccaaggtac taaaaaacaa atttcgaacc    5040
aaaaggtatt ttgcgaagca tccccgaatg ggctacctgc cagtgcagac tgtcttagag    5100
ggggacaaca tggaaactcc cgttactctg atcaacttct ggccagtaga ttctgcgcct    5160
gcctcgtccc ctcagctttc acacgatgat actcattcac gcattgaaca ttatgctagc    5220
aggctagcag aaatggaaaa cagcaatgga tcttatctaa atgatagcat ctctcctaat    5280
gagagcatag atgatgaaca tttgttaatc cagcattact gccaaagttt gaaccaggac    5340
tccccctga gccagcctcg tagtcctgcc cagatcttga tttccttaga gagtgaggaa      5400
agaggggagc tagagagaat cctagcagat cttgaggaag aaaacaggaa tctgcaagca    5460
gaatatgacc gtctaaagca gcagcacgaa cataaaggcc tgtccccact gccgtccct      5520
cctgaaatga tgcccacctc tccccagagt ccccgggatg ctgagctcat tgctgaggcc    5580
aagctactgc gtcaacacaa aggccgcctg gaagccagga tgcaaatcct ggaagaccac    5640
aataaacagc tggagtcaca gttacacagg ctaaggcagc tgctggagca accccaggca    5700
gaggccaaag tgaatggcac aacggtgtcc tctccttcta cctctctaca gaggtccgac    5760
agcagtcagc ctatgctgct ccgagtggtt ggcagtcaaa cttcggactc catgggtgag    5820
gaagatcttc tcagtcctcc ccaggacaca agcacagggt tagaggaggt gatggagcaa    5880
ctcaacaact ccttccctag ttcaagagga agaaatacc ctggaaagcc aatgagagag      5940
gacacaatgt ag                                                          5952
```

<210> SEQ ID NO 4
<211> LENGTH: 5751
<212> TYPE: DNA
<213> ORGANISM: Artificial Sequence
<220> FEATURE:
<223> OTHER INFORMATION: Synthetic oligonucleotide

<400> SEQUENCE: 4

```
atgctttggt gggaagaagt agaggactgt tatgaaagag aagatgttca aagaaaaca      60
ttcacaaaat gggtaaatgc acaattttct aagtttggga agcagcatat tgagaacctc    120
ttcagtgacc tacaggatgg gaggcgcctc ctagacctcc tcgaaggcct gacagggcaa    180
aaactgccaa agaaaaagg atccacaaga gttcatgccc tgaacaatgt caacaaggca      240
ctgcgggttt tgcagaacaa taatgttgat ttagtgaata ttggaagtac tgacatcgta    300
gatggaaatc ataaactgac tcttggttg atttggaata taatcctcca ctggcaggtc      360
aaaaatgtaa tgaaaatat catggctgga ttgcaacaaa ccaacagtga aaagattctc    420
ctgagctggg tccgacaatc aactcgtaat tatccacagg ttaatgtaat caacttcacc    480
accagctggt ctgatggcct ggctttgaat gctctcatcc atagtcatag gccagaccta    540
tttgactgga atagtgtggt ttgccagcag tcagccacac aacgactgga acatgcattc    600
aacatcgcca gatatcaatt aggcatagag aaactactcg atcctgaaga tgttgatacc    660
acctatccag ataagaagtc catcttaatg tacatcacat cactcttcca agttttgcct    720
```

```
caacaagtga gcattgaagc catccaggaa gtggaaatgt tgccaaggcc acctaaagtg     780
actaaagaag aacattttca gttacatcat caaatgcact attctcaaca gatcacggtc     840
agtctagcac agggatatga gagaacttct tcccctaagc ctcgattcaa gagctatgcc     900
tacacacagg ctgcttatgt caccacctct gaccctacac ggagcccatt tccttcacag     960
catttggaag ctcctgaaga caagtcattt ggcagttcat tgatggagag tgaagtaaac    1020
ctggaccgtt atcaaacagc tttagaagaa gtattatcgt ggcttctttc tgctgaggac    1080
acattgcaag cacaaggaga gatttctaat gatgtggaag tggtgaaaga ccagtttcat    1140
actcatgagg ggtacatgat ggatttgaca gcccatcagg gccgggttgg taatattcta    1200
caattgggaa gtaagctgat tggaacagga aaattatcag aagatgaaga aactgaagta    1260
caagagcaga tgaatctcct aaattcaaga tgggaatgcc tcagggtagc tagcatggaa    1320
aaacaaagca atttacatag agttttaatg gatctccaga atcagaaact gaaagagttg    1380
aatgactggc taacaaaaac agaagaaaga acaaggaaaa tggaggaaga gcctcttgga    1440
cctgatcttg aagacctaaa acgccaagta caacaacata aggtgcttca agaagatcta    1500
gaacaagaac aagtcagggt caattctctc actcacatgg tggtggtagt tgatgaatct    1560
agtggagatc acgcaactgc tgctttggaa gaacaactta aggtattggg agatcgatgg    1620
gcaaacatct gtagatggac agaagaccgc tgggttcttt tacaagacat ccttctcaaa    1680
tggcaacgtc ttactgaaga acagtgcctt tttagtgcat ggctttcaga aaaagaagat    1740
gcagtgaaca agattcacac aactggcttt aaagatcaaa atgaaatgtt atcaagtctt    1800
caaaaactgg ccgtttttaaa agcggatcta gaaaagaaaa agcaatccat gggcaaactg    1860
tattcactca aacaagatct tctttcaaca ctgaagaata agtcagtgac ccagaagacg    1920
gaagcatggc tggataactt tgcccggtgt tgggataatt tagtccaaaa acttgaaaag    1980
agtacagcac agatttcaca gcagcctgac ctagctcctg gactgaccac tattggagcc    2040
tctcctactc agactgttac tctggtgaca caacctgtgg ttactaagga aactgccatc    2100
tccaaactag aaatgccatc ttccttgatg ttggaggtac ctgctctggc agatttcaac    2160
cgggcttgga cagaacttac cgactggctt tctctgcttg atcaagttat aaaatcacag    2220
agggtgatgg tgggtgacct tgaggatatc aacgagatga tcatcaagca gaaggcaaca    2280
atgcaggatt tggaacagag gcgtccccag ttggaagaac tcattaccgc tgcccaaaat    2340
ttgaaaaaca agaccagcaa tcaagaggct agaacaatca ttacggatcg aattgaaaga    2400
attcagaatc agtgggatga agtacaagaa caccttcaga accggaggca acagttgaat    2460
gaaatgttaa aggattcaac acaatggctg gaagctaagg aagaagctga gcaggtctta    2520
ggacaggcca gagccaagct tgagtcatgg aaggagggtc cctatacagt agatgcaatc    2580
caaaagaaaa tcacagaaac caagcagttg gccaaagacc tccgccagtg gcagacaaat    2640
gtagatgtgg caaatgactt ggccctgaaa cttctccggg attattctgc agatgatacc    2700
agaaaagtcc acatgataac agagaatatc aatgcctctt ggagaagcat tcataaaagg    2760
gtgagtgagc gagaggctgc tttggaagaa actcatagat tactgcaaca gttcccctg    2820
gacctggaaa agtttcttgc ctggcttaca aagctgaaa caactgccaa tgtcctacag    2880
gatgctaccc gtaaggaaag gctcctagaa gactccaagg gagtaaaaga gctgatgaaa    2940
caatggcaag acctccaagg tgaaattgaa gctcacacag atgttttatca caacctggat    3000
gaaaacagcc aaaaaatcct gagatccctg gaaggttccg atgatgcagt cctgttacaa    3060
```

```
agacgtttgg ataacatgaa cttcaagtgg agtgaacttc ggaaaaagtc tctcaacatt    3120
aggtcccatt tggaagccag ttctgaccag tggaagcgtc tgcaccttc tctgcaggaa     3180
cttctggtgt ggctacagct gaaagatgat gaattaagcc ggcaggcacc tattggaggc    3240
gactttccag cagttcagaa gcagaacgat gtacataggg ccttcaagag ggaattgaaa    3300
actaaagaac ctgtaatcat gagtactctt gagactgtac gaatatttct gacagagcag    3360
cctttggaag gactagagaa actctaccag gagcccagag agctgcctcc tgaggagaga    3420
gcccagaatg tcactcggct tctacgaaag caggctgagg aggtcaatac tgagtgggaa    3480
aaattgaacc tgcactccgc tgactggcag agaaaaatag atgagaccct tgaaagactc    3540
caggaacttc aagaggccac ggatgagctg gacctcaagc tgcgccaagc tgaggtgatc    3600
aagggatcct ggcagcccgt gggcgatctc ctcattgact ctctccaaga tcacctcgag    3660
aaagtcaagg cacttcgagg agaaattgcg cctctgaaag agaacgtgag ccacgtcaat    3720
gaccttgctc gccagcttac cactttgggc attcagctct caccgtataa cctcagcact    3780
ctggaagacc tgaacaccag atggaagctt ctgcaggtgg ccgtcgagga ccgagtcagg    3840
cagctgcatg aagcccacag ggactttggt ccagcatctc agcactttct ttccacgtct    3900
gtccagggtc cctgggagag agccatctcg ccaaacaaag tgccctacta tatcaaccac    3960
gagactcaaa caacttgctg ggaccatccc aaaatgacag agctctacca gtctttagct    4020
gacctgaata atgtcagatt ctcagcttat aggactgcca tgaaactccg aagactgcag    4080
aaggcccttt gcttggatct cttgagcctg tcagctgcat gtgatgcctt ggaccagcac    4140
aacctcaagc aaaatgacca gcccatggat atcctgcaga ttattaattg tttgaccact    4200
atttatgacc gcctggagca agagcacaac aatttggtca acgtccctct ctgcgtggat    4260
atgtgtctga actggctgct gaatgtttat gatacgggac gaacagggag gatccgtgtc    4320
ctgtcttta aaactggcat catttccctg tgtaaagcac atttggaaga caagtacaga    4380
tacctttca agcaagtggc aagttcaaca ggattttgtg accagcgcag gctgggcctc    4440
cttctgcatg attctatcca aattccaaga cagttgggtg aagttgcatc ctttgggggc    4500
agtaacattg agccaagtgt ccggagctgc ttccaatttg ctaataataa gccagagatc    4560
gaagcggccc tcttcctaga ctggatgaga ctggaacccc agtccatggt gtggctgccc    4620
gtcctgcaca gagtggctgc tgcagaaact gccaagcatc aggccaaatg taacatctgc    4680
aaagagtgtc caatcattgg attcaggtac aggagtctaa agcactttaa ttatgacatc    4740
tgccaaagct gcttttttc tggtcgagtt gcaaaaggcc ataaaatgca ctatcccatg    4800
gtggaatatt gcactccgac tacatcagga gaagatgttc gagactttgc caaggtacta    4860
aaaaacaaat ttcgaaccaa aaggtatttt gcgaagcatc cccgaatggg ctacctgcca    4920
gtgcagactg tcttagaggg ggacaacatg gaaacgcctg cctcgtcccc tcagctttca    4980
cacgatgata ctcattcacg cattgaacat tatgctagca ggctagcaga aatggaaaac    5040
agcaatggat cttatctaaa tgatagcatc tctcctaatg agagcataga tgatgaacat    5100
ttgttaatcc agcattactg ccaaagtttg aaccaggact ccccctgag ccagcctcgt    5160
agtcctgccc agatcttgat ttccttagag agtgaggaaa gagggagct agagagaatc    5220
ctagcagatc ttgaggaaga aaacaggaat ctgcaagcag aatatgaccg tctaaagcag    5280
cagcacgaac ataaaggcct gtccccactg ccgtcccctc ctgaaatgat gcccacctct    5340
ccccagagtc cccgggatgc tgagctcatt gctgaggcca agctactgcg tcaacacaaa    5400
ggccgcctgg aagccaggat gcaaatcctg gaagaccaca ataaacagct ggagtcacag    5460
```

-continued

| | |
|---|---|
| ttacacaggc taaggcagct gctggagcaa ccccaggcag aggccaaagt gaatggcaca | 5520 |
| acggtgtcct ctccttctac ctctctacag aggtccgaca gcagtcagcc tatgctgctc | 5580 |
| cgagtggttg gcagtcaaac ttcggactcc atgggtgagg aagatcttct cagtcctccc | 5640 |
| caggacacaa gcacagggtt agaggaggtg atggagcaac tcaacaactc cttccctagt | 5700 |
| tcaagaggaa gaaatacccc tggaaagcca atgagagagg acacaatgta g | 5751 |

<210> SEQ ID NO 5
<211> LENGTH: 6396
<212> TYPE: DNA
<213> ORGANISM: Artificial Sequence
<220> FEATURE:
<223> OTHER INFORMATION: Synthetic oligonucleotide

<400> SEQUENCE: 5

| | |
|---|---|
| atgctttggt gggaagaagt agaggactgt tatgaaagag aagatgttca aaagaaaaca | 60 |
| ttcacaaaat gggtaaatgc acaattttct aagtttggga agcagcatat tgagaacctc | 120 |
| ttcagtgacc tacaggatgg gaggcgcctc ctagacctcc tcgaaggcct gacagggcaa | 180 |
| aaactgccaa agaaaaagg atccacaaga gttcatgccc tgaacaatgt caacaaggca | 240 |
| ctgcgggttt tgcagaacaa taatgttgat ttagtgaata ttggaagtac tgacatcgta | 300 |
| gatggaaatc ataaactgac tcttggtttg attttggaata taatcctcca ctggcaggtc | 360 |
| aaaaatgtaa tgaaaatat catggctgga ttgcaacaaa ccaacagtga aaagattctc | 420 |
| ctgagctggg tccgacaatc aactcgtaat tatccacagg ttaatgtaat caacttcacc | 480 |
| accagctggt ctgatggcct ggcttttgaat gctctcatcc atagtcatag gccagaccta | 540 |
| tttgactgga atagtgtggt ttgccagcag tcagccacac aacgactgga acatgcattc | 600 |
| aacatcgcca gatatcaatt aggcatagag aaactactcg atcctgaaga tgttgatacc | 660 |
| acctatccag ataagaagtc catcttaatg tacatcacat cactcttcca gttttgccct | 720 |
| caacaagtga gcattgaagc catccaggaa gtggaaatgt tgccaaggcc acctaaagtg | 780 |
| actaaagaag aacattttca gttacatcat caaatgcact attctcaaca gatcacggtc | 840 |
| agtctagcac agggatatga gagaacttct tcccctaagc ctcgattcaa gagctatgcc | 900 |
| tacacacagg ctgcttatgt caccacctct gaccctacac ggagcccatt tccttcacag | 960 |
| catttggaag ctcctgaaga caagtcattt ggcagttcat tgatggagag tgaagtaaac | 1020 |
| ctggaccgtt atcaaacagc tttagaagaa gtattatcgt ggcttctttc tgctgaggac | 1080 |
| acattgcaag cacaaggaga gatttctaat gatgtggaag tggtgaaaga ccagtttcat | 1140 |
| actcatgagg ggtacatgat ggatttgaca gcccatcagg gccgggttgg taatattcta | 1200 |
| caattgggaa gtaagctgat tggaacagga aaattatcag aagatgaaga aactgaagta | 1260 |
| caagagcaga tgaatctcct aaattcaaga tgggaatgcc tcagggtagc tagcatggaa | 1320 |
| aaacaaagca atttacatag agttttaatg gatctccaga atcagaaact gaaagagttg | 1380 |
| aatgactggc taacaaaaac agaagaaaga acaaggaaaa tggaggaaga gcctcttgga | 1440 |
| cctgatcttg aagacctaaa acgccaagta caacaacata aggtgcttca agaagatcta | 1500 |
| gaacaagaac aagtcagggt caattctctc actcacatgg tggtggtagt tgatgaatct | 1560 |
| agtggagatc acgcaactgc tgctttggaa gaacaactta aggtattggg agatcgatgg | 1620 |
| gcaaacatct gtagatggac agaagaccgc tgggttcttt tacaagacat ccttctcaaa | 1680 |
| tggcaacgtc ttactgaaga acagtgcctt tttagtgcat ggcttcagag aaaagaagat | 1740 |

```
gcagtgaaca agattcacac aactggcttt aaagatcaaa atgaaatgtt atcaagtctt    1800
caaaaactgg ccgttttaaa agcggatcta gaaaagaaaa agcaatccat gggcaaactg    1860
tattcactca aacaagatct tctttcaaca ctgaagaata agtcagtgac ccagaagacg    1920
gaagcatggc tggataactt tgcccggtgt tgggataatt tagtccaaaa acttgaaaag    1980
agtacagcac agatttcaca gcaaaagaat atcttgtcag aatttcaaag agatttaaat    2040
gaatttgttt tatggttgga ggaagcagat aacattgcta gtatcccact tgaacctgga    2100
aaagagcagc aactaaaaga aaagcttgag caagtcaagt tactggtgga agagttgccc    2160
ctgcgccagg gaattctcaa acaattaaat gaaactggag acccgtgct tgtaagtgct    2220 cccataagcc cagaagagca agataaactt gaaataagc tcaagcagac aaatctccag    2280
tggataaagg tttccagagc tttacctgag aaacaaggag aaattgaagc tcaaataaaa    2340
gaccttgggc agcttgaaaa aaagcttgaa gaccttgaag agcagttaaa tcatctgctg    2400
ctgtggttat ctcctattag gaatcagttg gaaatttata accaaccaaa ccaagaagga    2460
ccatttgacg ttcaggaaac tgaaatagca gttcaagcta acaaccgga tgtggaagag    2520 attttgtcta aagggcagca tttgtacaag gaaaaaccag ccactcagcc agtgaagagg    2580
aagttagaag atctgagctc tgagtggaag gcggtaaacc gtttacttca agagctgagg    2640
gcaaagcagc ctgacctagc tcctggactg accactattg gagcctctcc tactcagact    2700
gttactctgg tgacacaacc tgtggttact aaggaaactg ccatctccaa actagaaatg    2760
ccatcttcct tgatgttgga ggtacctgct ctggcagatt caaccgggc ttggacagaa    2820 cttaccgact ggctttctct gcttgatcaa gttataaaat cacagagggt gatggtgggt    2880
gaccttgagg atatcaacga gatgatcatc aagcagaagg caacaatgca ggatttggaa    2940
cagaggcgtc cccagttgga agaactcatt accgctgccc aaaatttgaa aaacaagacc    3000
agcaatcaag aggctagaac aatcattacg gatcgaattg aaagaattca gaatcagtgg    3060
gatgaagtac aagaacacct tcagaaccgg aggcaacagt tgaatgaaat gttaaaggat    3120
tcaacacaat ggctggaagc taaggaagaa gctgagcagg tcttaggaca ggccagagcc    3180
aagcttgagt catggaagga gggtcctat acagtagatg caatccaaaa gaaaatcaca    3240
gaaaccaagc agttggccaa agacctccgc cagtggcaga caaatgtaga tgtggcaaat    3300
gacttggccc tgaaacttct ccgggattat tctgcagatg ataccagaaa agtccacatg    3360
ataacagaga atatcaatgc ctcttggaga agcattcata aaagggtgag tgagcgagag    3420
gctgctttgg aagaaactca tagattactg caacagttcc ccctggacct ggaaaagttt    3480
cttgcctggc ttacagaagc tgaaacaact gccaatgtcc tacaggatgc tacccgtaag    3540
gaaaggctcc tagaagactc caagggagta aaagagctga tgaaacaatg gcaagacctc    3600
caaggtgaaa ttgaagctca cacagatgtt tatcacaacc tggatgaaaa cagccaaaaa    3660
atcctgagat ccctggaagg ttccgatgat gcagtcctgt tacaaagacg tttggataac    3720
atgaacttca gtggagtgaa acttcggaaa aagtctctca acattaggtc ccatttggaa    3780
gccagttctg accagtggaa gcgtctgcac ctttctctgc aggaacttct ggtgtggcta    3840
cagctgaaag atgatgaatt aagccggcag gcacctattg gaggcgactt tccagcagtt    3900
cagaagcaga acgatgtaca tagggccttc aagagggaat tgaaaactaa agaacctgta    3960
atcatgagta ctcttgagac tgtacgaata tttctgacag agcagccttt ggaaggacta    4020
gagaaactct accaggagcc cagagagctg cctcctgagg agagagccca gaatgtcact    4080
cggcttctac gaaagcaggc tgaggaggtc aatactgagt gggaaaaatt gaacctgcac    4140
```

-continued

```
tccgctgact ggcagagaaa aatagatgag acccttgaaa gactccagga acttcaagag    4200
gccacggatg agctggacct caagctgcgc caagctgagg tgatcaaggg atcctggcag    4260
cccgtgggcg atctcctcat tgactctctc caagatcacc tcgagaaagt caaggcactt    4320
cgaggagaaa ttgcgcctct gaaagagaac gtgagccacg tcaatgacct tgctcgccag    4380
cttaccactt tgggcattca gctctcaccg tataacctca gcactctgga agacctgaac    4440
accagatgga agcttctgca ggtggccgtc gaggaccgag tcaggcagct gcatgaagcc    4500
cacagggact tggtccagc atctcagcac tttctttcca cgtctgtcca gggtccctgg     4560
gagagagcca tctcgccaaa caaagtgccc tactatatca accacgagac tcaaacaact    4620
tgctgggacc atcccaaaat gacagagctc taccagtctt tagctgacct gaataatgtc    4680
agattctcag cttataggac tgccatgaaa ctccgaagac tgcagaaggc cctttgcttg    4740
gatctcttga gcctgtcagc tgcatgtgat gccttggacc agcacaacct caagcaaaat    4800
gaccagccca tggatatcct gcagattatt aattgtttga ccactattta tgaccgcctg    4860
gagcaagagc acaacaattt ggtcaacgtc cctctctgcg tggatatgtg tctgaactgg    4920
ctgctgaatg tttatgatac gggacgaaca gggaggatcc gtgtcctgtc ttttaaaact    4980
ggcatcattt ccctgtgtaa agcacatttg aagacaagt acagataccc tttcaagcaa    5040
gtggcaagtt caacaggatt ttgtgaccag cgcaggctgg gcctccttct gcatgattct    5100
atccaaattc caagacagtt gggtgaagtt gcatcctttg ggggcagtaa cattgagcca    5160
agtgtccgga gctgcttcca atttgctaat aataagccag atcgaagc ggccctcttc      5220
ctagactgga tgagactgga accccagtcc atggtgtggc tgcccgtcct gcacagagtg    5280
gctgctgcag aaactgccaa gcatcaggcc aaatgtaaca tctgcaaaga gtgtccaatc    5340
attggattca ggtacaggag tctaaagcac tttaattatg acatctgcca aagctgcttt    5400
ttttctggtc gagttgcaaa aggccataaa atgcactatc ccatggtgga atattgcact    5460
ccgactacat caggagaaga tgttcgagac tttgccaagg tactaaaaaa caaatttcga    5520
accaaaaggt attttgcgaa gcatccccga atgggctacc tgccagtgca gactgtctta    5580
gaggggaca acatggaaac gcctgcctcg tcccctcagc tttcacacga tgatactcat    5640
tcacgcattg aacattatgc tagcaggcta gcagaaatgg aaaacagcaa tggatcttat    5700
ctaaatgata gcatctctcc taatgagagc atagatgatg aacatttgtt aatccagcat    5760
tactgccaaa gtttgaacca ggactccccc ctgagccagc ctcgtagtcc tgcccagatc    5820
ttgatttcct tagagagtga ggaaagaggg gagctagaga gaatcctagc agatcttgag    5880
gaagaaaaca ggaatctgca agcagaatat gaccgtctaa agcagcagca cgaacataaa    5940
ggcctgtccc cactgccgtc ccctcctgaa atgatgccca cctctcccca gagtccccgg    6000
gatgctgagc tcattgctga ggccaagcta ctgcgtcaac acaaaggccg cctggaagcc    6060
aggatgcaaa tcctggaaga ccacaataaa cagctggagt cacagttaca caggctaagg    6120
cagctgctgg agcaaccca ggcagaggcc aaagtgaatg gcacaacggt gtcctctcct    6180
tctacctctc tacagaggtc cgacagcagt cagcctatgc tgctccgagt ggttggcagt    6240
caaacttcgg actccatggg tgaggaagat cttctcagtc ctccccagga cacaagcaca    6300
gggttagagg aggtgatgga gcaactcaac aactccttcc ctagttcaag aggaagaaat    6360
accccctggaa agccaatgag agaggacaca atgtag                             6396
```

<210> SEQ ID NO 6

<211> LENGTH: 6717
<212> TYPE: DNA
<213> ORGANISM: Artificial Sequence
<220> FEATURE:
<223> OTHER INFORMATION: Synthetic oligonucleotide

<400> SEQUENCE: 6

```
atgctttggt gggaagaagt agaggactgt tatgaaagag aagatgttca aaagaaaaca      60
ttcacaaaat gggtaaatgc acaatttttct aagtttggga agcagcatat tgagaacctc    120
ttcagtgacc tacaggatgg gaggcgcctc ctagacctcc tcgaaggcct gacagggcaa     180
aaactgccaa agaaaaagg atccacaaga gttcatgccc tgaacaatgt caacaaggca     240
ctgcgggttt tgcagaacaa taatgttgat ttagtgaata ttggaagtac tgacatcgta    300
gatggaaatc ataaactgac tcttggtttg atttggaata taatcctcca ctggcaggtc    360
aaaaatgtaa tgaaaaatat catggctgga ttgcaacaaa ccaacagtga aaagattctc    420
ctgagctggg tccgacaatc aactcgtaat tatccacagg ttaatgtaat caacttcacc    480
accagctggt ctgatggcct ggctttgaat gctctcatcc atagtcatag gccagaccta    540
tttgactgga atagtgtggt ttgccagcag tcagccacac aacgactgga acatgcattc    600
aacatcgcca gatatcaatt aggcatagag aaactactcg atcctgaaga tgttgatacc    660
acctatccag ataagaagtc catcttaatg tacatcacat cactcttcca agttttgcct    720
caacaagtga gcattgaagc catccaggaa gtggaaatgt gccaaggcc acctaaagtg     780
actaaagaag aacattttca gttacatcat caaatgcact attctcaaca gatcacggtc    840
agtctagcac agggatatga gagaacttct tcccctaagc ctcgattcaa gagctatgcc    900
tacacacagg ctgcttatgt caccacctct gaccctacac ggagcccatt tccttcacag    960
catttggaag ctcctgaaga caagtcattt ggcagttcat tgatggagag tgaagtaaac   1020
ctggaccgtt atcaaacagc tttagaagaa gtattatcgt ggcttctttc tgctgaggac   1080
acattgcaag cacaaggaga gatttctaat gatgtggaag tggtgaaaga ccagtttcat   1140
actcatgagg ggtacatgat ggatttgaca gcccatcagg gccgggttgg taatattcta   1200
caattgggaa gtaagctgat tggaacagga aaattatcag aagatgaaga aactgaagta   1260
caagagcaga tgaatctcct aaattcaaga tgggaatgcc tcagggtagc tagcatggaa   1320
aaacaaagca atttacatag agttttaatg gatctccaga atcagaaact gaaagagttg   1380
aatgactggc taacaaaaac agaagaaaga acaaggaaaa tggaggaaga gcctcttgga   1440
cctgatcttg aagacctaaa acgccaagta caacaacata aggtgcttca agaagatcta   1500
gaacaagaac aagtcagggt caattctctc actcacatgg tggtggtagt tgatgaatct   1560
agtggagatc acgcaactgc tgctttggaa gaacaactta aggtattggg agatcgatgg   1620
gcaaacatct gtagatggac agaagaccgc tgggttcttt tacaagacat ccttctcaaa   1680
tggcaacgtc ttactgaaga acagtgcctt tttagtgcat ggctttcaga aaagaagat    1740
gcagtgaaca agattcacac aactggcttt aaagatcaaa atgaaatgtt atcaagtctt   1800
caaaaactgg ccgttttaaa agcggatcta gaaagaaaa agcaatccat gggcaaactg   1860
tattcactca aacaagatct tctttcaaca ctgaagaata agtcagtgac ccagaagacg   1920
gaagcatggc tggataactt tgcccggtgt gggataatt tagtccaaaa acttgaaaag   1980
agtacagcac agatttcaca gtctgttgag aaatggcggc gttttcatta tgatataaag   2040
atatttaatc agtggctaac agaagctgaa cagtttctca aaagacaca aattcctgag   2100
aattgggaac atgctaaata caaatggtat cttaaggaac tccaggatgg cattgggcag   2160
```

-continued

```
cggcaaactg ttgtcagaac attgaatgca actggggaag aaataattca gcaatcctca    2220
aaaacagatg ccagtattct acaggaaaaa ttgggaagcc tgaatctgcg gtggcaggag    2280
gtctgcaaac agctgtcaga cagaaaaaag aggctagaaa acaaaagaa tatcttgtca     2340
gaatttcaaa gagatttaaa tgaatttgtt ttatggttgg aggaagcaga taacattgct    2400
agtatcccac ttgaacctgg aaaagagcag caactaaaag aaaagcttga gcaagtcaag    2460
ttactggtgg aagagttgcc cctgcgccag ggaattctca acaattaaa tgaaactgga     2520
ggacccgtgc ttgtaagtgc tcccataagc ccagaagagc aagataaact tgaaaataag    2580
ctcaagcaga caaatctcca gtggataaag gtttccagag ctttacctga gaaacaagga    2640
gaaattgaag ctcaaataaa agaccttggg cagcttgaaa aaaagcttga agaccttgaa    2700
gagcagttaa atcatctgct gctgtggtta tctcctatta ggaatcagtt ggaaatttat    2760
aaccaaccaa accaagaagg accatttgac gttcaggaaa ctgaaatagc agttcaagct    2820
aaacaaccgg atgtggaaga gattttgtct aaagggcagc atttgtacaa ggaaaaacca    2880
gccactcagc cagtgaagag gaagttagaa gatctgagct ctgagtggaa ggcggtaaac    2940
cgtttacttc aagagctgag ggcaaagcag cctgacctag ctcctggact gaccactatt    3000
ggagcctctc ctactcagac tgttactctg gtgacacaac ctgtggttac taaggaaact    3060
gccatctcca aactagaaat gccatcttcc ttgatgttgg aggtacctgc tctggcagat    3120
ttcaaccggg cttggacaga acttaccgac tggctttctc tgcttgatca agttataaaa    3180
tcacagaggg tgatggtggg tgaccttgag gatatcaacg agatgatcat caagcagaag    3240
gcaacaatgc aggatttgga acagaggcgt ccccagttgg aagaactcat taccgctgcc    3300
caaaatttga aaaacaagac cagcaatcaa gaggctagaa caatcattac ggatcgaatt    3360
gaaagaattc agaatcagtg ggatgaagta caagaacacc ttcagaaccg gaggcaacag    3420
ttgaatgaaa tgttaaagga ttcaacacaa tggctgaaag ctaaggaaga agctgagcag    3480
gtcttaggac aggccagagc caagcttgag tcatggaagg agggtcccta tacagtagat    3540
gcaatccaaa agaaaatcac agaaaccaag cagttggcca aagacctccg ccagtggcag    3600
acaaatgtag atgtggcaaa tgacttggcc ctgaaacttc tccgggatta ttctgcagat    3660
gataccagaa aagtccacat gataacagag aatatcaatg cctcttggag aagcattcat    3720
aaaagggtga gtgagcgaga ggctgctttg gaagaaactc atagattact gcaacagttc    3780
cccctggacc tggaaaagtt tcttgcctgg cttacagaag ctgaaacaac tgccaatgtc    3840
ctacaggatg ctacccgtaa ggaaaggctc ctagaagact ccaagggagt aaaagagctg    3900
atgaaacaat ggcaagacct ccaaggtgaa attgaagctc acacagatgt ttatcacaac    3960
ctggatgaaa acagccaaaa aatcctgaga tccctggaag gttccgatga tgcagtcctg    4020
ttacaaagac gtttggataa catgaacttc aagtggagtg aacttcggaa aaagtctctc    4080
aacattaggt cccatttgga agccagttct gaccagtgga agcgtctgca cctttctctg    4140
caggaacttc tggtgtggct acagctgaaa gatgatgaat taagccggca ggcacctatt    4200
ggaggcgact ttccagcagt tcagaagcag aacgatgtac ataggccctt caagagggaa    4260
ttgaaaacta agaacctgt aatcatgagt actcttgaga ctgtacgaat atttctgaca    4320
gagcagcctt tggaaggact agagaaactc taccaggagc ccagagagct gcctcctgag    4380
gagagagccc agaatgtcac tcggcttcta cgaaagcagg ctgaggaggt caatactgag    4440
tgggaaaaat tgaacctgca ctccgctgac tggcagagaa aaatagatga gacccttgaa    4500
```

```
agactccagg aacttcaaga ggccacggat gagctggacc tcaagctgcg ccaagctgag    4560
gtgatcaagg atcctggca gcccgtgggc gatctcctca ttgactctct ccaagatcac    4620
ctcgagaaag tcaaggcact tcgaggagaa attgcgcctc tgaaagagaa cgtgagccac    4680
gtcaatgacc ttgctcgcca gcttaccact ttgggcattc agctctcacc gtataacctc    4740
agcactctgg aagacctgaa caccagatgg aagcttctgc aggtggccgt cgaggaccga    4800
gtcaggcagc tgcatgaagc ccacagggac tttggtccag catctcagca ctttctttcc    4860
acgtctgtcc agggtccctg ggagagagcc atctcgccaa acaaagtgcc ctactatatc    4920
aaccacgaga ctcaaacaac ttgctgggac catcccaaaa tgacagagct ctaccagtct    4980
ttagctgacc tgaataatgt cagattctca gcttatagga ctgccatgaa actccgaaga    5040
ctgcagaagg ccctttgctt ggatctcttg agcctgtcag ctgcatgtga tgccttggac    5100
cagcacaacc tcaagcaaaa tgaccagccc atggatatcc tgcagattat taattgtttg    5160
accactattt atgaccgcct ggagcaagag cacaacaatt tggtcaacgt ccctctctgc    5220
gtggatatgt gtctgaactg gctgctgaat gtttatgata cgggacgaac agggaggatc    5280
cgtgtcctgt cttttaaaac tggcatcatt tccctgtgta agcacatttt ggaagacaag    5340
tacagatacc ttttcaagca agtggcaagt tcaacaggat tttgtgacca gcgcaggctg    5400
ggcctccttc tgcatgattc tatccaaatt ccaagacagt tgggtgaagt tgcatccttt    5460 ggggcagta acattgagcc aagtgtccgg agctgcttcc aatttgctaa taataagcca    5520
gagatcgaag cggccctctt cctagactgg atgagactgg aacccagtc catggtgtgg    5580 ctgcccgtcc tgcacagagt ggctgctgca gaaactgcca agcatcaggc caaatgtaac    5640
atctgcaaag agtgtccaat cattggattc aggtacagga gtctaaagca ctttaattat    5700
gacatctgcc aaagctgctt ttttttctggt cgagttgcaa aaggccataa aatgcactat    5760
cccatggtgg aatattgcac tccgactaca tcaggagaag atgttcgaga ctttgccaag    5820
gtactaaaaa acaaatttcg aaccaaaagg tattttgcga agcatccccg aatgggctac    5880
ctgccagtgc agactgtctt agagggggac aacatggaaa cgcctgcctc gtcccctcag    5940
cttccacacg atgatactca ttcacgcatt gaacattatg ctagcaggct agcagaaatg    6000
gaaaacagca atggatctta tctaaatgat agcatctctc ctaatgagag catagatgat    6060
gaacatttgt taatccagca ttactgccaa agtttgaacc aggactcccc cctgagccag    6120
cctcgtagtc ctgcccagat cttgatttcc ttagagagtg aggaaagagg ggagctagag    6180
agaatcctag cagatcttga ggaagaaaac aggaatctgc aagcagaata tgaccgtcta    6240
aagcagcagc acgaacataa aggcctgtcc ccactgccgt cccctcctga aatgatgccc    6300
acctctcccc agagtccccg ggatgctgag ctcattgctg aggccaagct actgcgtcaa    6360
cacaaaggcc gcctggaagc caggatgcaa atcctggaag accacaataa acagctggag    6420
tcacagttac acaggctaag gcagctgctg agcaaccccc aggcagaggc caaagtgaat    6480
ggcacaacgg tgtcctctcc ttctacctct ctacagaggt ccgacagcag tcagcctatg    6540
ctgctccgag tggttggcag tcaaacttcg gactccatgg gtgaggaaga tcttctcagt    6600
cctccccagg acacaagcac agggttagag gaggtgatgg agcaactcaa caactccttc    6660
cctagttcaa gaggaagaaa taccccctgga aagccaatga gagaggacac aatgtag     6717
```

<210> SEQ ID NO 7
<211> LENGTH: 7047
<212> TYPE: DNA
<213> ORGANISM: Artificial Sequence
<220> FEATURE:
<223> OTHER INFORMATION: Synthetic oligonucleotide

<400> SEQUENCE: 7

```
atgctttggt gggaagaagt agaggactgt tatgaaagag aagatgttca aaagaaaaca      60
ttcacaaaat gggtaaatgc acaattttct aagtttggga agcagcatat tgagaacctc     120
ttcagtgacc tacaggatgg gaggcgcctc ctagacctcc tcgaaggcct gacagggcaa     180
aaactgccaa agaaaaagg atccacaaga gttcatgccc tgaacaatgt caacaaggca      240
ctgcgggttt tgcagaacaa taatgttgat ttagtgaata ttggaagtac tgacatcgta     300
gatggaaatc ataaactgac tcttggtttg atttggaata taatcctcca ctggcaggtc     360
aaaaatgtaa tgaaaatat catggctgga ttgcaacaaa ccaacagtga aaagattctc      420
ctgagctggg tccgacaatc aactcgtaat tatccacagg ttaatgtaat caacttcacc     480
accagctggt ctgatggcct ggctttgaat gctctcatcc atagtcatag gccagaccta     540
tttgactgga atagtgtggt tgccagcag tcagccacac aacgactgga acatgcattc      600
aacatcgcca gatatcaatt aggcatagag aaactactcg atcctgaaga tgttgatacc     660
acctatccag ataagaagtc catcttaatg tacatcacat cactcttcca agttttgcct     720
caacaagtga gcattgaagc catccaggaa gtggaaatgt tgccaaggcc acctaaagtg     780
actaagaag aacattttca gttacatcat caaatgcact attctcaaca gatcacggtc      840
agtctagcac agggatatga gagaacttct tcccctaagc ctcgattcaa gagctatgcc     900
tacacacagg ctgcttatgt caccacctct gaccctacac ggagcccatt tccttcacag     960
catttggaag ctcctgaaga caagtcattt ggcagttcat tgatggagag tgaagtaaac    1020
ctggaccgtt atcaaacagc tttagaagaa gtattatcgt ggcttctttc tgctgaggac    1080
acattgcaag cacaaggaga gatttctaat gatgtggaag tggtgaaaga ccagtttcat    1140
actcatgagg ggtacatgat ggatttgaca gcccatcagg gccgggttgg taatattcta    1200
caattgggaa gtaagctgat tggaacagga aaattatcag aagatgaaga aactgaagta    1260
caagagcaga tgaatctcct aaattcaaga tgggaatgcc tcagggtagc tagcatggaa    1320
aaacaaagca atttacatag agttttaatg gatctccaga atcagaaact gaaagagttg    1380
aatgactggc taacaaaaac agaagaaaga acaaggaaaa tggaggaaga gcctcttgga    1440
cctgatcttg aagacctaaa acgccaagta caacaacata aggtgcttca agaagatcta    1500
gaacaagaac aagtcagggt caattctctc actcacatgg tggtggtagt tgatgaatct    1560
agtggagatc acgcaactgc tgctttggaa gaacaactta aggtattggg agatcgatgg    1620
gcaaacatct gtagatggac agaagaccgc tgggttcttt tacaagacat ccttctcaaa    1680
tggcaacgtc ttactgaaga acagtgcctt tttagtgcat ggctttcaga aaaagaagat    1740
gcagtgaaca agattcacac aactggcttt aaagatcaaa atgaaatgtt atcaagtctt    1800
caaaaactgg ccgttttaaa agcggatcta gaaaagaaaa agcaatccat gggcaaactg    1860
tattcactca aacaagatct tctttcaaca ctgaagaata gtcagtgac ccagaagacg     1920
gaagcatggc tggataactt tgcccggtgt tgggataatt tagtccaaaa acttgaaaag    1980
agtacagcac agatttcaca ggaaatttct tatgtgcctt ctacttattt gactgaaatc    2040
actcatgtct cacaagccct attagaagtg gaacaacttc tcaatgctcc tgacctctgt    2100
gctaaggact ttgaagatct cttttaagcaa gaggagtctc tgaagaatat aaaagatagt    2160
ctacaacaaa gctcaggtcg gattgacatt attcatagca agaagacagc agcattgcaa    2220
```

```
agtgcaacgc ctgtggaaag ggtgaagcta caggaagctc tctcccagct tgatttccaa   2280
tgggaaaaag ttaacaaaat gtacaaggac cgacaagggc gatttgacag atctgttgag   2340
aaatggcggc gttttcatta tgatataaag atatttaatc agtggctaac agaagctgaa   2400
cagtttctca gaaagacaca aattcctgag aattgggaac atgctaaata caaatggtat   2460
cttaaggaac tccaggatgg cattgggcag cggcaaactg ttgtcagaac attgaatgca   2520
actggggaag aaataattca gcaatcctca aaaacagatg ccagtattct acaggaaaaa   2580
ttgggaagcc tgaatctgcg gtggcaggag gtctgcaaac agctgtcaga cagaaaaaag   2640
aggctagaag aacaaaagaa tatcttgtca gaatttcaaa gagatttaaa tgaatttgtt   2700
ttatggttgg aggaagcaga taacattgct agtatcccac ttgaacctgg aaaagagcag   2760
caactaaaag aaaagcttga gcaagtcaag ttactggtgg aagagttgcc cctgcgccag   2820
ggaattctca acaattaaa tgaaactgga ggacccgtgc ttgtaagtgc tcccataagc   2880
ccagaagagc aagataaact tgaaaataag ctcaagcaga caaatctcca gtggataaag   2940
gtttccagag ctttacctga gaaacaagga gaaattgaag ctcaaataaa agaccttggg   3000
cagcttgaaa aaagcttga agaccttgaa gagcagttaa atcatctgct gctgtggtta   3060
tctcctatta ggaatcagtt ggaaatttat aaccaaccaa accaagaagg accatttgac   3120
gttcaggaaa ctgaaatagc agttcaagct aaacaaccgg atgtggaaga gattttgtct   3180
aaagggcagc atttgtacaa ggaaaaacca gccactcagc cagtgaagag aagttagaa   3240 gatctgagct ctgagtggaa ggcggtaaac cgtttacttc aagagctgag ggcaaagcag   3300
cctgacctag ctcctggact gaccactatt ggagcctctc ctactcagac tgttactctg   3360
gtgacacaac ctgtggttac taaggaaact gccatctcca aactagaaat gccatcttcc   3420
ttgatgttgg aggtacctgc tctggcagat ttcaaccggg cttggacaga acttaccgac   3480
tggctttctc tgcttgatca agttataaaa tcacagaggg tgatggtggg tgaccttgag   3540
gatatcaacg agatgatcat caagcagaag gcaacaatgc aggatttgga acagaggcgt   3600
ccccagttgg aagaactcat taccgctgcc caaaatttga aaaacaagac cagcaatcaa   3660
gaggctagaa caatcattac ggatcgaatt gaaagaattc agaatcagtg ggatgaagta   3720
caagaacacc ttcagaaccg gaggcaacag ttgaatgaaa tgttaaagga ttcaacacaa   3780
tggctggaag ctaaggaaga agctgagcag gtcttaggac aggccagagc caagcttgag   3840
tcatggaagg agggtcccta tacagtagat gcaatccaaa agaaaatcac agaaaccaag   3900
cagttggcca aagacctccg ccagtggcag acaaatgtag atgtggcaaa tgacttggcc   3960
ctgaaacttc tccgggatta ttctgcagat gataccagaa aagtccacat gataacagag   4020
aatatcaatg cctcttggag aagcattcat aaaagggtga gtgagcgaga ggctgctttg   4080
gaagaaactc atagattact gcaacagttc cccctggacc tggaaaagtt tcttgcctgg   4140
cttacagaag ctgaaacaac tgccaatgtc ctacaggatg ctacccgtaa ggaaaggctc   4200
ctagaagact ccaagggagt aaaagagctg atgaaacaat ggcaagacct ccaaggtgaa   4260
attgaagctc acacagatgt ttatcacaac ctggatgaaa cagccaaaaa atcctgaga   4320 tccctggaag gttccgatga tgcagtcctg ttacaaagac gtttggataa catgaacttc   4380
aagtggagtg aacttcggaa aaagtctctc aacattaggt cccatttgga agccagttct   4440
gaccagtgga agcgtctgca ccttctctg caggaacttc tggtgtggct acagctgaaa   4500
gatgatgaat taagccggca ggcacctatt ggaggcgact ttccagcagt tcagaagcag   4560
aacgatgtac ataggggcctt caagagggaa ttgaaaacta agaacctgt aatcatgagt   4620
```

```
actcttgaga ctgtacgaat atttctgaca gagcagcctt tggaaggact agagaaactc    4680
taccaggagc ccagagagct gcctcctgag gagagagccc agaatgtcac tcggcttcta    4740
cgaaagcagg ctgaggaggt caatactgag tgggaaaaat tgaacctgca ctccgctgac    4800
tggcagagaa aaatagatga gacccttgaa agactccagg aacttcaaga ggccacggat    4860
gagctggacc tcaagctgcg ccaagctgag gtgatcaagg gatcctggca gcccgtgggc    4920
gatctcctca ttgactctct ccaagatcac ctcgagaaag tcaaggcact tcgaggagaa    4980
attgcgcctc tgaaagagaa cgtgagccac gtcaatgacc ttgctcgcca gcttaccact    5040
ttgggcattc agctctcacc gtataacctc agcactctgg aagacctgaa caccagatgg    5100
aagcttctgc aggtggccgt cgaggaccga gtcaggcagc tgcatgaagc ccacagggac    5160
tttggtccag catctcagca ctttctttcc acgtctgtcc agggtccctg ggagagagcc    5220
atctcgccaa acaaagtgcc ctactatatc aaccacgaga ctcaaacaac ttgctgggac    5280
catcccaaaa tgacagagct ctaccagtct ttagctgacc tgaataatgt cagattctca    5340
gcttatagga ctgccatgaa actccgaaga ctgcagaagg ccctttgctt ggatctcttg    5400
agcctgtcag ctgcatgtga tgccttggac cagcacaacc tcaagcaaaa tgaccagccc    5460
atggatatcc tgcagattat taattgtttg accactattt atgaccgcct ggagcaagag    5520
cacaacaatt tggtcaacgt ccctctctgc gtggatatgt gtctgaactg gctgctgaat    5580
gtttatgata cgggacgaac agggaggatc cgtgtcctgt cttttaaaac tggcatcatt    5640
tccctgtgta aagcacattt ggaagacaag tacagatacc ttttcaagca gtggcaagt    5700 tcaacaggat tttgtgacca gcgcaggctg ggcctccttc tgcatgattc tatccaaatt    5760
ccaagacagt tgggtgaagt tgcatccttt gggggcagta acattgagcc aagtgtccgg    5820
agctgcttcc aatttgctaa taataagcca gagatcgaag cggccctctt cctagactgg    5880
atgagactgg aaccccagtc catggtgtgg ctgcccgtcc tgcacagagt ggctgctgca    5940
gaaactgcca agcatcaggc caaatgtaac atctgcaaag agtgtccaat cattggattc    6000
aggtacagga gtctaaagca ctttaattat gacatctgcc aaagctgctt ttttctggt    6060 cgagttgcaa aaggccataa aatgcactat cccatggtgg aatattgcac tccgactaca    6120
tcaggagaag atgttcgaga ctttgccaag gtactaaaaa acaaatttcg aaccaaaagg    6180
tattttgcga agcatccccg aatgggctac ctgccagtgc agactgtctt agaggggac    6240 aacatggaaa cgcctgcctc gtcccctcag cttcacacg atgatactca ttcacgcatt    6300
gaacattatg ctagcaggct agcagaaatg gaaaacagca atggatctta tctaaatgat    6360
agcatctctc ctaatgagag catagatgat gaacatttgt taatccagca ttactgccaa    6420
agtttgaacc aggactcccc cctgagccag cctcgtagtc ctgcccagat cttgatttcc    6480
ttagagagtg aggaaagagg ggagctgag agaatcctag cagatcttga ggaagaaaac    6540
aggaatctgc aagcagaata tgaccgtcta aagcagcagc acgaacataa aggcctgtcc    6600
ccactgccgt cccctcctga aatgatgccc acctctcccc agagtccccg ggatgctgag    6660
ctcattgctg aggccaagct actgcgtcaa cacaaaggcc gcctggaagc caggatgcaa    6720
atcctggaag accacaataa acagctggag tcacagttac acaggctaag gcagctgctg    6780 gagcaaccc aggcagaggc caaagtgaat ggcacaacgg tgtcctctcc ttctacctct    6840
ctacagaggt ccgacagcag tcagcctatg ctgctccgag tggttggcag tcaaacttcg    6900
gactccatgg gtgaggaaga tcttctcagt cctccccagg acacaagcac agggttagag    6960
```

```
gaggtgatgg agcaactcaa caactccttc cctagttcaa gaggaagaaa tacccctgga   7020
aagccaatga gagaggacac aatgtag                                      7047

<210> SEQ ID NO 8
<211> LENGTH: 6402
<212> TYPE: DNA
<213> ORGANISM: Artificial Sequence
<220> FEATURE:
<223> OTHER INFORMATION: Synthetic oligonucleotide

<400> SEQUENCE: 8
atgctttggt gggaagaagt agaggactgt tatgaaagag aagatgttca aaagaaaaca     60
ttcacaaaat gggtaaatgc acaattttct aagtttggga agcagcatat tgagaacctc    120
ttcagtgacc tacaggatgg gaggcgcctc ctagacctcc tcgaaggcct gacagggcaa    180
aaactgccaa agaaaaagg atccacaaga gttcatgccc tgaacaatgt caacaaggca    240
ctgcgggttt tgcagaacaa taatgttgat ttagtgaata ttggaagtac tgacatcgta    300
gatggaaatc ataaactgac tcttggtttg atttggaata taatcctcca ctggcaggtc    360
aaaaatgtaa tgaaaaatat catggctgga ttgcaacaaa ccaacagtga aaagattctc    420
ctgagctggg tccgacaatc aactcgtaat tatccacagg ttaatgtaat caacttcacc    480
accagctggt ctgatggcct ggctttgaat gctctcatcc atagtcatag gccagaccta    540
tttgactgga atagtgtggt tgccagcag tcagccacac aacgactgga acatgcattc    600
aacatcgcca gatatcaatt aggcatagag aaaactactcg atcctgaaga tgttgatacc    660
acctatccag ataagaagtc catcttaatg tacatcacat cactcttcca agttttgcct    720
caacaagtga gcattgaagc catccaggaa gtggaaatgt tgccaaggcc acctaaagtg    780 actaagaag aacattttca gttacatcat caaatgcact attctcaaca gatcacggtc    840
agtctagcac agggatatga gagaacttct tcccctaagc ctcgattcaa gagctatgcc    900
tacacacagg ctgcttatgt caccacctct gaccctacac ggagcccatt tccttcacag    960
catttggaag ctcctgaaga caagtcattt ggcagttcat tgatggagag tgaagtaaac   1020
ctggaccgtt atcaaacagc tttagaagaa gtattatcgt ggcttctttc tgctgaggac   1080
acattgcaag cacaaggaga gatttctaat gatgtggaag tggtgaaaga ccagtttcat   1140
actcatgagg ggtacatgat ggatttgaca gcccatcagg gccgggttgg taatattcta   1200
caattgggaa gtaagctgat tggaacagga aaattatcag aagatgaaga aactgaagta   1260
caagagcaga tgaatctcct aaattcaaga tgggaatgcc tcagggtagc tagcatggaa   1320
aaacaaagca atttacatag agttttaatg gatctccaga atcagaaact gaaagagttg   1380
aatgactggc taacaaaaac agaagaaaga acaaggaaaa tggaggaaga gcctcttgga   1440
cctgatcttg aagacctaaa acgccaagta caacaacata ggtgcttca agaagatcta   1500 gaacaagaac aagtcagggt caattctctc actcacatgg tggtggtagt tgatgaatct   1560
agtggagatc acgcaactgc tgctttggaa gaacaactta aggtattggg agatcgatgg   1620
gcaaacatct gtagatggac agaagaccgc tgggttcttt tacaagacat ccttctcaaa   1680
tggcaacgtc ttactgaaga acagtgcctt tttagtgcat ggcttttcaga aaagaagat   1740 gcagtgaaca agattcacac aactggcttt aagatcaaa atgaaatgtt atcaagtctt   1800
caaaaactgg ccgttttaaa agcggatcta gaaagaaaa agcaatccat gggcaaactg   1860
tattcactca aacaagatct tctttcaaca ctgaagaata agtcagtgac ccagaagacg   1920
gaagcatggc tggataactt tgcccggtgt tgggataatt tagtccaaaa acttgaaaag   1980
```

```
agtacagcac agatttcaca ggaaatttct tatgtgcctt ctacttattt gactgaaatc   2040
actcatgtct cacaagccct attagaagtg aacaacttc tcaatgctcc tgacctctgt    2100
gctaaggact ttgaagatct ctttaagcaa gaggagtctc tgaagaatat aaaagatagt   2160
ctacaacaaa gctcaggtcg gattgacatt attcatagca agaagacagc agcattgcaa   2220
agtgcaacgc ctgtggaaag ggtgaagcta caggaagctc tctcccagct tgatttccaa   2280
tgggaaaaag ttaacaaaat gtacaaggac cgacaagggc gatttgacag atctgttgag   2340
aaatggcggc gttttcatta tgatataaag atatttaatc agtggctaac agaagctgaa   2400
cagtttctca gaaagacaca aattcctgag aattgggaac atgctaaata caaatggtat   2460
cttaaggaac tccaggatgg cattgggcag cggcaaactg ttgtcagaac attgaatgca   2520
actggggaag aaataattca gcaatcctca aaaacagatg ccagtattct acaggaaaaa   2580
ttgggaagcc tgaatctgcg gtggcaggag gtctgcaaac agctgtcaga cagaaaaaag   2640
aggctagaag aacagcctga cctagctcct ggactgacca ctattggagc ctctcctact   2700
cagactgtta ctctggtgac acaacctgtg gttactaagg aaactgccat ctccaaacta   2760
gaaatgccat cttccttgat gttggaggta cctgctctgg cagatttcaa ccgggcttgg   2820
acagaactta ccgactggct ttctctgctt gatcaagtta taaaatcaca gagggtgatg   2880
gtgggtgacc ttaggatat caacgagatg atcatcaagc agaaggcaac aatgcaggat    2940 ttgaacaga ggcgtcccca gttgaagaa ctcattaccg ctgcccaaaa tttgaaaaac      3000
aagaccagca atcaagaggc tagaacaatc attacgatc gaattgaaag aattcagaat     3060
cagtgggatg aagtacaaga acaccttcag aaccggaggc aacagttgaa tgaaatgtta   3120
aaggattcaa cacaatggct ggaagctaag gaagaagctg agcaggtctt aggacaggcc   3180
agagccaagc ttgagtcatg gaaggagggt ccctatacag tagatgcaat ccaaaagaaa   3240
atcacagaaa ccaagcagtt ggccaaagac ctccgccagt ggcagacaaa tgtagatgtg   3300
gcaaatgact tggcccctgaa acttctccgg gattattctg cagatgatac cagaaaagtc   3360
cacatgataa cagagaatat caatgcctct tggagaagca ttcataaaag ggtgagtgag   3420
cgagaggctg ctttggaaga aactcataga ttactgcaac agttcccct ggacctggaa     3480 aagtttcttg cctggcttac agaagctgaa acaactgcca atgtcctaca ggatgctacc   3540
cgtaaggaaa ggctcctaga agactccaag ggagtaaaag agctgatgaa acaatggcaa   3600
gacctccaag gtgaaattga agctcacaca gatgtttatc acaacctgga tgaaaacagc   3660
caaaaaatcc tgagatccct ggaaggttcc gatgatgcag tcctgttaca aagacgtttg   3720
gataacatga acttcaagtg gagtgaactt cggaaaaagt ctctcaacat taggtcccat   3780
ttggaagcca gttctgacca gtggaagcgt ctgcacctt ctctgcagga acttctggtg     3840
tggctacagc tgaaagatga tgaattaagc cggcaggcac ctattggagg cgactttcca   3900
gcagttcaga agcagaacga tgtacatagg gccttcaaga gggaattgaa aactaaagaa   3960
cctgtaatca tgagtactct tgagactgta cgaatatttc tgacagagca gcctttggaa   4020
ggactagaga aactctacca ggagcccaga gagctgcctc ctgaggagag agcccagaat   4080
gtcactcggc ttctacgaaa gcaggctgag gaggtcaata ctgagtggga aaaattgaac   4140
ctgcactccg ctgactggca gagaaaaata gatgagaccc ttgaaagact ccaggaactt   4200
caagaggcca cggatgagct ggacctcaag ctgcgccaag ctgaggtgat caagggatcc   4260
tggcagcccg tgggcgatct cctcattgac tctctccaag atcacctcga gaaagtcaag   4320
```

-continued

```
gcacttcgag gagaaattgc gcctctgaaa gagaacgtga gccacgtcaa tgaccttgct    4380
cgccagctta ccactttggg cattcagctc tcaccgtata acctcagcac tctggaagac    4440
ctgaacacca gatggaagct tctgcaggtg gccgtcgagg accgagtcag gcagctgcat    4500
gaagcccaca gggactttgg tccagcatct cagcactttc tttccacgtc tgtccagggt    4560
ccctgggaga gagccatctc gccaaacaaa gtgccctact atatcaacca cgagactcaa    4620
acaacttgct gggaccatcc caaaatgaca gagctctacc agtctttagc tgacctgaat    4680
aatgtcagat tctcagctta taggactgcc atgaaactcc gaagactgca gaaggccctt    4740
tgcttggatc tcttgagcct gtcagctgca tgtgatgcct tggaccagca caacctcaag    4800
caaaatgacc agcccatgga tatcctgcag attattaatt gtttgaccac tatttatgac    4860
cgcctggagc aagagcacaa caatttggtc aacgtccctc tctgcgtgga tatgtgtctg    4920
aactggctgc tgaatgttta tgatacggga cgaacaggga ggatccgtgt cctgtctttt    4980
aaaactggca tcatttccct gtgtaaagca catttggaag acaagtacag ataccttttc    5040
aagcaagtgg caagttcaac aggattttgt gaccagcgca ggctgggcct ccttctgcat    5100
gattctatcc aaattccaag acagttgggt gaagttgcat cctttggggg cagtaacatt    5160
gagccaagtg tccggagctg cttccaattt gctaataata agccagagat cgaagcggcc    5220
ctcttcctag actggatgag actggaaccc cagtccatgg tgtggctgcc cgtcctgcac    5280
agagtggctg ctgcagaaac tgccaagcat caggccaaat gtaacatctg caaagagtgt    5340
ccaatcattg gattcaggta caggagtcta aagcacttta attatgacat ctgccaaagc    5400 tgctttttt ctggtcgagt tgcaaaaggc cataaaatgc actatcccat ggtggaatat    5460
tgcactccga ctacatcagg agaagatgtt cgagactttg ccaaggtact aaaaaacaaa    5520
tttcgaacca aaaggtattt tgcgaagcat ccccgaatgg gctacctgcc agtgcagact    5580
gtcttagagg gggacaacat ggaaacgcct gcctcgtccc ctcagctttc acacgatgat    5640
actcattcac gcattgaaca ttatgctagc aggctagcag aaatggaaaa cagcaatgga    5700
tcttatctaa atgatagcat ctctcctaat gagagcatag atgatgaaca tttgttaatc    5760
cagcattact gccaaagttt gaaccaggac tcccccctga gccagcctcg tagtcctgcc    5820
cagatcttga tttccttaga gagtgaggaa agaggggagc tagagagaat cctagcagat    5880
cttgaggaag aaaacaggaa tctgcaagca gaatatgacc gtctaaagca gcagcacgaa    5940
cataaaggcc tgtccccact gccgtcccct cctgaaatga tgcccacctc tccccagagt    6000 cccccgggatg ctgagctcat tgctgaggcc aagctactgc gtcaacacaa aggccgcctg    6060
gaagccagga tgcaaatcct ggaagaccac aataaacagc tggagtcaca gttacacagg    6120
ctaaggcagc tgctggagca accccaggca gaggccaaag tgaatggcac aacggtgtcc    6180
tctccttcta cctctctaca gaggtccgac agcagtcagc ctatgctgct ccgagtggtt    6240
ggcagtcaaa cttcggactc catgggtgag gaagatcttc tcagtcctcc ccaggacaca    6300
agcacagggt tagaggaggt gatggagcaa ctcaacaact ccttccctag ttcaagagga    6360
agaaataccc ctggaaagcc aatgagagag gacacaatgt ag                        6402
```

<210> SEQ ID NO 9
<211> LENGTH: 6081
<212> TYPE: DNA
<213> ORGANISM: Artificial Sequence
<220> FEATURE:
<223> OTHER INFORMATION: Synthetic oligonucleotide

<400> SEQUENCE: 9

```
atgctttggt gggaagaagt agaggactgt tatgaaagag aagatgttca aaagaaaaca    60
ttcacaaaat gggtaaatgc acaattttct aagtttggga agcagcatat tgagaacctc   120
ttcagtgacc tacaggatgg gaggcgcctc ctagacctcc tcgaaggcct gacagggcaa   180
aaactgccaa agaaaaagg atccacaaga gttcatgccc tgaacaatgt caacaaggca   240
ctgcgggttt tgcagaacaa taatgttgat ttagtgaata ttggaagtac tgacatcgta   300
gatggaaatc ataaactgac tcttggtttg atttggaata taatcctcca ctggcaggtc   360
aaaaatgtaa tgaaaatat catggctgga ttgcaacaaa ccaacagtga aaagattctc   420
ctgagctggg tccgacaatc aactcgtaat tatccacagg ttaatgtaat caacttcacc   480
accagctggt ctgatggcct ggctttgaat gctctcatcc atagtcatag gccagaccta   540
tttgactgga atagtgtggt tgccagcag tcagccacac aacgactgga acatgcattc   600
aacatcgcca gatatcaatt aggcatagag aaactactcg atcctgaaga tgttgatacc   660
acctatccag ataagaagtc catcttaatg tacatcacat cactcttcca agttttgcct   720
caacaagtga gcattgaagc catccaggaa gtggaaatgt tgccaaggcc acctaaagtg   780
actaagaag aacattttca gttacatcat caaatgcact attctcaaca gatcacggtc   840
agtctagcac agggatatga gagaacttct tcccctaagc ctcgattcaa gagctatgcc   900
tacacacagg ctgcttatgt caccacctct gaccctacac ggagcccatt tccttcacag   960
catttggaag ctcctgaaga caagtcattt ggcagttcat tgatggagag tgaagtaaac  1020
ctggaccgtt atcaaacagc tttagaagaa gtattatcgt ggcttctttc tgctgaggac  1080
acattgcaag cacaaggaga gatttctaat gatgtggaag tggtgaaaga ccagtttcat  1140
actcatgagg ggtacatgat ggatttgaca gcccatcagg gccgggttgg taatattcta  1200
caattgggaa gtaagctgat tggaacagga aaattatcag aagatgaaga aactgaagta  1260
caagagcaga tgaatctcct aaattcaaga tgggaatgcc tcagggtagc tagcatggaa  1320
aaacaaagca atttacatag agttttaatg gatctccaga atcagaaact gaaagagttg  1380
aatgactggc taacaaaaac agaagaaaga acaaggaaaa tggaggaaga gcctcttgga  1440
cctgatcttg aagacctaaa acgccaagta caacaacata aggtgcttca agaagatcta  1500
gaacaagaac aagtcagggt caattctctc actcacatgg tggtggtagt tgatgaatct  1560
agtggagatc acgcaactgc tgctttggaa gaacaactta aggtattggg agatcgatgg  1620
gcaaacatct gtagatggac agaagaccgc tgggttcttt tacaagacat ccttctcaaa  1680
tggcaacgtc ttactgaaga acagtgcctt tttagtgcat ggctttcaga aaaagaagat  1740
gcagtgaaca agattcacac aactggcttt aaagatcaaa atgaaatgtt atcaagtctt  1800
caaaaactgg ccgtttaaa agcggatcta gaaaagaaaa agcaatccat gggcaaactg  1860
tattcactca aacaagatct tctttcaaca ctgaagaata gtcagtgac ccagaagacg  1920
gaagcatggc tggataactt tgcccggtgt tgggataatt tagtccaaaa acttgaaaag  1980
agtacagcac agatttcaca ggaaatttct tatgtgcctt ctacttattt gactgaaatc  2040
actcatgtct cacaagccct attagaagtg gaacaacttc tcaatgctcc tgacctctgt  2100
gctaaggact ttgaagatct ctttaagcaa gaggagtctc tgaagaatat aaaagatagt  2160
ctacaacaaa gctcaggtcg gattgacatt attcatagca agaagacagc agcattgcaa  2220
agtcaacgc ctgtggaaag ggtgaagcta caggaagctc tctcccagct tgatttccaa  2280
tgggaaaaag ttaacaaaat gtacaaggac cgacaagggc gatttgacag acagcctgac  2340
```

```
ctagctcctg gactgaccac tattggagcc tctcctactc agactgttac tctggtgaca    2400
caacctgtgg ttactaagga aactgccatc tccaaactag aaatgccatc ttccttgatg    2460
ttggaggtac ctgctctggc agatttcaac cgggcttgga cagaacttac cgactggctt    2520
tctctgcttg atcaagttat aaaatcacag agggtgatgg tgggtgacct tgaggatatc    2580
aacgagatga tcatcaagca gaaggcaaca atgcaggatt tggaacagag gcgtccccag    2640
ttggaagaac tcattaccgc tgcccaaaat ttgaaaaaca agaccagcaa tcaagaggct    2700
agaacaatca ttacggatcg aattgaaaga attcagaatc agtgggatga agtacaagaa    2760
caccttcaga accggaggca acagttgaat gaaatgttaa aggattcaac acaatggctg    2820
gaagctaagg aagaagctga gcaggtctta ggacaggcca gagccaagct tgagtcatgg    2880
aaggagggtc cctatacagt agatgcaatc caaaagaaaa tcacagaaac caagcagttg    2940
gccaaagacc tccgccagtg cagacaaat gtagatgtgg caaatgactt ggccctgaaa    3000
cttctccggg attattctgc agatgatacc agaaaagtcc acatgataac agagaatatc    3060
aatgcctctt ggagaagcat tcataaaagg gtgagtgagc gagaggctgc tttggaagaa    3120
actcatagat tactgcaaca gttccccctg gacctggaaa agtttcttgc ctggcttaca    3180
gaagctgaaa caactgccaa tgtcctacag gatgctaccc gtaaggaaag gctcctagaa    3240
gactccaagg gagtaaaaga gctgatgaaa caatggcaag acctccaagg tgaaattgaa    3300
gctcacacag atgtttatca aacctggat gaaaacagcc aaaaaatcct gagatccctg    3360
gaaggttccg atgatgcagt cctgttacaa agacgtttgg ataacatgaa cttcaagtgg    3420
agtgaacttc ggaaaaagtc tctcaacatt aggtcccatt tggaagccag ttctgaccag    3480
tggaagcgtc tgcaccttc tctgcaggaa cttctggtgt ggctacagct gaaagatgat    3540
gaattaagcc ggcaggcacc tattggaggc gactttccag cagttcagaa gcagaacgat    3600
gtacataggg ccttcaagag ggaattgaaa actaaagaac tgtaatcat gagtactctt    3660 gagactgtac gaatatttct gacagagcag cctttggaag gactagagaa actctaccag    3720
gagcccagag agctgcctcc tgaggagaga gcccagaatg tcactcggct tctacgaaag    3780
caggctgagg aggtcaatac tgagtgggaa aaattgaacc tgcactccgc tgactggcag    3840 agaaaatag atgagaccct tgaaagactc caggaacttc aagaggccac ggatgagctg    3900
gacctcaagc tgcgccaagc tgaggtgatc aagggatcct ggcagcccgt gggcgatctc    3960
ctcattgact ctctccaaga tcacctcgag aaagtcaagg cacttcgagg agaaattgcg    4020
cctctgaaag agaacgtgag ccacgtcaat gaccttgctc gccagcttac cactttgggc    4080
attcagctct caccgtataa cctcagcact ctggaagacc tgaacaccag atggaagctt    4140
ctgcaggtgg ccgtcgagga ccgagtcagg cagctgcatg aagcccacag ggactttggt    4200
ccagcatctc agcactttct ttccacgtct gtccagggtc cctgggagag agccatctcg    4260
ccaaacaaag tgccctacta tatcaaccac gagactcaaa caacttgctg ggaccatccc    4320
aaaatgacag agctctacca gtctttagct gacctgaata atgtcagatt ctcagcttat    4380
aggactgcca tgaaactccg aagactgcag aaggccttt gcttggatct cttgagcctg    4440
tcagctgcat gtgatgcctt ggaccagcac aacctcaagc aaaatgacca gcccatggat    4500
atcctgcaga ttattaattg tttgaccact atttatgacc gcctggagca agagcacaac    4560
aatttggtca acgtccctct ctgcgtggat atgtgtctga actggctgct gaatgtttat    4620
gatacgggac gaacagggag gatccgtgtc ctgtctttta aaactggcat catttccctg    4680
tgtaaagcac atttggaaga caagtacaga taccttttca agcaagtggc aagttcaaca    4740
```

```
ggattttgtg accagcgcag gctgggcctc cttctgcatg attctatcca aattccaaga    4800
cagttgggtg aagttgcatc ctttgggggc agtaacattg agccaagtgt ccggagctgc    4860
ttccaatttg ctaataataa gccagagatc gaagcggccc tcttcctaga ctggatgaga    4920
ctggaacccc agtccatggt gtggctgccc gtcctgcaca gagtggctgc tgcagaaact    4980
gccaagcatc aggccaaatg taacatctgc aaagagtgtc caatcattgg attcaggtac    5040
aggagtctaa agcactttaa ttatgacatc tgccaaagct gctttttttc tggtcgagtt    5100
gcaaaaggcc ataaaatgca ctatcccatg gtggaatatt gcactccgac tacatcagga    5160
gaagatgttc gagactttgc caaggtacta aaaacaaat ttcgaaccaa aaggtatttt     5220
gcgaagcatc cccgaatggg ctacctgcca gtgcagactg tcttagaggg ggacaacatg    5280
gaaacgcctg cctcgtcccc tcagctttca cacgatgata ctcattcacg cattgaacat    5340
tatgctagca ggctagcaga aatggaaaac agcaatggat cttatctaaa tgatagcatc    5400
tctcctaatg agagcataga tgatgaacat ttgttaatcc agcattactg ccaaagtttg    5460
aaccaggact cccccctgag ccagcctcgt agtcctgccc agatcttgat ttccttagag    5520
agtgaggaaa gaggggagct agagagaatc ctagcagatc ttgaggaaga aaacaggaat    5580
ctgcaagcag aatatgaccg tctaaagcag cagcacgaac ataaaggcct gtccccactg    5640
ccgtcccctc ctgaaatgat gcccacctct ccccagagtc cccgggatgc tgagctcatt    5700
gctgaggcca agctactgcg tcaacacaaa ggccgcctgg aagccaggat gcaaatcctg    5760
gaagaccaca taaacagct ggagtcacag ttacacaggc taaggcagct gctggagcaa     5820
ccccaggcag aggccaaagt gaatggcaca acggtgtcct ctccttctac ctctctacag    5880
aggtccgaca gcagtcagcc tatgctgctc cgagtggttg gcagtcaaac ttcggactcc    5940
atgggtgagg aagatcttct cagtcctccc caggacacaa gcacagggtt agaggaggtg    6000
atggagcaac tcaacaactc cttccctagt tcaagaggaa gaaataccccc tggaaagcca   6060 atgagagagg acacaatgta g                                              6081
```

<210> SEQ ID NO 10
<211> LENGTH: 6264
<212> TYPE: DNA
<213> ORGANISM: Artificial Sequence
<220> FEATURE:
<223> OTHER INFORMATION: Synthetic oligonucleotide

<400> SEQUENCE: 10

```
atgctttggt gggaagaagt agaggactgt tatgaaagag aagatgttca aaagaaaaca     60
ttcacaaaat gggtaaatgc acaatttttct aagtttggga agcagcatat tgagaacctc   120
ttcagtgacc tacaggatgg gaggcgcctc ctagacctcc tcgaaggcct gacagggcaa    180
aaactgccaa agaaaaagg atccacaaga gttcatgccc tgaacaatgt caacaaggca    240
ctgcgggttt tgcagaacaa taatgttgat ttagtgaata ttggaagtac tgacatcgta    300
gatggaaatc ataaactgac tcttggtttg atttggaata taatcctcca ctggcaggtc    360
aaaaatgtaa tgaaaatat catggctgga ttgcaacaaa ccaacagtga aaagattctc    420
ctgagctggg tccgacaatc aactcgtaat tatccacagg ttaatgtaat caacttcacc   480
accagctggt ctgatggcct ggctttgaat gctctcatcc atagtcatag gccagaccta   540
tttgactgga atagtgtggt ttgccagcag tcagccacac aacgactgga acatgcattc    600
aacatcgcca gatatcaatt aggcatagag aaactactcg atcctgaaga tgttgatacc    660
```

| | |
|---|---|
| acctatccag ataagaagtc catcttaatg tacatcacat cactcttcca agtttttgcct | 720 |
| caacaagtga gcattgaagc catccaggaa gtggaaatgt tgccaaggcc acctaaagtg | 780 |
| actaaagaag aacatttttca gttacatcat caaatgcact attctcaaca gatcacggtc | 840 |
| agtctagcac agggatatga gagaacttct tccccctaagc ctcgattcaa gagctatgcc | 900 |
| tacacacagg ctgcttatgt caccacctct gaccctacac ggagcccatt tccttcacag | 960 |
| catttggaag ctcctgaaga caagtcattt ggcagttcat tgatggagag tgaagtaaac | 1020 |
| ctggaccgtt atcaaacagc tttagaagaa gtattatcgt ggcttctttc tgctgaggac | 1080 |
| acattgcaag cacaaggaga gatttctaat gatgtggaag tggtgaaaga ccagtttcat | 1140 |
| actcatgagg ggtacatgat ggatttgaca gcccatcagg gccgggttgg taatattcta | 1200 |
| caattgggaa gtaagctgat tggaacagga aaattatcag aagatgaaga aactgaagta | 1260 |
| caagagcaga tgaatctcct aaattcaaga tgggaatgcc tcagggtagc tagcatggaa | 1320 |
| aaacaaagca atttacatag agttttaatg gatctccaga atcagaaact gaaagagttg | 1380 |
| aatgactggc taacaaaaac agaagaaaga acaaggaaaa tggaggaaga gcctcttgga | 1440 |
| cctgatcttg aagacctaaa acgccaagta caacaacata aggtgcttca agaagatcta | 1500 |
| gaacaagaac aagtcagggt caattctctc actcacatgg tggtggtagt tgatgaatct | 1560 |
| agtggagatc acgcaactgc tgctttggaa gaacaactta aggtattggg agatcgatgg | 1620 |
| gcaaacatct gtagatggac agaagaccgc tgggttcttt tacaagacat ccttctcaaa | 1680 |
| tggcaacgtc ttactgaaga acagtgcctt tttagtgcat ggctttcaga aaaagaagat | 1740 |
| gcagtgaaca agattcacac aactggcttt aaagatcaaa atgaaatgtt atcaagtctt | 1800 |
| caaaaactgg ccgttttaaa agcggatcta gaaaagaaaa agcaatccat gggcaaactg | 1860 |
| tattcactca aacaagatct tctttcaaca ctgaagaata agtcagtgac ccagaagacg | 1920 |
| gaagcatggc tggataactt tgcccggtgt tgggataatt tagtccaaaa acttgaaaag | 1980 |
| agtacagcac agatttcaca ggaaatttct tatgtgcctt ctacttattt gactgaaatc | 2040 |
| actcatgtct cacaagccct attagaagtg gaacaacttc tcaatgctcc tgacctctgt | 2100 |
| gctaaggact ttgaagatct cttttaagcaa gaggagtctc tgaagaatat aaaagatagt | 2160 |
| ctacaacaaa gctcaggtcg gattgacatt attcatagca agaagacagc agcattgcaa | 2220 |
| agtgcaacgc ctgtggaaag ggtgaagcta caggaagctc tctcccagct tgatttccaa | 2280 |
| tgggaaaaag ttaacaaaat gtacaaggac cgacaagggc gatttgacag atctgttgag | 2340 |
| aaatggcggc gttttcatta tgatataaag atatttaatc agtggctaac agaagctgaa | 2400 |
| cagtttctca gaaagacaca aattcctgag aattgggaac atgctaaata caaatggtat | 2460 |
| cttaaggaac tccaggatgg cattgggcag cggcaaactg ttgtcagaac attgaatgca | 2520 |
| actggggaag aaataattca gcaatcctca aaaacagatg ccagtattct acaggaaaaa | 2580 |
| ttgggaagcc tgaatctgcg gtggcaggag gtctgcaaac agctgtcaga cagaaaaaag | 2640 |
| aggctagaag aacaaagaa tatcttgtca gaatttcaaa gagatttaaa tgaatttgtt | 2700 |
| ttatggttgg aggaagcaga taacattgct agtatcccac ttgaacctgg aaaagagcag | 2760 |
| caactaaaag aaaagcttga gcaagtcaag ttactggtgg aagagttgcc cctgcgccag | 2820 |
| ggaattctca acaattaaaa tgaaactgga ggacccgtgc ttgtaagtgc tcccataagc | 2880 |
| ccagaagagc aagataaact tgaaaataag ctcaagcaga caaatctcca gtggataaag | 2940 |
| gtttccagag ctttacctga gaacaaggga gaaattgaag ctcaaataaa agaccttggg | 3000 |
| cagcttgaaa aaaagcttga agaccttgaa gagcagttaa atcatctgct gctgtggtta | 3060 |

```
tctcctatta ggaatcagtt ggaaatttat aaccaaccaa accaagaagg accatttgac    3120
gttcaggaaa ctgaaatagc agttcaagct aaacaaccgg atgtggaaga gattttgtct    3180
aaagggcagc atttgtacaa ggaaaaacca gccactcagc cagtgaagag gaagttagaa    3240
gatctgagct ctgagtggaa ggcggtaaac cgtttacttc aagagctgag ggcaaagcag    3300
cctgacctag ctcctggact gaccactatt ggagcctctc ctactcagac tgttactctg    3360
gtgacacaac ctgtggttac taaggaaact gccatctcca aactagaaat gccatcttcc    3420
ttgatgttgg aggtacctgc tctggcagat ttcaaccggg cttggacaga acttaccgac    3480
tggctttctc tgcttgatca agttataaaa tcacagaggg tgatggtggg tgaccttgag    3540
gatatcaacg agatgatcat caagcagaag gcaacaatgc aggatttgga acagaggcgt    3600
ccccagttgg aagaactcat taccgctgcc caaaatttga aaacaagac cagcaatcaa    3660 gaggctagaa caatcattac ggatcgaatt gaaagaattc agaatcagtg ggatgaagta    3720
caagaacacc ttcagaaccg gaggcaacag ttgaatgaaa tgttaaagga ttcaacacaa    3780
tggctgaaag ctaaggaaga agctgagcag gtcttaggac aggccagagc caagcttgag    3840
tcatggaagg agggtcccta tacagtagat gcaatccaaa agaaaatcac agaaaccaag    3900
cagttggcca agacctccg ccagtggcag acaaatgtag atgtggcaaa tgacttggcc    3960
ctgaaacttc tccgggatta ttctgcagat gataccagaa aagtccacat gataacagag    4020
aatatcaatg cctcttggag aagcattcat aaaaggtga gtgagcgaga ggctgctttg    4080
gaagaaactc atagattact gcaacagttc cccctggacc tggaaaagtt tcttgcctgg    4140
cttacagaag ctgaaacaac tgccaatgtc ctacaggatg ctacccgtaa ggaaaggctc    4200
ctagaagact ccaagggagt aaaagagctg atgaaacaat ggcaagacct ccaaggtgaa    4260
attgaagctc acacagatgt ttatcacaac ctggatgaaa acagccaaaa aatcctgaga    4320
tccctggaag gttccgatga tgcagtcctg ttacaaagac gtttggataa catgaacttc    4380
aagtggagtg aacttcggaa aaagtctctc aacattaggt cccatttgga agccagttct    4440
gaccagtgga gcgtctgca cctttctctg caggaacttc tggtgtggct acagctgaaa    4500
gatgatgaat taagccggca ggcacctatt ggaggcgact ttccagcagt tcagaagcag    4560
aacgatgtac atagggcctt caagagggaa ttgaaaacta agaacctgt aatcatgagt    4620 actcttgaga ctgtacgaat atttctgaca gagcagcctt ggaaggact agagaaactc    4680 taccaggagc ccagagagct gcctcctgag gagagagccc agaatgtcac tcggcttcta    4740
cgaaagcagg ctgaggaggt caatactgag tgggaaaaat tgaacctgca ctccgctgac    4800
tggcagagaa aaatagatga gacccttgaa agactccagg aacttcaaga ggccacggat    4860
gagctggacc tcaagctgcg ccaagctgag gtgatcaagg atcctggca gcccgtgggc    4920 gatctcctca ttgactctct ccaagatcac ctcgagaaag tcaaggcact tcgaggagaa    4980
attgcgcctc tgaaagagaa cgtgagccac gtcaatgacc ttgctcgcca gcttaccact    5040
ttgggcattc agctctcacc gtataacctc agcactctgg aagacctgaa caccagatgg    5100
aagcttctgc aggtggccgt cgaggaccga gtcaggcagc tgcatgaagc ccacagggac    5160
tttggtccag catctcagca ctttctttcc acgtctgtcc agggtccctg ggagagagcc    5220
atctcgccaa acaaagtgcc ctactatatc aaccacgaga ctcaaacaac ttgctgggac    5280
catcccaaaa tgacagagct ctaccagtct ttagctgacc tgaataatgt cagattctca    5340
gcttatagga ctgccatgaa actccgaaga ctgcagaagg ccctttgctt ggatctcttg    5400
```

```
agcctgtcag ctgcatgtga tgccttggac cagcacaacc tcaagcaaaa tgaccagccc    5460
atggatatcc tgcagattat taattgtttg accactattt atgaccgcct ggagcaagag    5520
cacaacaatt tggtcaacgt ccctctctgc gtggatatgt gtctgaactg gctgctgaat    5580
gtttatgata cgggacgaac agggaggatc cgtgtcctgt cttttaaaac tggcatcatt    5640
tccctgtgta agcacatttt ggaagacaag tacagatacc ttttcaagca agtggcaagt    5700
tcaacaggat tttgtgacca gcgcaggctg ggcctccttc tgcatgattc tatccaaatt    5760
ccaagacagt tgggtgaagt tgcatccttt ggggcagta acattgagcc aagtgtccgg    5820
agctgcttcc aatttgctaa taataagcca gagatcgaag cggccctctt cctagactgg    5880
atgagactgg aaccccagtc catggtgtgg ctgcccgtcc tgcacagagt ggctgctgca    5940
gaaactgcca agcatcaggc caaatgtaac atctgcaaag agtgtccaat cattggattc    6000
aggtacagga gtctaaagca ctttaattat gacatctgcc aaagctgctt tttttctggt    6060
cgagttgcaa aaggccataa aatgcactat cccatggtgg aatattgcac tccgactaca    6120
tcaggagaag atgttcgaga ctttgccaag gtactaaaaa acaaatttcg aaccaaaagg    6180
tattttgcga agcatccccg aatgggctac ctgccagtgc agactgtctt agaggggac    6240 aacatggaaa ctgacacaat gtag                                            6264

<210> SEQ ID NO 11
<211> LENGTH: 4080
<212> TYPE: DNA
<213> ORGANISM: Artificial Sequence
<220> FEATURE:
<223> OTHER INFORMATION: Synthetic oligonucleotide

<400> SEQUENCE: 11
atgctttggt gggaagaagt agaggactgt tatgaaagag aagatgttca aagaaaaca      60 ttcacaaaat gggtaaatgc acaatttctt aagtttggga agcagcatat tgagaacctc    120
ttcagtgacc tacaggatgg gaggcgcctc ctagacctcc tcgaaggcct gacagggcaa    180
aaactgccaa agaaaaaggg atccacaaga gttcatgccc tgaacaatgt caacaaggca    240
ctgcgggttt tgcagaacaa taatgttgat ttagtgaata ttggaagtac tgacatcgta    300
gatggaaatc ataaactgac tcttggtttg atttggaata taatcctcca ctggcaggtc    360
aaaaatgtaa tgaaaatat catggctgga ttgcaacaaa ccaacagtga aaagattctc    420
ctgagctggg tccgacaatc aactcgtaat tatccacagg ttaatgtaat caacttcacc    480
accagctggt ctgatggcct ggctttgaat gctctcatcc atagtcatag gccagaccta    540
tttgactgga atagtgtggt ttgccagcag tcagccacac aacgactgga acatgcattc    600
aacatcgcca gatatcaatt aggcatagag aaactactcg atcctgaaga tgttgatacc    660
acctatccag ataagaagtc catcttaatg tacatcacat cactcttcca agttttgcct    720
caacaagtga gcattgaagc catccaggaa gtggaaatgt gccaaggcc acctaaagtg    780 actaagaag aacattttca gttacatcat caaatgcact attctcaaca gatcacggtc    840
agtctagcac agggatatga gagaacttct tcccctaagc ctcgattcaa gagctatgcc    900
tacacacagg ctgcttatgt caccacctct gaccctacac ggagcccatt tccttcacag    960
catttggaag ctcctgaaga caagtcattt ggcagttcat tgatggagag tgaagtaaac    1020
ctggaccgtt atcaaacagc tttagaagaa gtattatcgt ggcttcttc tgctgaggac    1080 acattgcaac acaaggaga gatttctaat gatgtggaag tggtgaaaga ccagtttcat    1140
actcatgagg ggtacatgat ggatttgaca gcccatcagg gccgggttgg taatattcta    1200
```

```
caattgggaa gtaagctgat tggaacagga aaattatcag aagatgaaga aactgaagta    1260
caagagcaga tgaatctcct aaattcaaga tgggaatgcc tcagggtagc tagcatggaa    1320
aaacaaagca atttcatag agaaatttct tatgtgcctt ctacttattt gactgaaatc     1380
actcatgtct cacaagccct attagaagtg aacaacttc tcaatgctcc tgacctctgt     1440
gctaaggact ttgaagatct ctttaagcaa gaggagtctc tgaagaatat aaaagatagt    1500
ctacaacaaa gctcaggtcg gattgacatt attcatagca agaagacagc agcattgcaa    1560
agtgcaacgc ctgtggaaag ggtgaagcta caggaagctc tctcccagct tgatttccaa    1620
tgggaaaaag ttaacaaaat gtacaaggac cgacaagggc gatttgacag atctgttgag    1680
aaatggcggc gttttcatta tgatataaag atatttaatc agtggctaac agaagctgaa    1740
cagtttctca gaaagacaca aattcctgag aattgggaac atgctaaata caatggtat    1800 cttaaggaac tccaggatgg cattgggcag cggcaaactg ttgtcagaac attgaatgca    1860
actggggaag aaataattca gcaatcctca aaaacagatg ccagtattct acaggaaaaa    1920
ttgggaagcc tgaatctgcg gtggcaggag gtctgcaaac agctgtcaga cagaaaaaag    1980
aggctagaag aacaaaagaa tatcttgtca gaatttcaaa gagatttaaa tgaatttgtt    2040
ttatggttgg aggaagcaga taacattgct agtatcccac ttgaacctgg aaaagagcag    2100
caactaaaag aaaagcttga gcaagtcaag ttactggtgg aagagttgcc cctgcgccag    2160
ggaattctca acaattaaa tgaaactgga ggacccgtgc ttgtaagtgc tcccataagc     2220
ccagaagagc aagataaact tgaaaataag ctcaagcaga caaatctcca gtggataaag    2280
gtttccagag cttttacctga gaaacaagga gaaattgaag ctcaaataaa agaccttggg    2340
cagcttgaaa aaaagcttga agaccttgaa gagcagttaa atcatctgct gctgtggtta    2400
tctcctatta ggaatcagtt ggaaatttat aaccaaccaa accaagaagg accatttgac    2460
gttcaggaaa ctgaaatagc agttcaagct aaacaaccgg atgtggaaga gattttgtct    2520
aaagggcagc atttgtacaa ggaaaaacca gccactcagc cagtgaagag gaagttagaa    2580
gatctgagct ctgagtggaa ggcggtaaac cgtttacttc aagagctgag ggcaaagacc    2640
cttgaaagac tccaggaact tcaagaggcc acggatgagc tggacctcaa gctgcgccaa    2700
gctgaggtga tcaagggatc ctggcagccc gtgggcgatc tcctcattga ctctctccaa    2760
gatcacctcg agaaagtcaa ggcacttcga ggagaaattg cgcctctgaa agagaacgtg    2820
agccacgtca atgaccttgc tcgccagctt accactttgg gcattcagct ctcaccgtat    2880
aacctcagca ctctggaaga cctgaacacc agatggaagc ttctgcaggt ggccgtcgag    2940
gaccgagtca ggcagctgca tgaagcccac agggactttg gtccagcatc tcagcacttt    3000 cttttccacgt ctgtccaggg tccctgggag agagccatct cgccaaacaa agtgccctac    3060
tatatcaacc acgagactca aacaacttgc tgggaccatc ccaaaatgac agagctctac    3120
cagtctttag ctgacctgaa taatgtcaga ttctcagctt ataggactgc catgaaactc    3180
cgaagactgc agaaggccct ttgcttggat ctcttgagcc tgtcagctgc atgtgatgcc    3240
ttggaccagc acaacctcaa gcaaaatgac cagcccatgg atatcctgca gattattaat    3300
tgtttgacca ctatttatga ccgcctggag caagagcaca caatttggt caacgtccct    3360 ctctgcgtgg atatgtgtct gaactggctg ctgaatgttt atgatacggg acgaacaggg    3420
aggatccgtg tcctgtcttt taaaactggc atcatttccc tgtgtaaagc acatttggaa    3480
gacaagtaca gataccttttt caagcaagtg gcaagttcaa caggatttg tgaccagcgc    3540
```

| aggctgggcc tccttctgca tgattctatc caaattccaa gacagttggg tgaagttgca | 3600 |
| tcctttgggg gcagtaacat tgagccaagt gtccggagct gcttccaatt tgctaataat | 3660 |
| aagccagaga tcgaagcggc cctcttccta gactggatga gactggaacc ccagtccatg | 3720 |
| gtgtggctgc ccgtcctgca cagagtggct gctgcagaaa ctgccaagca tcaggccaaa | 3780 |
| tgtaacatct gcaaagagtg tccaatcatt ggattcaggt acaggagtct aaagcacttt | 3840 |
| aattatgaca tctgccaaag ctgcttttt tctggtcgag ttgcaaaagg ccataaaatg | 3900 |
| cactatccca tggtggaata ttgcactccg actacatcag gagaagatgt tcgagacttt | 3960 |
| gccaaggtac taaaaaacaa atttcgaacc aaaaggtatt ttgcgaagca tccccgaatg | 4020 |
| ggctacctgc cagtgcagac tgtcttagag ggggacaaca tggaaactga cacaatgtag | 4080 |

<210> SEQ ID NO 12
<211> LENGTH: 3762
<212> TYPE: DNA
<213> ORGANISM: Artificial Sequence
<220> FEATURE:
<223> OTHER INFORMATION: Synthetic oligonucleotide

<400> SEQUENCE: 12

| atgctttggt gggaagaagt agaggactgt tatgaaagag aagatgttca aaagaaaaca | 60 |
| ttcacaaaat gggtaaatgc acaattttct aagtttggga agcagcatat tgagaacctc | 120 |
| ttcagtgacc tacaggatgg gaggcgcctc ctagacctcc tcgaaggcct gacagggcaa | 180 |
| aaactgccaa agaaaaagg atccacaaga gttcatgccc tgaacaatgt caacaaggca | 240 |
| ctgcgggttt tgcagaacaa taatgttgat ttagtgaata ttggaagtac tgacatcgta | 300 |
| gatggaaatc ataaactgac tcttggtttg atttggaata taatcctcca ctggcaggtc | 360 |
| aaaaatgtaa tgaaaatat catggctgga ttgcaacaaa ccaacagtga aaagattctc | 420 |
| ctgagctggg tccgacaatc aactcgtaat tatccacagg ttaatgtaat caacttcacc | 480 |
| accagctggt ctgatggcct ggctttgaat gctctcatcc atagtcatag gccagaccta | 540 |
| tttgactgga atagtgtggt ttgccagcag tcagccacac aacgactgga acatgcattc | 600 |
| aacatcgcca gatatcaatt aggcatagag aaactactcg atcctgaaga tgttgatacc | 660 |
| acctatccag ataagaagtc catcttaatg tacatcacat cactcttcca agttttgcct | 720 |
| caacaagtga gcattgaagc catccaggaa gtggaaatgt tgccaaggcc acctaaagtg | 780 |
| actaagaag aacattttca gttacatcat caaatgcact attctcaaca gatcacggtc | 840 |
| agtctagcac agggatatga gagaacttct tcccctaagc ctcgattcaa gagctatgcc | 900 |
| tacacacagg ctgcttatgt caccacctct gaccctacac ggagcccatt tccttcacag | 960 |
| catttggaag ctcctgaaga caagtcatt ggcagttcat tgatggagag tgaagtaaac | 1020 |
| ctggaccgtt atcaaacagc tttagaagaa gtattatcgt ggcttctttc tgctgaggac | 1080 |
| acattgcaag cacaaggaga gatttctaat gatgtggaag tggtgaaaga ccagtttcat | 1140 |
| actcatgagg ggtacatgat ggatttgaca gcccatcagg gccgggttgg taatattcta | 1200 |
| caattgggaa gtaagctgat tggaacagga aaattatcag aagatgaaga aactgaagta | 1260 |
| caagagcaga tgaatctcct aaattcaaga tgggaatgcc tcagggtagc tagcatggaa | 1320 |
| aaacaaagca atttacatag agtttttaatg gatctccaga atcagaaact gaagagttg | 1380 |
| aatgactggc taacaaaaac agaagaaaga acaaggaaaa tggaggaaga gcctcttgga | 1440 |
| cctgatcttg aagacctaaa acgccaagta caacaacata aggtgcttca agaagatcta | 1500 |
| gaacaagaac aagtcagggt caattctctc actcacatgg tggtggtagt tgatgaatct | 1560 |

```
agtggagatc acgcaactgc tgctttggaa gaacaactta aggtattggg agatcgatgg    1620
gcaaacatct gtagatggac agaagaccgc tgggttcttt tacaagacga aatttcttat    1680
gtgccttcta cttatttgac tgaaatcact catgtctcac aagccctatt agaagtggaa    1740
caacttctca atgctcctga cctctgtgct aaggactttg aagatctctt taagcaagag    1800
gagtctctga gaatataaa agatagtcta caacaaagct caggtcggat tgacattatt    1860
catagcaaga agacagcagc attgcaaagt gcaacgcctg tggaaagggt gaagctacag    1920
gaagctctct cccagcttga tttccaatgg gaaaaagtta acaaaatgta caaggaccga    1980
caagggcgat ttgacagatc tgttgagaaa tggcggcgtt ttcattatga tataaagata    2040
tttaatcagt ggctaacaga agctgaacag tttctcagaa agacacaaat tcctgagaat    2100
tgggaacatg ctaaatacaa atggtatctt aaggaactcc aggatggcat tgggcagcgg    2160
caaactgttg tcagaacatt gaatgcaact ggggaagaaa taattcagca atcctcaaaa    2220
acagatgcca gtattctaca ggaaaaattg ggaagcctga atctgcggtg gcaggaggtc    2280
tgcaaacagc tgtcagacag aaaaaagagg ctagaagaaa cccttgaaag actccaggaa    2340
cttcaagagg ccacggatga gctggacctc aagctgcgcc aagctgaggt gatcaaggga    2400
tcctggcagc ccgtgggcga tctcctcatt gactctctcc aagatcacct cgagaaagtc    2460
aaggcacttc gaggagaaat tgcgcctctg aaagagaacg tgagccacgt caatgacctt    2520
gctcgccagc ttaccacttt gggcattcag ctctcaccgt ataacctcag cactctggaa    2580
gacctgaaca ccagatggaa gcttctgcag gtggccgtcg aggaccgagt caggcagctg    2640
catgaagccc acagggactt tggtccagca tctcagcact ttctttccac gtctgtccag    2700
ggtccctggg agagagccat ctcgccaaac aaagtgccct actatatcaa ccacgagact    2760
caaacaactt gctgggacca tcccaaaatg acagagctct accagtcttt agctgacctg    2820
aataatgtca gattctcagc ttataggact gccatgaaac tccgaagact gcagaaggcc    2880
ctttgcttgg atctcttgag cctgtcagct gcatgtgatg ccttggacca gcacaacctc    2940
aagcaaaatg accagcccat ggatatcctg cagattatta attgtttgac cactatttat    3000
gaccgcctgg agcaagagca caacaatttg gtcaacgtcc ctctctgcgt ggatatgtgt    3060
ctgaactggc tgctgaatgt ttatgatacg ggacgaacag ggaggatccg tgtcctgtct    3120
tttaaaactg gcatcatttc cctgtgtaaa gcacatttgg aagacaagta cagatacctt    3180
ttcaagcaag tggcaagttc aacaggattt tgtgaccagc gcaggctggg cctccttctg    3240
catgattcta tccaaattcc aagacagttg ggtgaagttg catcctttgg gggcagtaac    3300
attgagccaa gtgtccggag ctgcttccaa tttgctaata ataagccaga gatcgaagcg    3360
gccctcttcc tagactggat gagactggaa ccccagtcca tggtgtggct gccgtcctg    3420 cacagagtgg ctgctgcaga aactgccaag catcaggcca aatgtaacat ctgcaaagag    3480
tgtccaatca ttggattcag gtacaggagt ctaaagcact ttaattatga catctgccaa    3540
agctgctttt tttctggtcg agttgcaaaa ggccataaaa tgcactatcc catggtggaa    3600
tattgcactc cgactacatc aggagaagat gttcgagact ttgccaaggt actaaaaaac    3660
aaatttcgaa ccaaaaggta ttttgcgaag catccccgaa tgggctacct gccagtgcag    3720
actgtcttag aggggacaa catggaaact gacacaatgt ag                        3762
```

<210> SEQ ID NO 13
<211> LENGTH: 3435
<212> TYPE: DNA

<213> ORGANISM: Artificial Sequence
<220> FEATURE:
<223> OTHER INFORMATION: Synthetic oligonucleotide

<400> SEQUENCE: 13

| | | | | | |
|---|---|---|---|---|---|
| atgctttggt | gggaagaagt | agaggactgt | tatgaaagag | aagatgttca | aaagaaaaca | 60 |
| ttcacaaaat | gggtaaatgc | acaatttct | aagtttggga | agcagcatat | tgagaacctc | 120 |
| ttcagtgacc | tacaggatgg | gaggcgcctc | ctagacctcc | tcgaaggcct | gacagggcaa | 180 |
| aaactgccaa | agaaaaagg | atccacaaga | gttcatgccc | tgaacaatgt | caacaaggca | 240 |
| ctgcgggttt | tgcagaacaa | taatgttgat | ttagtgaata | ttggaagtac | tgacatcgta | 300 |
| gatggaaatc | ataaactgac | tcttggtttg | atttggaata | taatcctcca | ctggcaggtc | 360 |
| aaaaatgtaa | tgaaaatat | catggctgga | ttgcaacaaa | ccaacagtga | aaagattctc | 420 |
| ctgagctggg | tccgacaatc | aactcgtaat | tatccacagg | ttaatgtaat | caacttcacc | 480 |
| accagctggt | ctgatggcct | ggctttgaat | gctctcatcc | atagtcatag | gccagaccta | 540 |
| tttgactgga | atagtgtggt | ttgccagcag | tcagccacac | aacgactgga | acatgcattc | 600 |
| aacatcgcca | gatatcaatt | aggcatagag | aaactactcg | atcctgaaga | tgttgatacc | 660 |
| acctatccag | ataagaagtc | catcttaatg | tacatcacat | cactcttcca | agttttgcct | 720 |
| caacaagtga | gcattgaagc | catccaggaa | gtggaaatgt | tgccaaggcc | acctaaagtg | 780 |
| actaaagaag | aacattttca | gttacatcat | caaatgcact | attctcaaca | gatcacggtc | 840 |
| agtctagcac | agggatatga | gagaacttct | tcccctaagc | ctcgattcaa | gagctatgcc | 900 |
| tacacacagg | ctgcttatgt | caccacctct | gaccctacac | ggagcccatt | tccttcacag | 960 |
| catttggaag | ctcctgaaga | caagtcattt | ggcagttcat | tgatggagag | tgaagtaaac | 1020 |
| ctggaccgtt | atcaaacagc | tttagaagaa | gtattatcgt | ggcttctttc | tgctgaggac | 1080 |
| acattgcaag | cacaaggaga | gatttctaat | gatgtggaag | tggtgaaaga | ccagtttcat | 1140 |
| actcatgagg | ggtacatgat | ggatttgaca | gcccatcagg | gccgggttgg | taatattcta | 1200 |
| caattgggaa | gtaagctgat | tggaacagga | aaattatcag | aagatgaaga | aactgaagta | 1260 |
| caagagcaga | tgaatctcct | aaattcaaga | tgggaatgcc | tcagggtagc | tagcatggaa | 1320 |
| aaacaaagca | atttacatag | agaaatttct | tatgtgcctt | ctacttattt | gactgaaatc | 1380 |
| actcatgtct | cacaagccct | attagaagtg | gaacaacttc | tcaatgctcc | tgacctctgt | 1440 |
| gctaaggact | ttgaagatct | ctttaagcaa | gaggagtctc | tgaagaatat | aaaagatagt | 1500 |
| ctacaacaaa | gctcaggtcg | gattgacatt | attcatagca | agaagacagc | agcattgcaa | 1560 |
| agtgcaacgc | ctgtggaaag | ggtgaagcta | caggaagctc | tctcccagct | tgatttccaa | 1620 |
| tgggaaaaag | ttaacaaaat | gtacaaggac | cgacaagggc | gatttgacag | atctgttgag | 1680 |
| aaatggcggc | gttttcatta | tgatataaag | atatttaatc | agtggctaac | agaagctgaa | 1740 |
| cagtttctca | gaaagacaca | aattcctgag | aattgggaac | atgctaaata | caaatggtat | 1800 |
| cttaaggaac | tccaggatgg | cattgggcag | cggcaaactg | ttgtcagaac | attgaatgca | 1860 |
| actggggaag | aaataattca | gcaatcctca | aaaacagatg | ccagtattct | acaggaaaaa | 1920 |
| ttgggaagcc | tgaatctgcg | gtggcaggag | gtctgcaaac | agctgtcaga | cagaaaaaag | 1980 |
| aggctagaag | aaaccccttga | aagactccag | gaacttcaag | aggccacgga | tgagctggac | 2040 |
| ctcaagctgc | gccaagctga | ggtgatcaag | ggatcctggc | agcccgtggg | cgatctcctc | 2100 |
| attgactctc | tccaagatca | cctcgagaaa | gtcaaggcac | ttcgaggaga | aattgcgcct | 2160 |
| ctgaaagaga | acgtgagcca | cgtcaatgac | cttgctcgcc | agcttaccac | tttgggcatt | 2220 |

```
cagctctcac cgtataacct cagcactctg gaagacctga acaccagatg gaagcttctg      2280
caggtggccg tcgaggaccg agtcaggcag ctgcatgaag cccacaggga ctttggtcca      2340
gcatctcagc actttctttc cacgtctgtc cagggtccct gggagagagc catctcgcca      2400
aacaaagtgc cctactatat caaccacgag actcaaacaa cttgctggga ccatcccaaa      2460
atgacagagc tctaccagtc tttagctgac ctgaataatg tcagattctc agcttatagg      2520
actgccatga aactccgaag actgcagaag gccctttgct ggatctctt gagcctgtca       2580 gctgcatgtg atgccttgga ccagcacaac ctcaagcaaa atgaccagcc catggatatc      2640
ctgcagatta ttaattgttt gaccactatt tatgaccgcc tggagcaaga gcacaacaat      2700
ttggtcaacg tccctctctg cgtggatatg tgtctgaact ggctgctgaa tgtttatgat      2760
acgggacgaa cagggaggat ccgtgtcctg tcttttaaaa ctggcatcat tccctgtgt      2820 aaagcacatt tggaagacaa gtacagatac cttttcaagc aagtggcaag ttcaacagga      2880
ttttgtgacc agcgcaggct gggcctcctt ctgcatgatt ctatccaaat tccaagacag      2940
ttgggtgaag ttgcatcctt tgggggcagt aacattgagc caagtgtccg gagctgcttc      3000
caatttgcta ataataagcc agagatcgaa gcggccctct tcctagactg gatgagactg      3060 gaacccagt ccatggtgtg gctgcccgtc ctgcacagag tggctgctgc agaaactgcc       3120
aagcatcagg ccaaatgtaa catctgcaaa gagtgtccaa tcattggatt caggtacagg     3180
agtctaaagc actttaatta tgacatctgc caaagctgct ttttttctgg tcgagttgca     3240
aaaggccata aaatgcacta tcccatggtg gaatattgca ctccgactac atcaggagaa     3300
gatgttcgag actttgccaa ggtactaaaa aacaaatttc gaaccaaaag gtattttgcg     3360
aagcatcccc gaatgggcta cctgccagtg cagactgtct tagaggggga caacatggaa     3420
actgacacaa tgtag                                                      3435

<210> SEQ ID NO 14
<211> LENGTH: 3441
<212> TYPE: DNA
<213> ORGANISM: Artificial Sequence
<220> FEATURE:
<223> OTHER INFORMATION: Synthetic oligonucleotide

<400> SEQUENCE: 14
atgctttggt gggaagaagt agaggactgt tatgaaagag aagatgttca aaagaaaaca         60
ttcacaaaat gggtaaatgc acaattttct aagtttggga agcagcatat tgagaacctc       120
ttcagtgacc tacaggatgg gaggcgcctc ctagacctcc tcgaaggcct gacagggcaa       180
aaactgccaa agaaaaagg atccacaaga gttcatgccc tgaacaatgt caacaaggca       240
ctgcgggttt tgcagaacaa taatgttgat ttagtgaata ttggaagtac tgacatcgta       300
gatgaaaatc ataaactgac tcttggtttg atttggaata taatcctcca ctggcaggtc       360
aaaaatgtaa tgaaaatat catggctgga ttgcaacaaa ccaacagtga aaagattctc       420
ctgagctggg tccgacaatc aactcgtaat tatccacagg ttaatgtaat caacttcacc      480
accagctggt ctgatggcct ggctttgaat gctctcatcc atagtcatag gccagaccta      540
tttgactgga atagtgtggt ttgccagcag tcagccacac aacgactgga acatgcattc      600
aacatcgcca gatatcaatt aggcatagag aaactactcg atcctgaaga tgttgatacc      660
acctatccag ataagaagtc catcttaatg tacatcacat cactcttcca agttttgcct      720
caacaagtga gcattgaagc catccaggaa gtggaaatgt tgccaaggcc acctaaagtg      780
```

```
actaaagaag aacatttca gttacatcat caaatgcact attctcaaca gatcacggtc      840
agtctagcac agggatatga gagaacttct tcccctaagc ctcgattcaa gagctatgcc      900
tacacacagg ctgcttatgt caccacctct gaccctacac ggagcccatt tccttcacag      960
catttggaag ctcctgaaga caagtcattt ggcagttcat tgatggagag tgaagtaaac     1020
ctggaccgtt atcaaacagc tttagaagaa gtattatcgt ggcttctttc tgctgaggac     1080
acattgcaag cacaaggaga gatttctaat gatgtggaag tggtgaaaga ccagtttcat     1140
actcatgagg ggtacatgat ggatttgaca gcccatcagg gccgggttgg taatattcta     1200
caattgggaa gtaagctgat tggaacagga aaattatcag aagatgaaga aactgaagta     1260
caagagcaga tgaatctcct aaattcaaga tgggaatgcc tcagggtagc tagcatggaa     1320
aaacaaagca atttacatag agttttaatg gatctccaga atcagaaact gaaagagttg     1380
aatgactggc taacaaaaac agaagaaaga acaaggaaaa tggaggaaga gcctcttgga     1440
cctgatcttg aagacctaaa acgccaagta caacaacata aggtgcttca agaagatcta     1500
gaacaagaac aagtcagggt caattctctc actcacatgg tggtggtagt tgatgaatct     1560
agtggagatc acgcaactgc tgctttggaa gaacaactta aggtattggg agatcgatgg     1620
gcaaacatct gtagatggac agaagaccgc tgggttcttt tacaagacga aatttcttat     1680
gtgccttcta cttatttgac tgaaatcact catgtctcac aagccctatt agaagtggaa     1740
caacttctca atgctcctga cctctgtgct aaggactttg aagatctctt taagcaagag     1800
gagtctctga agaatataaa agatagtcta caacaaagct caggtcggat tgacattatt     1860
catagcaaga agacagcagc attgcaaagt gcaacgcctg tggaaagggt gaagctacag     1920
gaagctctct cccagcttga tttccaatgg gaaaaagtta acaaaatgta caaggaccga     1980
caagggcgat ttgacagaac ccttgaaaga ctccaggaac ttcaagaggc cacggatgag     2040
ctggacctca gctgcgccca agctgaggtg atcaagggat cctggcagcc cgtgggcgat     2100
ctcctcattg actctctcca agatcacctc gagaaagtca aggcacttcg aggagaaatt     2160
gcgcctctga aagagaacgt gagccacgtc aatgaccttg ctcgccagct taccactttg     2220
ggcattcagc tctcaccgta taacctcagc actctggaag acctgaacac cagatggaag     2280
cttctgcagg tggccgtcga ggaccgagtc aggcagctgc atgaagccca cagggacttt     2340
ggtccagcat ctcagcactt tctttccacg tctgtccagg gtccctggga gagagccatc     2400
tcgccaaaca aagtgcccta ctatatcaac cacgagactc aaacaacttg ctgggaccat     2460
cccaaaatga cagagctcta ccagtcttta gctgacctga ataatgtcag attctcagct     2520
tataggactg ccatgaaact ccgaagactg cagaaggccc tttgcttgga tctcttgagc     2580
ctgtcagctg catgtgatgc cttggaccag cacaacctca agcaaaatga ccagcccatg     2640
gatatcctgc agattattaa ttgttttgacc actatttatg accgcctgga gcaagagcac     2700
aacaatttgg tcaacgtccc tctctgcgtg gatatgtgtc tgaactggct gctgaatgtt     2760
tatgatacgg gacgaacagg gaggatccgt gtcctgtctt ttaaaactgg catcatttcc     2820
ctgtgtaaag cacatttgga agacaagtac agatacctttt tcaagcaagt ggcaagttca     2880
acaggatttt gtgaccagcg caggctgggc ctccttctgc atgattctat ccaaattcca     2940
agacagttgg tgaagttgc atccttttggg ggcagtaaca ttgagccaag tgtccggagc     3000
tgcttccaat ttgctaataa taagccagag atcgaagcgg ccctcttcct agactggatg     3060
agactggaac cccagtccat ggtgtggctg ccgtcctgc acagagtggc tgctgcagaa     3120
actgccaagc atcaggccaa atgtaacatc tgcaaagagt gtccaatcat tggattcagg     3180
```

| | |
|---|---|
| tacaggagtc taaagcactt taattatgac atctgccaaa gctgctttt ttctggtcga | 3240 |
| gttgcaaaag gccataaaat gcactatccc atggtggaat attgcactcc gactacatca | 3300 |
| ggagaagatt ttcgagactt tgccaaggta ctaaaaaaca aatttcgaac caaaaggtat | 3360 |
| tttgcgaagc atccccgaat gggctacctg ccagtgcaga ctgtcttaga gggggacaac | 3420 |
| atggaaactg acacaatgta g | 3441 |

<210> SEQ ID NO 15
<211> LENGTH: 8316
<212> TYPE: DNA
<213> ORGANISM: Artificial Sequence
<220> FEATURE:
<223> OTHER INFORMATION: Synthetic oligonucleotide

<400> SEQUENCE: 15

| | |
|---|---|
| cattaatgaa tcggccaacg cgcggggaga ggcggtttgc gtattgggcg ctcttccgct | 60 |
| tcctcgctca ctgactcgct gcgctcggtc gttcggctgc ggcgagcggt atcagctcac | 120 |
| tcaaaggcgg taatacggtt atccacagaa tcagggggata acgcaggaaa gaacatgtga | 180 |
| gcaaaaggcc agcaaaaggc caggaaccgt aaaaaggccg cgttgctggc gtttttccat | 240 |
| aggctccgcc cccctgacga gcatcacaaa aatcgacgct caagtcagag gtggcgaaac | 300 |
| ccgacaggac tataaagata ccaggcgttt ccccctggaa gctccctcgt gcgctctcct | 360 |
| gttccgaccc tgccgcttac cggatacctg tccgcctttc tcccttcggg aagcgtggcg | 420 |
| ctttctcata gctcacgctg taggtatctc agttcggtgt aggtcgttcg ctccaagctg | 480 |
| ggctgtgtgc acgaaccccc cgttcagccc gaccgctgcg ccttatccgg taactatcgt | 540 |
| cttgagtcca acccggtaag acacgactta tcgccactgg cagcagccac tggtaacagg | 600 |
| attagcagag cgaggtatgt aggcggtgct acagagttct tgaagtggtg cctaactac | 660 |
| ggctacacta gaaggacagt atttggtatc tgcgctctgc tgaagccagt taccttcgga | 720 |
| aaaagagttg gtagctcttg atccggcaaa caaaccaccg ctggtagcgg tggttttttt | 780 |
| gtttgcaagc agcagattac gcgcagaaaa aaggatctc aagaagatcc tttgatcttt | 840 |
| tctacggggt ctgacgctca gtggaacgaa aactcacgtt aagggatttt ggtcatgaga | 900 |
| ttatcaaaaa ggatcttcac ctagatcctt ttaaattaaa aatgaagttt taaatcaatc | 960 |
| taaagtatat atgagtaaac ttggtctgac agttaccaat gcttaatcag tgaggcacct | 1020 |
| atctcagcga tctgtctatt tcgttcatcc atagttgcct gactccccgt cgtgtagata | 1080 |
| actacgatac gggagggctt accatctggc cccagtgctg caatgatacc gcgagaccca | 1140 |
| cgctcaccgg ctccagattt atcagcaata aaccagccag ccggaagggc cgagcgcaga | 1200 |
| agtggtcctg caactttatc cgcctccatc cagtctatta attgttgccg ggaagctaga | 1260 |
| gtaagtagtt cgccagttaa tagtttgcgc aacgttgttg ccattgctac aggcatcgtg | 1320 |
| gtgtcacgct cgtcgtttgg tatggcttca ttcagctccg gttcccaacg atcaaggcga | 1380 |
| gttacatgat cccccatgtt gtgcaaaaaa gcggttagct ccttcggtcc tccgatcgtt | 1440 |
| gtcagaagta agttggccgc agtgttatca ctcatggtta tggcagcact gcataattct | 1500 |
| cttactgtca tgccatccgt aagatgcttt tctgtgactg gtgagtactc aaccaagtca | 1560 |
| ttctgagaat agtgtatgcg gcgaccgagt tgctcttgcc cggcgtcaat acgggataat | 1620 |
| accgcgccac atagcagaac tttaaaagtg ctcatcattg gaaaacgttc ttcggggcga | 1680 |
| aaactctcaa ggatcttacc gctgttgaga tccagttcga tgtaacccac tcgtgcaccc | 1740 |

```
aactgatctt cagcatcttt tactttcacc agcgtttctg ggtgagcaaa acaggaagg      1800
caaaatgccg caaaaaggg aataagggcg acacggaaat gttgaatact catactcttc      1860
cttttcaat attattgaag catttatcag ggttattgtc tcatgagcgg atacatattt      1920
gaatgtattt agaaaaataa acaaataggg gttccgcgca catttccccg aaaagtgcca     1980
cctgacgtct aagaaaccat tattatcatg acattaacct ataaaaatag gcgtatcacg     2040
aggccctttc gtctcgcgcg tttcggtgat gacggtgaaa acctctgaca catgcagctc     2100
ccggagacgg tcacagcttg tctgtaagcg gatgccggga gcagacaagc ccgtcagggc     2160
gcgtcagcgt gttggcgg gtgtcggggc tggcttaact atgcggcatc agagcagatt       2220
gtactgagag tgcaccatat gcggtgtgaa ataccgcaca gatgcgtaag gagaaaatac    2280
cgcatcagga attccaacat ccaataaatc atacaggcaa ggcaaagaat tagcaaaatt    2340
aagcaataaa gcctcagagc ataaagctaa atcggttgta ccaaaaacat tatgaccctg    2400
taatactttt gcgggagaag cctttatttc aacgcaagga taaaattttt tagaaccctc    2460
atatattta aatgcaatgc ctgagtaatg tgtaggtaaa gattcaaacg ggtgagaaag     2520
gccggagaca gtcaaatcac catcaatatg atattcaacc gttctagctg ataaattcat    2580
gccggagagg gtagctattt ttgagaggtc tctacaaagg ctatcaggtc attgcctgag    2640
agtctggagc aaacaagaga atcgatgaac ggtaatcgta aaactagcat gtcaatcata    2700
tgtaccccgg ttgataatca gaaaagcccc aaaaacagga agattgtata agcaaatatt    2760
taaattgtaa acgttaatat tttgttaaaa ttcgcgttaa atttttgtta aatcagctca    2820
ttttttaacc aataggccga atcggcaaaa tcccttata aatcaaaaga atagaccgag     2880
atagggttga gtgttgttcc agtttggaac aagagtccac tattaaagaa cgtggactcc    2940
aacgtcaaag ggcgaaaaac cgtctatcag ggcgatggcc cactacgtga accatcaccc    3000
taatcaagtt ttttgggggtc gaggtgccgt aaagcactaa atcggaaccc taaagggagc    3060
ccccgattta gagcttgacg gggaaagccg gcgaacgtgg cgagaaagga agggaagaaa    3120
gcgaaaggag cgggcgctag ggcgctggca agtgtagcgg tcacgctgcg cgtaaccacc    3180
acaccgccg cgcttaatgc gccgctacag ggcgcgtact atggttgctt tgacgagcac    3240
gtataacgtg ctttcctcgt tagaatcaga gcgggagcta acaggaggc cgattaaagg     3300
gattttagac aggaacggta cgccagaatc ctgagaagtg ttttttataat cagtgaggcc    3360
accgagtaaa agagtctgtc catcacgcaa attaaccgtt gtcgcaatac ttctttgatt    3420
agtaataaca tcacttgcct gagtagaaga actcaaacta tcggccttgc tggtaatatc    3480
cagaacaata ttaccgccag ccattgcaac aggaaaaacg ctcatggaaa tacctacatt    3540
ttgacgctca atcgtctgga attccattcg ccattcaggc tgcgcaactg ttgggaaggg    3600
cgatcggtgc gggcctcttc gctattacgc cagctggcgc gctcgctcgc tcactgaggc    3660
cgcccgggca aagcccgggc gtcgggcgac ctttggtcgc ccggcctcag tgagcgagcg    3720
agcgcgcaga gagggagtgg ccaactccat cactagggt tccttgtagt taatgattaa     3780
cccgccatgc tacttatcta cggccgcggt accgcgttac ataacttacg gtaaatggcc    3840
cgcctggctg accgcccaac gaccccgcc cattgacgtc aataatgacg tatgttccca     3900
tagtaacgcc aatagggact ttccattgac gtcaatgggt ggagtattta cggtaaactg    3960
cccacttggc agtacatcaa gtgtatcata tgccaagtac gccccctatt gacgtcaatg    4020
acggtaaatg gcccgcctgg cattatgccc agtacatgac cttatgggac ttcctactt     4080
ggcagtacat ctacgtatta gtcatcgcta ttaccatggt gatgcggttt tggcagtaca    4140
```

```
tcaatgggcg tggatagcgg tttgactcac ggggatttcc aagtctccac cccattgacg   4200
tcaatgggag tttgttttgg caccaaaatc aacgggactt tccaaaatgt cgtaacaact   4260 ccgcccatt gacgcaaatg ggcggtaggc gtgtacggtg ggaggtctat ataagcagag    4320
ctcgtttagt gaaccgtcta gacggccgcg gttttttta tcgctgcctt gatatacact    4380
ttccaccatg ctttggtggg aagaagtaga ggactgttat gaaagagaag atgttcaaaa   4440
gaaaacattc acaaaatggg taaatgcaca atttctaag tttgggaagc agcatattga    4500
gaacctcttc agtgacctac aggatgggag gcgcctccta gacctcctcg aaggcctgac   4560
agggcaaaaa ctgccaaaag aaaaaggatc cacaagagtt catgccctga caatgtcaa    4620 caaggcactg cgggttttgc agaacaataa tgttgattta gtgaatattg gaagtactga   4680
catcgtagat ggaaatcata aactgactct tggtttgatt tggaatataa tcctccactg   4740
gcaggtcaaa aatgtaatga aaatatcat ggctggattg caacaaacca acagtgaaaa    4800
gattctcctg agctgggtcc gacaatcaac tcgtaattat ccacaggtta atgtaatcaa   4860
cttcaccacc agctggtctg atggcctggc tttgaatgct ctcatccata gtcataggcc   4920
agacctattt gactggaata gtgtggtttg ccagcagtca gccacacaac gactggaaca   4980
tgcattcaac atcgccagat atcaattagg catagagaaa ctactcgatc ctgaagatgt   5040
tgataccacc tatccagata agaagtccat cttaatgtac atcacatcac tcttccaagt   5100
tttgcctcaa caagtgagca ttgaagccat ccaggaagtg aaatgttgc caaggccacc    5160 taaagtgact aaagaagaac attttcagtt acatcatcaa atgcactatt ctcaacagat   5220
cacggtcagt ctagcacagg gatatgagag aacttcttcc cctaagcctc gattcaagag   5280
ctatgcctac acacaggctg cttatgtcac cacctctgac cctacacgga gcccatttcc   5340
ttcacagcat ttggaagctc ctgaagacaa gtcatttggc agttcattga tggagagtga   5400
agtaaacctg gaccgttatc aaacagcttt agaagaagta ttatcgtggc ttctttctgc   5460
tgaggacaca ttgcaagcac aaggagagat ttctaatgat gtggaagtgg tgaaagacca   5520
gtttcatact catgaggggt acatgatgga tttgacagcc catcagggcc gggttggtaa   5580
tattctacaa ttgggaagta agctgattgg aacaggaaaa ttatcagaag atgaagaaac   5640
tgaagtacaa gagcagatga atctcctaaa ttcaagatgg gaatgcctca gggtagctag   5700
catggaaaaa caaagcaatt tacatagaga aatttcttat gtgccttcta cttatttgac   5760
tgaaatcact catgtctcac aagcccctatt agaagtggaa caacttctca atgctcctga   5820
cctctgtgct aaggactttg aagatctctt taagcaagag gagtctctga gaatataaa    5880 agatagtcta caacaaagct caggtcggat tgacattatt catagcaaga agacagcagc   5940
attgcaaagt gcaacgcctg tggaaagggt gaagctacag gaagctctct cccagcttga   6000
tttccaatgg gaaaaagtta acaaaatgta caaggaccga caagggcgat ttgacagatc   6060
tgttgagaaa tggcggcgtt ttcattatga tataaagata tttaatcagt ggctaacaga   6120
agctgaacag tttctcagaa agacacaaat tcctgagaat tgggaacatg ctaaatacaa   6180
atggtatctt aaggaactcc aggatggcat tgggcagcgg caaactgttg tcagaacatt   6240
gaatgcaact ggggaagaaa taattcagca atcctcaaaa acagatgcca gtattctaca   6300
ggaaaaattg ggaagcctga atctgcggtg gcaggaggtc tgcaaacagc tgtcagacag   6360
aaaaaagagg ctagaagaaa cccttgaaag actccaggaa cttcaagagg ccacggatga   6420
gctggaccct aagctgcgcc aagctgaggt gatcaaggga tcctggcagc ccgtgggcga   6480
```

```
tctcctcatt gactctctcc aagatcacct cgagaaagtc aaggcacttc gaggagaaat    6540
tgcgcctctg aaagagaacg tgagccacgt caatgacctt gctcgccagc ttaccacttt    6600
gggcattcag ctctcaccgt ataacctcag cactctggaa gacctgaaca ccagatggaa    6660
gcttctgcag gtggccgtcg aggaccgagt caggcagctg catgaagccc acagggactt    6720
tggtccagca tctcagcact ttcttttcca c gtctgtccag gtccctggga agagagccat   6780
ctcgccaaac aaagtgccct actatatcaa ccacgagact caaacaactt gctgggacca    6840
tcccaaaatg acagagctct accagtcttt agctgacctg aataatgtca gattctcagc    6900
ttataggact gccatgaaac tccgaagact gcagaaggcc ctttgcttgg atctcttgag    6960
cctgtcagct gcatgtgatg ccttggacca gcacaacctc aagcaaaatg accagcccat    7020
ggatatcctg cagattatta attgtttgac cactatttat gaccgcctgg agcaagagca    7080
caacaatttg gtcaacgtcc ctctctgcgt ggatatgtgt ctgaactggc tgctgaatgt    7140
ttatgatacg ggacgaacag ggaggatccg tgtcctgtct tttaaaactg gcatcatttc    7200
cctgtgtaaa gcacatttgg aagacaagta cagatacctt ttcaagcaag tggcaagttc    7260
aacaggattt tgtgaccagc gcaggctggg cctccttctg catgattcta tccaaattcc    7320
aagacagttg ggtgaagttg catccttttg gggcagtaac attgagccaa gtgtccggag    7380
ctgcttccaa tttgctaata taagccaga gatcgaagcg ccctcttcc tagactggat     7440 gagactggaa ccccagtcca tggtgtggct gcccgtcctg cacagagtgg ctgctgcaga    7500
aactgccaag catcaggcca aatgtaacat ctgcaaagag tgtccaatca ttggattcag    7560
gtacaggagt ctaaagcact taattatga catctgccaa agctgctttt tttctggtcg    7620
agttgcaaaa ggccataaaa tgcactatcc catggtggaa tattgcactc cgactacatc    7680
aggagaagat gttcgagact tgccaaggt actaaaaaac aaatttcgaa ccaaaaggta    7740
ttttgcgaag catccccgaa tgggctacct gccagtgcag actgtcttag aggggggacaa   7800 catggaaact gacacaatgt aggaagtctt ttccacatgg cagatgattt gggcagagcg    7860
atggagtcct tagtatcagt catgacagat gaagaaggag cagaataaat gttttacaac    7920
tcctgattcc cgcatgcggc cgatccagac atgataagat acattgatga gtttggacaa    7980
accacaacta gaatgcagtg aaaaaaatgc tttatttgtg aaatttgtga tgctattgct    8040
ttatttgtaa ccattataag ctgcaataaa caagttaaca acaacaattg cattcatttt    8100
atgtttcagg ttcagggga ggtgtgggag gttttttgcg gccgtagata agtagcatgg     8160
cgggttaatc attaactaca aggaaccct agtgatgag ttggccactc cctctctgcg      8220
cgctcgctcg ctcactgagg ccgggcgacc aaaggtcgcc cgacgcccgg gctttgcccg    8280
ggcggcctca gtgagcgagc gagcgcgcag ctgctg                               8316
```

<210> SEQ ID NO 16
<211> LENGTH: 8294
<212> TYPE: DNA
<213> ORGANISM: Artificial Sequence
<220> FEATURE:
<223> OTHER INFORMATION: Synthetic oligonucleotide

<400> SEQUENCE: 16

```
cattaatgaa tcggccaacg cgcggggaga ggcggtttgc gtattgggcg ctcttccgct      60
tcctcgctca ctgactcgct gcgctcggtc gttcggctgc ggcgagcggt atcagctcac     120
tcaaaggcgg taatacggtt atccacagaa tcaggggata acgcaggaaa gaacatgtga    180
gcaaaaggcc agcaaaaggc caggaaccgt aaaaaggccg cgttgctggc gtttttccat    240
```

-continued

```
aggctccgcc cccctgacga gcatcacaaa aatcgacgct caagtcagag gtggcgaaac    300
ccgacaggac tataaagata ccaggcgttt cccctggaa gctccctcgt gcgctctcct    360
gttccgaccc tgccgcttac cggatacctg tccgcctttc tcccttcggg aagcgtggcg    420
ctttctcata gctcacgctg taggtatctc agttcggtgt aggtcgttcg ctccaagctg    480
ggctgtgtgc acgaaccccc cgttcagccc gaccgctgcg ccttatccgg taactatcgt    540
cttgagtcca acccggtaag acacgactta tcgccactgg cagcagccac tggtaacagg    600
attagcagag cgaggtatgt aggcggtgct acagagttct tgaagtggtg cctaactac    660
ggctacacta aaggacagt atttggtatc tgcgctctgc tgaagccagt taccttcgga    720
aaaagagttg gtagctcttg atccggcaaa caaaccaccg ctggtagcgg tggtttttt    780
gtttgcaagc agcagattac gcgcagaaaa aaggatctc aagaagatcc tttgatcttt    840
tctacggggt ctgacgctca gtggaacgaa aactcacgtt aagggatttt ggtcatgaga    900
ttatcaaaaa ggatcttcac ctagatcctt ttaaattaaa aatgaagttt taaatcaatc    960
taaagtatat atgagtaaac ttggtctgac agttaccaat gcttaatcag tgaggcacct   1020
atctcagcga tctgtctatt tcgttcatcc atagttgcct gactccccgt cgtgtagata   1080
actacgatac gggagggctt accatctggc cccagtgctg caatgatacc gcgagaccca   1140
cgctcaccgg ctccagattt atcagcaata aaccagccag ccggaagggc cgagcgcaga   1200
agtggtcctg caactttatc cgcctccatc cagtctatta attgttgccg ggaagctaga   1260
gtaagtagtt cgccagttaa tagtttgcgc aacgttgttg ccattgctac aggcatcgtg   1320
gtgtcacgct cgtcgtttgg tatggcttca ttcagctccg gttcccaacg atcaaggcga   1380
gttacatgat cccccatgtt gtgcaaaaaa gcggttagct ccttcggtcc tccgatcgtt   1440
gtcagaagta agttggccgc agtgttatca ctcatggtta tggcagcact gcataattct   1500
cttactgtca tgccatccgt aagatgcttt tctgtgactg gtgagtactc aaccaagtca   1560
ttctgagaat agtgtatgcg gcgaccgagt tgctcttgcc cggcgtcaat acgggataat   1620
accgcgccac atagcagaac tttaaaagtg ctcatcattg gaaaacgttc ttcggggcga   1680
aaactctcaa ggatcttacc gctgttgaga tccagttcga tgtaacccac tcgtgcaccc   1740
aactgatctt cagcatcttt tactttcacc agcgtttctg ggtgagcaaa aacaggaagg   1800
caaaatgccg caaaaaaggg aataagggcg acacggaaat gttgaatact catactcttc   1860
cttttcaat attattgaag catttatcag ggttattgtc tcatgagcgg atacatattt   1920
gaatgtattt agaaaaataa acaaataggg gttccgcgca catttccccg aaaagtgcca   1980
cctgacgtct aagaaaccat tattatcatg acattaacct ataaaaatag gcgtatcacg   2040
aggccctttc gtctcgcgcg tttcggtgat gacggtgaaa acctctgaca catgcagctc   2100
ccggagacgg tcagacttg tctgtaagcg atgccggga gcagacaagc ccgtcagggc   2160
gcgtcagcgg gtgttggcgg gtgtcgggc tggcttaact atgcggcatc agagcagatt   2220
gtactgagag tgcaccatat gcggtgtgaa ataccgcaca gatgcgtaag gagaaaatac   2280
cgcatcagga attccaacat ccaataaatc atacaggcaa ggcaaagaat tagcaaaatt   2340
aagcaataaa gcctcagagc ataaagctaa atcggttgta ccaaaacat tatgaccctg   2400
taatactttt gcgggagaag cctttatttc aacgcaagga taaaaatttt tagaaccctc   2460
atatatttta aatgcaatgc ctgagtaatg tgtaggtaaa gattcaaacg ggtgagaaag   2520
gccggagaca gtcaaatcac catcaatatg atattcaacc gttctagctg ataaattcat   2580
```

-continued

```
gccggagagg gtagctattt ttgagaggtc tctacaaagg ctatcaggtc attgcctgag    2640
agtctggagc aaacaagaga atcgatgaac ggtaatcgta aaactagcat gtcaatcata    2700
tgtaccccgg ttgataatca gaaaagcccc aaaaacagga agattgtata agcaaatatt    2760
taaattgtaa acgttaatat tttgttaaaa ttcgcgttaa attttttgtta aatcagctca   2820 tttttaacc aataggccga aatcggcaaa atcccttata aatcaaaaga atagaccgag    2880
atagggttga gtgttgttcc agtttggaac aagagtccac tattaaagaa cgtggactcc   2940
aacgtcaaag ggcgaaaaac cgtctatcag ggcgatggcc cactacgtga accatcaccc   3000
taatcaagtt ttttggggtc gaggtgccgt aaagcactaa atcggaaccc taaagggagc   3060
ccccgattta gagcttgacg gggaaagccg gcgaacgtgg cgagaaagga agggaagaaa   3120
gcgaaaggag cgggcgctag ggcgctggca agtgtagcgg tcacgctgcg cgtaaccacc   3180 acaccgccg cgcttaatgc gccgctacag ggcgcgtact atggttgctt tgacgagcac   3240 gtaacgtg ctttcctcgt tagaatcaga gcgggagcta aacaggaggc cgattaaagg    3300
gattttagac aggaacggta cgccagaatc ctgagaagtg ttttttataat cagtgaggcc   3360 accgagtaaa agagtctgtc catcacgcaa attaaccgtt gtcgcaatac ttctttgatt    3420
agtaataaca tcacttgcct gagtagaaga actcaaacta tcggccttgc tggtaatatc   3480
cagaacaata ttaccgccag ccattgcaac aggaaaaacg ctcatggaaa tacctacatt    3540
ttgacgctca atcgtctgga attccattcg ccattcaggc tgcgcaactg ttgggaaggg   3600
cgatcggtgc gggcctcttc gctattacgc cagctggcgc gctcgctcgc tcactgaggc   3660
cgcccgggca aagcccgggc gtcgggcgac ctttggtcgc ccggcctcag tgagcgagcg   3720
agcgcgcaga gagggagtgg ccaactccat cactaggggt tccttgtagt taatgattaa   3780
cccgccatgc tacttatcta cggccgcggt accactcacg gggatttcca agtctccacc   3840
ccattgacgt caatgggagt ttgttttggc accaaaatca acgggacttt ccaaaatgtc    3900
gtaataaccc cgccccgttg acgcaaatgg gcggtaggcg tgtacggtgg gaggtctata   3960
taagcagagc tcgtttagtg aaccgtctct agacggccgc ggtttttttt atcgctgcct    4020
tgatatacac tttccaccat gctttggtgg gaagaagtag aggactgtta tgaaagagaa   4080
gatgttcaaa agaaaacatt cacaaaatgg gtaaatgcac aattttctaa gtttgggaag   4140
cagcatattg agaacctctt cagtgaccta caggatggga ggcgcctcct agacctcctc   4200
gaaggcctga cagggcaaaa actgccaaaa gaaaaaggat ccacaagagt tcatgccctg   4260
aacaatgtca acaaggcact gcgggttttg cagaacaata atgttgattt agtgaatatt   4320
ggaagtactg acatcgtaga tggaaatcat aaactgactc ttggtttgat ttggaatata   4380
atcctccact ggcaggtcaa aaatgtaatg aaaaatatca tggctggatt gcaacaaacc   4440
aacagtgaaa agattctcct gagctgggtc cgacaatcaa ctcgtaatta tccacaggtt   4500
aatgtaatca acttccaccac cagctggtct gatggcctgg ctttgaatgc tctcatccat   4560
agtcataggc cagacctatt tgactggaat agtgtggttt gccagcagtc agccacacaa   4620
cgactggaac atgcattcaa catcgccaga tatcaattag gcatagagaa actactcgat   4680
cctgaagatg ttgataccac ctatccagat aagaagtcca tcttaatgta catcacatca   4740
ctcttccaag ttttgcctca acaagtgagc attgaagcca tccaggaagt ggaaatgttg   4800
ccaaggccac ctaaagtgac taaagaagaa cattttcagt tacatcatca aatgcactat   4860
tctcaacaga tcacggtcag tctagcacag ggatatgaga gaacttcttc ccctaagcct   4920
cgattcaaga gctatgccta cacacaggct gcttatgtca ccacctctga ccctacacgg   4980
```

```
agcccatttc cttcacagca tttggaagct cctgaagaca agtcatttgg cagttcattg    5040
atggagagtg aagtaaacct ggaccgttat caaacagctt tagaagaagt attatcgtgg    5100
cttctttctg ctgaggacac attgcaagca caaggagaga tttctaatga tgtggaagtg    5160
gtgaaagacc agtttcatac tcatgagggg tacatgatgg atttgacagc ccatcagggc    5220
cgggttggta atattctaca attgggaagt aagctgattg aacaggaaa attatcagaa     5280
gatgaagaaa ctgaagtaca agagcagatg aatctcctaa attcaagatg gaatgcctc    5340
agggtagcta gcatggaaaa acaaagcaat ttacatagag ttttaatgga tctccagaat    5400
cagaaactga aagagttgaa tgactggcta acaaaaacag aagaagaac aaggaaaatg     5460
gaggaagagc tcttggacc tgatcttgaa gacctaaaac gccaagtaca acaacataag     5520
gtgcttcaag aagatctaga acaagaacaa gtcagggtca attctctcac tcacatggtg    5580
gtggtagttg atgaatctag tggagatcac gcaactgctg ctttggaaga caacttaag    5640
gtattgggag atcgatgggc aaacatctgt agatggacag aagaccgctg ggttctttta    5700
caagacgaaa tttcttatgt gccttctact tatttgactg aaatcactca tgtctcacaa    5760
gccctattag aagtggaaca acttctcaat gctcctgacc tctgtgctaa ggactttgaa    5820
gatctcttta gcaagagga gtctctgaag aatataaaag atagtctaca acaaagctca    5880
ggtcggattg acattattca tagcaagaag acagcagcat gcaaagtgc aacgcctgtg     5940
gaaagggtga agctacagga agctctctcc cagcttgatt tccaatggga aaaagttaac    6000
aaaatgtaca aggaccgaca agggcgattt gacagatctg ttgagaaatg gcggcgtttt    6060
cattatgata taaagatatt taatcagtgg ctaacagaag ctgaacagtt tctcagaaag    6120
acacaaattc ctgagaattg ggaacatgct aaatacaaat ggtatcttaa ggaactccag    6180
gatggcattg ggcagcggca aactgttgtc agaacattga atgcaactgg gaagaaata    6240
attcagcaat cctcaaaaac agatgccagt attctacagg aaaaattggg aagcctgaat    6300
ctgcggtggc aggaggtctg caaacagctg tcagacagaa aaaagaggct agaagaaacc    6360
cttgaaagac tccaggaact tcaagaggcc acggatgagc tggacctcaa gctgcgccaa    6420
gctgaggtga tcaagggatc ctggcagccc gtgggcgatc tcctcattga ctctctccaa    6480
gatcacctcg agaaagtcaa ggcacttcga ggagaaattg cgcctctgaa agagaacgtg    6540
agccacgtca atgaccttgc tcgccagctt accactttgg gcattcagct ctcaccgtat    6600
aacctcagca ctctggaaga cctgaacacc agatggaagc ttctgcaggt ggccgtcgag    6660
gaccgagtca ggcagctgca tgaagcccac agggactttg gtccagcatc tcagcacttt    6720
ctttccacgt ctgtccaggg tcctgggag agagccatct cgccaaacaa agtgccctac    6780
tatatcaacc acgagactca acaacttgc tgggaccatc ccaaaatgac agagctctac    6840
cagtctttag ctgacctgaa taatgtcaga ttctcagctt ataggactgc catgaaactc    6900
cgaagactgc agaaggccct tgcttggat ctcttgagcc tgtcagctgc atgtgatgcc     6960
ttggaccagc acaacctcaa gcaaaatgac cagcccatgg atatcctgca gattattaat    7020
tgtttgacca ctatttatga ccgcctggag caagagcaca caatttggt caacgtccct    7080
ctctgcgtgg atatgtgtct gaactggctg ctgaatgttt atgatacggg acgaacaggg    7140
aggatccgtg tcctgtctt taaaactggc atcatttccc tgtgtaaagc acatttggaa    7200
gacaagtaca gatacctttt caagcaagtg gcaagttcaa caggattttg tgaccagcgc    7260
aggctgggcc tccttctgca tgattctatc caaattccaa gacagttggg tgaagttgca    7320
```

```
tcctttgggg gcagtaacat tgagccaagt gtccggagct gcttccaatt tgctaataat    7380
aagccagaga tcgaagcggc cctcttccta gactggatga gactggaacc ccagtccatg    7440
gtgtggctgc ccgtcctgca cagagtggct gctgcagaaa ctgccaagca tcaggccaaa    7500
tgtaacatct gcaaagagtg tccaatcatt ggattcaggt acaggagtct aaagcacttt    7560
aattatgaca tctgccaaag ctgctttttt tctggtcgag ttgcaaaagg ccataaaatg    7620
cactatccca tggtggaata ttgcactccg actacatcag gagaagatgt tcgagacttt    7680
gccaaggtac taaaaaacaa atttcgaacc aaaaggtatt ttgcgaagca tccccgaatg    7740
ggctacctgc cagtgcagac tgtcttagag ggggacaaca tggaaactga cacaatgtag    7800
gaagtctttt ccacatggca gatgatttgg gcagagcgat ggagtcctta gtatcagtca    7860
tgacagatga agaaggagca gaataaatgt tttacaactc ctgattcccg catgcggccg    7920
atccagacat gataagatac attgatgagt ttggacaaac cacaactaga atgcagtgaa    7980
aaaaatgctt tatttgtgaa atttgtgatg ctattgcttt atttgtaacc attataagct    8040
gcaataaaca agttaacaac aacaattgca ttcattttat gtttcaggtt caggggagg     8100 tgtgggaggt ttttgcggc cgtagataag tagcatggcg ggttaatcat taactacaag    8160 gaaccccctag tgatggagtt ggccactccc tctctgcgcg ctcgctcgct cactgaggcc    8220
gggcgaccaa aggtcgcccg acgcccgggc tttgcccggg cggcctcagt gagcgagcga    8280
gcgcgcagct gctg                                                      8294

<210> SEQ ID NO 17
<211> LENGTH: 756
<212> TYPE: DNA
<213> ORGANISM: Homo sapiens

<400> SEQUENCE: 17
atgctttggt gggaagaagt agaggactgt tatgaaagag aagatgttca aaagaaaaca     60
ttcacaaaat gggtaaatgc acaatttct aagtttggga agcagcatat tgagaacctc    120
ttcagtgacc tacaggatgg gaggcgcctc ctagacctcc tcgaaggcct gacagggcaa    180
aaactgccaa agaaaaagg atccacaaga gttcatgccc tgaacaatgt caacaaggca    240
ctgcgggttt tgcagaacaa taatgttgat ttagtgaata ttggaagtac tgacatcgta    300
gatggaaatc ataaactgac tcttggtttg atttggaata taatcctcca ctggcaggtc    360
aaaaatgtaa tgaaaatat catggctgga ttgcaacaaa ccaacagtga aaagattctc    420
ctgagctggg tccgacaatc aactcgtaat tatccacagg ttaatgtaat caacttcacc    480
accagctggt ctgatggcct ggctttgaat gctctcatcc atagtcatag gccagaccta    540
tttgactgga atagtgtggt ttgccagcag tcagccacac aacgactgga acatgcattc    600
aacatcgcca gatatcaatt aggcatagag aaactactcg atcctgaaga tgttgatacc    660
acctatccag ataagaagtc catcttaatg tacatcacat cactcttcca agttttgcct    720
caacaagtga gcattgaagc catccaggaa gtggaa                              756

<210> SEQ ID NO 18
<211> LENGTH: 252
<212> TYPE: DNA
<213> ORGANISM: Homo sapiens

<400> SEQUENCE: 18
atgttgccaa ggccacctaa agtgactaaa gaagaacatt tcagttaca tcatcaaatg       60 cactattctc aacagatcac ggtcagtcta gcacagggat atgagagaac ttcttcccct    120
```

```
aagcctcgat tcaagagcta tgcctacaca caggctgctt atgtcaccac ctctgaccct    180
acacggagcc catttccttc acagcatttg gaagctcctg aagacaagtc atttggcagt    240
tcattgatgg ag                                                        252

<210> SEQ ID NO 19
<211> LENGTH: 333
<212> TYPE: DNA
<213> ORGANISM: Homo sapiens

<400> SEQUENCE: 19
agtgaagtaa acctggaccg ttatcaaaca gctttagaag aagtattatc gtggcttctt     60
tctgctgagg acacattgca agcacaagga gagattccta atgatgtgga agtggtgaaa    120
gaccagtttc atactcatga ggggtacatg atggatttga cagcccatca gggccgggtt    180
ggtaatattc tacaattggg aagtaagctg attggaacag gaaaattatc agaagatgaa    240
gaaactgaag tacaagagca gatgaatctc ctaaattcaa gatgggaatg cctcagggta    300
gctagcatgg aaaaacaaag caatttacat aga                                 333

<210> SEQ ID NO 20
<211> LENGTH: 327
<212> TYPE: DNA
<213> ORGANISM: Homo sapiens

<400> SEQUENCE: 20
gttttaatgg atctccagaa tcagaaactg aaagagttga atgactggct aacaaaaaca     60
gaagaaagaa caaggaaaat ggaggaagag cctcttggac ctgatcttga agacctaaaa    120
cgccaagtac aacaacataa ggtgcttcaa gaagatctag aacaagaaca agtcagggtc    180
aattctctca ctcacatggt ggtggtagtt gatgaatcta gtggagatca cgcaactgct    240
gctttggaag aacaacttaa ggtattggga gatcgatggg caaacatctg tagatggaca    300
gaagaccgct gggttctttt acaagac                                        327

<210> SEQ ID NO 21
<211> LENGTH: 333
<212> TYPE: DNA
<213> ORGANISM: Homo sapiens

<400> SEQUENCE: 21
atccttctca aatggcaacg tcttactgaa gaacagtgcc tttttagtgc atggctttca     60 gaaaagaag atgcagtgaa caagattcac acaactggct ttaaagatca aaatgaaatg    120
ttatcaagtc ttcaaaaact ggccgtttta aagcggatc tagaaaagaa aaagcaatcc    180
atgggcaaac tgtattcact caaacaagat cttctttcaa cactgaagaa taagtcagtg    240
acccagaaga cggaagcatg gctggataac tttgcccggt gttgggataa tttagtccaa    300
aaacttgaaa agagtacagc acagatttca cag                                 333

<210> SEQ ID NO 22
<211> LENGTH: 150
<212> TYPE: DNA
<213> ORGANISM: Homo sapiens

<400> SEQUENCE: 22
gctgtcacca ccactcagcc atcactaaca cagacaactg taatggaaac agtaactacg     60
gtgaccacaa gggaacagat cctggtaaag catgctcaag aggaacttcc accaccacct    120
```

```
cccaaaaga agaggcagat tactgtggat                                      150

<210> SEQ ID NO 23
<211> LENGTH: 262
<212> TYPE: DNA
<213> ORGANISM: Homo sapiens

<400> SEQUENCE: 23
tctgaaatta ggaaaaggtt ggatgttgat ataactgaac ttcacagctg gattactcgc    60
tcagaagctg tgttgcagag tcctgaattt gcaatctttc ggaaggaagg caacttctca   120
gacttaaaag aaaaagtcaa tgccatagag cgagaaaaag ctgagaagtt cagaaaactg   180
caagatgcca gcagatcagc tcaggccctg gtggaacaga tggtgaatga gggtgttaat   240
gcagatagca tcaaacaagc ct                                            262

<210> SEQ ID NO 24
<211> LENGTH: 389
<212> TYPE: DNA
<213> ORGANISM: Homo sapiens

<400> SEQUENCE: 24
cagaacaact gaacagccgg tggatcgaat tctgccagtt gctaagtgag agacttaact    60
ggctggagta tcagaacaac atcatcgctt tctataatca gctacaacaa ttggagcaga   120
tgacaactac tgctgaaaac tggttgaaaa tccaacccac caccccatca gagccaacag   180
caattaaaag tcagttaaaa atttgtaagg atgaagtcaa ccggctatca ggtcttcaac   240
ctcaaattga acgattaaaa attcaaagca tagccctgaa agagaaagga caaggaccca   300
tgttcctgga tgcagacttt gtggccttta caaatcattt taagcaagtc ttttctgatg   360
tgcaggccag agagaaagag ctacagaca                                     389

<210> SEQ ID NO 25
<211> LENGTH: 333
<212> TYPE: DNA
<213> ORGANISM: Homo sapiens

<400> SEQUENCE: 25
atttttgaca ctttgccacc aatgcgctat caggagacca tgagtgccat caggacatgg    60
gtccagcagt cagaaaccaa actctccata cctcaactta gtgtcaccga ctatgaaatc   120
atggagcaga gactcgggga attgcaggct ttacaaagtt ctctgcaaga gcaacaaagt   180
ggcctatact atctcagcac cactgtgaaa gagatgtcga agaaagcgcc ctctgaaatt   240
agccggaaat atcaatcaga atttgaagaa attgagggac gctggaagaa gctctcctcc   300
cagctggttg agcattgtca aaagctagag gag                                333

<210> SEQ ID NO 26
<211> LENGTH: 327
<212> TYPE: DNA
<213> ORGANISM: Homo sapiens

<400> SEQUENCE: 26
caaatgaata aactccgaaa aattcagaat cacatacaaa ccctgaagaa atggatggct    60
gaagttgatg ttttttctgaa ggaggaatgg cctgcccttg gggattcaga aattctaaaa   120
aagcagctga acagtgcag acttttagtc agtgatattc agacaattca gcccagtcta   180
aacagtgtca atgaaggtgg gcagaagata aagaatgaag cagagccaga gtttgcttcg   240
agacttgaga cagaactcaa agaacttaac actcagtggg atcacatgtg ccaacaggtc   300
```

```
tatgccagaa aggaggcctt gaaggga                                       327

<210> SEQ ID NO 27
<211> LENGTH: 327
<212> TYPE: DNA
<213> ORGANISM: Homo sapiens

<400> SEQUENCE: 27
ggtttggaga aaactgtaag cctccagaaa gatctatcag agatgcacga atggatgaca   60
caagctgaag aagagtatct tgagagagat tttgaatata aaactccaga tgaattacag  120
aaagcagttg aagagatgaa gagagctaaa gaagaggccc aacaaaaaga agcgaaagtg  180
aaactcctta ctgagtctgt aaatagtgtc atagctcaag ctccaccgt agcacaagag   240 gccttaaaaa aggaacttga aactctaacc accaactacc agtggctctg cactaggctg  300
aatgggaaat gcaagacttt ggaagaa                                      327

<210> SEQ ID NO 28
<211> LENGTH: 312
<212> TYPE: DNA
<213> ORGANISM: Homo sapiens

<400> SEQUENCE: 28
gtttgggcat gttggcatga gttattgtca tacttggaga aagcaaacaa gtggctaaat   60
gaagtagaat ttaaacttaa aaccactgaa aacattcctg gcggagctga ggaaatctct  120
gaggtgctag attcacttga aaatttgatg cgacattcag aggataaccc aaatcagatt  180
cgcatattgg cacagaccct aacagatggc ggagtcatgg atgagctaat caatgaggaa  240
cttgagacat ttaattctcg ttgggggaa ctacatgaag aggctgtaag gaggcaaaag   300
ttgcttgaac ag                                                      312

<210> SEQ ID NO 29
<211> LENGTH: 288
<212> TYPE: DNA
<213> ORGANISM: Homo sapiens

<400> SEQUENCE: 29
agcatccagt ctgcccagga gactgaaaaa tccttacact taatccagga gtccctcaca   60
ttcattgaca agcagttggc agcttatatt gcagacaagg tggacgcagc tcaaatgcct  120
caggaagccc agaaaatcca atctgatttg acaagtcatg agatcagttt agaagaaatg  180
aagaaacata atcaggggaa ggaggctgcc caaagagtcc tgtctcagat tgatgttgca  240
cagaaaaaat tacaagatgt ctccatgaag tttcgattat tccagaaa               288

<210> SEQ ID NO 30
<211> LENGTH: 315
<212> TYPE: DNA
<213> ORGANISM: Homo sapiens

<400> SEQUENCE: 30
ccagccaatt ttgagctgcg tctacaagaa agtaagatga ttttagatga agtgaagatg   60
cacttgcctg cattggaaac aaagagtgtg aacaggaag agtacagtc acagctaaat   120 cattgtgtga acttgtataa aagtctgagt gaagtgaagt ctgaagtgga aatggtgata  180
aagactggac gtcagattgt acagaaaaag cagacgaaa atcccaaaga acttgatgaa   240
agagtaacag ctttgaaatt gcattataat gagctgggag caaaggtaac agaaagaaag  300
```

-continued

```
caacagttgg agaaa                                                   315

<210> SEQ ID NO 31
<211> LENGTH: 324
<212> TYPE: DNA
<213> ORGANISM: Homo sapiens

<400> SEQUENCE: 31
tgcttgaaat tgtcccgtaa gatgcgaaag gaaatgaatg tcttgacaga atggctggca    60
gctacagata tggaattgac aaagagatca gcagttgaag gaatgcctag taatttggat   120
tctgaagttg cctggggaaa ggctactcaa aaagagatta agaaacagaa ggtgcacctg   180
aagagtatca cagaggtagg agaggccttg aaaacagttt tgggcaagaa ggagacgttg   240
gtggaagata aactcagtct tctgaatagt aactggatag ctgtcacctc ccgagcagaa   300
gagtggttaa atcttttgtt ggaa                                         324

<210> SEQ ID NO 32
<211> LENGTH: 306
<212> TYPE: DNA
<213> ORGANISM: Homo sapiens

<400> SEQUENCE: 32
taccagaaac acatggaaac ttttgaccag aatgtggacc acatcacaaa gtggatcatt    60
caggctgaca cacttttgga tgaatcagag aaaagaaac cccagcaaaa agaagacgtg    120
cttaagcgtt taaaggcaga actgaatgac atacgcccaa aggtggactc tacacgtgac   180
caagcagcaa acttgatggc aaaccgcggt gaccactgca ggaaattagt agagccccaa   240
atctcagagc tcaaccatcg atttgcagcc atttcacaca gaattaagac tggaaaggcc   300
tccatt                                                             306

<210> SEQ ID NO 33
<211> LENGTH: 288
<212> TYPE: DNA
<213> ORGANISM: Homo sapiens

<400> SEQUENCE: 33
cctttgaagg aattggagca gtttaactca gatatacaaa aattgcttga accactggag    60
gctgaaattc agcagggggt gaatctgaaa gaggaagact tcaataaaga tatgaatgaa   120
gacaatgagg gtactgtaaa agaattgttg caaagaggag acaacttaca acaaagaatc   180
acagatgaga gaaagagaga ggaaataaag ataaaacagc agctgttaca gacaaaacat   240
aatgctctca aggatttgag gtctcaaaga agaaaaaagg ctctagaa               288

<210> SEQ ID NO 34
<211> LENGTH: 297
<212> TYPE: DNA
<213> ORGANISM: Homo sapiens

<400> SEQUENCE: 34
atttctcatc agtggtatca gtacaagagg caggctgatg atctcctgaa atgcttggat    60
gacattgaaa aaaattagc cagcctacct gagcccagag atgaaaggaa aataaaggaa   120
attgatcggg aattgcagaa gaagaaagag agctgaatg cagtgcgtag gcaagctgag   180
ggcttgtctg aggatggggc cgcaatggca gtggagccaa ctcagatcca gctcagcaag   240
cgctggcggg aaattgagag caaatttgct cagtttcgaa gactcaactt tgcacaa     297
```

<210> SEQ ID NO 35
<211> LENGTH: 384
<212> TYPE: DNA
<213> ORGANISM: Homo sapiens

<400> SEQUENCE: 35

```
attcacactg tccgtgaaga acgatgatg gtgatgactg aagacatgcc tttggaaatt      60
tcttatgtgc cttctactta tttgactgaa atcactcatg tctcacaagc cctattagaa     120
gtggaacaac ttctcaatgc tcctgacctc tgtgctaagg actttgaaga tctctttaag     180
caagaggagt ctctgaagaa tataaaagat agtctacaac aaagctcagg tcggattgac     240
attattcata gcaagaagac agcagcattg caaagtgcaa cgcctgtgga aagggtgaag     300
ctacaggaag ctctctccca gcttgatttc caatgggaaa agttaacaa aatgtacaag      360
gaccgacaag ggcgatttga caga                                            384
```

<210> SEQ ID NO 36
<211> LENGTH: 321
<212> TYPE: DNA
<213> ORGANISM: Homo sapiens

<400> SEQUENCE: 36

```
tctgttgaga aatggcggcg ttttcattat gatataaaga tatttaatca gtggctaaca     60
gaagctgaac agtttctcag aaagacacaa attcctgaga attgggaaca tgctaaatac    120
aaatggtatc ttaaggaact ccaggatggc attgggcagc ggcaaactgt tgtcagaaca    180
ttgaatgcaa ctggggaaga ataattcag caatcctcaa aaacagatgc cagtattcta    240
caggaaaaat tgggaagcct gaatctgcgg tggcaggagg tctgcaaaca gctgtcagac    300
agaaaaaaga ggctagaaga a                                              321
```

<210> SEQ ID NO 37
<211> LENGTH: 330
<212> TYPE: DNA
<213> ORGANISM: Homo sapiens

<400> SEQUENCE: 37

```
caaaagaata tcttgtcaga atttcaaaga gatttaaatg aatttgtttt atggttggag      60
gaagcagata acattgctag tatcccactt gaacctggaa aagagcagca actaaaagaa    120
aagcttgagc aagtcaagtt actggtggaa gagttgcccc tgcgccaggg aattctcaaa    180
caattaaatg aaactggagg acccgtgctt gtaagtgctc ccataagccc agaagagcaa    240
gataaacttg aaaataagct caagcagaca atctccagt ggataaaggt ttccagagct     300
ttacctgaga acaaggaga aattgaagct                                      330
```

<210> SEQ ID NO 38
<211> LENGTH: 315
<212> TYPE: DNA
<213> ORGANISM: Homo sapiens

<400> SEQUENCE: 38

```
caaataaaag accttgggca gcttgaaaaa aagcttgaag accttgaaga gcagttaaat     60
catctgctgc tgtggttatc tcctattagg aatcagttgg aaatttataa ccaaccaaac    120
caagaaggac catttgacgt tcaggaaact gaaatagcag ttcaagctaa acaaccggat    180
gtggaagaga ttttgtctaa agggcagcat ttgtacaagg aaaaaccagc cactcagcca    240
gtgaagagga agttagaaga tctgagctct gagtggaagg cggtaaaccg tttacttcaa    300
```

```
gagctgaggg caaag                                              315

<210> SEQ ID NO 39
<211> LENGTH: 141
<212> TYPE: DNA
<213> ORGANISM: Homo sapiens

<400> SEQUENCE: 39
cagcctgacc tagctcctgg actgaccact attggagcct ctcctactca gactgttact    60
ctggtgacac aacctgtggt tactaaggaa actgccatct ccaaactaga aatgccatct   120
tccttgatgt tggaggtacc t                                             141

<210> SEQ ID NO 40
<211> LENGTH: 321
<212> TYPE: DNA
<213> ORGANISM: Homo sapiens

<400> SEQUENCE: 40
gctctggcag atttcaaccg ggcttggaca gaacttaccg actggctttc tctgcttgat    60
caagttataa atcacagag gtgatggtg ggtgaccttg aggatatcaa cgagatgatc    120
atcaagcaga aggcaacaat gcaggatttg aacagaggc gtccccagtt ggaagaactc   180
attaccgctg cccaaaattt gaaaaacaag accagcaatc aagaggctag aacaatcatt   240
acggatcgaa ttgaaagaat tcagaatcag tgggatgaag tacaagaaca ccttcagaac   300
cggaggcaac agttgaatga a                                             321

<210> SEQ ID NO 41
<211> LENGTH: 327
<212> TYPE: DNA
<213> ORGANISM: Homo sapiens

<400> SEQUENCE: 41
atgttaaagg attcaacaca atggctggaa gctaaggaag aagctgagca ggtcttagga    60
caggccagag ccaagcttga gtcatggaag gagggtccct atacagtaga tgcaatccaa   120
aagaaaatca cagaaaccaa gcagttggcc aaagacctcc gccagtggca gacaaatgta   180
gatgtggcaa atgacttggc cctgaaactt ctccgggatt attctgcaga tgataccaga   240
aaagtccaca tgataacaga gaatatcaat gcctcttgga gaagcattca taaagggtg    300 agtgagcgag aggctgccttt ggaagaa                                      327

<210> SEQ ID NO 42
<211> LENGTH: 348
<212> TYPE: DNA
<213> ORGANISM: Homo sapiens

<400> SEQUENCE: 42
actcatagat tactgcaaca gttccccctg gacctggaaa gtttcttgc ctggcttaca    60 gaagctgaaa caactgccaa tgtcctacag gatgctaccc gtaaggaaag gctcctagaa   120
gactccaagg gagtaaaaga gctgatgaaa caatggcaag acctccaagg tgaaattgaa   180
gctcacacag atgttttatca caacctggat gaaaacagcc aaaaaatcct gagatccctg   240
gaaggttccg atgatgcagt cctgttacaa agacgtttgg ataacatgaa cttcaagtgg   300
agtgaacttc ggaaaaagtc tctcaacatt aggtcccatt tggaagcc              348

<210> SEQ ID NO 43
<211> LENGTH: 387
```

```
<212> TYPE: DNA
<213> ORGANISM: Homo sapiens

<400> SEQUENCE: 43
agttctgacc agtggaagcg tctgcacctt tctctgcagg aacttctggt gtggctacag      60
ctgaaagatg atgaattaag ccggcaggca cctattggag gcgactttcc agcagttcag     120
aagcagaacg atgtacatag gccttcaag agggaattga aaactaaaga acctgtaatc      180
atgagtactc ttgagactgt acgaatattt ctgacagagc agcctttgga aggactagag     240
aaactctacc aggagcccag agagctgcct cctgaggaga gagcccagaa tgtcactcgg     300
cttctacgaa agcaggctga ggaggtcaat actgagtggg aaaaattgaa cctgcactcc     360
gctgactggc agagaaaaat agatgag                                          387

<210> SEQ ID NO 44
<211> LENGTH: 327
<212> TYPE: DNA
<213> ORGANISM: Homo sapiens

<400> SEQUENCE: 44
acccttgaaa gactccagga acttcaagag gccacggatg agctggacct caagctgcgc      60
caagctgagg tgatcaaggg atcctggcag cccgtgggcg atctcctcat tgactctctc     120
caagatcacc tcgagaaagt caaggcactt cgaggagaaa ttgcgcctct gaaagagaac     180
gtgagccacg tcaatgacct tgctcgccag cttaccactt tgggcattca gctctcaccg     240
tataacctca gcactctgga agacctgaac accagatgga gcttctgca ggtggccgtc      300 gaggaccgag tcaggcagct gcatgaa                                          327

<210> SEQ ID NO 45
<211> LENGTH: 216
<212> TYPE: DNA
<213> ORGANISM: Homo sapiens

<400> SEQUENCE: 45
gcccacaggg actttggtcc agcatctcag cactttcttt ccacgtctgt ccagggtccc      60
tgggagagag ccatctcgcc aaacaaagtg ccctactata tcaaccacga gactcaaaca     120
acttgctggg accatcccaa aatgacagag ctctaccagt cttagctga cctgaataat      180 gtcagattct cagcttatag gactgccatg aaactc                               216

<210> SEQ ID NO 46
<211> LENGTH: 888
<212> TYPE: DNA
<213> ORGANISM: Homo sapiens

<400> SEQUENCE: 46
cgaagactgc agaaggccct ttgcttggat ctcttgagcc tgtcagctgc atgtgatgcc      60
ttggaccagc acaacctcaa gcaaaatgac cagcccatgg atatcctgca gattattaat     120
tgtttgacca ctatttatga ccgcctggag caagagcaca caatttggt caacgtccct     180 ctctgcgtgg atatgtgtct gaactggctg ctgaatgttt atgatacggg acgaacaggg     240
aggatccgtg tcctgtcttt taaaactggc atcatttccc tgtgtaaagc acatttggaa     300
gacaagtaca gataccttt caagcaagtg gcaagttcaa caggattttg tgaccagcgc     360
aggctgggcc tccttctgca tgattctatc caaattccaa gacagttggg tgaagttgca     420
tcctttgggg gcagtaacat tgagccaagt gtccggagct gcttccaatt tgctaataat     480
```

| | | |
|---|---|---|
| aagccagaga tcgaagcggc cctcttccta gactggatga gactggaacc ccagtccatg | 540 | |
| gtgtggctgc ccgtcctgca cagagtggct gctgcagaaa ctgccaagca tcaggccaaa | 600 | |
| tgtaacatct gcaaagagtg tccaatcatt ggattcaggt acaggagtct aaagcacttt | 660 | |
| aattatgaca tctgccaaag ctgcttttt tctggtcgag ttgcaaaagg ccataaaatg | 720 | |
| cactatccca tggtggaata ttgcactccg actacatcag agaagatgt tcgagacttt | 780 | |
| gccaaggtac taaaaaacaa atttcgaacc aaaaggtatt ttgcgaagca tccccgaatg | 840 | |
| ggctacctgc cagtgcagac tgtcttagag ggggacaaca tggaaact | 888 | |

<210> SEQ ID NO 47
<211> LENGTH: 834
<212> TYPE: DNA
<213> ORGANISM: Homo sapiens

<400> SEQUENCE: 47

| | | |
|---|---|---|
| cccgttactc tgatcaactt ctggccagta gattctgcgc ctgcctcgtc ccctcagctt | 60 | |
| tcacacgatg atactcattc acgcattgaa cattatgcta gcaggctagc agaaatggaa | 120 | |
| aacagcaatg gatcttatct aaatgatagc atctctccta atgagagcat agatgatgaa | 180 | |
| catttgttaa tccagcatta ctgccaaagt ttgaaccagg actccccct gagccagcct | 240 | |
| cgtagtcctg cccagatctt gatttcctta gagagtgagg aaagagggga gctagagaga | 300 | |
| atcctagcag atcttgagga agaaaacagg aatctgcaag cagaatatga ccgtctaaag | 360 | |
| cagcagcacg aacataaagg cctgtcccca ctgccgtccc ctcctgaaat gatgcccacc | 420 | |
| tctcccccaga gtccccggga tgctgagctc attgctgagg ccaagctact gcgtcaacac | 480 | |
| aaaggccgcc tggaagccag gatgcaaatc ctggaagacc acaataaaca gctggagtca | 540 | |
| cagttacaca ggctaaggca gctgctggag caaccccagg cagaggccaa agtgaatggc | 600 | |
| acaacggtgt cctctccttc tacctctcta cagaggtccg acagcagtca gcctatgctg | 660 | |
| ctccgagtgg ttggcagtca aacttcggac tccatgggtg aggaagatct tctcagtcct | 720 | |
| ccccaggaca caagcacagg gttagaggag gtgatggagc aactcaacaa ctccttccct | 780 | |
| agttcaagag gaagaaatac ccctggaaag ccaatgagag aggacacaat gtag | 834 | |

<210> SEQ ID NO 48
<211> LENGTH: 11043
<212> TYPE: DNA
<213> ORGANISM: Canis familiaris

<400> SEQUENCE: 48

| | | |
|---|---|---|
| atgctttggt gggaagaagt agaggactgt tatgaaagag aagatgttca aaagaaaaca | 60 | |
| ttcacaaaat gggtaaatgc acagttttct aagtttggga agcagcacat agagaacctc | 120 | |
| ttcagtgacc tacaggatgg gagacgcctc ctagaccttt tggaaggcct gacagggcaa | 180 | |
| aaactgccaa agaaaaagg atccacaaga gttcatgccc tgaacaatgt caacaaggca | 240 | |
| ctgcgcgtct tgcagaaaaa taatgttgat ttagtgaaca ttggaagtac tgacatagta | 300 | |
| gatggaaatc acaaactgac tcttggtttg atttggaata taatcctcca ctggcaggtc | 360 | |
| aaaaatgtaa tgaaaatat catggctgga ttgcaacaaa ccaacagtga aaagattctc | 420 | |
| ctgagctggg tccgacaatc aactcgtaat tatccacagg ttaatgtcat taacttcacc | 480 | |
| accagctggt ctgatggcct ggctttgaac gctctcatcc acagtcatag gccagacctg | 540 | |
| tttgattgga ataagtgtgt ttgccagcag tcagccacac aacgcctgga acatgcattc | 600 | |
| aacattgcca aatatcaatt aggcatagag aaactgcttg atcctgaaga tgttgccacc | 660 | |

-continued

```
acttatccag ataagaagtc catcttaatg tatatcacat cactcttcca agttttgcct      720
caacaagtga gcattgaagc catccaggaa gtggaaatgt tgccaaggcc atctcaagtt      780
actagagaag aacattttca gatacatcat caaatgcact attctcaaca gatcacagtc      840
agtctagcac agggatatga acgagcccct tcctttccta agcctcggtt caagagctat      900
gcctacacac aggctgctta tgtcaccact tctgacccca cacggagccc acttccttca      960
cagcatttgg aaactcctga agacaagtca tttggccggt cattgacaga gaccgaagca     1020
aacctggaca gttatcaaac agcttttgaa gaagtactct cgtggcttct ttcagctgag     1080
gatgcactgc aagcccaagg agagatttct aatgatgtcg aagaagtgaa agaacaattt     1140
catactcatg agggatatat gatggacttg acatcccatc agggacgggt cggtaatgtt     1200
ctccaactgg gaagtcaact gattggaaca gggaaattat cagaagatga gaaaccgaa      1260
gtgcaggaac aaatgaatct cctcaattca agatgggaat gcctcagggt agctagcatg     1320
gaaaaacaaa gcaattttaca taaagttcta atggatctcc agaatcagca actgaaagag     1380
ttaaatgact ggctaaccaa aacagaagag agaacaagga aaatggagaa ggagcccctt     1440
ggacctgata ttgaagacct aaaacgccaa gtacaacaac ataaggtgct tcaagaagac     1500
ttagaacagg aacaagtcag ggtcaattcc ctcactcata tggtggtggt agtcgatgaa     1560
tctagtggag accatgcaac tgctgctttg gaagaacaac ttaaggtact gggagatcga     1620
tgggcaaaca tctgtaggtg gacagaagat cgctgggttc ttttacaaga catcctccta     1680
aaatggcagc gttttactga agaacagtgc cttttttagtg catggctttc ggagaaggaa     1740
gatgcagtga acaagattca cacaactggc tttaaggatc aaagtgaagt gttatcaaat     1800
cttcagaaac tggctgtctt aaaaacagat ctggaaaaga gaagcaaac catggacaaa      1860
ctctgctcac tcaaccaaga ccttctttca gcgctgaaaa acacagtggt agcccacaag     1920
atggaagcat ggctggacaa cttttgcccag cgctgggata atttagtcca gaaacttgaa     1980
aaaagttcag cacagatttc acaggctgtc accaccactc agccatcact aacacagaca     2040
actgtaatgg aaacagtaac tatggtgacc acgagggaac acatcttggt aaagcatgcc     2100
caagaggaac tgccaccacc acccctcag aagaagaggc agattatcgt ggattctgaa       2160
attaggaaaa ggttggatgt cgatataact gaacttcaca gttggattac tcgttcagaa     2220
gctgtgttgc agagtcctga atttgcaatc tatcggaagg aaggcaactt ctcagacctt     2280
aaagaaaaag tcaatgccat agagcgagaa aaagccgaga agttcagaaa actgcaagat     2340
gccagcagat cagctcaggc cctggtggaa cagatggtga atgagggtgt taatgctgac     2400
agcatcaaac aagcctccga acaactgaac agccggtgga tagagttctg ccaattgcta     2460
agcgagagac ttaactggct ggagtatcag aacaacatca tcactttcta taatcagcta     2520
caacaattgg agcagatgac aactactgct gaaaactggt tgaaaaccca gcctaccacc     2580
acatcagagc caacagcaat taaaagccag ttaaaaattt gtaaggatga aatcaaccga     2640
ctgtcagctc ttcagcctca aatcgagcga ttaaaaattc aaagcatagc cctgaaagag     2700
aaaggacaag ggccaatgtt cctggatgca gactttgtgg cctttacaaa tcattttaac     2760
caagtctttg ctgatgtgca ggcaagagaa aaagagctac aaacaatttt tgacagtttg     2820
ccacccatgc gctatcagga gactatgagt accatcctga catggatcca gcagtcagaa     2880
accaaactct ctatacctca ggttactgtc actgaatatg acatcatgga acagagactc     2940
ggagagctac aggctttaca aagctctctg caagagcaac aaaatggcct aaactatctc     3000
```

```
agcaccactg tgaaagagat gtcaaagaaa gcaccactgt ctgatattag tcggaaatat   3060
caatcagaat ttgaagagat tgagggacgt tggaagaagc tgtcttccca gctggttgaa   3120
cattgtcaaa agttggagga gcaaatggct aaacttcgaa aaattcagaa tcacataaaa   3180
actctgaaga aatggatcac tgaagtcgat gttttcctga aggaggaatg gcctgccctt   3240
ggggattcag aaattctgaa agacagctg aacagtgca ggcttttagt caatgacatt    3300
cagaccatcc agcctagtct caacagtgtc aatgaagggg ctcagaagat gaagaatgaa   3360
gcagaaccag agtttgctgg cagacttgag acagagctcc gagaacttaa cacccagtgg   3420
gattacatgt gccgccaggt ctatgccagg aaggaagcct taaaggagg tttggataaa    3480
actgtaagtc ttcagaaaga tctgtcagag atgcatgagt ggatgacaca agctgaagaa   3540
gaatacctag agagagattt cgaatacaag acccctgatg aattacagac agcagttgaa   3600
gagatgaaga gagctaaaga agaggcccag caaaagaag caaaagtgaa actcctaacc    3660
gagtccgtca atagtgtcat agctcaggct ccacctgcag cacaagaggc cttaaaaaag   3720
gaacttgaca ctctccaccac caactaccag tggctctgca ccaggctcaa tggcaaatgc   3780
aagaccttgg aagaagtttg gcgtgctgg catgagttat tgtcctactt ggagaaggca    3840
aacaagtggc taagtgaagt agaagtcaag cttaaaacca ctgaaaatat ttctggggga   3900
gctgaggaaa tcgccgaggt gcttgattcg cttgaaaatt tgatgcaaca ttcagaggat   3960
aacccgaatc agattcgcat attggcacag accttgacag atggtggagt catggatgaa   4020
ctgatcaatg aggagcttga gacatttaat tctcgttgga gagaactcca tgaagaggct   4080
gtgaggaggc aaaagttgct tgagcagagt atccagtcgg cccaggagat agaaaaatcc   4140
ttgcacttaa ttcaggagtc cctctcttcc attgacaagc agttggcagc ttatattgct   4200
gacaaagtgg atgcagctca gatgcctcag gaagcccaga aaatccaatc agatttgaca   4260
agtcatgaga tcagtttaga agaaatgaag aaacataacc agggaaagga gactgcccaa   4320
agggtactat cccaaattga tgtggcacag aaaaaattgc aggatgtttc catgaagttt   4380
cgattattcc agaagccagc caattttgag cagcgcctac aagaaagtaa aatgatttta   4440
gatgaagtga agatgcattt acctgcgttg gaaacaaaga gtgtggaaca ggaagtagta   4500
cagtcacagt taaatcattg tgtgaacttg tataaaagtc tgagtgaagt gaagtctgaa   4560
gtggaaatgg taataaaaac tggacgtcag attgtacaga agaagcagac ggaaaacccg   4620
aaagagcttg atgaaagagt tacagctttg aaattgcatt ataatgagct gggagcaaag   4680
gtgacagaaa gaaagcaaca gttggaaaaa tgcttgaaat tgtcccgtaa gatgcgaaag   4740
gaaatgaatg ccctgacaga atggctggca gctacagata tggaactgac aaagagatcg   4800
gcagttgaag gaatgcctag taatttggat tctgaagttg cctggggaaa ggctactcag   4860
aaagagattg agaaacagaa ggttcaccta aagagtgtca cagaggtagg agaggccttg   4920
aaaacggttt tgggcaagaa ggaaatgttg gtggaagata aactgagtct tctgaatagt   4980
aactggatag ccgtcacttc ccgagcagaa gagtggttaa accttttatt ggaataccag   5040
aaacacatgg aaacttttga ccagaatgtg gattacatca caaactggat cattcaggct   5100
gatgcacttt tggatgaatc tgagaaaaag aaacctcagc aaaaagaaga catacttaag   5160
cgtttaaagg ctgaaatgaa tgacatacgt ccaaggtgg attctacacg tgaccaagca    5220
gcaaacctga tggcaaaccg cggcgaccac tgcaggaaag tagtagagcc caaaatctca   5280
gagctcaacc atcgatttgc agccatttct cacagaatta agactggaaa ggcctccatt   5340
cctttgaagg aattggagca gtttaactca gatatacaaa aattgcttga accactggag   5400
```

```
gctgaaattc agcagggggt gaatctgaaa gaggaagact tcaataaaga tatgagtgaa     5460
gacaatgagg gtactgtaaa agaattgttg caaagaggag acaacttaca acaaagaatc     5520
acagatgaga gaaagcgaga ggaaataaag ataaaacaac agctgttaca gacaaaacat     5580
aatgctctca aggatttgag gtctcaaaga agaaaaaagg ctctagaaat ttctcaccag     5640
tggtatcagt acaagaggca ggctgatgat ctcctgaaat gcttggatga cattgaaaaa     5700
aaattagcca gcctacctga acccagagat gaaaggaaaa taaaggaaat tgatcgtgaa     5760
ttgcagaaga agaaagagga gctgaatgca gtgcgtaggc aagctgaggg cttgtctgag     5820
gatggggccg caatggcagt ggagccaact cagatccagc tcagcaagcg ctggcgggaa     5880
attgagagca aatttgctca gtttcgaaga ctcaactttg cacaaattca cactgtccat     5940
gaagagtcag tggtggcgat gactgaagac atgcctttgg aaatttctta tgtgccttct     6000
acttacctga ctgagatcac tcatgtctca caagccctat cagaagtgga agagcttctt     6060
aatgctcccg acctttgtgc tcaagatttt gaagatctct ttaaacaaga ggaatccttg     6120
aagaacataa aagacagcct gcaacaaatc tcaggtcgga ttgacatcat tcacaataaa     6180
aagacagcag cattgcacag tgccactcct gcagaaaggg caaagctcca ggaagctctc     6240
tcacggcttg atttccaatg ggaaagagtt aacaatatgt acaaggaccg acaagggaga     6300
tttgacagat ctgtggaaaa atggcggcgg tttcattatg atatgaagat acttaatcaa     6360
tggctaacag aagctgaaca gtttctcaaa aagacacaaa ttcctgagaa ttgggaacat     6420
gccaaataca aatggtatct taaggaactc caggatggca ttggacagcg gcaaagtgtt     6480
gtcagggtat tgaatgcaac tggggaagaa ataattcaac agtcctcaaa aacagatgcc     6540
agtattctcc aagaaaaact gggaagcctg aatctgcggt ggcaggaggt ctgcaaacag     6600
ctggcagaaa gaaaaaagag gctagaggaa cagaagaata tcttgtcaga atttcaaaga     6660
gatgtaaatg aatttgtttt atggttggaa gaagcggata acgttgctaa tattccactt     6720
gaacctggaa atgagcagca gctaaaagaa aaacttgaac aagtcaagtt actggcagaa     6780
gagttgcccc tgcgccaggg aattctaaaa caattaaatg aaactggagg aacagtgctt     6840
gtaagtgctc ccctaagccc agaagagcaa gataaacttg aaaataagct caagcagaca     6900
aatcttcagt ggataaaggt ttctagaaat ctgcctgaga agcaagaaga aattgaggca     6960
cacgtaaaag accttggaca gctggaagag cagttaaatc atctgcttct atggctgtct     7020
cctattagga atcagttgga aatttacaat cagccaaatc aaacaggacc atttgacatc     7080
aaggaaattg aagtagcagt tcaagctaaa cagccggatg tggaagggat tttgtctaaa     7140
gggcagcatt tgtacaagga aaaccagcc actcagccag cgaagagaaa gctgaagat      7200 ctcagctctg attggaaggt ggtaactcag ttgcttcaag agctgcgggc aaagcaacct     7260
ggcccagctc ctggactgac cactgtcaga gcccctccca gtcagactgt tactctggtg     7320
acacaacccg cggttaccaa ggaaactgcc atctccaaac tagaaatgcc atcttcattg     7380
ctgttggagg tacctgcact ggcagatttc aaccgagctt ggacagaact taccgactgg     7440
ctgtctctgc ttgatcgagt tataaaatca cagagggtga tggtgggtga tcttgaagac     7500
attaacgaga tgatcatcaa gcagaaggca acgctgcagg atttggaaca gaggcgcccc     7560
cagttggaag aactcattac cgctgcccag aatttgaaaa acaagaccag caatcaagag     7620
gctagaacaa tcattactga tcgaattgaa agaattcaga gtcagtggga tgaagtacag     7680
gaacatcttc agaaccggag gctacagttg actgaaatgt taaggattc cacacaatgg     7740
```

```
ctggaagcta aagaggaggc tgagcaggtg ttggggcagg ccagagccaa gcttgagtca    7800
tggaaggagg ctccctacac agtagatgca atccaaaaga aaatcacaga aaccaagcag    7860
ttggccaaag acctccgcca gtggcagata aatgtagatg ttgcaaatga tttggcactg    7920
aaacttctcc gagattattc tgcagatgat accagaaaag tacacatgat aacagagaac    7980
atcaatgcct cttgggcaag catccataaa agattgagtg agcgagaggc tgctctggaa    8040
gaaacccaca gattactgca acagttcccc ttggacctgg agaagttcct tgcctggctt    8100
acagaagccg aaacaactgc caacgtcctg caggatgcca cccataagga aaggcttcta    8160
gaagattcca agggagtaag agagctgatg aaacaatggc aagacctcca aggagaaatc    8220
gaagctcaca cagatatcta tcacaacctg gacgaaaatg gccaaaaagt cctgagatcc    8280
ctggaaggtt ctgacgatgc agccttgttg caaagacgtt tggataacat gaacttcaag    8340
tggagcgaac ttcggaaaaa gtctctcaac attaggtctc acttggaagc cagttctgac    8400
cagtggaagc gtctgcacct ttctcttcag gaacttctgg tatggctcca gctgaaagat    8460
gatgagttaa gccggcaggc acccattgga ggagactttc cagcggtgca aagcagaat    8520 gatgtacaca gggccttcaa gagggaattg aaacgaaag aacctgtaat catgagtact    8580
cttgagactg tacgaatatt tctgacagag cagcctttag aaggactaga gaaactctac    8640
caggagccca gagagctgcc tcctgaagag agagcccaga atgtcacacg ctcctacga    8700 aagcaagctg aggaggtcaa cactcagtgg gaaaaactga acgtgcactc tgcagactgg    8760
cagagaaaaa tagacgaggc cctcgaaaga ctccaggagc ttcaggaagc aacagatgag    8820
ctggatctca aactacgtca ggcagaggtg atcaaaggat cctggcagcc tgtgggtgac    8880
ctcctcattg actctctcca agatcacctc gaaaaagtca aggcgcttcg aggagaaatt    8940
acacctctga aagagaatgt cagctacgtc aatgaccttg ctcgccaact cactacgttg    9000
ggcattcagc tgtcaccata taacctcaac actctggaag acctgaacac cagatggaag    9060
cttctgcagg tggccattga ggaccgcatc aggcagctgc atgaagcgca cagggacttt    9120
ggaccagcct cccagcactt cctttccact tctgtccagg gtccctggga gagagccatc    9180
tcaccaaaca aagtgcccta ctatatcaac cacgagaccc aaacaacttg ctgggaccat    9240
cccaaaatga cagagctcta ccagtcttta gctgacctga ataatgtcag gttctcagct    9300
tacaggactg ccatgaaact ccgaagactg cagaaggccc tttgcttgga tctcttgagc    9360
ctatcggctg catgcgatgc cttgaccag cacaacctca agcaaaatga ccagcccatg    9420
gatatcctgc aggtcattaa ctgtctgacc actatttatg atcgcctaga gcaagagcac    9480
aacaatctgg tcaacgtccc ctctctgcgtg gatatgtgtc tcaattggct gctgaatgtt    9540
tatgacacgg gacgaacggg gaggatccgg gtcctgtctt ttaaaactgg catcattct    9600 ctgtgtaaag cccatttgga agacaagtac agatacctct tcaagcaagt ggcaagttcg    9660
acaggatttt gtgaccagcg caggctgggc ctcctcctgc atgactctat ccagatccca    9720
agacagttgg gtgaagtcgc atcgttcggg gcagtaaca ttgagccgag tgtcaggagc    9780
tgcttccagt ttgctaataa taagcctgag atcgaagcgg ccctcttcct agactggatg    9840
cgcctggagc cccagtccat ggtgtggctg cctgtcctgc accgagtggc tgccgcggaa    9900
actgccaagc accaggccaa gtgcaacatc tgcaaggagt gtcccatcat cggattcagg    9960
tacaggagtc taaagcactt taattatgac atctgccaaa gttgcttttt ttctggtcga   10020
gttgcaaaag gccataaaat gcactatccc atggtggaat actgcactcc gactacatcg   10080
ggagaagatg tccgtgactt tgccaaggta ctaaaaaaca aatttcgaac caaaaggtat   10140
```

-continued

```
tttgcgaagc atccccgaat gggctacctg ccagtgcaga ctgtcttaga gggggacaac   10200
atggaaactc ctgtcactct gatcaacttc tggccggtag attctgcgcc tgcctcgtcc   10260
cctcagcttt cacacgatga tactcattca cgcattgagc attatgctag caggctaaaa   10320
aaaatggaaa acagcaatgg atcttatcta aatgatagca tctctcctaa tgagagcata   10380
gatgatgaac atttgttaat ccagcattac tggcgaagtt tgaaccagga atccccctg    10440 agccagcctc gtagtcctgc ccagatcttg atttccttag agagtgagga agaggggag    10500 ctagagagaa tcctagcaga tcttgagggg agaaacagaa atctgcaagc agagtatgat   10560
cgtctaaagc agcagcatga acacaaaggc ctgtccccac tgccatcccc tcctgaaatg   10620
atgcctactt ctccccaaag tccccgggat gctgagctca tcgctgaggc caagctgctg   10680
cgtcaacaca aaggccgcct ggaagccagg atgcaaatcc ttgaagacca taacaaacaa   10740
ctggaatccc agttacacag gctcaggcag ctgctggagc aaccccaggc agaggccaag   10800
gtgaatggta caacggtgtc ttctccttct acctctcttc agaggtcaga tagcagtcag   10860
cctatgctgc tccgggtggt cggcagtcag acttcagaat ccatgggcga ggaagacctg   10920
ctcagccctc cccaggacac aagcacaggg ttagaggaag tgatggagca gctcaaccac   10980
tccttcccta gttccagagg aagaaatacc cctgggaagc caatgagaga ggacacaatg   11040
tag                                                                 11043
```

<210> SEQ ID NO 49
<211> LENGTH: 3680
<212> TYPE: PRT
<213> ORGANISM: Canis familiaris

<400> SEQUENCE: 49

```
Met Leu Trp Trp Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Lys Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Lys Tyr Gln Leu Gly
        195                 200                 205
```

```
Ile Glu Lys Leu Leu Asp Pro Glu Asp Val Ala Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Met Leu Pro Arg
                245                 250                 255

Pro Ser Gln Val Thr Arg Glu Glu His Phe Gln Ile His His Gln Met
            260                 265                 270

His Tyr Ser Gln Gln Ile Thr Val Ser Leu Ala Gln Gly Tyr Glu Arg
        275                 280                 285

Ala Pro Ser Phe Pro Lys Pro Arg Phe Lys Ser Tyr Ala Tyr Thr Gln
    290                 295                 300

Ala Ala Tyr Val Thr Thr Ser Asp Pro Thr Arg Ser Pro Leu Pro Ser
305                 310                 315                 320

Gln His Leu Glu Thr Pro Glu Asp Lys Ser Phe Gly Arg Ser Leu Thr
                325                 330                 335

Glu Thr Glu Ala Asn Leu Asp Ser Tyr Gln Thr Ala Leu Glu Glu Val
            340                 345                 350

Leu Ser Trp Leu Leu Ser Ala Glu Asp Ala Leu Gln Ala Gln Gly Glu
        355                 360                 365

Ile Ser Asn Asp Val Glu Val Lys Glu Gln Phe His Thr His Glu
    370                 375                 380

Gly Tyr Met Met Asp Leu Thr Ser His Gln Gly Arg Val Gly Asn Val
385                 390                 395                 400

Leu Gln Leu Gly Ser Gln Leu Ile Gly Thr Gly Lys Leu Ser Glu Asp
                405                 410                 415

Glu Glu Thr Glu Val Gln Glu Gln Met Asn Leu Leu Asn Ser Arg Trp
            420                 425                 430

Glu Cys Leu Arg Val Ala Ser Met Glu Lys Gln Ser Asn Leu His Lys
        435                 440                 445

Val Leu Met Asp Leu Gln Asn Gln Gln Leu Lys Glu Leu Asn Asp Trp
450                 455                 460

Leu Thr Lys Thr Glu Glu Arg Thr Arg Lys Met Glu Lys Glu Pro Leu
465                 470                 475                 480

Gly Pro Asp Ile Glu Asp Leu Lys Arg Gln Val Gln Gln His Lys Val
                485                 490                 495

Leu Gln Glu Asp Leu Glu Gln Glu Gln Val Arg Val Asn Ser Leu Thr
            500                 505                 510

His Met Val Val Val Asp Glu Ser Ser Gly Asp His Ala Thr Ala
        515                 520                 525

Ala Leu Glu Glu Gln Leu Lys Val Leu Gly Asp Arg Trp Ala Asn Ile
    530                 535                 540

Cys Arg Trp Thr Glu Asp Arg Trp Val Leu Leu Gln Asp Ile Leu Leu
545                 550                 555                 560

Lys Trp Gln Arg Phe Thr Glu Glu Gln Cys Leu Phe Ser Ala Trp Leu
                565                 570                 575

Ser Glu Lys Glu Asp Ala Val Asn Lys Ile His Thr Thr Gly Phe Lys
            580                 585                 590

Asp Gln Ser Glu Val Leu Ser Asn Leu Gln Lys Leu Ala Val Leu Lys
        595                 600                 605

Thr Asp Leu Glu Lys Lys Gln Thr Met Asp Lys Leu Cys Ser Leu
    610                 615                 620
```

-continued

```
Asn Gln Asp Leu Leu Ser Ala Leu Lys Asn Thr Val Val Ala His Lys
625                 630                 635                 640

Met Glu Ala Trp Leu Asp Asn Phe Ala Gln Arg Trp Asp Asn Leu Val
            645                 650                 655

Gln Lys Leu Glu Lys Ser Ser Ala Gln Ile Ser Gln Ala Val Thr Thr
        660                 665                 670

Thr Gln Pro Ser Leu Thr Gln Thr Thr Val Met Glu Thr Val Thr Met
    675                 680                 685

Val Thr Thr Arg Glu His Ile Leu Val Lys His Ala Gln Glu Glu Leu
690                 695                 700

Pro Pro Pro Pro Gln Lys Lys Arg Gln Ile Ile Val Asp Ser Glu
705                 710                 715                 720

Ile Arg Lys Arg Leu Asp Val Asp Ile Thr Glu Leu His Ser Trp Ile
            725                 730                 735

Thr Arg Ser Glu Ala Val Leu Gln Ser Pro Glu Phe Ala Ile Tyr Arg
        740                 745                 750

Lys Glu Gly Asn Phe Ser Asp Leu Lys Glu Lys Val Asn Ala Ile Glu
    755                 760                 765

Arg Glu Lys Ala Glu Lys Phe Arg Lys Leu Gln Asp Ala Ser Arg Ser
770                 775                 780

Ala Gln Ala Leu Val Glu Gln Met Val Asn Glu Gly Val Asn Ala Asp
785                 790                 795                 800

Ser Ile Lys Gln Ala Ser Glu Gln Leu Asn Ser Arg Trp Ile Glu Phe
            805                 810                 815

Cys Gln Leu Leu Ser Glu Arg Leu Asn Trp Leu Glu Tyr Gln Asn Asn
        820                 825                 830

Ile Ile Thr Phe Tyr Asn Gln Leu Gln Gln Leu Glu Gln Met Thr Thr
    835                 840                 845

Thr Ala Glu Asn Trp Leu Lys Thr Gln Pro Thr Thr Thr Ser Glu Pro
850                 855                 860

Thr Ala Ile Lys Ser Gln Leu Lys Ile Cys Lys Asp Glu Ile Asn Arg
865                 870                 875                 880

Leu Ser Ala Leu Gln Pro Gln Ile Glu Arg Leu Lys Ile Gln Ser Ile
            885                 890                 895

Ala Leu Lys Glu Lys Gly Gln Gly Pro Met Phe Leu Asp Ala Asp Phe
        900                 905                 910

Val Ala Phe Thr Asn His Phe Asn Gln Val Phe Ala Asp Val Gln Ala
    915                 920                 925

Arg Glu Lys Glu Leu Gln Thr Ile Phe Asp Ser Leu Pro Pro Met Arg
930                 935                 940

Tyr Gln Glu Thr Met Ser Thr Ile Leu Thr Trp Ile Gln Gln Ser Glu
945                 950                 955                 960

Thr Lys Leu Ser Ile Pro Gln Val Thr Val Thr Glu Tyr Asp Ile Met
            965                 970                 975

Glu Gln Arg Leu Gly Glu Leu Gln Ala Leu Gln Ser Ser Leu Gln Glu
        980                 985                 990

Gln Gln Asn Gly Leu Asn Tyr Leu Ser Thr Thr Val Lys Glu Met Ser
    995                 1000                1005

Lys Lys Ala Pro Leu Ser Asp Ile Ser Arg Lys Tyr Gln Ser Glu
    1010                1015                1020

Phe Glu Glu Ile Glu Gly Arg Trp Lys Lys Leu Ser Ser Gln Leu
    1025                1030                1035

Val Glu His Cys Gln Lys Leu Glu Glu Gln Met Ala Lys Leu Arg
```

```
              1040                1045                1050

Lys Ile Gln Asn His Ile Lys Thr Leu Lys Lys Trp Ile Thr Glu
1055                1060                1065

Val Asp Val Phe Leu Lys Glu Glu Trp Pro Ala Leu Gly Asp Ser
1070                1075                1080

Glu Ile Leu Lys Arg Gln Leu Lys Gln Cys Arg Leu Leu Val Asn
1085                1090                1095

Asp Ile Gln Thr Ile Gln Pro Ser Leu Asn Ser Val Asn Glu Gly
1100                1105                1110

Ala Gln Lys Met Lys Asn Glu Ala Glu Pro Glu Phe Ala Gly Arg
1115                1120                1125

Leu Glu Thr Glu Leu Arg Glu Leu Asn Thr Gln Trp Asp Tyr Met
1130                1135                1140

Cys Arg Gln Val Tyr Ala Arg Lys Glu Ala Leu Lys Gly Gly Leu
1145                1150                1155

Asp Lys Thr Val Ser Leu Gln Lys Asp Leu Ser Glu Met His Glu
1160                1165                1170

Trp Met Thr Gln Ala Glu Glu Glu Tyr Leu Glu Arg Asp Phe Glu
1175                1180                1185

Tyr Lys Thr Pro Asp Glu Leu Gln Thr Ala Val Glu Glu Met Lys
1190                1195                1200

Arg Ala Lys Glu Glu Ala Gln Gln Lys Glu Ala Lys Val Lys Leu
1205                1210                1215

Leu Thr Glu Ser Val Asn Ser Val Ile Ala Gln Ala Pro Pro Ala
1220                1225                1230

Ala Gln Glu Ala Leu Lys Lys Glu Leu Asp Thr Leu Thr Thr Asn
1235                1240                1245

Tyr Gln Trp Leu Cys Thr Arg Leu Asn Gly Lys Cys Lys Thr Leu
1250                1255                1260

Glu Glu Val Trp Ala Cys Trp His Glu Leu Leu Ser Tyr Leu Glu
1265                1270                1275

Lys Ala Asn Lys Trp Leu Ser Glu Val Glu Val Lys Leu Lys Thr
1280                1285                1290

Thr Glu Asn Ile Ser Gly Gly Ala Glu Glu Ile Ala Glu Val Leu
1295                1300                1305

Asp Ser Leu Glu Asn Leu Met Gln His Ser Glu Asp Asn Pro Asn
1310                1315                1320

Gln Ile Arg Ile Leu Ala Gln Thr Leu Thr Asp Gly Gly Val Met
1325                1330                1335

Asp Glu Leu Ile Asn Glu Glu Leu Glu Thr Phe Asn Ser Arg Trp
1340                1345                1350

Arg Glu Leu His Glu Glu Ala Val Arg Arg Gln Lys Leu Leu Glu
1355                1360                1365

Gln Ser Ile Gln Ser Ala Gln Glu Ile Glu Lys Ser Leu His Leu
1370                1375                1380

Ile Gln Glu Ser Leu Ser Ser Ile Asp Lys Gln Leu Ala Ala Tyr
1385                1390                1395

Ile Ala Asp Lys Val Asp Ala Ala Gln Met Pro Gln Glu Ala Gln
1400                1405                1410

Lys Ile Gln Ser Asp Leu Thr Ser His Glu Ile Ser Leu Glu Glu
1415                1420                1425

Met Lys Lys His Asn Gln Gly Lys Glu Thr Ala Gln Arg Val Leu
1430                1435                1440
```

```
Ser Gln Ile Asp Val Ala Gln Lys Lys Leu Gln Asp Val Ser Met
    1445                1450                1455

Lys Phe Arg Leu Phe Gln Lys Pro Ala Asn Phe Glu Gln Arg Leu
    1460                1465                1470

Gln Glu Ser Lys Met Ile Leu Asp Glu Val Lys Met His Leu Pro
    1475                1480                1485

Ala Leu Glu Thr Lys Ser Val Glu Gln Glu Val Val Gln Ser Gln
    1490                1495                1500

Leu Asn His Cys Val Asn Leu Tyr Lys Ser Leu Ser Glu Val Lys
    1505                1510                1515

Ser Glu Val Glu Met Val Ile Lys Thr Gly Arg Gln Ile Val Gln
    1520                1525                1530

Lys Lys Gln Thr Glu Asn Pro Lys Glu Leu Asp Glu Arg Val Thr
    1535                1540                1545

Ala Leu Lys Leu His Tyr Asn Glu Leu Gly Ala Lys Val Thr Glu
    1550                1555                1560

Arg Lys Gln Gln Leu Glu Lys Cys Leu Lys Leu Ser Arg Lys Met
    1565                1570                1575

Arg Lys Glu Met Asn Ala Leu Thr Glu Trp Leu Ala Ala Thr Asp
    1580                1585                1590

Met Glu Leu Thr Lys Arg Ser Ala Val Glu Gly Met Pro Ser Asn
    1595                1600                1605

Leu Asp Ser Glu Val Ala Trp Gly Lys Ala Thr Gln Lys Glu Ile
    1610                1615                1620

Glu Lys Gln Lys Val His Leu Lys Ser Val Thr Glu Val Gly Glu
    1625                1630                1635

Ala Leu Lys Thr Val Leu Gly Lys Lys Glu Met Leu Val Glu Asp
    1640                1645                1650

Lys Leu Ser Leu Leu Asn Ser Asn Trp Ile Ala Val Thr Ser Arg
    1655                1660                1665

Ala Glu Glu Trp Leu Asn Leu Leu Leu Glu Tyr Gln Lys His Met
    1670                1675                1680

Glu Thr Phe Asp Gln Asn Val Asp Tyr Ile Thr Asn Trp Ile Ile
    1685                1690                1695

Gln Ala Asp Ala Leu Leu Asp Glu Ser Glu Lys Lys Lys Pro Gln
    1700                1705                1710

Gln Lys Glu Asp Ile Leu Lys Arg Leu Lys Ala Glu Met Asn Asp
    1715                1720                1725

Ile Arg Pro Lys Val Asp Ser Thr Arg Asp Gln Ala Ala Asn Leu
    1730                1735                1740

Met Ala Asn Arg Gly Asp His Cys Arg Lys Val Val Glu Pro Lys
    1745                1750                1755

Ile Ser Glu Leu Asn His Arg Phe Ala Ala Ile Ser His Arg Ile
    1760                1765                1770

Lys Thr Gly Lys Ala Ser Ile Pro Leu Lys Glu Leu Glu Gln Phe
    1775                1780                1785

Asn Ser Asp Ile Gln Lys Leu Leu Glu Pro Leu Glu Ala Glu Ile
    1790                1795                1800

Gln Gln Gly Val Asn Leu Lys Glu Glu Asp Phe Asn Lys Asp Met
    1805                1810                1815

Ser Glu Asp Asn Glu Gly Thr Val Lys Glu Leu Leu Gln Arg Gly
    1820                1825                1830
```

-continued

```
Asp Asn Leu Gln Gln Arg Ile Thr Asp Glu Arg Lys Arg Glu Glu
    1835                1840                1845

Ile Lys Ile Lys Gln Gln Leu Leu Gln Thr Lys His Asn Ala Leu
    1850                1855                1860

Lys Asp Leu Arg Ser Gln Arg Arg Lys Lys Ala Leu Glu Ile Ser
    1865                1870                1875

His Gln Trp Tyr Gln Tyr Lys Arg Gln Ala Asp Leu Leu Lys
    1880                1885                1890

Cys Leu Asp Asp Ile Glu Lys Lys Leu Ala Ser Leu Pro Glu Pro
    1895                1900                1905

Arg Asp Glu Arg Lys Ile Lys Glu Ile Asp Arg Glu Leu Gln Lys
    1910                1915                1920

Lys Lys Glu Glu Leu Asn Ala Val Arg Arg Gln Ala Glu Gly Leu
    1925                1930                1935

Ser Glu Asp Gly Ala Ala Met Ala Val Glu Pro Thr Gln Ile Gln
    1940                1945                1950

Leu Ser Lys Arg Trp Arg Glu Ile Glu Ser Lys Phe Ala Gln Phe
    1955                1960                1965

Arg Arg Leu Asn Phe Ala Gln Ile His Thr Val His Glu Glu Ser
    1970                1975                1980

Val Val Ala Met Thr Glu Asp Met Pro Leu Glu Ile Ser Tyr Val
    1985                1990                1995

Pro Ser Thr Tyr Leu Thr Glu Ile Thr His Val Ser Gln Ala Leu
    2000                2005                2010

Ser Glu Val Glu Glu Leu Leu Asn Ala Pro Asp Leu Cys Ala Gln
    2015                2020                2025

Asp Phe Glu Asp Leu Phe Lys Gln Glu Glu Ser Leu Lys Asn Ile
    2030                2035                2040

Lys Asp Ser Leu Gln Gln Ile Ser Gly Arg Ile Asp Ile Ile His
    2045                2050                2055

Asn Lys Lys Thr Ala Ala Leu His Ser Ala Thr Pro Ala Glu Arg
    2060                2065                2070

Ala Lys Leu Gln Glu Ala Leu Ser Arg Leu Asp Phe Gln Trp Glu
    2075                2080                2085

Arg Val Asn Asn Met Tyr Lys Asp Arg Gln Gly Arg Phe Asp Arg
    2090                2095                2100

Ser Val Glu Lys Trp Arg Arg Phe His Tyr Asp Met Lys Ile Leu
    2105                2110                2115

Asn Gln Trp Leu Thr Glu Ala Glu Gln Phe Leu Lys Lys Thr Gln
    2120                2125                2130

Ile Pro Glu Asn Trp Glu His Ala Lys Tyr Lys Trp Tyr Leu Lys
    2135                2140                2145

Glu Leu Gln Asp Gly Ile Gly Gln Arg Gln Ser Val Val Arg Val
    2150                2155                2160

Leu Asn Ala Thr Gly Glu Glu Ile Ile Gln Gln Ser Ser Lys Thr
    2165                2170                2175

Asp Ala Ser Ile Leu Gln Glu Lys Leu Gly Ser Leu Asn Leu Arg
    2180                2185                2190

Trp Gln Glu Val Cys Lys Gln Leu Ala Glu Arg Lys Lys Arg Leu
    2195                2200                2205

Glu Glu Gln Lys Asn Ile Leu Ser Glu Phe Gln Arg Asp Val Asn
    2210                2215                2220

Glu Phe Val Leu Trp Leu Glu Glu Ala Asp Asn Val Ala Asn Ile
```

-continued

```
             2225                2230                2235

Pro Leu Glu Pro Gly Asn Glu Gln Gln Leu Lys Glu Lys Leu Glu
         2240                2245                2250

Gln Val Lys Leu Leu Ala Glu Glu Leu Pro Leu Arg Gln Gly Ile
         2255                2260                2265

Leu Lys Gln Leu Asn Glu Thr Gly Gly Thr Val Leu Val Ser Ala
         2270                2275                2280

Pro Leu Ser Pro Glu Glu Gln Asp Lys Leu Glu Asn Lys Leu Lys
         2285                2290                2295

Gln Thr Asn Leu Gln Trp Ile Lys Val Ser Arg Asn Leu Pro Glu
         2300                2305                2310

Lys Gln Glu Glu Ile Glu Ala His Val Lys Asp Leu Gly Gln Leu
         2315                2320                2325

Glu Glu Gln Leu Asn His Leu Leu Leu Trp Leu Ser Pro Ile Arg
         2330                2335                2340

Asn Gln Leu Glu Ile Tyr Asn Gln Pro Asn Gln Thr Gly Pro Phe
         2345                2350                2355

Asp Ile Lys Glu Ile Glu Val Ala Val Gln Ala Lys Gln Pro Asp
         2360                2365                2370

Val Glu Gly Ile Leu Ser Lys Gly Gln His Leu Tyr Lys Glu Lys
         2375                2380                2385

Pro Ala Thr Gln Pro Ala Lys Arg Lys Leu Glu Asp Leu Ser Ser
         2390                2395                2400

Asp Trp Lys Val Val Thr Gln Leu Leu Gln Glu Leu Arg Ala Lys
         2405                2410                2415

Gln Pro Gly Pro Ala Pro Gly Leu Thr Thr Val Arg Ala Pro Pro
         2420                2425                2430

Ser Gln Thr Val Thr Leu Val Thr Gln Pro Ala Val Thr Lys Glu
         2435                2440                2445

Thr Ala Ile Ser Lys Leu Glu Met Pro Ser Ser Leu Leu Leu Glu
         2450                2455                2460

Val Pro Ala Leu Ala Asp Phe Asn Arg Ala Trp Thr Glu Leu Thr
         2465                2470                2475

Asp Trp Leu Ser Leu Leu Asp Arg Val Ile Lys Ser Gln Arg Val
         2480                2485                2490

Met Val Gly Asp Leu Glu Asp Ile Asn Glu Met Ile Ile Lys Gln
         2495                2500                2505

Lys Ala Thr Leu Gln Asp Leu Glu Gln Arg Arg Pro Gln Leu Glu
         2510                2515                2520

Glu Leu Ile Thr Ala Ala Gln Asn Leu Lys Asn Lys Thr Ser Asn
         2525                2530                2535

Gln Glu Ala Arg Thr Ile Ile Thr Asp Arg Ile Glu Arg Ile Gln
         2540                2545                2550

Ser Gln Trp Asp Glu Val Gln Glu His Leu Gln Asn Arg Arg Leu
         2555                2560                2565

Gln Leu Thr Glu Met Leu Lys Asp Ser Thr Gln Trp Leu Glu Ala
         2570                2575                2580

Lys Glu Glu Ala Glu Gln Val Leu Gly Gln Ala Arg Ala Lys Leu
         2585                2590                2595

Glu Ser Trp Lys Glu Ala Pro Tyr Thr Val Asp Ala Ile Gln Lys
         2600                2605                2610

Lys Ile Thr Glu Thr Lys Gln Leu Ala Lys Asp Leu Arg Gln Trp
         2615                2620                2625
```

-continued

```
Gln Ile Asn Val Asp Val Ala Asn Asp Leu Ala Leu Lys Leu Leu
    2630                2635                2640

Arg Asp Tyr Ser Ala Asp Asp Thr Arg Lys Val His Met Ile Thr
    2645                2650                2655

Glu Asn Ile Asn Ala Ser Trp Ala Ser Ile His Lys Arg Leu Ser
    2660                2665                2670

Glu Arg Glu Ala Ala Leu Glu Glu Thr His Arg Leu Leu Gln Gln
    2675                2680                2685

Phe Pro Leu Asp Leu Glu Lys Phe Leu Ala Trp Leu Thr Glu Ala
    2690                2695                2700

Glu Thr Thr Ala Asn Val Leu Gln Asp Ala Thr His Lys Glu Arg
    2705                2710                2715

Leu Leu Glu Asp Ser Lys Gly Val Arg Glu Leu Met Lys Gln Trp
    2720                2725                2730

Gln Asp Leu Gln Gly Glu Ile Glu Ala His Thr Asp Ile Tyr His
    2735                2740                2745

Asn Leu Asp Glu Asn Gly Gln Lys Val Leu Arg Ser Leu Glu Gly
    2750                2755                2760

Ser Asp Asp Ala Ala Leu Leu Gln Arg Arg Leu Asp Asn Met Asn
    2765                2770                2775

Phe Lys Trp Ser Glu Leu Arg Lys Lys Ser Leu Asn Ile Arg Ser
    2780                2785                2790

His Leu Glu Ala Ser Ser Asp Gln Trp Lys Arg Leu His Leu Ser
    2795                2800                2805

Leu Gln Glu Leu Leu Val Trp Leu Gln Leu Lys Asp Asp Glu Leu
    2810                2815                2820

Ser Arg Gln Ala Pro Ile Gly Gly Asp Phe Pro Ala Val Gln Lys
    2825                2830                2835

Gln Asn Asp Val His Arg Ala Phe Lys Arg Glu Leu Lys Thr Lys
    2840                2845                2850

Glu Pro Val Ile Met Ser Thr Leu Glu Thr Val Arg Ile Phe Leu
    2855                2860                2865

Thr Glu Gln Pro Leu Glu Gly Leu Glu Lys Leu Tyr Gln Glu Pro
    2870                2875                2880

Arg Glu Leu Pro Pro Glu Arg Ala Gln Asn Val Thr Arg Leu
    2885                2890                2895

Leu Arg Lys Gln Ala Glu Glu Val Asn Thr Gln Trp Glu Lys Leu
    2900                2905                2910

Asn Val His Ser Ala Asp Trp Gln Arg Lys Ile Asp Glu Ala Leu
    2915                2920                2925

Glu Arg Leu Gln Glu Leu Gln Glu Ala Thr Asp Glu Leu Asp Leu
    2930                2935                2940

Lys Leu Arg Gln Ala Glu Val Ile Lys Gly Ser Trp Gln Pro Val
    2945                2950                2955

Gly Asp Leu Leu Ile Asp Ser Leu Gln Asp His Leu Glu Lys Val
    2960                2965                2970

Lys Ala Leu Arg Gly Glu Ile Thr Pro Leu Lys Glu Asn Val Ser
    2975                2980                2985

Tyr Val Asn Asp Leu Ala Arg Gln Leu Thr Thr Leu Gly Ile Gln
    2990                2995                3000

Leu Ser Pro Tyr Asn Leu Asn Thr Leu Glu Asp Leu Asn Thr Arg
    3005                3010                3015
```

-continued

```
Trp Lys Leu Leu Gln Val Ala Ile Glu Asp Arg Ile Arg Gln Leu
3020                3025                3030

His Glu Ala His Arg Asp Phe Gly Pro Ala Ser Gln His Phe Leu
3035                3040                3045

Ser Thr Ser Val Gln Gly Pro Trp Glu Arg Ala Ile Ser Pro Asn
3050                3055                3060

Lys Val Pro Tyr Tyr Ile Asn His Glu Thr Gln Thr Thr Cys Trp
3065                3070                3075

Asp His Pro Lys Met Thr Glu Leu Tyr Gln Ser Leu Ala Asp Leu
3080                3085                3090

Asn Asn Val Arg Phe Ser Ala Tyr Arg Thr Ala Met Lys Leu Arg
3095                3100                3105

Arg Leu Gln Lys Ala Leu Cys Leu Asp Leu Leu Ser Leu Ser Ala
3110                3115                3120

Ala Cys Asp Ala Leu Asp Gln His Asn Leu Lys Gln Asn Asp Gln
3125                3130                3135

Pro Met Asp Ile Leu Gln Val Ile Asn Cys Leu Thr Thr Ile Tyr
3140                3145                3150

Asp Arg Leu Glu Gln Glu His Asn Asn Leu Val Asn Val Pro Leu
3155                3160                3165

Cys Val Asp Met Cys Leu Asn Trp Leu Leu Asn Val Tyr Asp Thr
3170                3175                3180

Gly Arg Thr Gly Arg Ile Arg Val Leu Ser Phe Lys Thr Gly Ile
3185                3190                3195

Ile Ser Leu Cys Lys Ala His Leu Glu Asp Lys Tyr Arg Tyr Leu
3200                3205                3210

Phe Lys Gln Val Ala Ser Ser Thr Gly Phe Cys Asp Gln Arg Arg
3215                3220                3225

Leu Gly Leu Leu Leu His Asp Ser Ile Gln Ile Pro Arg Gln Leu
3230                3235                3240

Gly Glu Val Ala Ser Phe Gly Gly Ser Asn Ile Glu Pro Ser Val
3245                3250                3255

Arg Ser Cys Phe Gln Phe Ala Asn Asn Lys Pro Glu Ile Glu Ala
3260                3265                3270

Ala Leu Phe Leu Asp Trp Met Arg Leu Glu Pro Gln Ser Met Val
3275                3280                3285

Trp Leu Pro Val Leu His Arg Val Ala Ala Glu Thr Ala Lys
3290                3295                3300

His Gln Ala Lys Cys Asn Ile Cys Lys Glu Cys Pro Ile Ile Gly
3305                3310                3315

Phe Arg Tyr Arg Ser Leu Lys His Phe Asn Tyr Asp Ile Cys Gln
3320                3325                3330

Ser Cys Phe Phe Ser Gly Arg Val Ala Lys Gly His Lys Met His
3335                3340                3345

Tyr Pro Met Val Glu Tyr Cys Thr Pro Thr Thr Ser Gly Glu Asp
3350                3355                3360

Val Arg Asp Phe Ala Lys Val Leu Lys Asn Lys Phe Arg Thr Lys
3365                3370                3375

Arg Tyr Phe Ala Lys His Pro Arg Met Gly Tyr Leu Pro Val Gln
3380                3385                3390

Thr Val Leu Glu Gly Asp Asn Met Glu Thr Pro Val Thr Leu Ile
3395                3400                3405

Asn Phe Trp Pro Val Asp Ser Ala Pro Ala Ser Ser Pro Gln Leu
```

-continued

```
                3410                3415                3420

Ser His Asp Asp Thr His Ser Arg Ile Glu His Tyr Ala Ser Arg
    3425                3430                3435

Leu Lys Lys Met Glu Asn Ser Asn Gly Ser Tyr Leu Asn Asp Ser
    3440                3445                3450

Ile Ser Pro Asn Glu Ser Ile Asp Asp Glu His Leu Leu Ile Gln
    3455                3460                3465

His Tyr Trp Arg Ser Leu Asn Gln Glu Ser Pro Leu Ser Gln Pro
    3470                3475                3480

Arg Ser Pro Ala Gln Ile Leu Ile Ser Leu Glu Ser Glu Glu Arg
    3485                3490                3495

Gly Glu Leu Glu Arg Ile Leu Ala Asp Leu Glu Gly Arg Asn Arg
    3500                3505                3510

Asn Leu Gln Ala Glu Tyr Asp Arg Leu Lys Gln Gln His Glu His
    3515                3520                3525

Lys Gly Leu Ser Pro Leu Pro Ser Pro Pro Glu Met Met Pro Thr
    3530                3535                3540

Ser Pro Gln Ser Pro Arg Asp Ala Glu Leu Ile Ala Glu Ala Lys
    3545                3550                3555

Leu Leu Arg Gln His Lys Gly Arg Leu Glu Ala Arg Met Gln Ile
    3560                3565                3570

Leu Glu Asp His Asn Lys Gln Leu Glu Ser Gln Leu His Arg Leu
    3575                3580                3585

Arg Gln Leu Leu Glu Gln Pro Gln Ala Glu Ala Lys Val Asn Gly
    3590                3595                3600

Thr Thr Val Ser Ser Pro Ser Thr Ser Leu Gln Arg Ser Asp Ser
    3605                3610                3615

Ser Gln Pro Met Leu Leu Arg Val Val Gly Ser Gln Thr Ser Glu
    3620                3625                3630

Ser Met Gly Glu Glu Asp Leu Leu Ser Pro Pro Gln Asp Thr Ser
    3635                3640                3645

Thr Gly Leu Glu Glu Val Met Glu Gln Leu Asn His Ser Phe Pro
    3650                3655                3660

Ser Ser Arg Gly Arg Asn Thr Pro Gly Lys Pro Met Arg Glu Asp
    3665                3670                3675

Thr Met
    3680

<210> SEQ ID NO 50
<211> LENGTH: 251
<212> TYPE: PRT
<213> ORGANISM: Homo sapiens

<400> SEQUENCE: 50

Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
                20                  25                  30

Gly Lys Gln His Ile Glu Asn Leu Phe Ser Asp Leu Gln Asp Gly Arg
            35                  40                  45

Arg Leu Leu Asp Leu Leu Glu Gly Leu Thr Gly Gln Lys Leu Pro Lys
        50                  55                  60

Glu Lys Gly Ser Thr Arg Val His Ala Leu Asn Asn Val Asn Lys Ala
65                  70                  75                  80
```

```
Leu Arg Val Leu Gln Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Val Met Lys Asn Ile Met Ala
            115                 120                 125

Gly Leu Gln Gln Thr Asn Ser Glu Lys Ile Leu Leu Ser Trp Val Arg
130                 135                 140

Gln Ser Thr Arg Asn Tyr Pro Gln Val Asn Val Ile Asn Phe Thr Thr
145                 150                 155                 160

Ser Trp Ser Asp Gly Leu Ala Leu Asn Ala Leu Ile His Ser His Arg
                165                 170                 175

Pro Asp Leu Phe Asp Trp Asn Ser Val Val Cys Gln Gln Ser Ala Thr
            180                 185                 190

Gln Arg Leu Glu His Ala Phe Asn Ile Ala Arg Tyr Gln Leu Gly Ile
            195                 200                 205

Glu Lys Leu Leu Asp Pro Glu Asp Val Asp Thr Thr Tyr Pro Asp Lys
210                 215                 220

Lys Ser Ile Leu Met Tyr Ile Thr Ser Leu Phe Gln Val Leu Pro Gln
225                 230                 235                 240

Gln Val Ser Ile Glu Ala Ile Gln Glu Val Glu
                245                 250

<210> SEQ ID NO 51
<211> LENGTH: 2860
<212> TYPE: PRT
<213> ORGANISM: Homo sapiens

<400> SEQUENCE: 51

Met Leu Pro Arg Pro Lys Val Thr Lys Glu Glu His Phe Gln Leu
1               5                   10                  15

His His Gln Met His Tyr Ser Gln Gln Ile Thr Val Ser Leu Ala Gln
                20                  25                  30

Gly Tyr Glu Arg Thr Ser Ser Pro Lys Pro Arg Phe Lys Ser Tyr Ala
            35                  40                  45

Tyr Thr Gln Ala Ala Tyr Val Thr Thr Ser Asp Pro Thr Arg Ser Pro
50                  55                  60

Phe Pro Ser Gln His Leu Glu Ala Pro Glu Asp Lys Ser Phe Gly Ser
65                  70                  75                  80

Ser Leu Met Glu Ser Glu Val Asn Leu Asp Arg Tyr Gln Thr Ala Leu
                85                  90                  95

Glu Glu Val Leu Ser Trp Leu Leu Ser Ala Glu Asp Thr Leu Gln Ala
            100                 105                 110

Gln Gly Glu Ile Ser Asn Asp Val Glu Val Val Lys Asp Gln Phe His
            115                 120                 125

Thr His Glu Gly Tyr Met Met Asp Leu Thr Ala His Gln Gly Arg Val
130                 135                 140

Gly Asn Ile Leu Gln Leu Gly Ser Lys Leu Ile Gly Thr Gly Lys Leu
145                 150                 155                 160

Ser Glu Asp Glu Glu Thr Glu Val Gln Glu Gln Met Asn Leu Leu Asn
                165                 170                 175

Ser Arg Trp Glu Cys Leu Arg Val Ala Ser Met Glu Lys Gln Ser Asn
            180                 185                 190

Leu His Arg Val Leu Met Asp Leu Gln Asn Gln Lys Leu Lys Glu Leu
            195                 200                 205
```

-continued

```
Asn Asp Trp Leu Thr Lys Thr Glu Glu Arg Thr Arg Lys Met Glu Glu
    210                 215                 220
Glu Pro Leu Gly Pro Asp Leu Glu Asp Leu Lys Arg Gln Val Gln Gln
225                 230                 235                 240
His Lys Val Leu Gln Glu Asp Leu Glu Gln Glu Gln Val Arg Val Asn
                245                 250                 255
Ser Leu Thr His Met Val Val Val Asp Glu Ser Ser Gly Asp His
                260                 265                 270
Ala Thr Ala Ala Leu Glu Glu Gln Leu Lys Val Leu Gly Asp Arg Trp
            275                 280                 285
Ala Asn Ile Cys Arg Trp Thr Glu Asp Arg Trp Val Leu Leu Gln Asp
        290                 295                 300
Ile Leu Leu Lys Trp Gln Arg Leu Thr Glu Glu Gln Cys Leu Phe Ser
305                 310                 315                 320
Ala Trp Leu Ser Glu Lys Glu Asp Ala Val Asn Lys Ile His Thr Thr
                325                 330                 335
Gly Phe Lys Asp Gln Asn Glu Met Leu Ser Ser Leu Gln Lys Leu Ala
                340                 345                 350
Val Leu Lys Ala Asp Leu Glu Lys Lys Lys Gln Ser Met Gly Lys Leu
            355                 360                 365
Tyr Ser Leu Lys Gln Asp Leu Leu Ser Thr Leu Lys Asn Lys Ser Val
        370                 375                 380
Thr Gln Lys Thr Glu Ala Trp Leu Asp Asn Phe Ala Arg Cys Trp Asp
385                 390                 395                 400
Asn Leu Val Gln Lys Leu Glu Lys Ser Thr Ala Gln Ile Ser Gln Ala
                405                 410                 415
Val Thr Thr Thr Gln Pro Ser Leu Thr Gln Thr Thr Val Met Glu Thr
                420                 425                 430
Val Thr Thr Val Thr Thr Arg Glu Gln Ile Leu Val Lys His Ala Gln
            435                 440                 445
Glu Glu Leu Pro Pro Pro Pro Pro Gln Lys Lys Arg Gln Ile Thr Val
        450                 455                 460
Asp Ser Glu Ile Arg Lys Arg Leu Asp Val Asp Ile Thr Glu Leu His
465                 470                 475                 480
Ser Trp Ile Thr Arg Ser Glu Ala Val Leu Gln Ser Pro Glu Phe Ala
                485                 490                 495
Ile Phe Arg Lys Glu Gly Asn Phe Ser Asp Leu Lys Glu Lys Val Asn
                500                 505                 510
Ala Ile Glu Arg Glu Lys Ala Glu Lys Phe Arg Lys Leu Gln Asp Ala
            515                 520                 525
Ser Arg Ser Ala Gln Ala Leu Val Glu Gln Met Val Asn Glu Gly Val
        530                 535                 540
Asn Ala Asp Ser Ile Lys Gln Ala Ser Glu Gln Leu Asn Ser Arg Trp
545                 550                 555                 560
Ile Glu Phe Cys Gln Leu Leu Ser Glu Arg Leu Asn Trp Leu Glu Tyr
                565                 570                 575
Gln Asn Asn Ile Ile Ala Phe Tyr Asn Gln Leu Gln Gln Leu Glu Gln
                580                 585                 590
Met Thr Thr Thr Ala Glu Asn Trp Leu Lys Ile Gln Pro Thr Thr Pro
            595                 600                 605
Ser Glu Pro Thr Ala Ile Lys Ser Gln Leu Lys Ile Cys Lys Asp Glu
        610                 615                 620
```

-continued

```
Val Asn Arg Leu Ser Gly Leu Gln Pro Gln Ile Glu Arg Leu Lys Ile
625                 630                 635                 640

Gln Ser Ile Ala Leu Lys Glu Lys Gly Gln Gly Pro Met Phe Leu Asp
            645                 650                 655

Ala Asp Phe Val Ala Phe Thr Asn His Phe Lys Gln Val Phe Ser Asp
                660                 665                 670

Val Gln Ala Arg Glu Lys Glu Leu Gln Thr Ile Phe Asp Thr Leu Pro
            675                 680                 685

Pro Met Arg Tyr Gln Glu Thr Met Ser Ala Ile Arg Thr Trp Val Gln
690                 695                 700

Gln Ser Glu Thr Lys Leu Ser Ile Pro Gln Leu Ser Val Thr Asp Tyr
705                 710                 715                 720

Glu Ile Met Glu Gln Arg Leu Gly Glu Leu Gln Ala Leu Gln Ser Ser
                725                 730                 735

Leu Gln Glu Gln Gln Ser Gly Leu Tyr Tyr Leu Ser Thr Thr Val Lys
            740                 745                 750

Glu Met Ser Lys Lys Ala Pro Ser Glu Ile Ser Arg Lys Tyr Gln Ser
            755                 760                 765

Glu Phe Glu Glu Ile Glu Gly Arg Trp Lys Lys Leu Ser Ser Gln Leu
770                 775                 780

Val Glu His Cys Gln Lys Leu Glu Glu Gln Met Asn Lys Leu Arg Lys
785                 790                 795                 800

Ile Gln Asn His Ile Gln Thr Leu Lys Lys Trp Met Ala Glu Val Asp
                805                 810                 815

Val Phe Leu Lys Glu Glu Trp Pro Ala Leu Gly Asp Ser Glu Ile Leu
            820                 825                 830

Lys Lys Gln Leu Lys Gln Cys Arg Leu Leu Val Ser Asp Ile Gln Thr
            835                 840                 845

Ile Gln Pro Ser Leu Asn Ser Val Asn Glu Gly Gly Gln Lys Ile Lys
850                 855                 860

Asn Glu Ala Glu Pro Glu Phe Ala Ser Arg Leu Glu Thr Glu Leu Lys
865                 870                 875                 880

Glu Leu Asn Thr Gln Trp Asp His Met Cys Gln Gln Val Tyr Ala Arg
                885                 890                 895

Lys Glu Ala Leu Lys Gly Gly Leu Glu Lys Thr Val Ser Leu Gln Lys
            900                 905                 910

Asp Leu Ser Glu Met His Glu Trp Met Thr Gln Ala Glu Glu Glu Tyr
            915                 920                 925

Leu Glu Arg Asp Phe Glu Tyr Lys Thr Pro Asp Glu Leu Gln Lys Ala
930                 935                 940

Val Glu Glu Met Lys Arg Ala Lys Glu Glu Ala Gln Gln Lys Glu Ala
945                 950                 955                 960

Lys Val Lys Leu Leu Thr Glu Ser Val Asn Ser Val Ile Ala Gln Ala
                965                 970                 975

Pro Pro Val Ala Gln Glu Ala Leu Lys Lys Glu Leu Glu Thr Leu Thr
            980                 985                 990

Thr Asn Tyr Gln Trp Leu Cys Thr Arg Leu Asn Gly Lys Cys Lys Thr
            995                 1000                1005

Leu Glu Glu Val Trp Ala Cys Trp His Glu Leu Leu Ser Tyr Leu
    1010                1015                1020

Glu Lys Ala Asn Lys Trp Leu Asn Glu Val Glu Phe Lys Leu Lys
    1025                1030                1035

Thr Thr Glu Asn Ile Pro Gly Gly Ala Glu Glu Ile Ser Glu Val
```

```
                1040                1045                1050
Leu Asp Ser Leu Glu Asn Leu Met Arg His Ser Glu Asp Asn Pro
    1055                1060                1065
Asn Gln Ile Arg Ile Leu Ala Gln Thr Leu Thr Asp Gly Gly Val
    1070                1075                1080
Met Asp Glu Leu Ile Asn Glu Glu Leu Glu Thr Phe Asn Ser Arg
    1085                1090                1095
Trp Arg Glu Leu His Glu Glu Ala Val Arg Arg Gln Lys Leu Leu
    1100                1105                1110
Glu Gln Ser Ile Gln Ser Ala Gln Glu Thr Glu Lys Ser Leu His
    1115                1120                1125
Leu Ile Gln Glu Ser Leu Thr Phe Ile Asp Lys Gln Leu Ala Ala
    1130                1135                1140
Tyr Ile Ala Asp Lys Val Asp Ala Ala Gln Met Pro Gln Glu Ala
    1145                1150                1155
Gln Lys Ile Gln Ser Asp Leu Thr Ser His Glu Ile Ser Leu Glu
    1160                1165                1170
Glu Met Lys Lys His Asn Gln Gly Lys Glu Ala Ala Gln Arg Val
    1175                1180                1185
Leu Ser Gln Ile Asp Val Ala Gln Lys Lys Leu Gln Asp Val Ser
    1190                1195                1200
Met Lys Phe Arg Leu Phe Gln Lys Pro Ala Asn Phe Glu Leu Arg
    1205                1210                1215
Leu Gln Glu Ser Lys Met Ile Leu Asp Glu Val Lys Met His Leu
    1220                1225                1230
Pro Ala Leu Glu Thr Lys Ser Val Glu Gln Glu Val Val Gln Ser
    1235                1240                1245
Gln Leu Asn His Cys Val Asn Leu Tyr Lys Ser Leu Ser Glu Val
    1250                1255                1260
Lys Ser Glu Val Glu Met Val Ile Lys Thr Gly Arg Gln Ile Val
    1265                1270                1275
Gln Lys Lys Gln Thr Glu Asn Pro Lys Glu Leu Asp Glu Arg Val
    1280                1285                1290
Thr Ala Leu Lys Leu His Tyr Asn Glu Leu Gly Ala Lys Val Thr
    1295                1300                1305
Glu Arg Lys Gln Gln Leu Glu Lys Cys Leu Lys Leu Ser Arg Lys
    1310                1315                1320
Met Arg Lys Glu Met Asn Val Leu Thr Glu Trp Leu Ala Ala Thr
    1325                1330                1335
Asp Met Glu Leu Thr Lys Arg Ser Ala Val Glu Gly Met Pro Ser
    1340                1345                1350
Asn Leu Asp Ser Glu Val Ala Trp Gly Lys Ala Thr Gln Lys Glu
    1355                1360                1365
Ile Glu Lys Gln Lys Val His Leu Lys Ser Ile Thr Glu Val Gly
    1370                1375                1380
Glu Ala Leu Lys Thr Val Leu Gly Lys Lys Glu Thr Leu Val Glu
    1385                1390                1395
Asp Lys Leu Ser Leu Leu Asn Ser Asn Trp Ile Ala Val Thr Ser
    1400                1405                1410
Arg Ala Glu Glu Trp Leu Asn Leu Leu Leu Glu Tyr Gln Lys His
    1415                1420                1425
Met Glu Thr Phe Asp Gln Asn Val Asp His Ile Thr Lys Trp Ile
    1430                1435                1440
```

```
Ile Gln Ala Asp Thr Leu Leu Asp Glu Ser Glu Lys Lys Lys Pro
    1445                1450                1455

Gln Gln Lys Glu Asp Val Leu Lys Arg Leu Lys Ala Glu Leu Asn
    1460                1465                1470

Asp Ile Arg Pro Lys Val Asp Ser Thr Arg Asp Gln Ala Ala Asn
    1475                1480                1485

Leu Met Ala Asn Arg Gly Asp His Cys Arg Lys Leu Val Glu Pro
    1490                1495                1500

Gln Ile Ser Glu Leu Asn His Arg Phe Ala Ala Ile Ser His Arg
    1505                1510                1515

Ile Lys Thr Gly Lys Ala Ser Ile Pro Leu Lys Glu Leu Glu Gln
    1520                1525                1530

Phe Asn Ser Asp Ile Gln Lys Leu Leu Glu Pro Leu Glu Ala Glu
    1535                1540                1545

Ile Gln Gln Gly Val Asn Leu Lys Glu Glu Asp Phe Asn Lys Asp
    1550                1555                1560

Met Asn Glu Asp Asn Glu Gly Thr Val Lys Glu Leu Leu Gln Arg
    1565                1570                1575

Gly Asp Asn Leu Gln Gln Arg Ile Thr Asp Glu Arg Lys Arg Glu
    1580                1585                1590

Glu Ile Lys Ile Lys Gln Gln Leu Leu Gln Thr Lys His Asn Ala
    1595                1600                1605

Leu Lys Asp Leu Arg Ser Gln Arg Arg Lys Lys Ala Leu Glu Ile
    1610                1615                1620

Ser His Gln Trp Tyr Gln Tyr Lys Arg Gln Ala Asp Asp Leu Leu
    1625                1630                1635

Lys Cys Leu Asp Asp Ile Glu Lys Lys Leu Ala Ser Leu Pro Glu
    1640                1645                1650

Pro Arg Asp Glu Arg Lys Ile Lys Glu Ile Asp Arg Glu Leu Gln
    1655                1660                1665

Lys Lys Lys Glu Glu Leu Asn Ala Val Arg Arg Gln Ala Glu Gly
    1670                1675                1680

Leu Ser Glu Asp Gly Ala Ala Met Ala Val Glu Pro Thr Gln Ile
    1685                1690                1695

Gln Leu Ser Lys Arg Trp Arg Glu Ile Glu Ser Lys Phe Ala Gln
    1700                1705                1710

Phe Arg Arg Leu Asn Phe Ala Gln Ile His Thr Val Arg Glu Glu
    1715                1720                1725

Thr Met Met Val Met Thr Glu Asp Met Pro Leu Glu Ile Ser Tyr
    1730                1735                1740

Val Pro Ser Thr Tyr Leu Thr Glu Ile Thr His Val Ser Gln Ala
    1745                1750                1755

Leu Leu Glu Val Glu Gln Leu Leu Asn Ala Pro Asp Leu Cys Ala
    1760                1765                1770

Lys Asp Phe Glu Asp Leu Phe Lys Gln Glu Glu Ser Leu Lys Asn
    1775                1780                1785

Ile Lys Asp Ser Leu Gln Gln Ser Ser Gly Arg Ile Asp Ile Ile
    1790                1795                1800

His Ser Lys Lys Thr Ala Ala Leu Gln Ser Ala Thr Pro Val Glu
    1805                1810                1815

Arg Val Lys Leu Gln Glu Ala Leu Ser Gln Leu Asp Phe Gln Trp
    1820                1825                1830
```

-continued

Glu Lys Val Asn Lys Met Tyr Lys Asp Arg Gln Gly Arg Phe Asp
1835                1840                1845

Arg Ser Val Glu Lys Trp Arg Arg Phe His Tyr Asp Ile Lys Ile
    1850                1855                1860

Phe Asn Gln Trp Leu Thr Glu Ala Glu Gln Phe Leu Arg Lys Thr
    1865                1870                1875

Gln Ile Pro Glu Asn Trp Glu His Ala Lys Tyr Lys Trp Tyr Leu
    1880                1885                1890

Lys Glu Leu Gln Asp Gly Ile Gly Gln Arg Gln Thr Val Val Arg
    1895                1900                1905

Thr Leu Asn Ala Thr Gly Glu Glu Ile Ile Gln Gln Ser Ser Lys
    1910                1915                1920

Thr Asp Ala Ser Ile Leu Gln Glu Lys Leu Gly Ser Leu Asn Leu
    1925                1930                1935

Arg Trp Gln Glu Val Cys Lys Gln Leu Ser Asp Arg Lys Lys Arg
    1940                1945                1950

Leu Glu Glu Gln Lys Asn Ile Leu Ser Glu Phe Gln Arg Asp Leu
    1955                1960                1965

Asn Glu Phe Val Leu Trp Leu Glu Glu Ala Asp Asn Ile Ala Ser
    1970                1975                1980

Ile Pro Leu Glu Pro Gly Lys Glu Gln Gln Leu Lys Glu Lys Leu
    1985                1990                1995

Glu Gln Val Lys Leu Leu Val Glu Glu Leu Pro Leu Arg Gln Gly
    2000                2005                2010

Ile Leu Lys Gln Leu Asn Glu Thr Gly Gly Pro Val Leu Val Ser
    2015                2020                2025

Ala Pro Ile Ser Pro Glu Glu Gln Asp Lys Leu Glu Asn Lys Leu
    2030                2035                2040

Lys Gln Thr Asn Leu Gln Trp Ile Lys Val Ser Arg Ala Leu Pro
    2045                2050                2055

Glu Lys Gln Gly Glu Ile Glu Ala Gln Ile Lys Asp Leu Gly Gln
    2060                2065                2070

Leu Glu Lys Lys Leu Glu Asp Leu Glu Glu Gln Leu Asn His Leu
    2075                2080                2085

Leu Leu Trp Leu Ser Pro Ile Arg Asn Gln Leu Glu Ile Tyr Asn
    2090                2095                2100

Gln Pro Asn Gln Glu Gly Pro Phe Asp Val Gln Glu Thr Glu Ile
    2105                2110                2115

Ala Val Gln Ala Lys Gln Pro Asp Val Glu Glu Ile Leu Ser Lys
    2120                2125                2130

Gly Gln His Leu Tyr Lys Glu Lys Pro Ala Thr Gln Pro Val Lys
    2135                2140                2145

Arg Lys Leu Glu Asp Leu Ser Ser Glu Trp Lys Ala Val Asn Arg
    2150                2155                2160

Leu Leu Gln Glu Leu Arg Ala Lys Gln Pro Asp Leu Ala Pro Gly
    2165                2170                2175

Leu Thr Thr Ile Gly Ala Ser Pro Thr Gln Thr Val Thr Leu Val
    2180                2185                2190

Thr Gln Pro Val Val Thr Lys Glu Thr Ala Ile Ser Lys Leu Glu
    2195                2200                2205

Met Pro Ser Ser Leu Met Leu Glu Val Pro Ala Leu Ala Asp Phe
    2210                2215                2220

Asn Arg Ala Trp Thr Glu Leu Thr Asp Trp Leu Ser Leu Leu Asp

-continued

```
            2225                2230                2235
Gln Val Ile Lys Ser Gln Arg Val Met Val Gly Asp Leu Glu Asp
        2240                2245                2250
Ile Asn Glu Met Ile Ile Lys Gln Lys Ala Thr Met Gln Asp Leu
        2255                2260                2265
Glu Gln Arg Arg Pro Gln Leu Glu Glu Leu Ile Thr Ala Ala Gln
        2270                2275                2280
Asn Leu Lys Asn Lys Thr Ser Asn Gln Glu Ala Arg Thr Ile Ile
        2285                2290                2295
Thr Asp Arg Ile Glu Arg Ile Gln Asn Gln Trp Asp Glu Val Gln
        2300                2305                2310
Glu His Leu Gln Asn Arg Arg Gln Gln Leu Asn Glu Met Leu Lys
        2315                2320                2325
Asp Ser Thr Gln Trp Leu Glu Ala Lys Glu Glu Ala Glu Gln Val
        2330                2335                2340
Leu Gly Gln Ala Arg Ala Lys Leu Glu Ser Trp Lys Glu Gly Pro
        2345                2350                2355
Tyr Thr Val Asp Ala Ile Gln Lys Lys Ile Thr Glu Thr Lys Gln
        2360                2365                2370
Leu Ala Lys Asp Leu Arg Gln Trp Gln Thr Asn Val Asp Val Ala
        2375                2380                2385
Asn Asp Leu Ala Leu Lys Leu Leu Arg Asp Tyr Ser Ala Asp Asp
        2390                2395                2400
Thr Arg Lys Val His Met Ile Thr Glu Asn Ile Asn Ala Ser Trp
        2405                2410                2415
Arg Ser Ile His Lys Arg Val Ser Glu Arg Glu Ala Ala Leu Glu
        2420                2425                2430
Glu Thr His Arg Leu Leu Gln Gln Phe Pro Leu Asp Leu Glu Lys
        2435                2440                2445
Phe Leu Ala Trp Leu Thr Glu Ala Glu Thr Thr Ala Asn Val Leu
        2450                2455                2460
Gln Asp Ala Thr Arg Lys Glu Arg Leu Leu Glu Asp Ser Lys Gly
        2465                2470                2475
Val Lys Glu Leu Met Lys Gln Trp Gln Asp Leu Gln Gly Glu Ile
        2480                2485                2490
Glu Ala His Thr Asp Val Tyr His Asn Leu Asp Glu Asn Ser Gln
        2495                2500                2505
Lys Ile Leu Arg Ser Leu Glu Gly Ser Asp Asp Ala Val Leu Leu
        2510                2515                2520
Gln Arg Arg Leu Asp Asn Met Asn Phe Lys Trp Ser Glu Leu Arg
        2525                2530                2535
Lys Lys Ser Leu Asn Ile Arg Ser His Leu Glu Ala Ser Ser Asp
        2540                2545                2550
Gln Trp Lys Arg Leu His Leu Ser Leu Gln Glu Leu Leu Val Trp
        2555                2560                2565
Leu Gln Leu Lys Asp Asp Glu Leu Ser Arg Gln Ala Pro Ile Gly
        2570                2575                2580
Gly Asp Phe Pro Ala Val Gln Lys Gln Asn Asp Val His Arg Ala
        2585                2590                2595
Phe Lys Arg Glu Leu Lys Thr Lys Glu Pro Val Ile Met Ser Thr
        2600                2605                2610
Leu Glu Thr Val Arg Ile Phe Leu Thr Glu Gln Pro Leu Glu Gly
        2615                2620                2625
```

```
Leu Glu Lys Leu Tyr Gln Glu Pro Arg Glu Leu Pro Pro Glu Glu
    2630                2635                2640

Arg Ala Gln Asn Val Thr Arg Leu Leu Arg Lys Gln Ala Glu Glu
    2645                2650                2655

Val Asn Thr Glu Trp Glu Lys Leu Asn Leu His Ser Ala Asp Trp
    2660                2665                2670

Gln Arg Lys Ile Asp Glu Thr Leu Glu Arg Leu Gln Glu Leu Gln
    2675                2680                2685

Glu Ala Thr Asp Glu Leu Asp Leu Lys Leu Arg Gln Ala Glu Val
    2690                2695                2700

Ile Lys Gly Ser Trp Gln Pro Val Gly Asp Leu Leu Ile Asp Ser
    2705                2710                2715

Leu Gln Asp His Leu Glu Lys Val Lys Ala Leu Arg Gly Glu Ile
    2720                2725                2730

Ala Pro Leu Lys Glu Asn Val Ser His Val Asn Asp Leu Ala Arg
    2735                2740                2745

Gln Leu Thr Thr Leu Gly Ile Gln Leu Ser Pro Tyr Asn Leu Ser
    2750                2755                2760

Thr Leu Glu Asp Leu Asn Thr Arg Trp Lys Leu Leu Gln Val Ala
    2765                2770                2775

Val Glu Asp Arg Val Arg Gln Leu His Glu Ala His Arg Asp Phe
    2780                2785                2790

Gly Pro Ala Ser Gln His Phe Leu Ser Thr Ser Val Gln Gly Pro
    2795                2800                2805

Trp Glu Arg Ala Ile Ser Pro Asn Lys Val Pro Tyr Tyr Ile Asn
    2810                2815                2820

His Glu Thr Gln Thr Thr Cys Trp Asp His Pro Lys Met Thr Glu
    2825                2830                2835

Leu Tyr Gln Ser Leu Ala Asp Leu Asn Asn Val Arg Phe Ser Ala
    2840                2845                2850

Tyr Arg Thr Ala Met Lys Leu
    2855                2860

<210> SEQ ID NO 52
<211> LENGTH: 296
<212> TYPE: PRT
<213> ORGANISM: Homo sapiens

<400> SEQUENCE: 52

Arg Arg Leu Gln Lys Ala Leu Cys Leu Asp Leu Leu Ser Leu Ser Ala
1               5                   10                  15

Ala Cys Asp Ala Leu Asp Gln His Asn Leu Lys Gln Asn Asp Gln Pro
                20                  25                  30

Met Asp Ile Leu Gln Ile Ile Asn Cys Leu Thr Thr Ile Tyr Asp Arg
            35                  40                  45

Leu Glu Gln Glu His Asn Asn Leu Val Asn Val Pro Leu Cys Val Asp
        50                  55                  60

Met Cys Leu Asn Trp Leu Leu Asn Val Tyr Asp Thr Gly Arg Thr Gly
65                  70                  75                  80

Arg Ile Arg Val Leu Ser Phe Lys Thr Gly Ile Ile Ser Leu Cys Lys
                85                  90                  95

Ala His Leu Glu Asp Lys Tyr Arg Tyr Leu Phe Lys Gln Val Ala Ser
            100                 105                 110

Ser Thr Gly Phe Cys Asp Gln Arg Arg Leu Gly Leu Leu Leu His Asp
```

```
                    115                 120                 125
Ser Ile Gln Ile Pro Arg Gln Leu Gly Glu Val Ala Ser Phe Gly Gly
    130                 135                 140

Ser Asn Ile Glu Pro Ser Val Arg Ser Cys Phe Gln Phe Ala Asn Asn
145                 150                 155                 160

Lys Pro Glu Ile Glu Ala Ala Leu Phe Leu Asp Trp Met Arg Leu Glu
                165                 170                 175

Pro Gln Ser Met Val Trp Leu Pro Val Leu His Arg Val Ala Ala Ala
            180                 185                 190

Glu Thr Ala Lys His Gln Ala Lys Cys Asn Ile Cys Lys Glu Cys Pro
        195                 200                 205

Ile Ile Gly Phe Arg Tyr Arg Ser Leu Lys His Phe Asn Tyr Asp Ile
    210                 215                 220

Cys Gln Ser Cys Phe Phe Ser Gly Arg Val Ala Lys Gly His Lys Met
225                 230                 235                 240

His Tyr Pro Met Val Glu Tyr Cys Thr Pro Thr Thr Ser Gly Glu Asp
                245                 250                 255

Val Arg Asp Phe Ala Lys Val Leu Lys Asn Lys Phe Arg Thr Lys Arg
            260                 265                 270

Tyr Phe Ala Lys His Pro Arg Met Gly Tyr Leu Pro Val Gln Thr Val
        275                 280                 285

Leu Glu Gly Asp Asn Met Glu Thr
    290                 295

<210> SEQ ID NO 53
<211> LENGTH: 277
<212> TYPE: PRT
<213> ORGANISM: Homo sapiens

<400> SEQUENCE: 53

Pro Val Thr Leu Ile Asn Phe Trp Pro Val Asp Ser Ala Pro Ala Ser
1               5                   10                  15

Ser Pro Gln Leu Ser His Asp Asp Thr His Ser Arg Ile Glu His Tyr
            20                  25                  30

Ala Ser Arg Leu Ala Glu Met Glu Asn Ser Asn Gly Ser Tyr Leu Asn
        35                  40                  45

Asp Ser Ile Ser Pro Asn Glu Ser Ile Asp Asp Glu His Leu Leu Ile
    50                  55                  60

Gln His Tyr Cys Gln Ser Leu Asn Gln Asp Ser Pro Leu Ser Gln Pro
65                  70                  75                  80

Arg Ser Pro Ala Gln Ile Leu Ile Ser Leu Glu Ser Glu Glu Arg Gly
                85                  90                  95

Glu Leu Glu Arg Ile Leu Ala Asp Leu Glu Glu Asn Arg Asn Leu
            100                 105                 110

Gln Ala Glu Tyr Asp Arg Leu Lys Gln Gln His Glu His Lys Gly Leu
        115                 120                 125

Ser Pro Leu Pro Ser Pro Pro Glu Met Met Pro Thr Ser Pro Gln Ser
    130                 135                 140

Pro Arg Asp Ala Glu Leu Ile Ala Glu Ala Lys Leu Leu Arg Gln His
145                 150                 155                 160

Lys Gly Arg Leu Glu Ala Arg Met Gln Ile Leu Glu Asp His Asn Lys
                165                 170                 175

Gln Leu Glu Ser Gln Leu His Arg Leu Arg Gln Leu Leu Glu Gln Pro
            180                 185                 190
```

```
Gln Ala Glu Ala Lys Val Asn Gly Thr Thr Val Ser Ser Pro Ser Thr
        195                 200                 205

Ser Leu Gln Arg Ser Asp Ser Gln Pro Met Leu Leu Arg Val Val
        210                 215                 220

Gly Ser Gln Thr Ser Asp Ser Met Gly Glu Glu Asp Leu Leu Ser Pro
225                 230                 235                 240

Pro Gln Asp Thr Ser Thr Gly Leu Glu Glu Val Met Glu Gln Leu Asn
                245                 250                 255

Asn Ser Phe Pro Ser Ser Arg Gly Arg Asn Thr Pro Gly Lys Pro Met
                260                 265                 270

Arg Glu Asp Thr Met
        275

<210> SEQ ID NO 54
<211> LENGTH: 110
<212> TYPE: PRT
<213> ORGANISM: Macaca mulatta

<400> SEQUENCE: 54

Glu Ile Ser Tyr Val Pro Ser Thr Tyr Leu Thr Glu Ile Thr His Val
1               5                   10                  15

Ser Gln Ala Leu Ser Glu Val Glu Gln Leu Leu Asn Ala Pro Asp Leu
            20                  25                  30

Cys Ala Lys Asp Phe Glu Asp Leu Phe Lys Gln Glu Glu Ser Leu Lys
        35                  40                  45

Asn Ile Lys Asp Ile Leu Gln Gln Ser Ser Gly Arg Ile Asp Ile Ile
    50                  55                  60

His Ser Lys Lys Thr Ala Ala Leu Gln Ser Ala Thr Pro Val Glu Arg
65                  70                  75                  80

Val Lys Leu Gln Glu Ala Leu Ser Gln Ile Asp Phe Gln Trp Glu Lys
                85                  90                  95

Val Asn Lys Met Tyr Lys Asp Arg Gln Gly Arg Phe Asp Arg
                100                 105                 110

<210> SEQ ID NO 55
<211> LENGTH: 107
<212> TYPE: PRT
<213> ORGANISM: Macaca mulatta

<400> SEQUENCE: 55

Ser Val Glu Lys Trp Arg Arg Phe His Tyr Asp Ile Lys Ile Phe Asn
1               5                   10                  15

Gln Trp Leu Thr Glu Ala Glu Gln Phe Leu Arg Lys Thr Gln Ile Pro
            20                  25                  30

Glu Asn Trp Glu His Ala Lys Tyr Lys Trp Tyr Leu Lys Glu Leu Gln
        35                  40                  45

Asp Gly Ile Gly Gln Arg Gln Thr Val Val Arg Thr Leu Asn Ala Thr
    50                  55                  60

Gly Glu Glu Ile Ile Gln Gln Ser Ser Lys Thr Asp Ala Ser Ile Leu
65                  70                  75                  80

Gln Glu Lys Leu Gly Ser Leu Asn Leu Arg Trp Gln Glu Val Cys Lys
                85                  90                  95

Gln Leu Ser Glu Arg Lys Lys Arg Leu Glu Glu
                100                 105

<210> SEQ ID NO 56
<211> LENGTH: 110
```

```
<212> TYPE: PRT
<213> ORGANISM: Sus scrofa

<400> SEQUENCE: 56

Glu Ile Ser Tyr Val Pro Ser Ala Tyr Leu Thr Glu Ile Thr His Val
1               5                   10                  15

Ser Gln Ala Leu Ser Glu Val Glu Gln Leu Leu Asn Ala Pro Asp Leu
            20                  25                  30

Cys Ala Lys Asp Phe Glu Asp Leu Phe Lys Gln Glu Glu Ser Leu Lys
        35                  40                  45

Asn Ile Lys Asp Ser Leu Gln Gln Ile Ser Gly Arg Val Lys Glu Glu
    50                  55                  60

His Asn Lys Lys Thr Ala Gly Leu Gln Ser Ala Thr Pro Val Glu Arg
65                  70                  75                  80

Thr Arg Leu Gln Glu Ala Leu Ser Gln Leu Asp Phe Gln Trp Glu Arg
                85                  90                  95

Val Asn Lys Met Tyr Lys Asp Arg Gln Gly Lys Phe Asp Arg
            100                 105                 110

<210> SEQ ID NO 57
<211> LENGTH: 107
<212> TYPE: PRT
<213> ORGANISM: Sus scrofa

<400> SEQUENCE: 57

Ser Val Glu Lys Trp Arg Arg Phe His Tyr Asp Met Lys Ile Phe Asn
1               5                   10                  15

Gln Trp Leu Thr Glu Ala Glu His Phe Leu Lys Lys Thr Gln Ile Pro
            20                  25                  30

Glu Asn Trp Glu His Ala Lys Tyr Lys Trp Tyr Leu Lys Glu Leu Gln
        35                  40                  45

Asp Gly Ile Gly Gln Arg Gln Thr Ile Val Arg Val Leu Asn Ala Thr
    50                  55                  60

Gly Glu Glu Val Ile Gln Gln Ser Ser Lys Thr Asp Ala Ser Ile Leu
65                  70                  75                  80

Gln Glu Lys Leu Gly Ser Leu Asn Leu Arg Trp Gln Glu Val Cys Lys
                85                  90                  95

Gln Leu Ala Glu Arg Lys Lys Arg Leu Glu Glu
            100                 105

<210> SEQ ID NO 58
<211> LENGTH: 110
<212> TYPE: PRT
<213> ORGANISM: Mus musculus

<400> SEQUENCE: 58

Asp Val Ser Tyr Val Pro Ser Thr Tyr Leu Thr Glu Ile Ser His Ile
1               5                   10                  15

Leu Gln Ala Leu Ser Glu Val Asp His Leu Leu Asn Thr Pro Glu Leu
            20                  25                  30

Cys Ala Lys Asp Phe Glu Asp Leu Phe Lys Gln Glu Glu Ser Leu Lys
        35                  40                  45

Asn Ile Lys Asp Asn Leu Gln Gln Ile Ser Gly Arg Ile Asp Ile Ile
    50                  55                  60

His Lys Lys Lys Thr Ala Ala Leu Gln Ser Ala Thr Ser Met Glu Lys
65                  70                  75                  80

Val Lys Val Gln Glu Ala Val Ala Gln Met Asp Phe Gln Gly Glu Lys
```

```
                   85                  90                  95

Leu His Arg Met Tyr Lys Glu Arg Gln Gly Arg Phe Asp Arg
            100                 105                 110

<210> SEQ ID NO 59
<211> LENGTH: 107
<212> TYPE: PRT
<213> ORGANISM: Mus musculus

<400> SEQUENCE: 59

Ser Val Glu Lys Trp Arg His Phe His Tyr Asp Met Lys Val Phe Asn
1               5                  10                  15

Gln Trp Leu Asn Glu Val Glu Gln Phe Phe Lys Lys Thr Gln Asn Pro
            20                  25                  30

Glu Asn Trp Glu His Ala Lys Tyr Lys Trp Tyr Leu Lys Glu Leu Gln
        35                  40                  45

Asp Gly Ile Gly Gln Arg Gln Ala Val Val Arg Thr Leu Asn Ala Thr
    50                  55                  60

Gly Glu Glu Ile Ile Gln Gln Ser Ser Lys Thr Asp Val Asn Ile Leu
65                  70                  75                  80

Gln Glu Lys Leu Gly Ser Leu Ser Leu Arg Trp His Asp Ile Cys Lys
                85                  90                  95

Glu Leu Ala Glu Arg Arg Lys Arg Ile Glu Glu
            100                 105

<210> SEQ ID NO 60
<211> LENGTH: 110
<212> TYPE: PRT
<213> ORGANISM: Gallus gallus

<400> SEQUENCE: 60

Glu Thr Thr Tyr Val Pro Ser Thr Tyr Leu Ala Glu Ile Leu Gln Leu
1               5                  10                  15

Leu Gln Ala Leu Ser Glu Val Glu Glu Arg Leu Asn Ser Pro Val Leu
            20                  25                  30

Gln Ala Lys Asp Cys Glu Asp Leu Leu Lys Gln Glu Glu Cys Leu Lys
        35                  40                  45

Asn Ile Lys Asp Cys Leu Gly Arg Leu Gln Gly His Ile Asp Ile Ile
    50                  55                  60

His Ser Lys Lys Thr Pro Ala Leu Gln Ser Ala Thr Pro Arg Glu Thr
65                  70                  75                  80

Ala Asn Ile Gln Asp Lys Leu Thr Gln Leu Asn Ser Gln Trp Glu Lys
                85                  90                  95

Val Asn Lys Met Tyr Arg Asp Arg Gln Ala Arg Phe Asp Lys
            100                 105                 110

<210> SEQ ID NO 61
<211> LENGTH: 106
<212> TYPE: PRT
<213> ORGANISM: Gallus gallus

<400> SEQUENCE: 61

Glu Lys Trp Arg Leu Phe His Cys Glu Met Lys Ser Phe Asn Glu Trp
1               5                  10                  15

Leu Thr Glu Thr Glu Glu Lys Leu Ser Arg Ala Gln Ile Glu Ala Gly
            20                  25                  30

Asp Val Gly His Val Lys Thr Lys Gln Phe Leu Gln Glu Leu Gln Asp
        35                  40                  45
```

```
Gly Ile Gly Arg Gln Gln Thr Val Val Lys Thr Leu Asn Val Thr Gly
    50                  55                  60

Glu Glu Ile Ile Glu Gln Ser Ser Ala Ala Asp Ala Asn Val Leu Lys
65                   70                  75                  80

Glu Gln Leu Gly Asn Leu Asn Thr Arg Trp Gln Glu Ile Cys Arg Gln
                85                  90                  95

Leu Val Glu Lys Arg Lys Arg Ile Glu Glu
            100             105
```

SYNTHETIC MINI/MICRO-DYSTROPHIN GENES TO RESTORE NNOS TO THE SARCOLEMMA

CROSS-REFERENCE TO RELATED APPLICATIONS

This application claims the benefit of U.S. Provisional Application Ser. Nos. 60/881,129 filed Jan. 18, 2007 and 60/999,321 filed Oct. 16, 2007.

STATEMENT OF GOVERNMENT RIGHTS

This invention was made at least in part from government support under Grant No. AR49419 from the National Institutes of Health of the United States of America. The U.S. Government may have certain rights in the invention.

FIELD OF THE INVENTION

The present invention relates to novel dystrophin mini/micro-genes that retain the essential biological functions of a full-length dystrophin gene. More particularly, the present invention relates to a series of synthetic mini/micro-dystrophin genes capable of restoring neuronal nitric oxide synthase (nNOS) to the sarcolemma.

BACKGROUND OF THE INVENTION

The dystrophin-deficient muscle diseases include Duchenne muscular dystrophy (DMD), Becker muscular dystrophy (BMD), and X-linked dilated cardiomyopathy (XLDC). They are among the most common genetic diseases and affect more than one male infant in every 3,000 newborns. The progressive muscle degeneration and weakness usually confine the patients to wheelchairs by their early teens, and lead to death by their early twenties. Women carriers are also affected in their 40s to 50s. The above mentioned muscle diseases are caused by mutations in the dystrophin gene, specifically, the X-linked recessive mutations. The dystrophin gene is the largest gene known to date, which spans nearly 2.4 million base-pairs on the X-chromosome with 79 exons, a coding sequence of about 11.5 kb, and a high rate of de novo mutations.

Currently, there is no effective treatment for dystrophin-deficient diseases. Novel genetic approaches including cell therapy and gene therapy have been actively explored. However, the tremendous size of the dystrophin gene and mRNA (14 kilobases; kb) are formidable obstacles to the development of gene therapy. For this reason, studies have focused on developing smaller abbreviated versions of the mini-dystrophin or micro-dystrophin genes. These abbreviated genes can be introduced via a viral vector (such as an AAV vector and a lentiviral vector) or via stem cells (such as mesoangioblasts, CD133+ stem cell, and side population cells) (Yuasa et al., 1998; Wang et al., 2000; Ferrer et al., 2000; Harper et al., 2002; Fabb et al., 2002; Sakamoto et al., 2002; Bachrach et al., 2004; Sampaolesi et al., 2006; Benchaouir et al 2007, Cell Stem Cell 1:646-657). The microgene generally refers to the naturally occurring and the synthetic dystrophin genes that have a coding sequence equal to or less than 5 kb and can be packaged in a single adeno-associated viral vector (AAV). The minigene refers to the synthetic dystrophin genes that have a coding sequence equal to or less than 10 kb, but larger than 5 kb. The minigene cannot be packaged in a single AAV vector but can be delivered through a variant of dual vectors such as the overlapping vector, the trans-splicing vector and the hybrid vector.

The wild type dystrophin gene carries two main biological functions. One is to provide a mechanic link between the cytoskeleton and the extracellular matrix so that the muscle membrane is stabilized during contraction. The other is to provide signaling function for a number of important cellular activities. The signaling function of dystrophin is accomplished mainly through a partner protein called neuronal nitric oxide synthase (nNOS) (Rando, 2001). Several studies have shown that nNOS is recruited to the sarcolemma by the full-length dystrophin protein (Brenman et al., 1995; Brenman et al., 1996). Recent studies further suggested that the loss of nNOS in dystrophin-deficient muscle contributed significantly to the disease progression in animal models of DMD and human DMD patients (Brenman et al., 1995; Chang et al., 1996; Thomas et al., 1998; Sander et al., 2000). Furthermore, transgenic over-expression of nNOS ameliorates muscle pathology in the mdx mouse model of DMD (Wehling et al., 2001; Tidball and Wehling-Henricks, 2004; Shiao et al., 2004; Wehling-Henricks et al., 2005).

Attempts to generate dystrophin minigenes and microgenes have been documented. For example, the ΔR4-R23/ΔC micro-dystrophin can reduce histopathology in mouse models of DMD. However, this micro-protein cannot recover muscle specific force to the normal level (Harper et al., 2002; Gregorevic et al., 2004; Liu et al., 2005; Yue et al., 2006; Gregorevic et al., 2006). The ΔH2-R19 mini-dystrophin gene is derived from a very mild patient (England et al., 1990; Harper et al., 2002). This minigene is better than the ΔR4-R23 microgene or the ΔR4-R23/ΔC microgene because it can recover the muscle specific force to the same level as the full-length dystrophin gene (Harper et al., 2002; Lai et al., 2005). However, the minigene cannot restore nNOS. As a matter of fact, none of the existing mini- or micro-dystrophin genes have the ability to recruit nNOS to the sarcolemma (Table 1) (Chao et al., 1996; Crawford et al., 2000; Warner et al., 2002; Wells et al., 2003; Torelli et al., 2004; Lai et al., 2005; Yue et al., 2006; Li et al., 2006; Judge et al., 2006). The failure to restore sarcolemmal nNOS will significantly reduce the therapeutic efficacy of the minimized dystrophin genes.

Previously it was thought that nNOS is recruited to the sarcolemma through the C-terminal domain of the dystrophin protein (Brenman et al., 1995; Brenman et al., 1996). The full-length dystrophin protein has four domains including the N-terminal domain, mid-rod domain, cysteine-rich domain, and C-terminal domain. The N-terminal domain and a portion of the mid-rod domain interact with cytoskeleton protein F-actin. The mid-rod domain contains 24 spectrin-like repeats and four hinges. The cysteine-rich domain interacts with transmembrane protein dystroglycan to connect dystrophin to the extracellular matrix. The C-terminal domain contains two syntrophin binding sites and one dystrobrevin binding site. Several studies suggest that nNOS is recruited to the sarcolemma through a PDZ/PDZ domain interaction between nNOS and α-syntrophin (Brenman et al., 1996; Hillier et al., 1999; Kameya et al., 1999; Tochio et al., 1999; Adams et al., 2001; Miyagoe-Suzuki and Takeda, 2001). This seems to suggest that a mini- or micro-gene with the C-terminal domain should be able to recruit nNOS to the sarcolemma. However, studies have repeatedly shown that none of the existing C-terminal domain containing mini/micro-dystrophin proteins can bring nNOS to the sarcolemma although syntrophin is perfectly localized to the sarcolemma in these occasions (Chao et al., 1996; Lai et al., 2005). Furthermore, a C-terminal truncated full-length dystrophin protein was shown to recruit nNOS to the sarcolemma (Crawford et al., 2000).

Table 1 evaluates and summarizes the structures and functions of several naturally occurring dystrophin genes and several representative synthetic dystrophin minigenes and microgenes. Among all the tested genes, only the natural isoform Dp427 (full-length dystrophin gene) and Dp260 (retinal isoform of the full-length gene), and a C-terminal truncated full-length gene (Δ71-78) have been confirmed to restore nNOS to the sarcolemma. However, as discussed above, these genes are too big for AAV or lentiviral vector packaging.

Therefore, there is a need for developing a novel mini/micro-dystrophin gene, or a series thereof, with the ability to restore nNOS to the sarcolemma, and to be used for gene therapy in the treatment of DMD, BMD and XLDC.

SUMMARY OF THE INVENTION

The present invention has identified novel dystrophin minigenes and micro-genes that is significantly reduced in size relative to the full-length dystrophin gene and can restore both the mechanic link function and signaling function, such as neuronal nitric oxide synthase (nNOS) to the sarcolemma.

In one aspect, the present invention is directed to a nucleic acid molecule (also referred to in the present application as minigene or microgene) that contains a nucleotide sequence coding for a modified or non-full-length dystrophin polypeptide that retains the N-terminal domain, the cysteine-rich domain, two or more repeats of the mid-rod domain, and two or more hinges of the mid-rod domain of a full-length dystrophin protein.

Preferably, the nucleic acid molecule retains at least R16 and R17 among the retained repeats of the mid-rod domain. H1 and H4 are among the preferred retained hinges of the mid-rod domain.

In a particular aspect, the modified or non-full-length dystrophin polypeptide encoded by the minigene or microgene of the present invention further retains the C-terminal domain of a full-length dystrophin protein.

In another particular aspect, the present invention provides modified or non-full-length dystrophin polypeptide molecules that have amino acid sequence as set forth in SEQ ID NOs: 1, which can be encoded by mini-dystrophin genes ΔH2-R15 (SEQ ID NO: 7), ΔH2-R15/ΔC (SEQ ID NO: 10), ΔH2-R15/ΔR18-19 (SEQ ID NO: 8), ΔR3-15/ΔR18-23/ΔC (SEQ ID NO: 12), ΔR2-15/ΔR18-23/ΔC (SEQ ID NO: 13), ΔR2-15/ΔH3-R23/ΔC (SEQ ID NO: 11), respectively, or modifications or variations thereof. See also FIGS. 1B and 1C.

In another aspect, the present invention is directed to recombinant adeno-associated viral vectors (AAVs) to deliver the nucleic acid molecule of the present invention (mini- and/or micro-dystrophin genes) that are capable of restoring neuronal nitric oxide synthase (nNOS) to the sarcolemma. A recombinant AAV vector (single vector or dual vectors) in accordance with the present invention includes any one of the nucleic acid molecule of the present invention (a mini- or micro-dystrophin gene) that is capable of restoring nNOS to the sarcolemma, an expression cassette (a promoter and a polyA), and viral inverted terminal repeats (ITRs). A particular aspect of the present invention provides exemplary AAV vectors that include, but are not limited to, AV.CMV.ΔR2-15/ΔR18-23/ΔC, AV.miniCMV.ΔR3-15/ΔR18-23/ΔC, AV.miniCMV.ΔR2-15/ΔH3-R23/ΔC, AV.ΔH2-R15Donor/AV.ΔH2-R15Acceptor, AV.ΔH2-R15/ΔR18-19.Head/AV.ΔH2-R15/ΔR18-19.Tail, and modifications or variations thereof. The present invention also provides exemplary lentiviral vectors that include, but are not limited to, Lenti.CK6.ΔR2-15/ΔR18-23/ΔC, Lenti.CK6.ΔR3-15/ΔR18-23/ΔC, and Lenti.CK6.ΔH2-R15. See FIG. 2.

According to the present invention, a dual recombinant AAV vector system contains two AAV vectors, wherein one of the two AAV vectors contains a part of the nucleic acid molecule, minigenes or microgene of the present invention, and the other vector comprise the remaining part of the nucleic acid molecule, minigenes or microgene, and wherein the two vectors further contain sequences that permit recombination with each other to produce the nucleic acid molecule, minigenes or microgene in full length.

In yet another aspect, the present invention is directed to a method for the treatments of DMD, BMD and/or XLDC in a subject by administering to the subject a therapeutically effective amount of the nucleic acid molecule of the present invention (mini/micro-dystrophin genes) with or without a pharmaceutically acceptable carrier. In a particular aspect, the route of the administration in accordance with the method of the present invention includes, but is not limited to, local or regional muscle injection to improve local muscle function in patients, systemic delivery (such as intravenous, intra-artery, intraperitoneal, and intra-heart) to all muscles in a region or in the whole body in patients, in vitro infection of myogenic stem cells with AAV or lentiviral vector followed by local and/or systemic delivery.

In still yet another aspect, the present invention is directed to a pharmaceutical composition comprising one or more of the AAV vectors and lentiviral vectors of the present invention and a pharmaceutically acceptable carrier.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1B shows the DNA sequence and the amino acid sequence of the R16 and R17 from the human dystrophin gene (nucleotides 5920-6624 of SEQ ID NO:2 and SEQ ID NOs:35-36) and the protein (residues 1722-1956 of SEQ ID NO:51), respectively. The sequences before the vertical line are R16 and the sequences after the vertical line are R17.

FIG. 1C shows the amino acid sequence alignment from R16 and R17 of the dystrophin gene from different species including human (residues 1740-1849 of SEQ ID NO:51 corresponding to R16 and residues 1850-1956 of SEQ ID NO:51 corresponding to R17), rhesus monkey (macaca mulatta; SEQ ID NOS:54-55), pig (sus scrofa; SEQ ID NOS: 56-57), dog (canis familliaris; residues 1994-2103 of SEQ ID NO:49 corresponding to R16 and residues 2104-2210 of SEQ ID NO:49, corresponding to R17), mouse (mus musculus; SEQ ID NOs:58-59), and chicken (gallus gallus; SEQ ID NOs:60-61). The amino acids that are identical among different species are marked by asterisks. The amino acids that are highly homologous among different species are marked by two dots. The amino acids that are moderately homologous among different species are marked by one dot.

FIG. 8A is a schematic outline of the constructs used in the yeast-two-hybrid assay. The nNOS PDZ domain is engineered in a construct containing the DNA binding domain. This construct also expresses tryptophan (Trp). It can grow in Trp deficient medium (Trp−). R16, R17, R16-17 or the syntrophin PDZ domain are engineered in constructs harboring the DNA activation domain. These constructs express leucine (Leu) and they can grow in Leu deficient medium (Leu−). The structure of R16-17 is different from that of R16 or R17. An interaction between the DNA binding domain and the DNA activation domain initiates histidine (His) production. Subsequently, these cells can grow in Leu-/Trp-/His-triple deficient medium. FIG. 8B is a representative yeast-two-hybrid assay on the Leu-/Trp-/His-triple deficient medium. FIG. 8C is a representative dot dilution assay on the Leu-/Trp-/His-triple deficient medium. Cotransformation of the syntrophin PDZ domain DNA activation construct or the R16-17 DNA activation construct resulted in yeast growth. Co-transformation with R16 or R17DNA activation constructs did not yield growth. √, yeast cells grew in the triple deficient medium; X, yeast cells did not grown in the triple deficient medium.

FIG. 12A shows specific twitch force (under single stimulation); FIG. 12B shows specific tetanic forces under different frequencies of tetanic stimulation; FIG. 12C shows force decline during 10 cycles of eccentric contraction. Asterisk, the results from AAV infected mice were significantly better than those of uninfected controls. Sample size for muscle function assay, N=4 for uninfected littermate control; N=14 for AV.CMV.ΔR2-15/ΔR18-23/ΔC infected m-dko mice. Sample size for the CK assay, N=3 for uninfected littermate control; N=6 for AV.CMV.ΔR2-15/ΔR18-23/ΔC infected m-dko mice.

DETAILED DESCRIPTION OF THE INVENTION

All publications, patent applications, patents, and other references mentioned herein are incorporated by reference in their entirety.

The present invention identifies a novel series of dystrophin minigenes and microgenes that are small enough to be packaged into AAV or lentiviral vectors, and yet retain the essential functions of a full-length, wild type dystrophin gene, including, but not limited to, the mechanic-link function and signal functions (such as sarcolemmal nNOS-related functions), needed for protecting muscle from dystrophic injury. The present invention recognizes that the inclusion of the R16 and R17 repeats of the mid-rod domain of a dystrophin protein in a synthetic mini/micro-dystrophin gene is critical for nNOS restoration. In other words, mini/micro-dystrophin genes retaining R16 and R17 can restore nNOS protein to the sarcolemma in a similar fashion as the full-length dystrophin protein. The present invention further recognizes that the restored nNOS protein, from treatment with the mini/micro-genes of the present invention, retains its biological functions (enzymatic activity).

By "dystrophin gene" is meant a nucleic acid molecule having a nucleotide sequence that encodes a full-length dystrophin protein. The present invention contemplates employing dystrophin gene derived from any mammalian species including, but not limited to, human, murine, and canine, particularly, from human. A particular full-length dystrophin gene has a DNA sequence as set forth in SEQ ID NO: 2, which encodes a full-length dystrophin protein having an amino acid sequence as set forth in SEQ ID NO: 1.

By "domain" is meant a portion of a protein structure. For example, the "N-terminal domain" of a human dystrophin protein, as referred to herein, includes amino acid residues from approximately 1 to approximately 252, particularly, from amino acid residues methionine 1 to glutamate 252 of SEQ ID NO: 1, more particularly, amino acid sequence encoded by a nucleotide sequence as set forth in SEQ ID NO: 17. Similarly, the "mid-rod domain" or "rod domain" of a dystrophin protein, as referred to herein, includes amino acid residues approximately from 253 to approximately 3112 of SEQ ID NO: 1, particularly, from amino acid residues methionine 253 to leucine 3112 as set forth in SEQ ID NO: 1; the "cysteine-rich domain" of a dystrophin protein, as referred to herehin, includes amino acid residues from approximately 3113 to approximately 3408 of SEQ ID NO: 1, particularly, from amino acid residues arginine 3113 to threonine 3048 as set forth in SEQ ID NO: 1, more particularly, amino acid sequence encoded by a nucleotide sequence as set forth in SEQ ID NO: 46 and the "C-terminal domain" of a dystrophin protein, as referred to herehin, includes amino acid residues from approximately 3409 to 3685 of SEQ ID NO: 1, particularly, from amino acid residues proline 3409 to methionine 3685 as set forth in SEQ ID NO: 47.

Figure 1A:
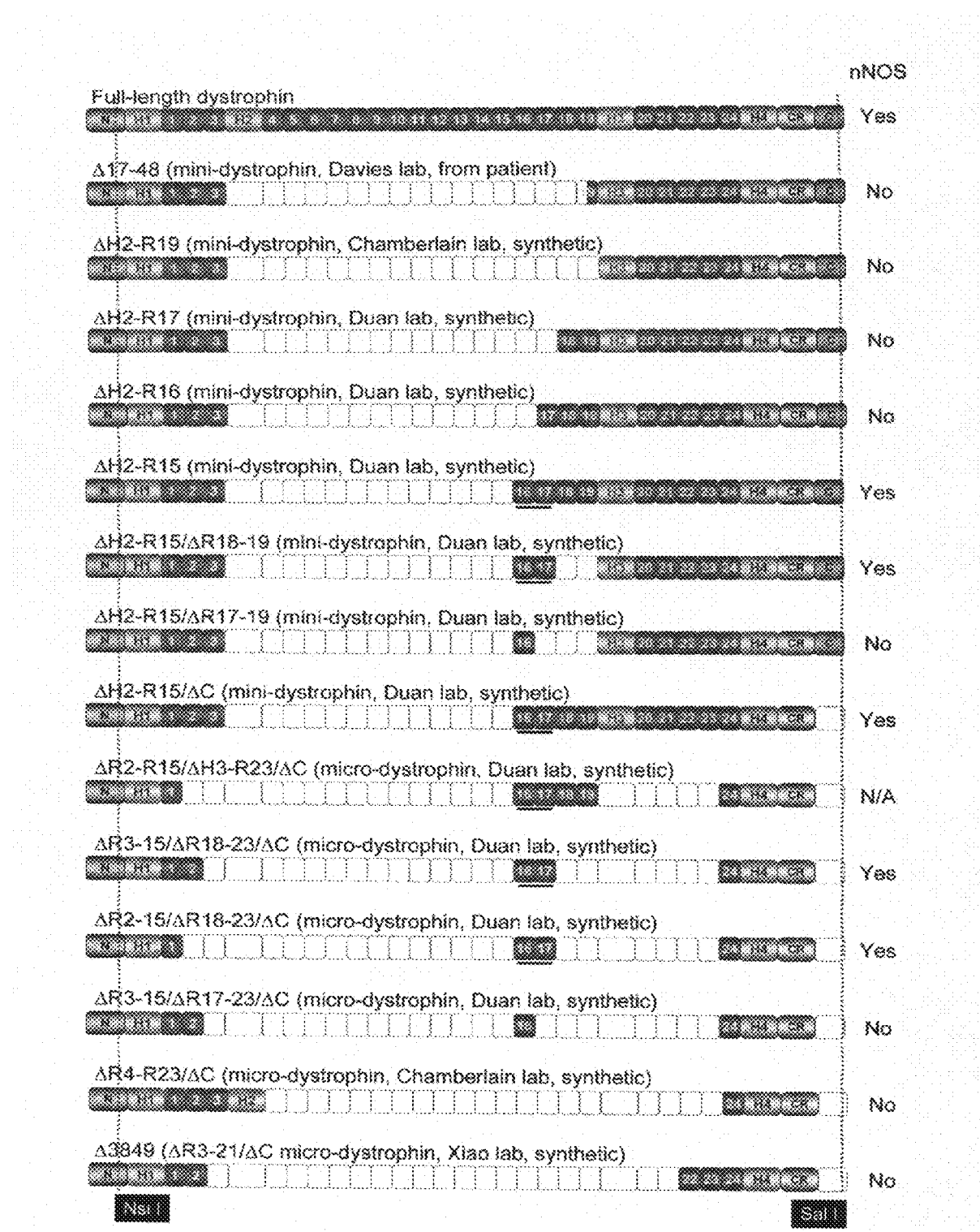
FIG. 1A shows the structure of the full-length dystrophin gene and a series of mini/micro-dystrophin genes and their corresponding nNOS restoration abilities.

By "dystrophin microgene" or "micro-dystrophin gene" or "microgene" is meant a nucleic acid molecule that is 5 kb or less in length and encodes a modified or non-full-length dystrophin polypeptide (also referred to as micro-dystrophin in the present application) that retains the N-terminal domain, the cysteine-rich domain, two or more repeats of the mid-rod domain, and two or more hinges of the mid-rod domain of a full-length dystrophin protein. By "micro-dystrophin" is meant a modified or non-full-length dystrophin protein molecule that retains biological function of a full-length dystrophin protein and the coding sequence of which is 5 kb or less. Examples of micro-dystrophin are illustrated in FIG. 1.

By "dystrophin minigene," "mini-dystrophin gene" or "minigene" is meant a nucleic acid molecule that is more than 5 kb in length but less than the full-length of dystrophin coding sequence, preferably, between 5 kb to about 10 kb in length, more preferably about 5 kb to about 8 kb in length, even more preferably, about 7 kb in length, and encodes a modified or non-full-length dystrophin polypeptide (also referred to as mini-dystrophin in the present application) that retains the N-terminal domain, the cysteine-rich domain, two or more repeats (also referred to by R and a number, e.g., R16 means repeat number 16) of the mid-rod domain, and two or more hinges of the mid-rod domain of a full-length dystrophin protein. By "mini-dystrophin" is meant a modified or non-full-length dystrophin protein molecule that retains the biological functions of a full-length dystrophin protein and the coding sequence of which is more than 5 kb in length but less than the full-length of dystrophin coding sequence.

By "biological functions" of a dystrophin protein is meant functions which include, but are not limited to providing a mechanic link between the cytoskeleton and the extracellular matrix and signaling function such as recruiting nNOS to the sarcolemma.

By "modified" in connection with dystrophin gene or dystrophin protein is meant a wild-type (or naturally-occurring) full-length dystrophin gene or dystrophin protein molecule is changed so that the modified dystrophin gene or dystrophin protein molecule does not include the full-length coding sequence of a dystrophin gene or the full-length amino acid sequence of a dystrophin protein, yet retain or substantially retain the biological functions of a full-length gene or protein.

By "modified N-terminal domain" is meant an N-terminal domain that is different in structure and/or sequence from that of wild type or naturally occurred but retain the function of a wild type or naturally occurred N-terminus. By "modifications or variations" is meant any changes to a nucleic acid molecule or polypeptide, such as by mutation, that retains substantial function of the nucleic acid molecule or polypeptides and/or is substantially homologous with, or similar/identical to, the nucleic acid molecule or polypeptide.

In one embodiment, the present invention is directed to a nucleic acid molecule (also referred to in the present application as minigene or microgene) that contains a nucleotide sequence coding for a modified or non-full-length dystrophin polypeptide that retains the N-terminal domain, two or more spectrin-like repeats of the mid-rod domain, two or more hinge regions of the mid-rod domain, and the cysteine-rich domain of a full-length dystrophin protein.

In a particular embodiment, the minigene or microgene of the present invention further includes a nucleotide sequence coding for the C-terminal domain of the dystrophin protein. Mutations in the C-terminal domain have been shown to correlate with cognitive phenotype in DMD patients (Tuffery et al., 1995; Kerr et al., 2001). Furthermore, C-terminal domain mutations have also been shown to cause DMD in a subset of patients (McCabe et al., 1989; Prior et al., 1995; Suminaga et al., 2004). Without intending to be limited to any particular theory, it is believed that a mini- or micro-dystrophin gene further including a DNA sequence coding for the C-terminal domain of the dystrophin protein can provide better protection or treatment against DMD. In a specific embodiment, the repeats of the mid-rod domain can be from any specifies including, but not limited to, human, canine, murine, swine, porcine, rabbit, chicken.

Preferably, the two or more spectrin-like repeats of the minigene or microgene of the present invention include R16 and R17 of the mid-rod domain. However, the present invention also contemplates minigenes and microgenes that include sequence encoding additional spectrin-like repeats besides R16 and R17, including one or more selected from R1-R15 and R18-R24. For example, as illustrated FIG. 1, a microgene can include R1, R16, R17 and R24 (e.g., ΔR2-15/ΔR18-23/ΔC of FIG. 1), or R1-R2, R16, R17 and R24 (e.g., ΔR3-15/ΔR18-23/ΔC of FIG. 1), or R1, R16-R19, and R24 (e.g., ΔR2-15/ΔH3-23/ΔC) of FIG. 1), which are specific embodiments of the present invention. The symbol "Δ" used in the present invention means deletion or missing of a particular sequence or region of a nucleotide or amino acid sequence. For example, ΔR2-15/ΔR18-23/ΔC represents one microgene, in which Repeats 2-15, 18-23 and C-terminal domain are deleted or missing. In another particular embodiment, the present invention contemplates a minigene that includes Repeats R1-R3, R16, R17, and R20-R24 (e.g., ΔR2-15/ΔR18-19 of FIG. 1), or R1-R3 and R16-R24 (e.g., ΔH2-R15 of FIG. 1).

The hinge region of a minigene or microgene of the present invention preferably includes, but is not limited to, H1 and H4 hinge regions. However, the present invention also contemplates minigenes and microgenes that include additional hinge regions besides H1 and H4. For example, FIG. 1 illustrates H3 can also be included in a minigene, e.g., ΔR2-15/ΔR18-19 and ΔH2-R15, which are specific embodiments of the present invention.

In one embodiment, the present invention is directed to a minigene or microgene that contains a nucleotide sequence, or a nucleotide sequence having substantial homology, similarity or identity to a nucleotide sequence coding for a modified or non-full-length dystrophin polypeptide that retains the N-terminal domain as set forth in (SEQ ID NO: 17), two or more spectrin-like repeats of the mid-rod domain as set forth in (SEQ ID NOs: 19-44), two or more hinge regions of the mid-rod domain, e.g., as set forth in (SEQ ID NOs: 18-45 and SEQ ID NO: 1) and the cysteine-rich domain as set forth in (SEQ ID NO: 46) of a full-length dystrophin protein.

By "substantial homology", "substantial similarity" or "substantial identity" is meant a nucleic acid or amino acid sequence having at least 70%, preferably, at least 80%, more preferably at least 90%, even more preferably, at least 95% of homology, similarity or identity in sequence.

In another embodiment, the minigenes or microgenes are those that hybridize to selected sequences under high, moderate or low stringent conditions. Reference herein to a low stringency at 37-42° C. includes and encompasses from at least about 1% v/v to at least about 15% v/v formamide and from at least about 1M to at least about 2M salt for hybridisation, and at least about 1M to at least about 2M salt for washing conditions. Alternative stringency conditions may be applied where necessary, such as medium stringency, which includes and encompasses from at least about 16% v/v to at least about 30% v/v formamide and from at least about 0.5M to at least about 0.9M salt for hybridisation, and at least about 0.5M to at least about 0.9M salt for washing conditions, or high stringency, which includes and encompasses from at least about 31% v/v to at least about 50% v/v formamide and from at least about 0.01M to at least about 0.15M salt for hybridisation, and at least about 0.01M to at least about 0.15M salt for washing conditions. Hybridization may be carried out at different temperatures and, where this occurs, other conditions may be adjusted accordingly. Examples of specific hybridization conditions include hybridization at 65° C., followed by one or more washes with 2×SSC, 0.1% SDS, and a final wash with 0.2×SSC, more preferably with 0.1× SSC and 0.1% SDS, at room temperature or a temperature up to 65° C. or 68° C.

In a particular embodiment, the modified dystrophin protein includes, but is not limited to, R16 as set forth in (SEQ ID NO:) and R17 as set forth in (SEQ ID NO:) of the mid-rod domain. However, the present invention also contemplates modified dystrophin proteins that in addition to R16 and R17, also include other spectrin-like repeats selected from R1-R15 as set forth in (SEQ ID NOs: 19-34, repectively) and R18-R24 as set forth in (SEQ ID NOs: 37-44 respectively). For example, as illustrated FIG. 1, a modified dystrophin protein can include R1, R16, R17 and R24 (e.g., ΔR2-15/ΔR18-23/ΔC of FIG. 1), or R1-R2, R16, R17 and R24 (e.g., ΔR3-15/ΔR18-23/ΔC of FIG. 1), or R1, R16-R19, and R24 (e.g., ΔR2-15/ΔH3-23/ΔC of FIG. 1), which are particular embodiments of the present invention. In another particular embodiment, the present invention contemplates a modified dystrophin protein that includes Repeats R1-R3, R16, R17, and R20-R24 (e.g., ΔR2-15/ΔR18-19 of FIG. 1), or R1-R3 and R16-R24 (e.g., ΔH2-R15 FIG. 1).

Similarly, a minigene or microgene of the present invention preferably includes, but is not limited to, H1 as set forth in (SEQ ID NO: 18) and H4 as set forth in (SEQ ID NO: 45) hinge regions. However, the present invention also contemplates minigenes and microgenes that include hinge regions in addition to H1 and H4. For example, FIG. 1 illustrates H3 can also be included in a minigene, e.g., ΔR2-15/ΔR18-19 and ΔH2-R15, which are particular embodiments of the present invention.

Even more preferably, the present invention is directed to modified dystrophin proteins ΔR2-15/ΔR18-23/ΔC as set forth in (SEQ ID NO: 13), ΔR3-15/ΔR18-23/ΔC as set forth in (SEQ ID NO: 12), AR-15/ΔH3-23/ΔC as set forth in (SEQ ID NO: 11); and modified dystrophin proteins ΔR-15/ΔR18-19 as set forth in (SEQ ID NO: 8) and ΔH2-R15 as set forth in (SEQ ID NO: 7). Any modifications or variations of the microgene and minigene of the present invention are also contemplated by the present invention. The degenerate nucleic acid molecules that encode the expression products of the above-mentioned minigene or microgene are particularly contemplated by the present invention.

According to the present invention, the micro-/mini-dystrophin genes can be synthesized, generated, obtained or assembled by convention technologies known to one skilled in the art and also as illustrated in the Examples provided below in the present application. For example, the minigenes and microgenes of the present invention can be synthesized by molecular biology techniques and as described and shown in Example 2 and FIG. 3. Polypeptides encoded by the minigenes and/or microgenes of the present invention are also contemplated and encompassed by the present invention.

In still another embodiment, the present invention provides vectors that can deliver the nucleic acid molecules of the present invention. Any vector suitable for the purpose is contemplated by the present invention. In particular, the present invention provides a series of recombinant adeno-associated viral vectors (AAVs) and lentiviral vectors to deliver the nucleic acid molecules of the present invention (mini/micro-dystrophin genes) that are capable of restoring nNOS to the sarcolemma. A recombinant AAV vector (single vector or dual vectors) in accordance with the present invention includes any one of the nucleic acid molecule of the present invention (the mini/micro-dystrophin genes) that is capable of restoring nNOS to the sarcolemma, operably linked to an expression cassette (a promoter and a polyA) and viral inverted terminal repeats (ITRs).

Preferably, the vectors contemplated by the present invention include, but are not limited to, AAV vectors such as AV.CMV.ΔR2-15/ΔR18-23/ΔC, AV.miniCMV.ΔR3-15/ΔR18-23/ΔC, AV.miniCMV.ΔR2-15/ΔH3-R23/ΔC, AV.ΔH2-R15Donor/AV.ΔH2-R15 Acceptor, AV.ΔH2-R15/ΔR18-19.Head/AV.ΔH2-R15/ΔR18-19.Tail. Modifications or variations of these vectors are also contemplated by the present invention.

The minigenes or microgenes which encode mini- or micro-dystrophin polypeptide molecules can be generated as described above and illustrated in Example 2 below by employing conventional techniques. The minigenes or microgenes can then be removed by use of appropriate restriction enzymes and spliced into a selected expression cassette, preferably suitable for AAV vectors. Alternatively, purified minigenes or microgenes nucleic acid molecules can be sequenced in its entirety using known methods, and any of several translationally equivalent synthetic DNA sequences can then be prepared which code for the sequence of amino acids, and this synthetic sequence can be inserted into an appropriate expression cassette, preferably suitable for AAV vectors.

Numerous expression cassettes and vectors are well known in the art. By "expression cassette" is meant a complete set of control sequences including initiation, promoter and termination sequences which function in a cell when they flank a structural gene in the proper reading frame. Expression cassettes frequently and preferably contain an assortmtent of restriction sites suitable for cleavage and insertion of any desired structural gene, e.g., the microgene or minigene of the present invention. It is important that the cloned gene have a start codon in the correct reading frame for the structural sequence. In addition, the expression cassette for the present invention preferably includes a strong constitutive promoter sequence, e.g., a CMV promoter, at one end to cause the gene to be transcribed at a high frequency, and a poly-A recognition sequence at the other end for proper processing and transport of the messenger RNA. Examples of such a preferred (empty) expression cassette into which the microgene of the present invention can be inserted are pcis.RSVmcs, pcis.CMVmcs, pcis.CMVmcs-intron, pcis.SV40mcs, pcis.SV40mcs-intron, pcis.CK6mcs, and pcis.CAGmcs as described in Yue et al (Yue & Duan 2002 *Biotechniques* 33(3):672-678). Examples of such a preferred (empty) expression cassette into which the minigene of the present invention can be inserted are pDD188, pDD293 and pDD295 as described in Duan et al (Duan, Yue and Engelhardt 2003 *Methods in Molecular Biology* 219:29-51) and pAG15, and pAG21 as described in Ghosh et al (Ghosh, Yue, Lai and Duan 2008 *Molecular Therapy* 16:124-130). Highly preferred expression cassettes will be designed to include one or more selectable marker genes, such as kanamycin resistance gene.

By the term "vector" is meant a DNA sequence which is able to replicate and express a foreign gene in a host cell. Typically, the vector has one or more endonuclease recognition sites which may be cut in a predictable fashion by use of the appropriate enzyme. Such vectors are preferably constructed to include additional structural gene sequences imparting markers for identifying and separating transformed cells. Preferred markers/selection agents include kanamycin, chlorosulfuron. phosphonothricin, hygromycin and methotrexate. A cell in which the foreign genetic material in a vector is functionally expressed has been "transformed" by the vector and is referred to as a "transformant."

A particularly preferred vector is a AAV vector, by which is a single-stranded DNA molecule which derives from the genome of Adeno-associated viruses but is non-pathogenic.

Promoters that may be used in the expression cassette include, but are not limited to nos, ocs, phaseolin, CaMV, RSV, CMV, SV40, CAG, CK6, and MCK promoters.

The expression cassette containing a minigene or microgene operably linked to the desired control sequences can be ligated into a suitable vector for delivery. In general, AAV and lentiviral vectors containing replication and control sequences compatible with the host cell are used. A suitable vector, such as a single AAV vector will typically carry viral inverted terminal repeats (ITR) at the ends, the promoters, and microgene and polyA.

By "dual vector system" meant a vector system composed of two vectors, e.g., AAV vectors, in which system both vector carry a part of a gene or sequence to be delivered and the entire gene is reconstituted by interaction between the two vectors.

In one embodiment, the two vectors of dual vector system, e.g., AAV dual vector system, of the present invention are trans-splicing vectors (ts vectors, e.g., tsAAV vectors).

In another embodiment, the two vectors of dual vector system, e.g., AAV dual vector system, of the present invention are hybrid vectors (e.g., hybrid AAV vectors).

Figure 2:
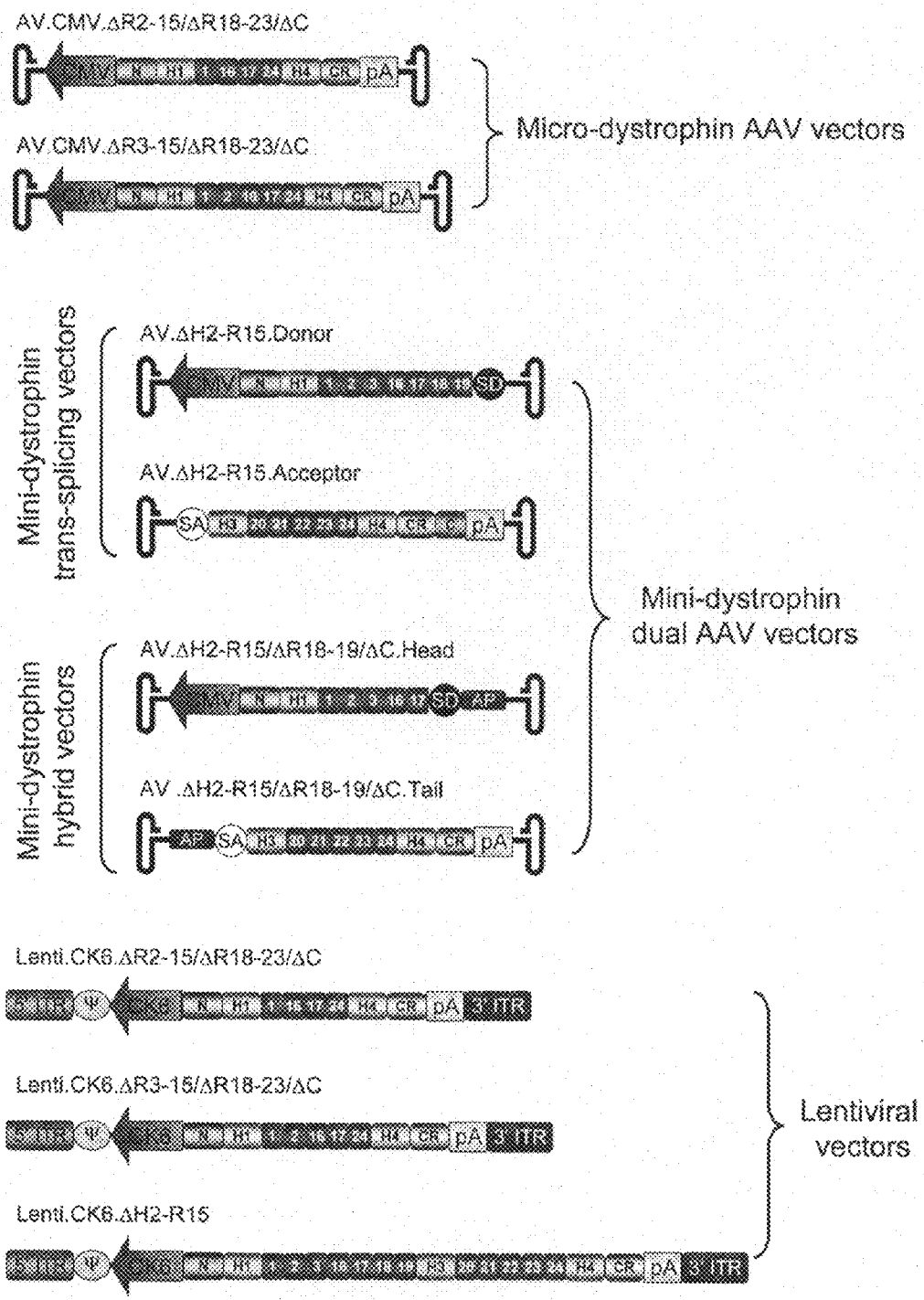
FIG. 2 shows the construction of AAV vectors and lentiviral vectors carrying an inventive dystrophin mini/micro-gene.

Trans-splicing AAV vectors typically carry (in addition to what are presented in a single AAV vector) a splicing donor signal and a splicing acceptor signal. Hybrid AAV vector will typically carry (in addition to what are presented in a single AAV vector and in the trans-splicing vector) a homologous overlapping sequence, preferably from the middle one-third of human placental alkaline phosphotase gene. A lentiviral vector will typically carry the 5' long terminal repeats (LTR), the 3' LTR and the packaging signal AAV as depicted in FIG. 2.

By "operably linked" is meant that a nucleic acid molecule is placed in a functional relationship with another nucleic acid molecule. For example, expression cassette (a promoter and a polyA) is operably linked to a mini/micro-dystrophin gene if the expression cassette affects the transcription of the sequence.

The information with respect to the structure, function and usage of AAV and lentiviral vectors have been well known and available in the art. Dual AAV vectors of the present invention have large, e.g., at least 10 kb, packaging capacity.

Three classical dual vectors are the cis-activation, trans-splicing (ts) and overlapping vectors (reviewed in Duan, D., Z. Yan, and J. F. Engelhardt. 2006. Expanding the capacity of AAV vectors, p. pp 525-32. In M. E. Bloom, S. F. Cotmore, R. M. Linden, C. R. Parrish, and J. R. Kerr (ed.), Parvoviruses. Hodder Arnold; Distributed in the U.S.A. by Oxford University Press, London, New York. Ghosh, A., and D. Duan. 2007. Expending Adeno-associated Viral Vector Capacity: A Tale of Two Vectors. Biotechnology and Genetic Engineering Reviews 24: 165-177, 2007.)

Only the ts and overlapping vectors can deliver the 6 kb minigene. In tsAAV, a large therapeutic gene is split into a donor vector and an acceptor vector. The donor vector carries the 5' part of the gene and a splicing donor signal. The acceptor vector carries a splicing acceptor signal and the 3' part of the gene. Expression is achieved by AAV inverted terminal repeat (ITR)-mediated intermolecular recombination and subsequent splicing of the recombinant genome (FIG. 13) See Duan, D., Y. Yue, and J. F. Engelhardt. 2001. Expanding AAV Packaging Capacity With Transsplicing Or Overlapping Vectors: A Quantitative Comparison. Mol Ther 4:383-91, Sun, L., J. Li, and X. Xiao. 2000. Overcoming adeno-associated virus vector size limitation through viral DNA heterodimerization. Nat. Med. 6:599-602, and Yan, Z., Y. Zhang, D. Duan, and J. F. Engelhardt. 2000. From the Cover: Trans-splicing vectors expand the utility of adeno-associated virus for gene therapy. Proc. Natl. Acad. Sci. USA 97:6716-6721.

Figure 13:
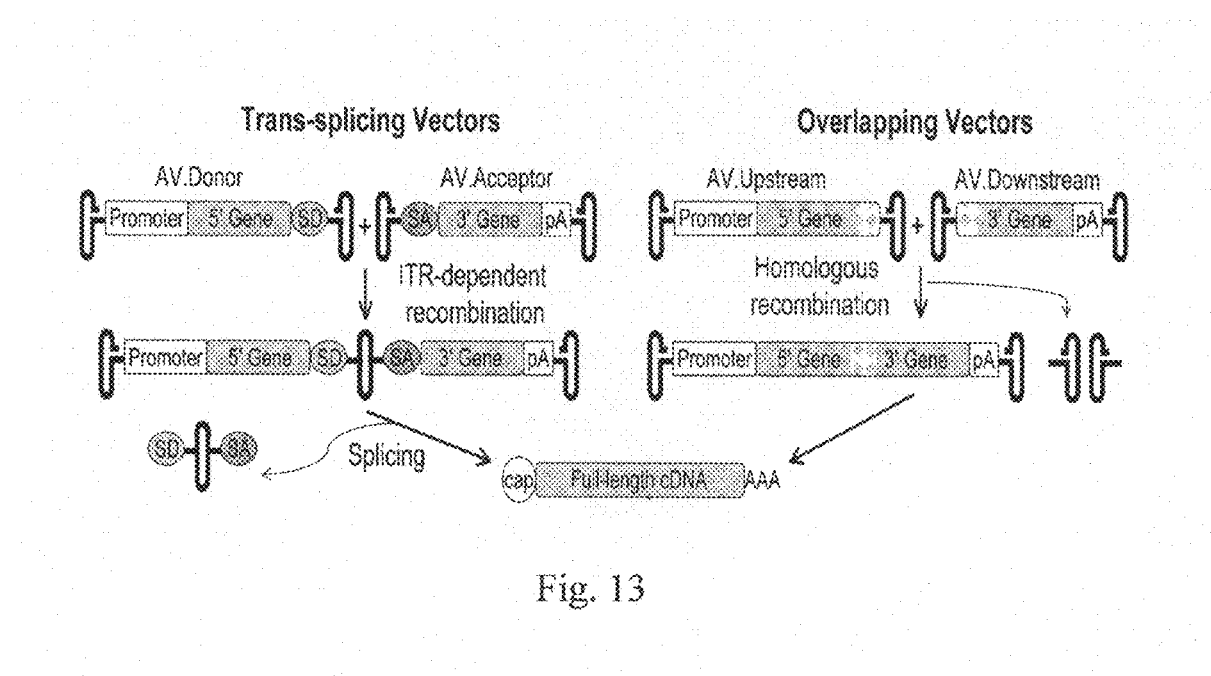
FIG. 13 shows schematic outline of transgene reconstitution in the trans-splicing AAV (tsAAV) vectors and the overlapping AAV vectors. In the tsAAV vectors, ITR-dependent recombination reconstitutes the full-length expression cassette. The double-D ITR junction is removed by engineered splicing donor (SD) and acceptor (SA) sequences. In the overlapping AAV vectors, the shared region recombines through homologous recombination. Viral ITRs are removed during this process.
Figure 14:
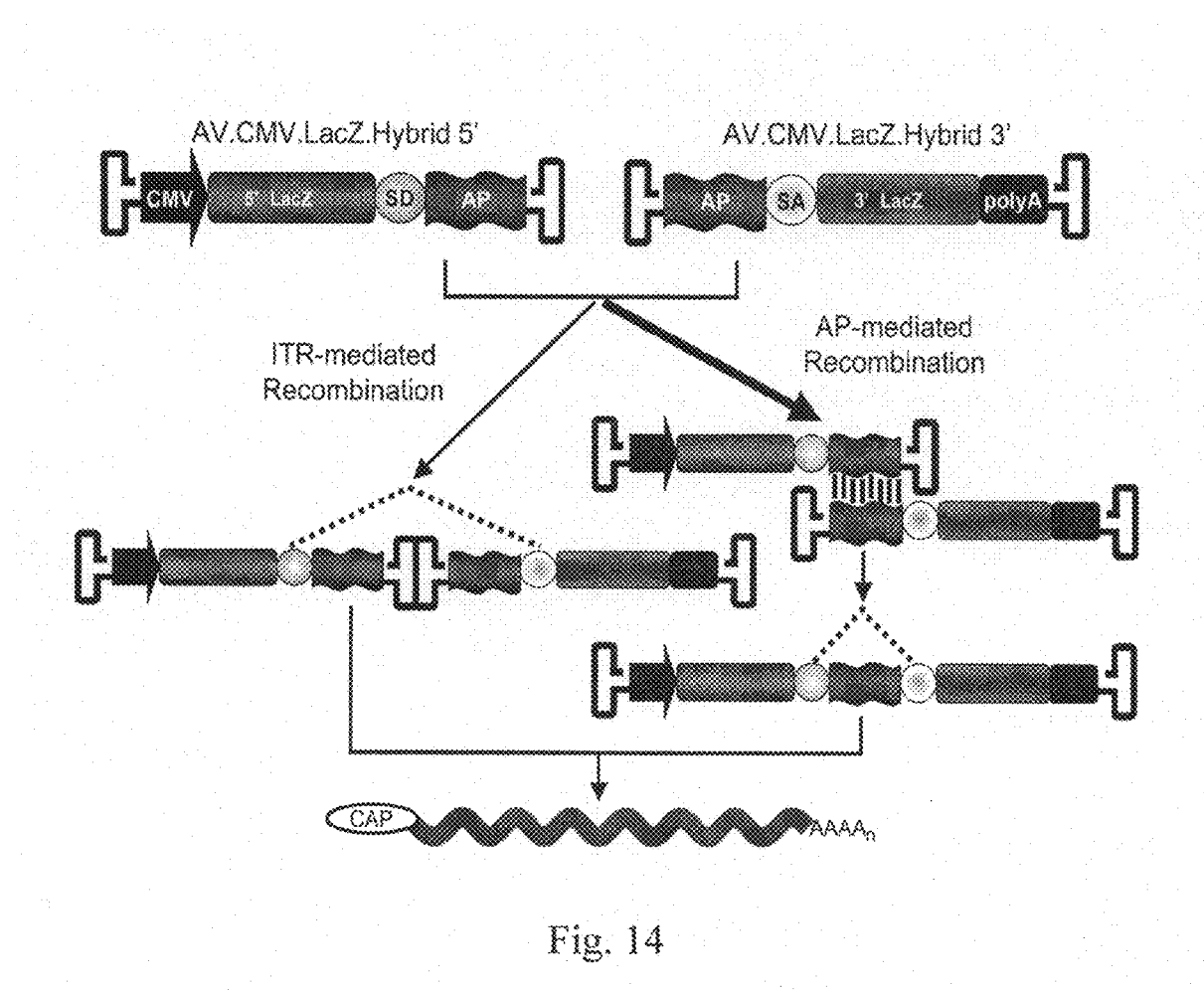
FIG. 14 shows schematic outline of transgene reconstitution in the hybrid AAV vectors. The AV.CMV.LacZ.Hybrid5' vector contains the CMV promoter, the 5' half of the LacZ gene, the splicing donor (SD) and the 872 bp alkaline phosphatase (AP) sequence. The AV.CMV.LacZ.Hybrid 3' vector contains the 872 bp AP sequence followed by the splicing acceptor (SA), the 3' half of the LacZ gene and the SV40 polyadenylation signal (polyA). Vector genomes are flanked by the AAV-2 ITRs. Upon co-infection, the complete LacZ expression cassette can be reconstituted via AP sequence-mediated homologous recombination. Alternatively, it can be generated via viral ITR-mediated head-to-tail recombination. LacZ expression is achieved after the junction sequences are removed by cellular splicing machinery (dotted lines).

In the overlapping vectors, a large therapeutic gene is split into an upstream vector and a downstream vector. The upstream and the downstream vectors share a region of homology (Duan, D., Y. Yue, and J. F. Engelhardt. 2001., Halbert, C. L., J. M. Allen, and A. D. Miller. 2002. Efficient mouse airway transduction following recombination between AAV vectors carrying parts of a larger gene. Nat Biotechnol 20:697-701.) Transgene reconstitution is achieved through homologous recombination (FIG. 13). By rational vector design, such as optimizing the gene splitting site, the transduction efficiency from tsAAV vectors can reach that of a single AAV vector (Lai et al 2005 *Nature Biotechnique*; Lai et al 2006 *Human Gene Therapy*). Furthermore, systemic delivery of the tsAAV vectors has been shown to efficiently transduce whole body muscle in rodents (Ghosh, Yue, Long, Bostic and Duan 2007 *Molecular Therapy* 16:124-130). tsAAV-mediated minigene therapy was demonstrated to reduce muscle pathology, improve muscle force and prevent contraction-induced injury in a single mdx muscle (Lai, Y., D. Li, Y. Yue, and D. Duan. 2007. Design of trans-splicing adeno-associated viral vectors for Duchenne muscular dystrophy gene therapy. *Method in Molecular Medicine*:In-press., Lai, Y., Y. Yue, M. Liu, and D. Duan. 2006. Synthetic intron improves transduction efficiency of transsplicing adeno-associated viral vectors. Hum Gene Ther 17:1036-42, and Lai, Y., Y. Yue, M. Liu, A. Ghosh, J. F. Engelhardt, J. S. Chamberlain, and D. Duan. 2005. Efficient in vivo gene expression by trans-splicing adeno-associated viral vectors. Nat Biotechnol 23:1435-9.)

Besides the classic dual AAV vectors, a hybrid AAV dual vector system has been developed recently (Ghosh, Yue, Lai and Duan 2008 *Molecular Therapvy* 16:124-130). The tsAAV is highly dependent on the optimal gene splitting site. This limitation is overcome in the hybrid vector system. In hybrid AAV vectors, transgene reconstitution can be achieved either through the traditional trans-splicing pathway as described in the tsAAV vectors or through homologous recombination via a highly recombinogenic foreign DNA sequence.

FIG. 1 shows the structures and their respective functions as to restoring nNOS to the sarcolemma of the full-length dystrophin gene, the mini/micro-dystrophin genes published/investigated by other researchers, and the representative mini/micro-dystrophin genes synthesized by the present inventors. In FIG. 1, N represents the N-terminal domain of the dystrophin protein; H1-4 represents the hinges 1 to 4 in the rod domain of the dystrophin protein; numeric numbers represent the spectrin-like repeats in the dystrophin rod domain (positively charged repeats are in white colored numeric numbers); CR represents the cysteine-rich domain in the dystrophin protein; C represents the C-terminal domain of the dystrophin protein; and the dotted boxes denote the regions that are deleted in each respective construct.

As shown in FIG. 1, prior to the present invention, minigene $\Delta$17-48, minigene $\Delta$H2-R19, microgene $\Delta$R4-R23/$\Delta$C and microgene $\Delta$3849 ($\Delta$R3-21/$\Delta$C) had been described/investigated. Though with other benefits, none of these mini/micro-genes retain the function of restoring nNOS to the sarcolemma, neither do other published mini/micro-dystrophin genes (not listed in FIG. 1). In work leading up to the present invention, novel mini/micro-genes were synthesized. It has been discovered that the mini/micro-genes containing R16-17 repeats, such as $\Delta$H2-R15, $\Delta$H2-R15/$\Delta$R18-19, $\Delta$H2-R15/$\Delta$C, $\Delta$R3-15/$\Delta$R18-23/$\Delta$C, and $\Delta$R2-15/$\Delta$R18-23/$\Delta$C, are shown to restore nNOS, while the mini/micro-genes without R16 or R17 repeat, such as, $\Delta$H2-R17, $\Delta$H2-R16, $\Delta$H2-R15/$\Delta$R17-19 and $\Delta$R3-15/$\Delta$R17-23, lack the capability. See FIG. 1 and the Examples provided below in the present application.

FIG. 1 further suggests that the function of the nNOS recruiting micro-domain is independent of its natural context/location. In the wild type dystrophin, R16-17 is surrounded by R15 and R18. In the inventive mini/micro-dystrophin genes, nNOS protein and its activity are restored to the sarcolemma when the R16-17 is placed adjacent to other repeats or hinges such as R1 (for example in $\Delta$R2-15/$\Delta$R18-23/$\Delta$C), R2 (for example in $\Delta$R3-15/$\Delta$R18-23/$\Delta$C), R3 (for example in $\Delta$H2-R15 and its derivatives), H3 (for example in $\Delta$H2-R15/$\Delta$R18-19) and R24 (for example in $\Delta$R2-15/$\Delta$R18-23/$\Delta$C and its derivatives).

Accordingly, in still another embodiment, the present invention is directed to a method for the treatments of DMD, BMD and/or XLDC in a subject by administering to the subject a therapeutically effective amount of the minigene and/or microgene of the present invention, preferably by administering a vector carrying the minigene and/or microgene, more preferably, by administering to the subject a therapeutically effective amount of a AAV vector containing the minigene and/or microgene of the present invention.

By "subject" is meant any mammalian subject, preferably, human.

The route of the administration accordance with the method of the present invention includes local or regional muscle injection to improve local muscle function in patients, systemic delivery (such as intravenous, intra-artery, intraperitoneal) to all muscles in a region or in the whole body in patients, in vitro infection of myogenic stem cells with AAV or lentiviral vector followed by local and/or systemic delivery.

By "therapeutically effective amount" is meant an amount high enough to significantly positively modify the condition to be treated but low enough to avoid serious side effects (at reasonable benefit/risk ratio) within the scope of sound medical judgment. The therapeutically effective amount will vary with the particular condition being treated, or the condition of the subject being treated and his/her physical condition, as well as the type of preparation, vector, or composition being used.

In a particular embodiment, the present invention contemplates intravascular administration. For example, in AAV-9 gene therapy with micro-dystrophin gene containing R16 and R17, the dosage to newborn mice (1 week or younger in age) is about 0.5 to about 1.5×10e11 vg particles/gram body weight or about 50 to about 75 μl/gram body weight; the dosage to young mice (1 week to 1 month in age) is about 0.5 to about 1.5×10e11 vg particles/gram body weight or about 75 to about 200 μl/gram body weight; the dosage to adult mice (1 to 20-month-old) is about 0.5 to about 1.5×10e11 vg particles/gram body weight or about 200 to about 400 μl/gram body weight; the dosage for newborn dog (three days or younger in age) is about 0.5 to about 2×10e11 vg particles/gram body weight or about 10 to about 25 μl/gram body weight; the dosage for young dog (3 days to 3 months in age) is about 0.5 to about 2×10e11 vg particles/gram body weight or about 10 to about 25 μl/gram body weight; the dosage for adult dog (3-month-old or older) is about 1 to about 3×10e11 vg particles/gram body weight or about 15 to about 30 μl/gram body weight.

According to the present invention, after identifying the R16-17 nNOS recruiting micro-domain in the dystrophin protein, the micro-domain can be incorporated into non-viral and/or viral gene therapy vectors, and/or cell therapy for the treatment of dystrophin deficient diseases such as DMD, BMD and XLDC. The present invention provides a series of AAV mini/micro-dystrophin vectors that can restore nNOS in a dystrophin-deficient muscle. An recombinant AAV vector includes any one of the nNOS restoring mini/micro-dystrophin genes, an expression cassette (a promoter and a polyA), and viral inverted terminal repeats (ITRs). FIG. 2 lists the exemplary constructs of the AAV vectors carrying the mini/micro-dystrophin genes of the present invention.

In yet another embodiment, the present invention is directed to a pharmaceutical composition containing one or more of the AAV vectors and lentiviral vectors of the present invention and unmodified plasmid DNA molecules and a pharmaceutically acceptable carrier.

Pharmaceutical formulations, dosages and routes of administration for nucleic acids are generally disclosed, for example, in U.S. Pat. No. 5,580,859 to Felgner et al. Both local and systemic administration are contemplated by the present invention. When the molecules of the invention are employed for prophylactic purposes, agents of the invention are amenable to chronic use, preferably by systemic administration. One or more suitable unit dosage forms comprising the therapeutic agents of the invention, which may optionally be formulated for sustained release, can be administered by a variety of routes including oral, or parenteral, including by rectal, transdermal, subcutaneous, intravenous, intramuscular, intraperitoneal, intrathoracic, intrapulmonary and intranasal routes. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for oral administration, they are preferably combined with a pharmaceutically acceptable carrier, diluent or excipient to form a pharmaceutical formulation, or unit dosage form.

By "pharmaceutically acceptable" is meant the carrier, diluent, excipient, and/or salt must be compatible with the other ingredients of the formulation, and not deleterious to the recipient thereof. The active ingredient for oral administration may be present as a powder or as granules; as a solution, a suspension or an emulsion; or in achievable base such as a synthetic resin for ingestion of the active ingredients from a chewing gum. The active ingredient may also be presented as a bolus, electuary or paste.

Pharmaceutical formulations containing the pharmaceutical composition of the present invention can be prepared by procedures known in the art using well known and readily available ingredients. For example, the agent can be formulated with common excipients, diluents, or carriers, and formed into tablets, capsules, suspensions, powders, and the like. Examples of excipients, diluents, and carriers that are suitable for such formulations include the following fillers and extenders such as starch, sugars, mannitol, and silicic derivatives; binding agents such as carboxymethyl cellulose, HPMC and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The therapeutic agents of the invention can also be formulated as elixirs or solutions for convenient oral administration or as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable vehicles and adjuvants which are well known in the prior art.

The compositions according to the invention can also contain thickening agents such as cellulose and/or cellulose derivatives. They can also contain gums such as xanthan, guar or carbo gum or gum arabic, or alternatively polyethylene glycols, bentones and montmorillonites, and the like.

It is possible to add, if necessary, an adjuvant chosen from antioxidants, surfactants, other preservatives, film-forming, keratolytic or comedolytic agents, perfumes and colorings. Also, other active ingredients may be added, whether for the conditions described or some other condition.

The local delivery of the pharmaceutical composition of the present invention can also be by a variety of techniques which administer the agent at or near the site of disease. Examples of site-specific or targeted local delivery techniques are not intended to be limiting but to be illustrative of the techniques available. Examples include local delivery catheters, such as an infusion or indwelling catheter, e.g., a needle infusion catheter, shunts and stents or other implantable devices, site specific carriers, direct injection, or direct applications.

In particular, for delivery of a vector of the invention to a tissue such as muscle, any physical or biological method that will introduce the vector into the muscle tissue of a host animal can be employed. Vector means both a bare recombinant vector and vector DNA packaged into viral coat proteins, as is well known for AAV administration. Simply dissolving an AAV vector in phosphate buffered saline (PBS) or in N-2-Hydroxyethylpiperazine-N'-2-ethanesulfonic acid (HEPES) buffered saline has been demonstrated to be sufficient to provide a vehicle useful for muscle tissue expression, and there are no known restrictions on the carriers or other components that can be coadministered with the vector (although compositions that degrade DNA should be avoided in the normal manner with vectors). Pharmaceutical compositions can be prepared as injectable formulations or as topical formulations to be delivered to the muscles by transdermal transport. Numerous formulations for both intramuscular injection and transdermal transport have been previously developed and can be used in the practice of the invention. The vectors can be used with any pharmaceutically acceptable carrier for ease of administration and handling.

For purposes of intramuscular injection, solutions in an adjuvant such as sesame or peanut oil or in aqueous propylene glycol can be employed, as well as sterile aqueous solutions. Such aqueous solutions can be buffered, if desired, and the liquid diluent first rendered isotonic with saline or glucose. Solutions of the AAV vector as a free acid (DNA contains acidic phosphate groups) or a pharmacologically acceptable salt can be prepared in water suitably mixed with a surfactant such as hydroxypropylcellulose. A dispersion of AAV viral particles can also be prepared in glycerol, liquid polyethylene glycols and mixtures thereof and in oils. Under ordinary conditions of storage and use, these preparations contain a preservative to prevent the growth of microorganisms. In this connection, the sterile aqueous media employed are all readily obtainable by standard techniques well-known to those skilled in the art.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating the AAV vector in the required amount in the appropriate solvent with various of the other ingredients enumerated above, as required, followed by filtered sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from the previously sterile-filtered solution thereof.

The therapeutic compounds of this invention may be administered to a mammal alone or in combination with pharmaceutically acceptable carriers. The relative proportions of active ingredient and carrier are determined by the solubility and chemical nature of the compound, chosen route of administration and standard pharmaceutical practice.

The dosage of the present therapeutic agents which will be most suitable for prophylaxis or treatment will vary with the form of administration, the particular compound chosen and the physiological characteristics of the particular patient under treatment. Generally, small dosages will be used initially and, if necessary, will be increased by small increments until the optimum effect under the circumstances is reached. Exemplary dosages are set out in the example below.

Since AAV has been shown to have a broad host range (for pulmonary expression) and persists in muscle, the vectors of the invention may be employed to express a gene in any animal, and particularly in mammals, birds, fish, and reptiles, especially domesticated mammals and birds such as cattle, sheep, pigs, horses, dogs, cats, chickens, and turkeys. Both human and veterinary uses are particularly preferred.

The gene being expressed can be either a DNA segment encoding a protein, with whatever control elements (e.g., promoters, operators) are desired by the user, or a non-coding DNA segment, the transcription of which produces all or part of some RNA-containing molecule (such as a transcription control element, +RNA, or anti-sense molecule).

Adeno-associated virus vectors have certain advantages over the above-mentioned vector systems. First, like adenovirus, AAV can efficiently infect non-dividing cells. Second, all the AAV viral genes are eliminated in the vector. Since the viral-gene-expression-induced immune reaction is no longer a concern, AAV vectors are safer than adenovirus vectors. Thirds, wild type AAV is an integration virus by nature, and integration into the host chromosome will stably maintain its transgene in the cells. Fourth, recombinant AAV vector can persist as episomal molecules for years in mammalian tissues such as muscle, in particular in rodent, dogs and human. The episomal form is considered the predominant form for AAV vector mediated transduction in tissues in vivo. Fifth, AAV is an extremely stable virus, which is resistant to many detergents, pH changes and heat (stable at 56.degree. C. for more than an hour). It can be lyophilized and redissolved without losing its activity. Therefore, it is a very promising delivery vehicle for gene therapy.

The invention further provides examples of fabrications of the inventive mini/micro-genes, detections of nNOS restoration, determinations of nNOS protein activity, expression of the inventive AAV vectors. The examples provided below are meant merely to exemplify several embodiments, and should

EXAMPLE 1

Experimental Protocol

Animal model and in vivo gene transfer. All animal experiments described in this disclosure have been approved by the institute Animal Care and Use Committee at the University of Missouri and are in accordance with NIH guidelines. Normal experimental mice (BL10 mice) and dystrophin-deficient experimental mice (the mck mouse and the mdx4cv mouse) were originally purchased from the Jackson Laboratory (Bar Harbor, Me.). The myoD/dystrophin double knockout (m-dko) mice were originally obtained from Dr. Michael Rudnicki at the Ottawa Research Institute. The colonies were subsequently established by in-house breeding at the University of Missouri and mice (including experimental mice and breeding pairs) were housed in a specific-pathogen-free animal facility at 20-23° C. with a 12 hr-12 light-dark cycle. Two muscles (the tibialis anterior (TA) muscle and the gastrocnemius muscle) were used to evaluate dystrophin expression, nNOS expression and nNOS activity by either nonviral plasmid in vivo local transfection or by AAV-mediated local gene transfer. The extensor digitorium longus (EDL) muscle was used to dystrophin expression, nNOS expression, nNOS activity and muscle force improvement after AAV-mediated gene transfer (local and systemic delivery). All body muscles (including skeletal and cardiac muscles) were analyzed for dystrophin expression, nNOS expression, nNOS activity and muscle pathology improvement after intravascular systemic gene delivery. To deliver plasmid or AAV to these muscles, the proximal end of the muscle was first exposed with a 2~3 mm incision. A 33 G Hamilton needle was then inserted into the middle belly of the muscle. Vectors (plasmid or AAV) were injected into the muscle while slowly backing out the injection needle. The wound was sutured and the animal was monitor until it recovered.

Double immunofluorescence staining for human dystrophin and nNOS. All the reported mini/micro-dystrophin genes as well as the inventive mini/micro-dystrophin genes were molded after human dystrophin cDNA. To evaluate synthetic mini/micro-gene expression, a monoclonal antibody that specifically reacts with an epitope in the hinge 1 region of human dystrophin, but not mouse dystrophin (Dys-3, clone Dy10/12B2, IgG2a; 1:20 dilution; Novocastra, Newcastle, UK), was used. To evaluate nNOS expression, a polyclonal anti-nNOS C-terminus antibody (1:2000 dilution; Santa Cruz, Santa Cruz, Calif.) was used. The polyclonal antibody had a very low background in mouse muscle.

Below is a description of the double immunostaining protocol. Briefly rinse 8 µm air-dried cryosections with KPBS (356 µM $KH_2PO_4$, 1.64 mM $K_2HPO_4$, 160 mM NaCl). Block with 1% goat serum KPBS at room temperature for 15 min. Wash with 0.2% gelatin (Sigma, St Louis, Mo.) KPBS. Apply anti-nNOS antibody at 4° C. overnight. Wash with 0.2% gelatin KPBS. Apply Alex 488-conjugated goat anti-rabbit antibody (1:100 dilution; Molecular Probe, Eugene, Oreg.) to reveal nNOS protein expression. The second step requires using a mouse monoclonal antibody in mouse muscle. First, the binding of the secondary antibody to endogenous mouse immunoglobulins (Igs) was blocked. Papain-digested rabbit anti-mouse IgG (including Fab and Fc fragments) was used for blocking. Briefly, rabbit anti-mouse IgG (Sigma, St Louis, Mo.) was digested with Papain (Sigma, St Louis, Mo.) in the presence of 1 mM EDTA and 22 mM L-cysteine (Sigma, St Louis, Mo.) at 37° C. for 16 hrs. Digestion reaction was stopped by iodoacetic acid (Sigma, St Louis, Mo.). For double immunostaining, the nNOS antibody stained cryosections were blocked in anti-mouse IgG blocking solution at room temperature for 60 min. After washing in PBS, the cryosections were blocked again with 20% rabbit serum (Jackson ImmunoResearch Laboratories, Inc., West Grove, Pa.) at room temperature for 30 min. After washing in PBS, the Dys-3 monoclonal antibody (diluted in 1% rabbit serum) was applied overnight at 4° C. After washing in PBS, human dystrophin epitope was revealed by an Alex 594-conjugated goat anti-mouse antibody (Molecular Probe, Eugene, Oreg.). To visualize nuclei and reduce photobleaching, slides were mounted with SlowFade Light Antifade Kit with DAPI (Molecular Probe, Eugene, Oreg.). Photomicrographs are taken with a Qimage Retiga 1300 camera using a Nikon E800 fluorescence microscope.

Histo-enzymatic staining to evaluate nNOS activity. Histochemical evaluation of nNOS activity was based on the reduced nicotinamide adenine dinucleotide phosphate (NADPH) diaphorase activity (Hope et al., 1991; Bredt et al., 1991; Dawson et al., 1991). nNOS is a NADPH diaphorase (Hope et al., 1991). Essentially, nNOS uses NADPH as an electronic donor to convert colorless soluble nitroblue tetrazolium (NBT) salt to blue insoluble formazan. To determine nNOS activity in muscle, 16 µm air-dried cryosections were first fixed in 4% paraformaldehyde for 2 hrs at 4° C. This step inactivates non-specific NADPH diaphorase activity in other cellular enzymes such as dehydrogenases and P450. nNOS derived NADPH diaphorase activity is resistant to paraformaldehyde fixation (Matsumoto et al., 1993; Spessert and Claassen, 1998).

After a brief rinse in phosphate buffered saline (PBS), the tissue sections were permeabilized with 0.2% Triton X-100 at 37° C. for 20 min. The NADPH diaphorase activity was then revealed by staining the slides at 37° C. for 4 hours in a solution containing 0.2% Triton X-100, 0.2 mM NADPH, and 0.16 mg/ml NBT. A functional nNOS enzyme appeared as blue staining under bright field microscope. Photomicrographs were taken with a Qimage Retiga 1300 camera using a Nikon E800 microscope.

Recombinant AAV-6 production. The cis plasmids used for AAV packaging carried the mini/micro-gene of the present invention such as theΔR2-15/R18-23/ΔC microgene. Without intending to be limited by any mechanism, it is believed that R16-17 micro-domain is responsible for nNOS restoration in these mini/micro-genes. To generate AAV vector, the packaging cell line (293 cells) were split at 1:6 to 150 mm culture plates at 48 hrs prior to plasmid transfection. A total of four plasmids were co-transfected to make AAV-6 vector. These included the cis plasmid, pMT-Rep2, pCMVCap6 and pHelper. For each vector preparation (15×150 mm plates), 187.5 µg of the cis plasmid, 187.5 µg pMT-Rep2, 562.5 µg pCMVCap6 and 562.5 µg pHelper (at a ratio of 1:1:3:3) were used. After all plasmids were thoroughly mixed in 15.2 ml $H_2O$, 1.68 ml of 2.5 M $CaCl_2$ was added to a final concentration of 250 mM. DNA-calcium-phosphate precipitate was then generated by slowly dropping the DNA/$CaCl_2$ mixture to 16.8 ml of 2×HBS. Then the DNA-calcium-phosphate precipitate was applied to 293 cells drop-by-drop while swirling the culture plate. At 72 hrs after transfection, cell lysate was collected with a cell lifter (Corning Incorporated, Corning, N.Y.). After a 20 min spin in a bench-top centrifuge (3,000 rpm at 4° C.), cell pellet was resuspended in 9 ml 10 mM Tris-HCl (pH 8.0). cell lysate was frozen/thawed 8 to 10 times using dry ice/ethanol and a 40° C. water bath. Cell lysate was sonicate at the power output of 5.5 for 10 min (on ice) (Misonic Cell Disruptor S3000; Misonix, N.Y.). Cell lysate was digest with DNase I at 37° C. for 45 min. Sonicate cell lysate again at the power output of 5.5 for 7 min (on ice). Lysate was digest with one-tenth volume of 0.25% trypsin and 10% sodium deoxycholate for 30 min at 37° C. Clear cell lysate was obtained by spinning at 4,000 rpm for 30 min at 4° C. Supernatant was transferred to a new tube. The volume was adjusted to 29 ml with 10 mM Tris (pH 8) and 18.2 g $CsCl_2$ (final concentration, 0.613 g $CsCl_2$/ml) was added. The solution was incubated for 30 min at 37° C. to dissolve $CsCl_2$ and then was spinned at 4,000 rpm for 30 min at 4° C. The supernatant ws loaded into six 5 ml Beckman ultracentrifugation tubes in an SW55Ti rotor And was spinned at 46,000 rpm for 40 hrs at 4° C. Fractions were collected from the bottom of the tube with a 20 Gauge needle. The viral containing fractions was identified by slot blot using a radio-labelled human dystrophin gene-specific probe. Fractions with the highest viral titer were combined and centrifuged again at 46,000 rpm for 40 hrs at 4° C. Fractions were collected and the highest viral fraction was identified by slot blot. Viral stock was dialyzed at 4° C. for 2×24 hrs in HEPES buffer (20 mM HEPES, 150 mM NaCl, pH 7.8).

Recombinant AAV-9 production. The same cis plasmids used for AAV-6 packaging was used for AAV-9 packaging. The transfection and purification protocols were essentially the same as in the AAV-6 production except for the packaging plasmids. Instead of using four-plasmid co-transfection, a triple plasmid transfection was performed using the cis plasmid, pRep2/Cap9 and pHelper at a ratio of 1:1:3 (187.5 μg of the cis plasmid, 187.5 μg pRep2/Cap9 and 562.5 μg pHelper) (Bostick et al., 2007; Ghosh et al., 2007).

EXAMPLE 2

Mini/micro-dystrophin Genes

Figure 3:
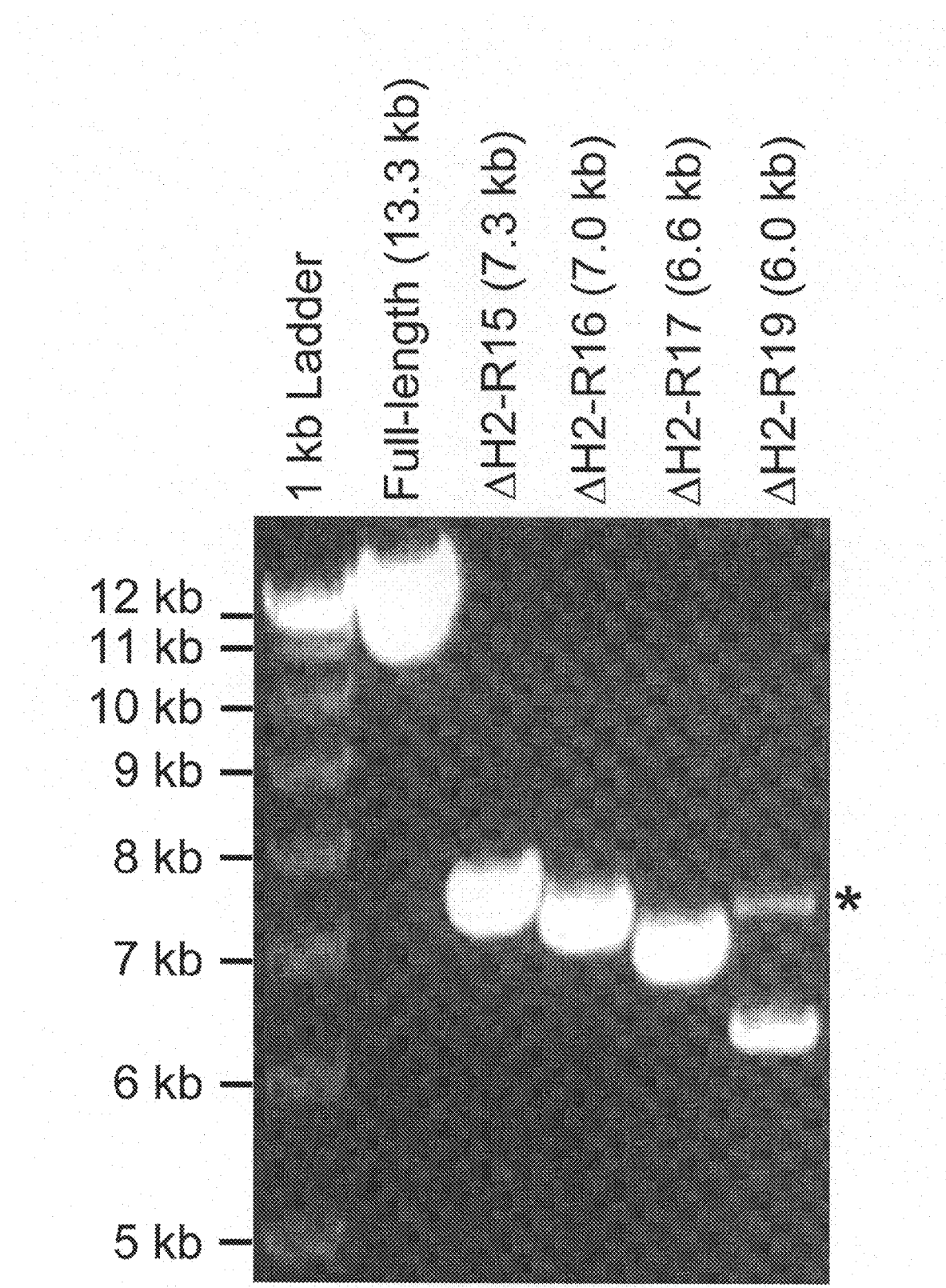
FIG. 3 shows the diagnostic cut of the full-length dystrophin gene and several synthetic mini-dystrophin genes developed by the inventors. The structures of these minigenes are outlined in FIG. 1. The biological function of these minigenes in terms of nNOS restoration is examined in detail in FIG. 4.

One example of dystrophin minigene, ΔH2-R15, can be developed using the ΔH2-R19 minigene as the template. FIG. 3 shows the diagnostic cut for the prototype constructs including the full-length gene, the ΔH2-R19 minigene and three newly synthesized minigenes. The ΔH2-R19 minigene, which cannot restore nNOS to the sarcolemma, is the minigene currently being evaluated for DMD gene therapy (Harper et al., 2002; Lai et al., 2005). The ΔH2-R17, ΔH2-R16 and ΔH2-R15 are minigenes that contain two (R18 and R19), three (R17, R18 and R19), and four (R16, R17, R18 and R19) additional repeats, respectively, than that of the ΔH2-R19 minigene. The extra repeats can be visualized by a gradual increase in the molecular weight of the diagnostic bands. Specifically, each respective construct was cut with Nsi I/Sal I double digestion to release the diagnostic fragment from the transgene. Digested DNA fragments were electrophoresed on an agrose gel. The size of the diagnostic band was determined with the molecular weight marker (1 kb ladder). The asterisk indicates residual leftover plasmid of the ΔH2-R19 construct due to incomplete digestion.

Similar to the synthetic mini-dystrophin genes, the synthetic micro-dystrophin genes were generated using standard molecular biology cloning procedures. Essentially, the relevant DNA sequences (such as repeats, hinges etc) were amplified by a high fidelity PCR reaction and then re-assembled by enzyme ligation using T4 DNA ligase. The recombined synthetic DNA molecules were then transformed into competent E. Coli. using standard recombinant DNA techniques. The correct clones were identified by restriction enzyme diagnostic cut. These clones were further confirmed by DNA sequencing.

EXAMPLE 3 nNOS Restoration

Figure 4:
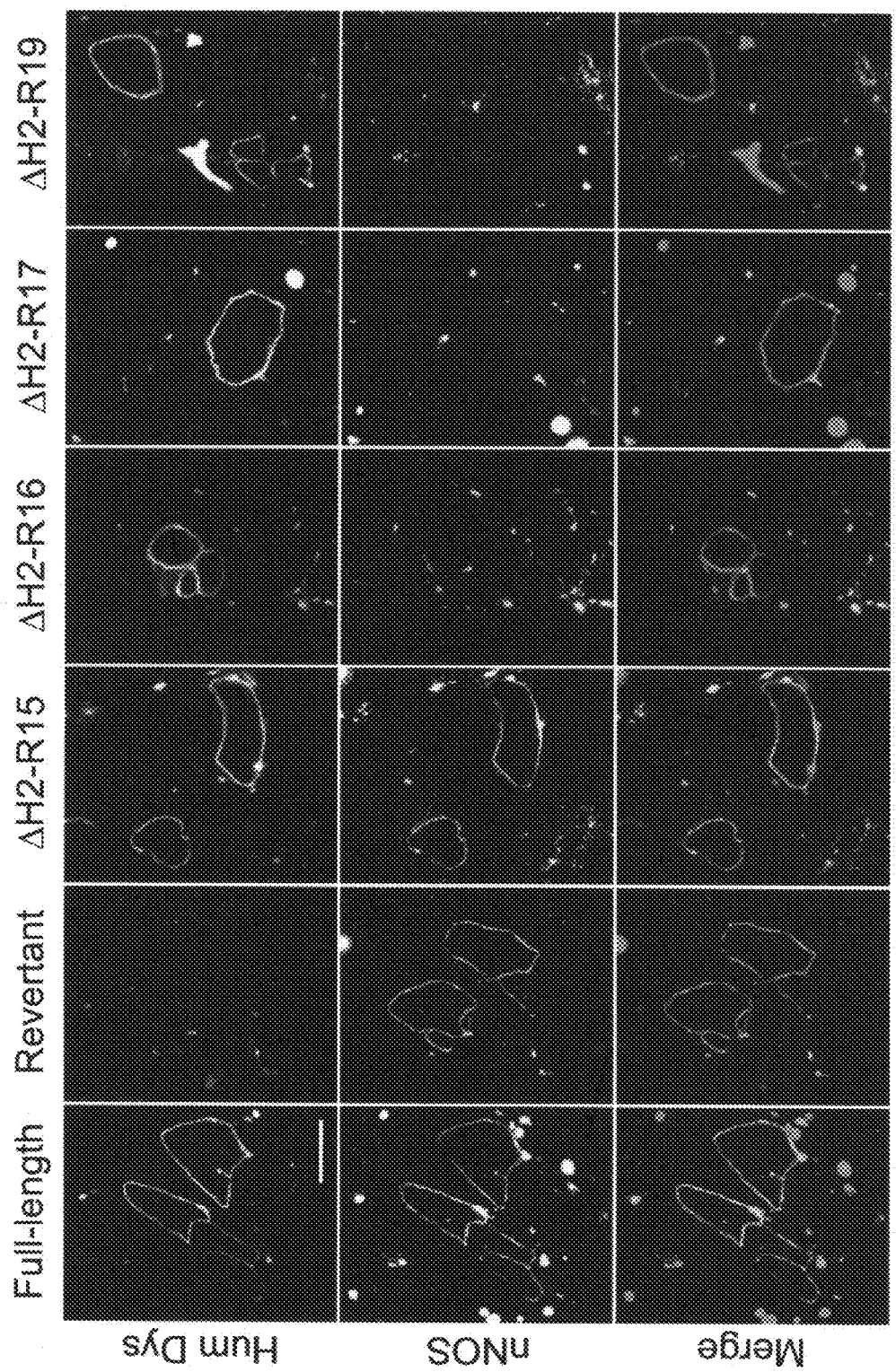
FIG. 4 shows immunofluorescence (IF) analysis of the nNOS restoration and dystrophin expression in skeletal muscle of 2-month-old dystrophin-deficient mdx mice after treatment with the plasmids carrying the full-length or some synthetic mini-dystrophin genes, ΔH2-R15, ΔH2-R16, ΔH2-R17, or ΔH2-R19. A clone of revertant fibers in an untreated mdx muscle is also presented. Expression was examined at 2 to 3 weeks after injection.

FIG. 4 shows immunofluorescence (IF) analysis of the nNOS restorations and dystrophin expressions in skeletal muscle of 2-month-old mdx mice after treatment with the full-length or some synthetic mini-dystrophin genes, ΔH2-R15, ΔH2-R16, ΔH2-R17, or ΔH2-R19. A clone of revertant fibers in an untreated mdx muscle is also presented.

During the experiments, the plasmids carrying the full-length human dystrophin cDNA, the ΔH2-R19, ΔH2-R17, ΔH2-R16, or the inventive ΔH2-R15 minigenes were injected to the tibialis anterior (TA) muscle and the gastrocnemius muscle of 2-month-old mdx mice. All the minigenes were derived from the human dystrophin gene and could be identified using a monoclonal antibody (Dys-3) specific for an epitope existing only in human dystrophin (This antibody is referred to as Hum Dys antibody in this application). In all these constructs, transgenes were expressed under the transcriptional regulation of the CMV promoter and the SV40 polyA.

At the time of injection, there was no dystrophin expression in mdx muscle except for a few revertant fibers. The absence of dystrophin expression in mdx muscle was due to a point mutation in exon 23 in the mouse dystrophin gene in this model. This mutation lead to pre-mature translation termination and the loss of dystrophin expression. Occasionally, an RNA transcript was generated by skipping the mutated exon. This lead to dystrophin expression only in the myofibers containing the skipped transcripts. These myofibers are called revertant. The frequency of revertant myofiber is usually <1%. Since revertant myofibers carry the mouse dystrophin protein, it cannot be recognized by human dystrophin-specific antibody.

To correlate dystrophin expression and nNOS expression in the mini-dystrophin gene (ΔH2-R15) as well as in the full-length human dystrophin gene control, and other control minigenes (ΔH2-R19, ΔH2-R17, ΔH2-R16), two different antibodies, Hum Dys and nNOS antibody, were used for immunostaining. As shown in FIG. 4, Hum Dys antibody (FIG. 4, top row) only reacted with human dystrophin and did not recognize mouse dystrophin in revertant fibers. nNOS antibody (FIG. 4, middle row) recognized sarcolemma-localized nNOS. Positive staining was found in the full-length dystrophin plasmid and the ΔH2-R15 mini-gene transfected cells, as well as in revertant fibers but not in the myofibers transfected by the ΔH2-R19, ΔH2-R17, or ΔH2-R16 minigenes. In the merged images (FIG. 4, bottom row), the constructs that can restore nNOS protein display as yellow (Full-length and ΔH2-R15), while the constructs that cannot restore nNOS display as red (ΔH2-R16, ΔH2-R17, and ΔH2-R19). The mouse dystrophin protein in revertant myofibers cannot be recognized by Dys-3 antibody and they appear as green in the merged image. The scale bar is 50 μm.

Table 2 shows the quantification of the immunostaining results displayed in FIG. 4. Table 2 provides conclusive evidence that the inventive ΔH2-R15 minigene can restore nNOS to the sarcolemma.

Figure 5:
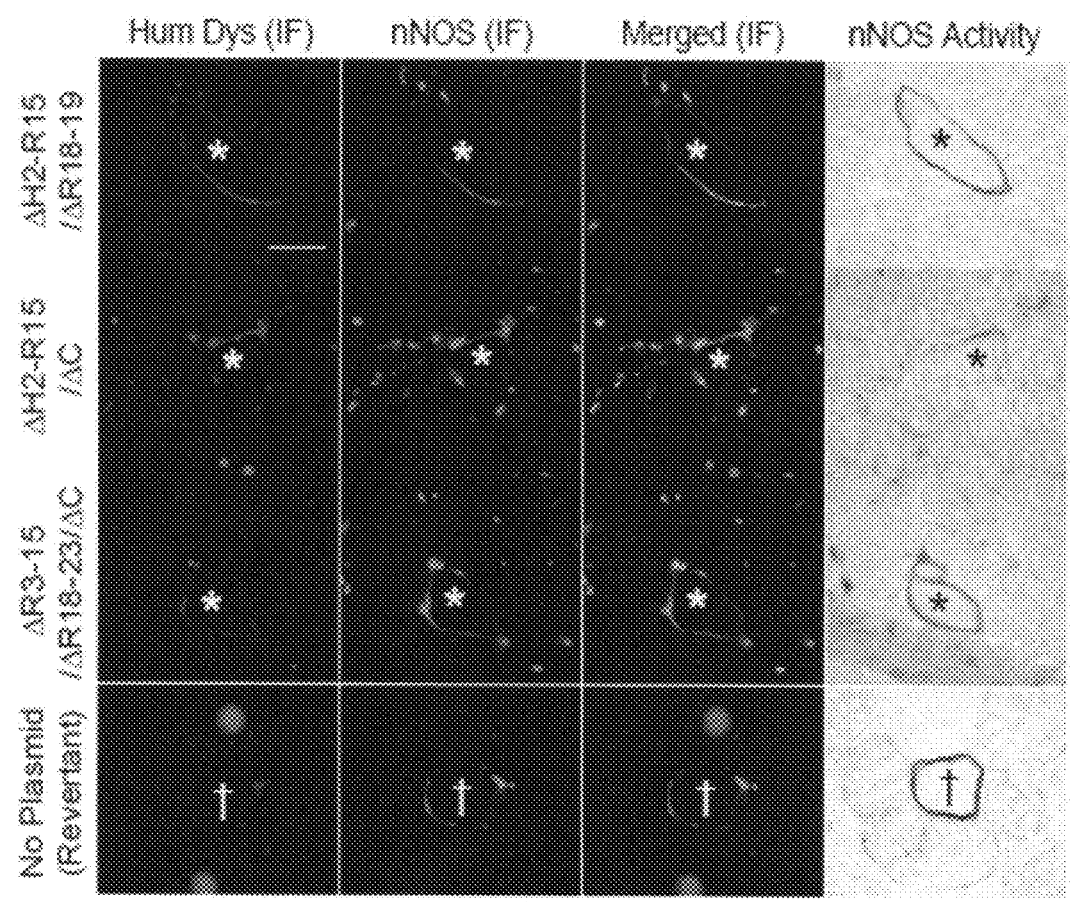
FIG. 5 shows additional IF analysis of nNOS restoration and dystrophin expression in skeletal muscle of dystrophin-deficient mdx mice after treatment with plasmids carrying additional mini/micro-genes (ΔH2-R15/ΔR18-19, ΔH2-R15/ΔC, and ΔR3-15/ΔR18-23/ΔC) synthesized in the inventors' lab, and the histo-enzymatic staining of nNOS activity. Also shown is a revertant fiber in an untreated (no plasmid) mdx muscle.

FIG. 5 shows additional IF analysis of nNOS restoration and dystrophin expression in skeletal muscle of dystrophin-deficient mdx mice after treatment with three additional mini/micro-genes ΔH2-R15/ΔR18-19, ΔH2-R15/ΔC, or ΔR3-15/ΔR18-23/ΔC synthesized. Also shown is a revertant fiber in an untreated mdx muscle.

Similarly, the expression of the additional mini/micro-genes was under transcriptional regulation of the CMV promoter and the SV40 polyA. The plasmids carrying these inventive genes were injected into the TA and/or gastrocnemius muscle in 2-month-old mdx mice. Dystrophin expression and nNOS restoration were examined at one to two weeks later. Expression of the inventive mini/micro-genes was demonstrated by an antibody specific to the human dystrophin epitope (in red color). nNOS expression was revealed by a nNOS specific antibody (in green color). The merged images show co-localization of the inventive mini/microdystrophin protein and the nNOS protein (in yellow). In these photomicrographs, the fibers carrying the inventive mini/microgenes are marked by asterisk. In untreated muscle (no plasmid), only revertant myofiber (cross) was detected. The scale bar is 50 μm.

EXAMPLE 4 nNOS Activity Test

A stringent histo-enzymatic assay has been performed to determine the biochemical function of the nNOS protein that is being recruited. The nNOS-activity results are also included in FIGS. 5, 6B-6E and 7A-7B, with nNOS activity staining shown in blue color in the bright field images. An important concern is whether the nNOS protein detected by immunofluorescence staining after the treatment of the inventive mini/micro-genes is indeed a functional protein. nNOS has an NADPH diaphorase activity (Hope et al., 1991; Bredt et al., 1991; Dawson et al., 1991). Essentially, this enzymatic activity allows electron transfer from NADPH to a colorless, soluble tetrazolium salt and eventually produces a colored, insoluble formazan derivative (Beesley, 1995; Rothe et al., 2005). The nNOS activity assay, i.e., histo-enzymatic assay employed by the inventors, has been previously used by other researchers to establish functional interaction between nNOS and α-syntrophin (Kameya et al., 1999). The myofibers that stained positive for nNOS protein by immunofluorescence staining also showed nNOS activity by the in situ enzymatic assay.

Table 3 shows the quantification of the immunostaining and nNOS activity assay results displayed in FIG. 5. Table 3 provides clear evidence that the mini/micro-genes with the R16-17 micro-domain can restore a functional nNOS protein to the sarcolemma. The nNOS recruiting activity of the R16-17 micro-domain is independent of its natural position in the full-length protein. Results in Table 3 further strengthen the conclusion that nNOS restoration by the inventive mini/micro-genes is independent of the dystrophin C-terminal domain.

EXAMPLE 5

AAV Vectors with the Mini/micro-genes

Figure 6A:
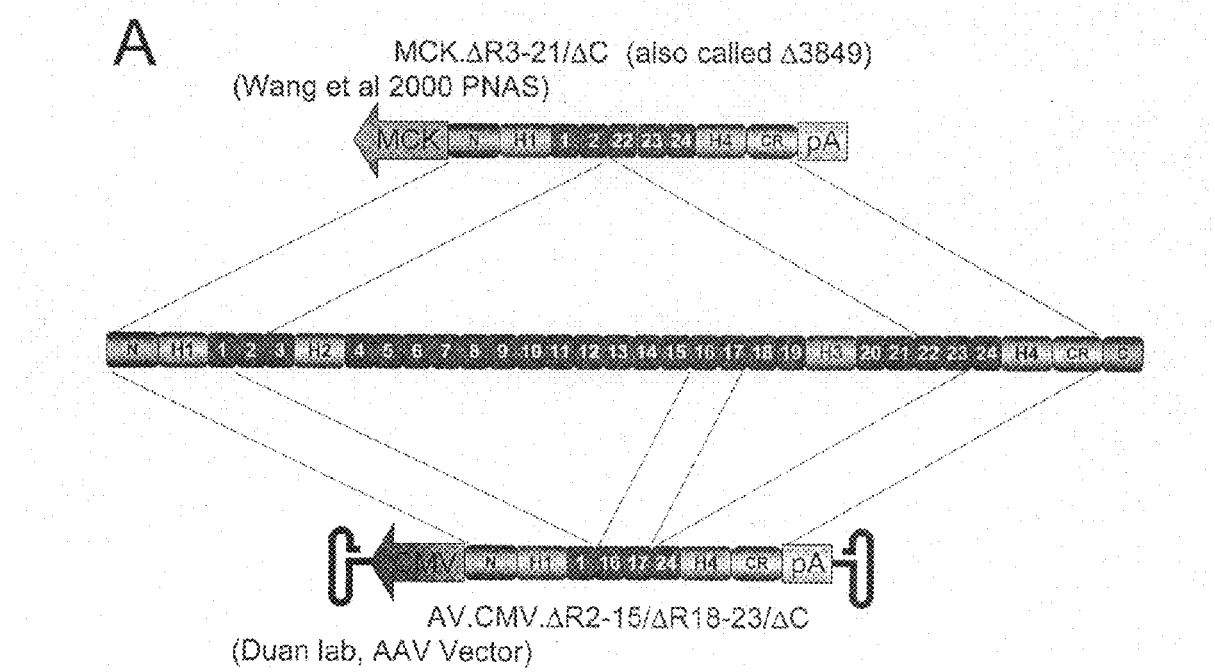
FIG. 6A compares the structure of the AAV vector carrying the microgene ΔR2-15/ΔR18-23/ΔC developed by the inventors to that of the Δ3849 microgene expression cassette developed by another researcher (Wang et al., 2000).

FIG. 6A shows an example of the AAV vectors, i.e., the AAV vector carrying ΔR2-15/ΔR18-23/ΔC microgene, and compares it to the full-length protein and an existing Δ3849 microgene expression cassette (Wang et al., 2000). The expression cassette of the AAV vector contains the CMV promoter, the ΔR2-15/ΔR18-23/ΔC microgene, and the SV40 polyA. The entire cassette is flanked by AAV ITRs at the ends. The AAV vector was generated by packaging the entire construct (AV.CMV. ΔR2-15/ΔR18-23/ΔC) into the capsid of a chosen AAV serotype such as AAV-6, AAV-8 and AAV-9. FIG. 6A also shows the structure of another micro-dystrophin expression cassette (MCK.ΔR3-22/ΔC). This microgene was originally called the "Δ3849 minigene" by its authors (Wang et al., 2000). To facilitate comparison, it is renamed as the ΔR3-22/ΔC microgene to reflect its molecular structure.

FIGS. 6B to 6E show the results of IF straining and nNOS activity staining. In FIGS. 6B-E, expression of the microgene (from a transgenic mdx mouse, as in 6D; or from the inventive AAV-6 vector, as in 6E) is highlighted in red color using a monoclonal antibody specific for a human dystrophin epitope. The nNOS protein is highlighted in green using a nNOS specific polyclonal antibody. Nuclei stained with DAPI are shown in blue. Enzymatic activity of nNOS is reflected as blue color on the sarcolemma in bright field microscopy. In these panels, the top row photomicrographs are low power images (Scale bar, 500 μm). The bottom row photomicrographs are enlarged images from the boxed areas in the top row photomicrographs, respectively (Scale bar, 100 μm). In these experiments, AV. CMV. ΔR2-15/ΔR18-23/ΔC was packed into AAV-6 using the previously published protocols and then the packaged AAV vector was delivered to the TA muscle of 2-month-old mdx mice (Lai et al., 2005; Ghosh et al., 2006; Yue et al., 2006; Lai et al., 2006). AAV infected muscles were harvested at three weeks later.

Figure 6B:
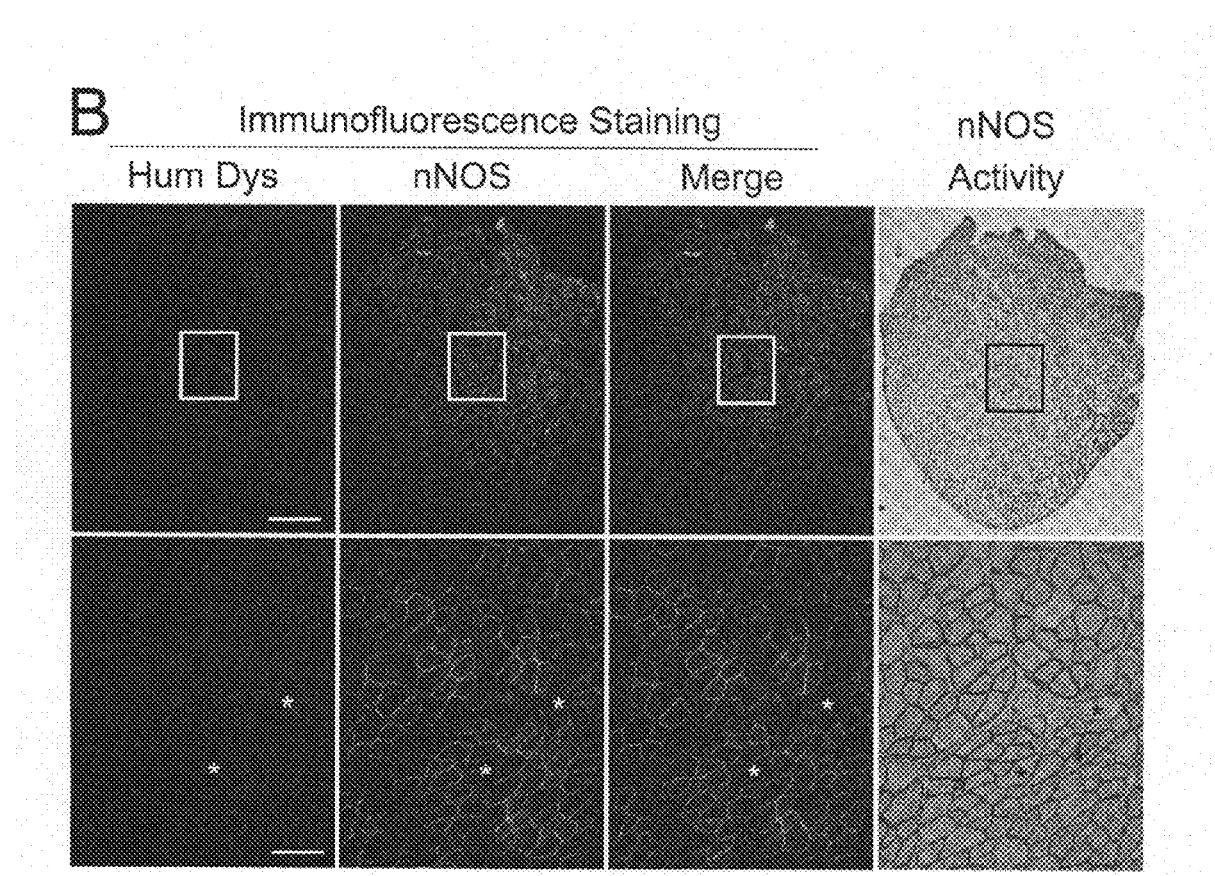
FIG. 6B shows IF and histo-enzymatic staining of nNOS, human dystrophin and nNOS activity in a normal mouse muscle.

FIG. 6B shows sarcolemma nNOS localization in a normal mouse TA muscle. In normal mouse muscle, no human dystrophin was detected with an antibody specific for human dystrophin epitope (Dys-3). Abundant nNOS protein and nNOS activity were detected in normal mouse muscle. nNOS has been shown to preferentially express in type II fibers. In the mouse TA muscle, 99% fibers are type II fibers. Asterisks show a few myofibers (<1%) that are negative for the nNOS protein and nNOS activity. These are type I fibers.

Figure 6C:
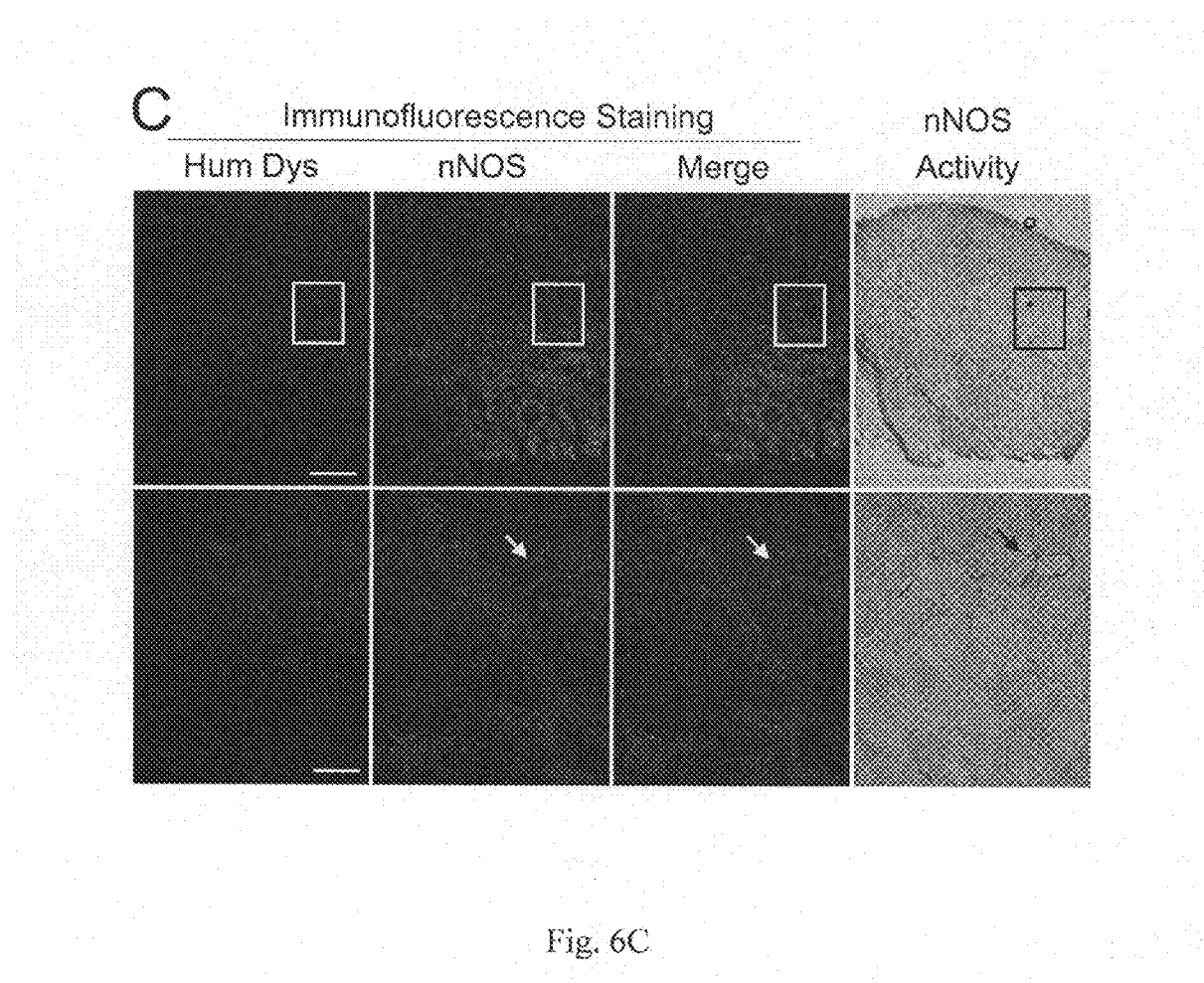
FIG. 6C shows IF and histo-enzymatic staining of nNOS, human dystrophin and nNOS activity in an mdx mouse muscle.

FIG. 6C shows a lack of nNOS protein and nNOS activity on the sarcolemma in mdx muscle. In mdx mouse muscle, no human dystrophin was detected with an antibody specific for human dystrophin epitope (Hum Dys). Arrow marks infrequent revertant fibers that are positive for the nNOS protein and nNOS activity.

Figure 6D:
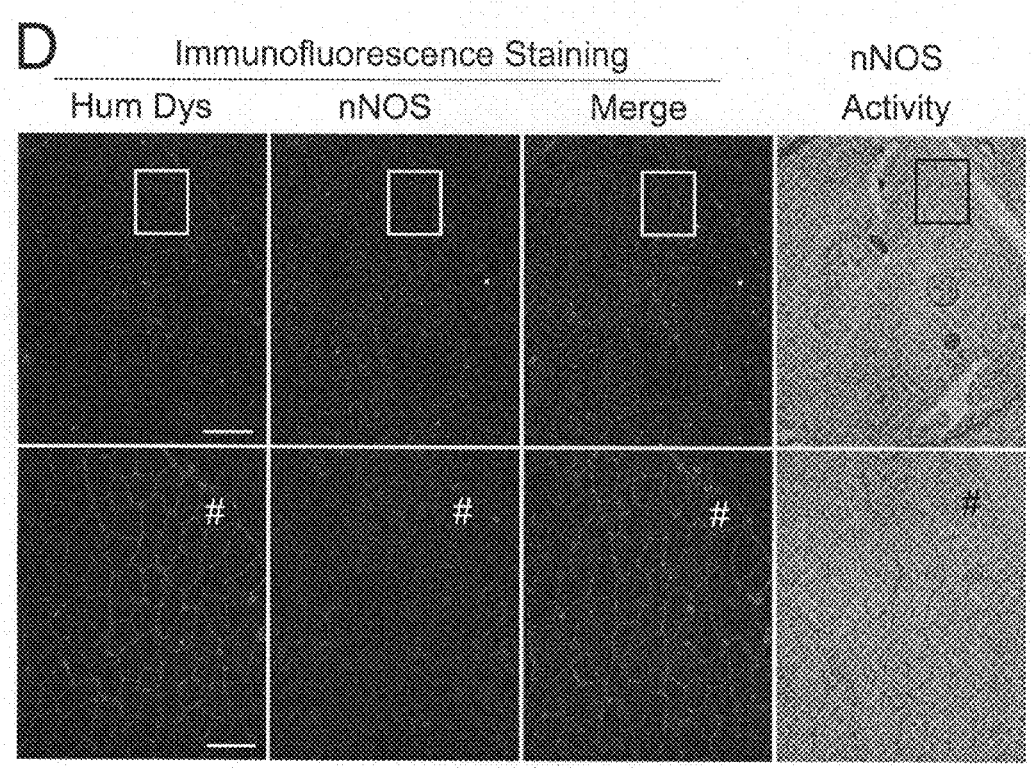
FIG. 6D shows IF and histo-enzymatic staining of nNOS, human dystrophin and nNOS activity in a transgenic mdx mouse muscle carrying the Δ3849 microgene.

FIG. 6D demonstrates that expression of a previously published ΔR3-21/ΔC microgene cannot restore nNOS to the sarcolemma. Pound sign stands for a representative myofiber that expressed the ΔR3-21/ΔC microgene but is negative for the nNOS protein and nNOS activity.

Figure 6E:
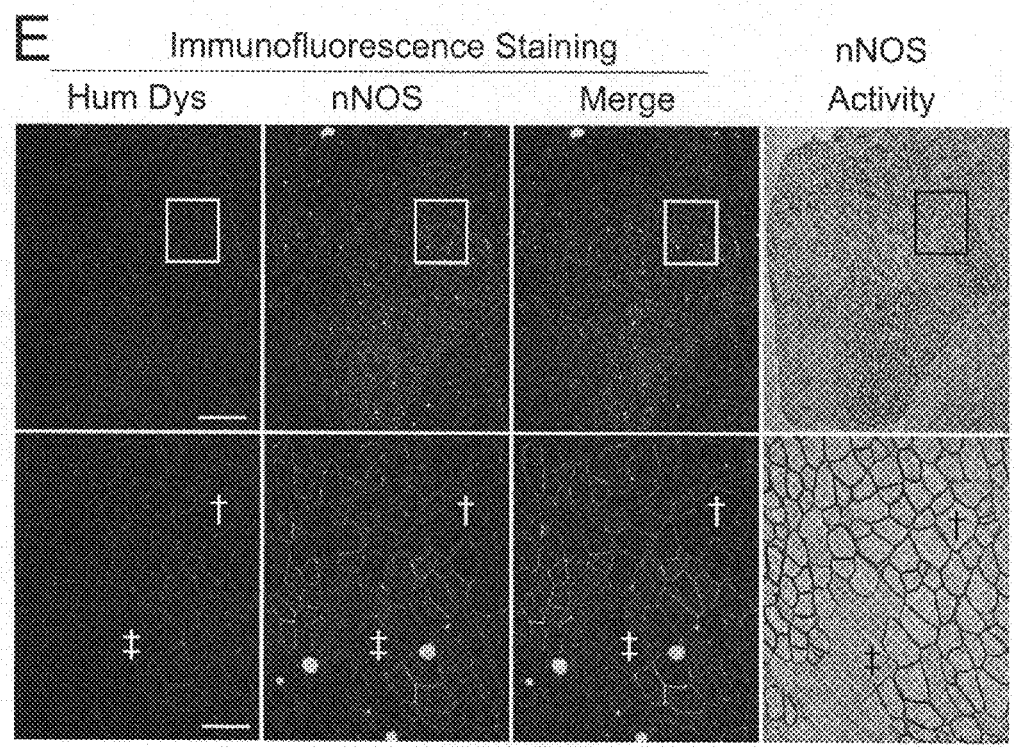
FIG. 6E shows IF and histo-enzymatic staining of nNOS, human dystrophin and nNOS activity in an mdx mouse muscle after treatment with an AAV-6 vector carrying the inventive ΔR2-15/ΔR18-23/ΔC microgene.

FIG. 6E reveals the successful restoration of the nNOS protein and nNOS activity by the inventive ΔR2-15/R18-23/ΔC microgene AAV vector. AAV-6 (AV.CMV. ΔR2-15/ΔR18-23/ΔC) efficiently infected the majority of myofibers in the mdx TA muscle. Cross represents a representative myofiber that expresses the ΔR2-15/R18-23/ΔC microgene and is also positive for nNOS. Double cross represents a representative myofiber that is missed by AAV infection with no sign of ΔR2-15/R18-23/ΔC microgene expression or nNOS protein/ activity. In contrast to the ΔR3-21/ΔC microgene expressing muscle, all the ΔR2-15/ΔR18-23/ΔC microgene positive fibers also showed positive staining for the nNOS protein and nNOS activity. While the ΔR2-15/ΔR18-23/ΔC microgene negative fibers were essentially negative for the nNOS protein and nNOS activity.

EXAMPLE 6

Figure 7A:
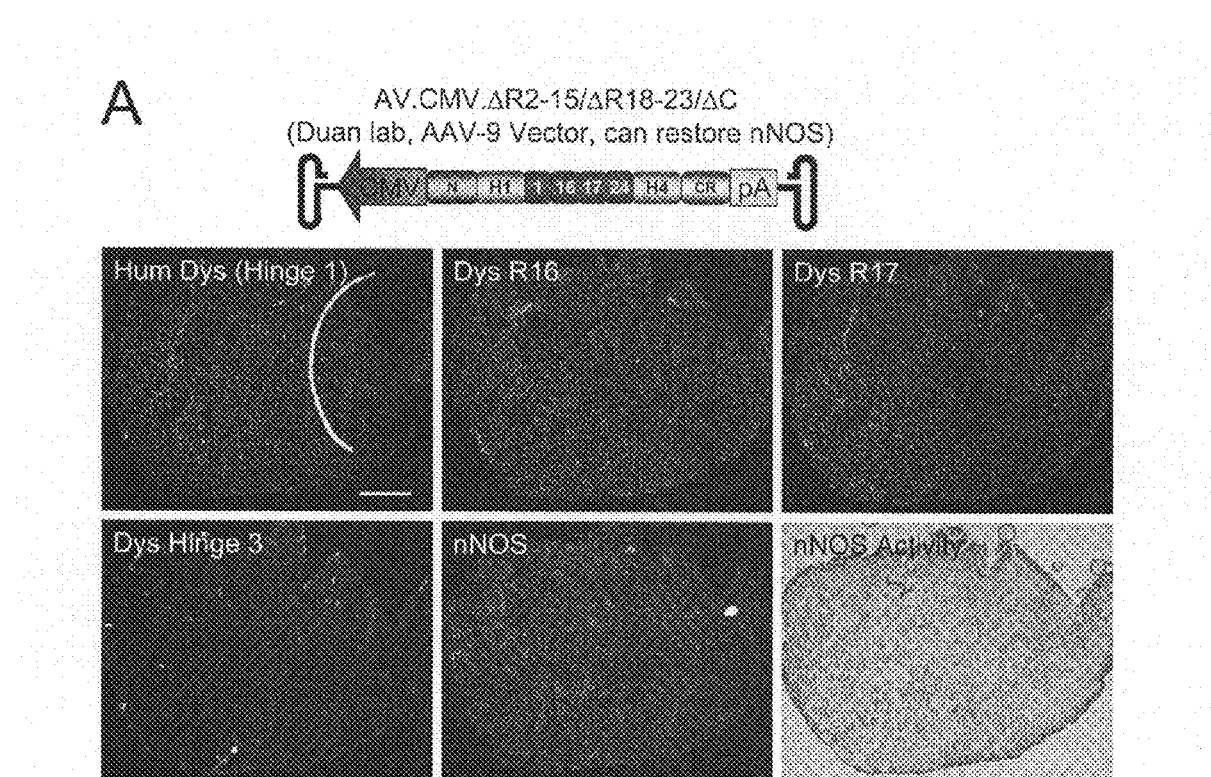
FIG. 7A shows IF and histo-enzymatic staining of nNOS, human dystrophin (N-terminal domain, R16, R17 and H3, respectively) and nNOS activity in an mdx mouse muscle after treatment with an AAV-9 vector carrying the inventive ΔR2-15/ΔR18-23/ΔC microgene. Also shown is the structure of the AAV vector.
Figure 7B:
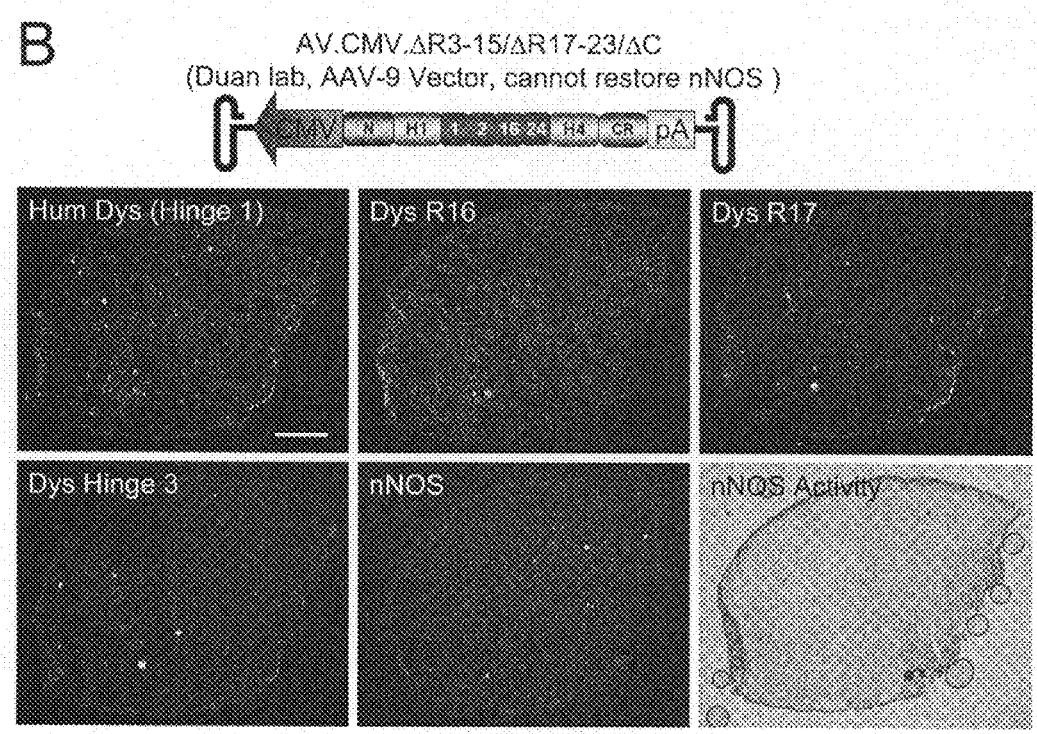
FIG. 7B shows IF and histo-enzymatic staining of nNOS, human dystrophin (N-terminal domain, R16, R17 and H3, respectively) and nNOS activity in an mdx mouse muscle after treatment with an AAV-9 vector carrying the inventive ΔR3-15/ΔR17-23/ΔC microgene. Also shown is the structure of the AAV vector.

Both R16 and R17 Repeats are Required in the Inventive Micro-genes AAV Vectors to Restore nNOS FIGS. 7A and 7B show the results of IF staining and nNOS activity staining. In these experiments, AV. CMV. ΔR2-15/ ΔR18-23/ΔC (FIG. 7A) and AV.CMV.ΔR3-15/ΔR17-23/ΔC (FIG. 7B) were packed into AAV-9 using the previously published protocols and then the packaged AAV vector was delivered to the TA muscle of 50-day-old mdx mice (Bostick et al., 2007; Ghosh et al., 2007). AAV infected muscles were harvested at 30 days later.

FIG. 7A reveals the successful restoration of the nNOS protein and nNOS activity by the inventive ΔR2-15/R18-23/ΔC microgene AAV-9 vector. Four different dystrophin antibodies were used to diagnose ΔR2-15/R18-23/ΔC microgene expression. The Hinge 1 antibody (also called Dys 3) only recognizes hinge 1 in human dystrophin. The R16 antibody (also called Mandys 106) recognizes dystrophin repeat 16. The R17 antibody (also called Manex 44A) recognizes dystrophin repeat 17. The Hinge 3 antibody (also called Manex 50) recognizes dystrophin hinge 3. The inventive ΔR2-15/R18-23/ΔC microgene does not carry H3. Thus, only a few revertant fibers were detected with the Hinge 3 antibody. The Hinge 1, R16 and R17 antibodies revealed abundant transduction with AV.CMV.ΔR2-15/R18-23/ΔC vector. These AAV transduced myofibers also expressed nNOS and showed nNOS activity (Scale bar, 500 μm).

FIG. 7B shows a lack of nNOS protein and nNOS activity on the sarcolemma in mdx muscle infected with AV.CMV.ΔR3-15/R17-23/ΔC AAV-9 vector. This microgene does not contain R17. Therefore, only a few revertant fibers were detected with the R17 antibody.

While the invention has been described in connection with specific embodiments thereof, it will be understood that the inventive method is capable of further modifications. This patent application is intended to cover any variations, uses, or adaptations of the invention following, in general, the principles of the invention and including such departures from the present disclosure as come within known or customary practice within the art to which the invention pertains and as may be applied to the essential features herein before set forth and as follows in the scope of the appended claims.

EXAMPLE 7

Yeast-two-hybrid Studies Revealed an Interaction Between R16-17 and the nNOS PDZ Domain Our in vivo studies in mdx mice suggest that the presence of either R16 alone (such as in the ΔR3-15/ΔR17-23/ΔC microgene) or R17 alone (such as in the ΔH2-R16 minigene) cannot restore sarcolemma nNOS expression. However, when both R16 and R17 are present (such as in the ΔR2-15/ΔR18-23/ΔC microgene), nNOS is recruited to the sarcolemma. To determine whether there is a direct interaction between R16-17 and the nNOS PDZ domain, we performed a yeast-two-hybrid assay (FIG. 8).

Figure 8A:
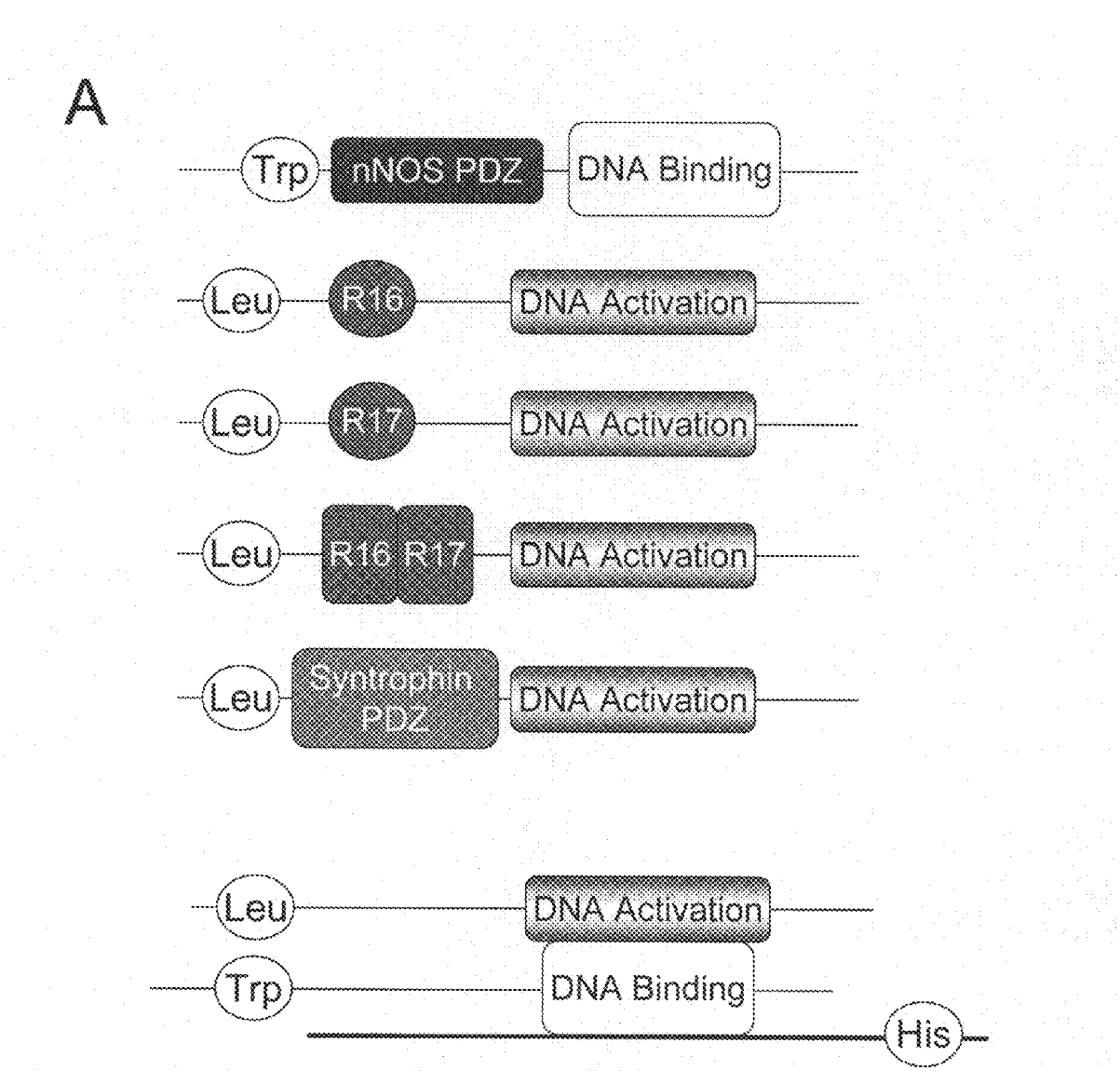
FIGS. 8A-8C illustrate a yeast-two-hybrid assay which revealed a positive interaction between the nNOS PDZ domain and R16-17, but not R16 or R17.
Figure 8B:
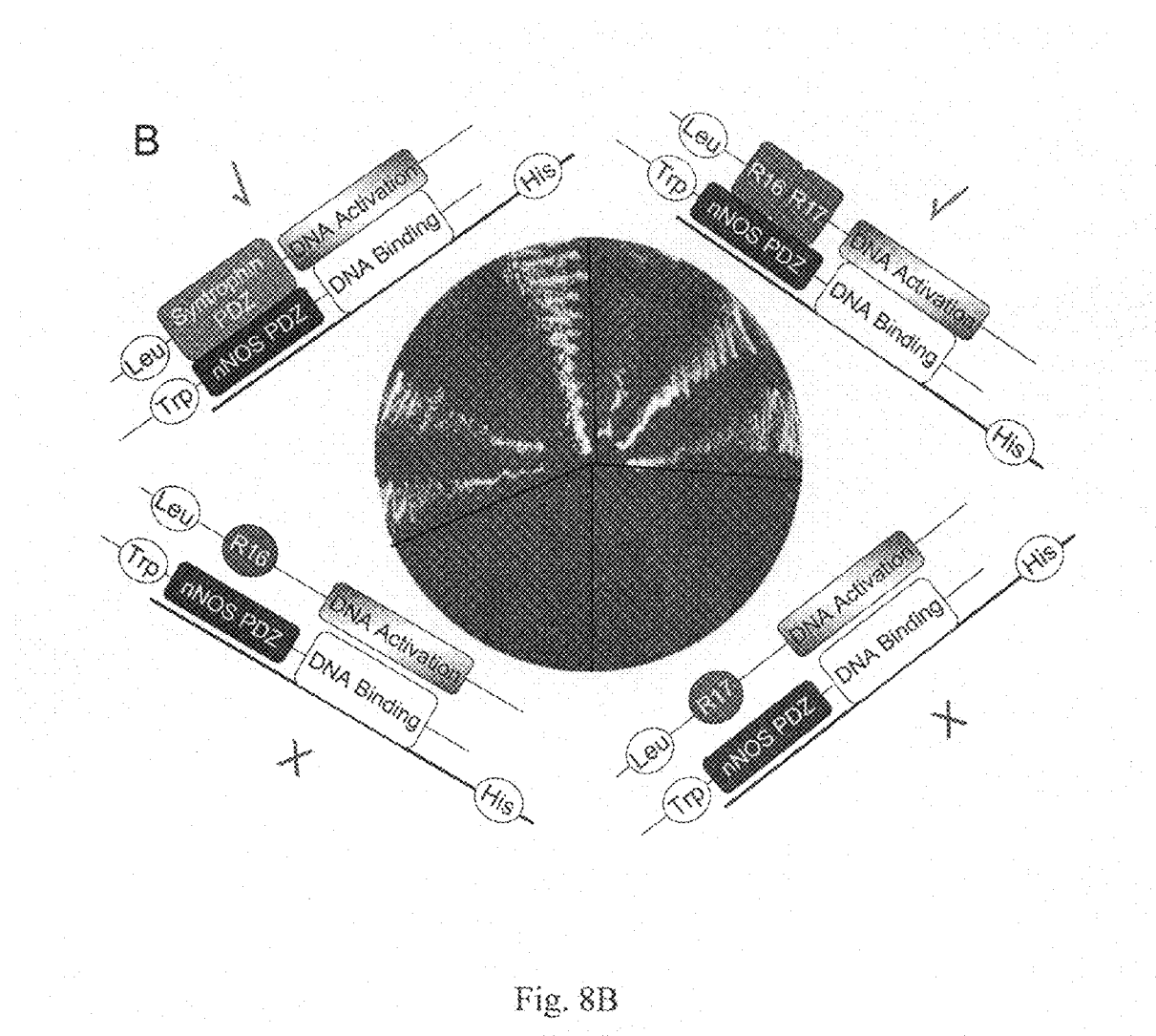
Figure 8C:
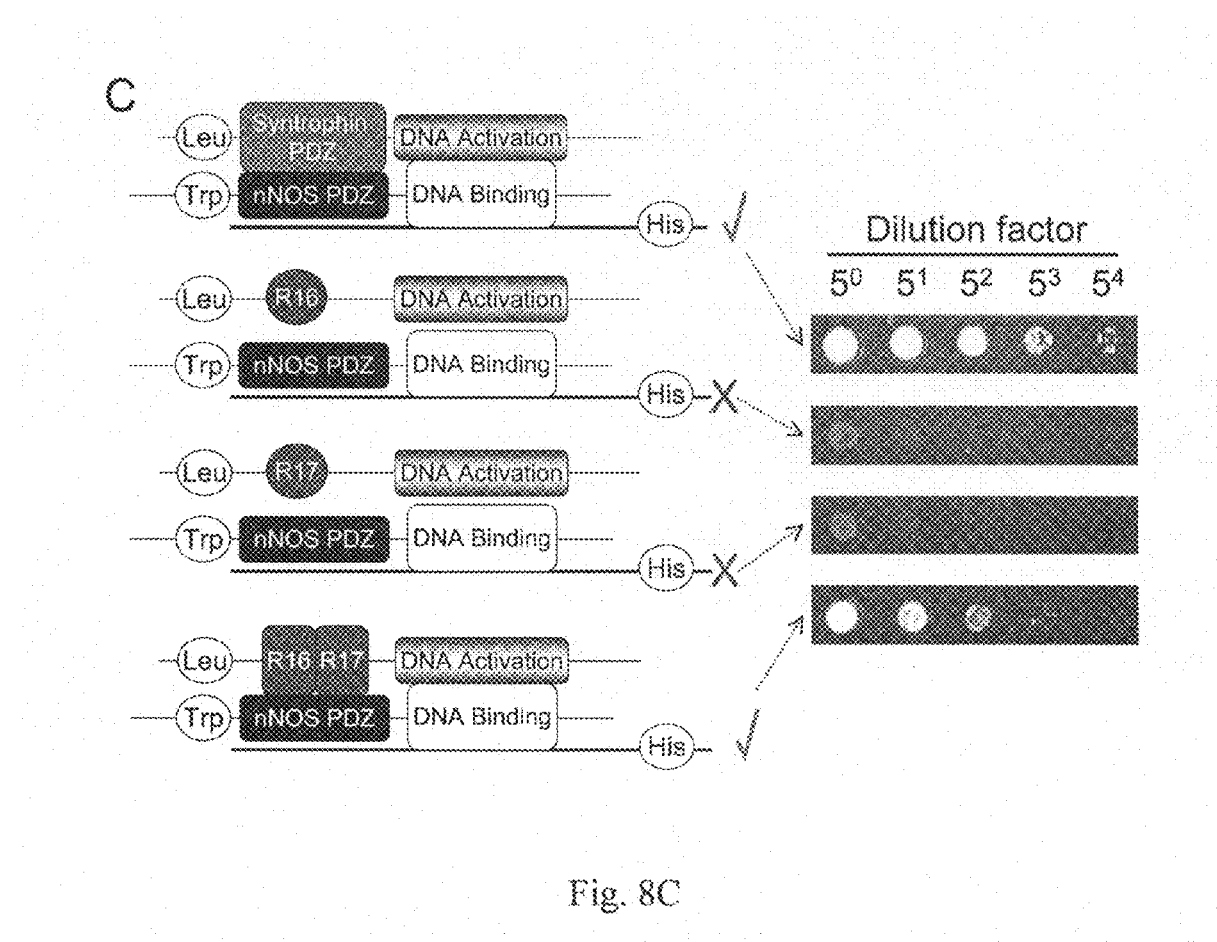

The binding construct expresses the DNA binding domain, tryptophan (Trp) and the nNOS PDZ domain (FIG. 8A). The activation constructs express DNA activation domain, leucine (Leu) and dystrophin spectrin-like repeats (R16 only, R17 only or both R16 and 17) (FIG. 8A). An activation construct carrying the syntrophin PDZ domain was also included as the positive control. An interaction between the DNA binding domain and DNA activation domain initiates histidine (His) production (FIG. 8A). Yeast cells transformed with individual construct did not grow on the Leu-/Trp-double deficient plates. Yeast cells co-transformed with both binding and activation constructs were able to grow on the Leu-/Trp-plates. In the positive control, interaction between the syntrophin PDZ domain and the nNOS PDZ domain resulted in histidine production. This allowed yeast cells to grow in Leu-/Trp-/His-triple deficient plates (FIG. 8B and FIG. 8C). We observed yeast cell growth in cells cotransfected with the R16-17 activation construct, but not in cells co-transfected with R16 or R17 activation constructs (FIGS. 8B and 8C). Taken together, our yeast-two-hybrid results suggest that there is a direct interaction between R16-17 and the nNOS PDZ domain. However, R16 alone or R17 alone cannot interact with the nNOS PDZ domain.

Figure 9A:
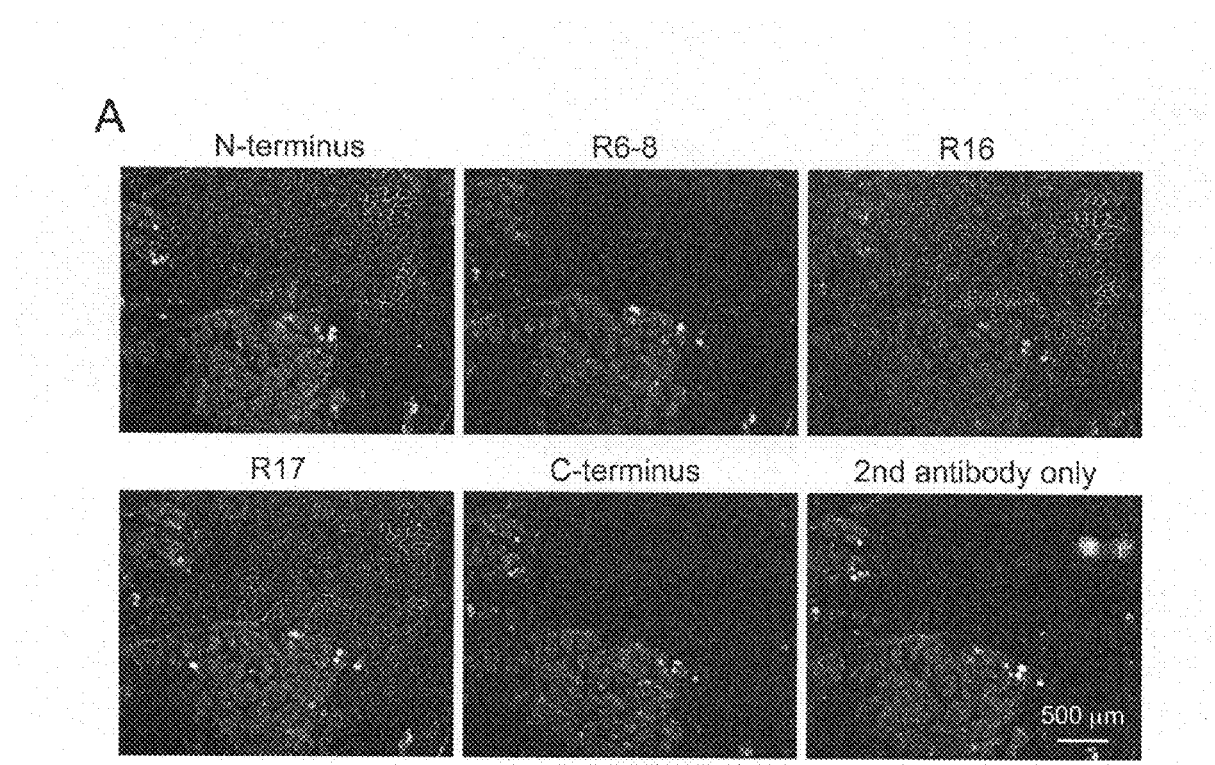
FIGS. 9A-9B show that the ΔR2-15/ΔR18-23/ΔC microgene strengthened the sarcolemma integrity in mdx skeletal muscle. AV.CMV.ΔR2-15/ΔR18-23/ΔC was packaged in AAV-6 vector. 6×10e10 vg particles of the vector were delivered to the gastrocnemius muscle in 2-m-old mdx mice (N=4). The Evans blue dye uptake assay was performed at 40 days after AAV infection. Representative low power (FIG. 9A) and high power (FIG. 9B) immunofluorescence staining photomicrographs on serial muscle sections in AAV infected muscle. The epitope recognized by the respective antibodies are marked for each photomicrograph. Micro-dystrophin is expressed along the sarcolemma. Evans blue dye accumulates inside injured myofibers.
Figure 9B:
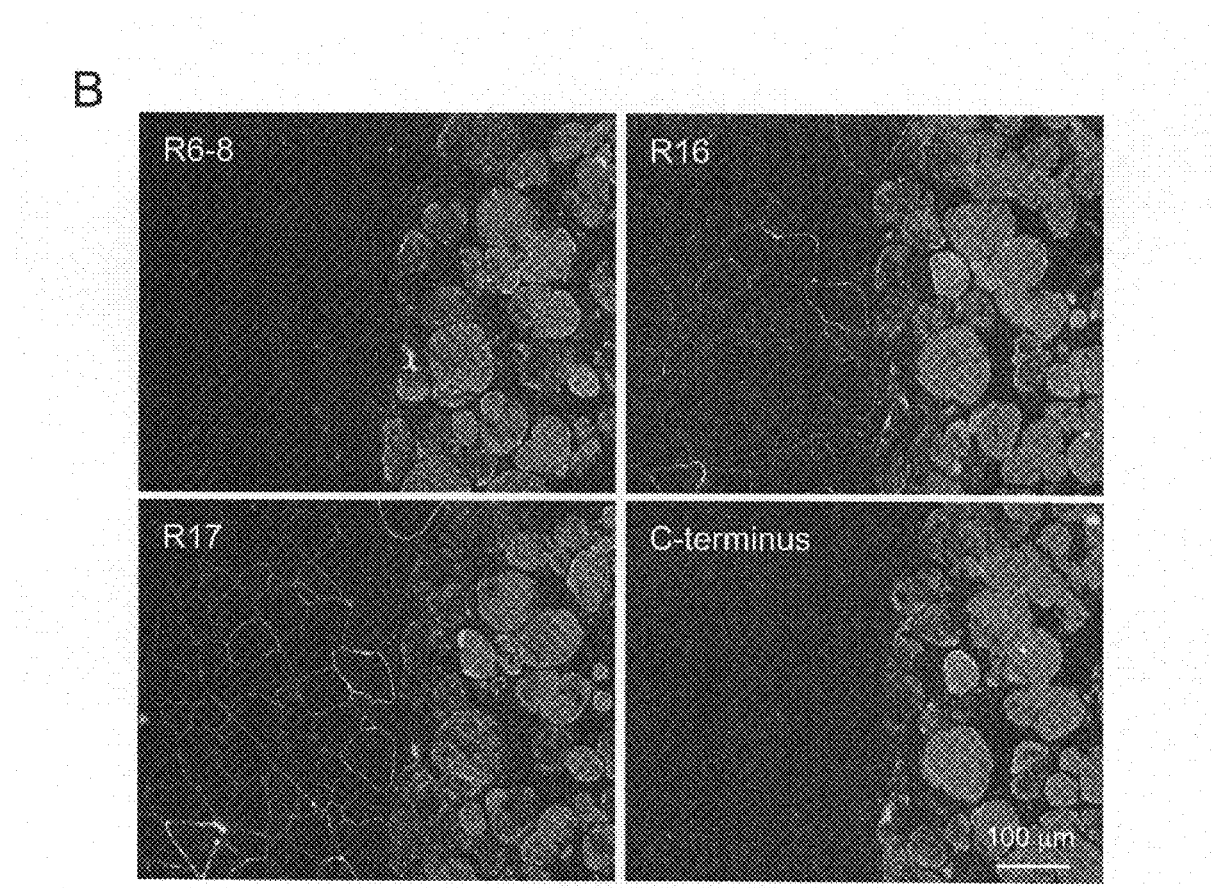

The R16-17 containing micro-dystrophin gene strengthens the sarcolemma. Dystrophin provides mechanical support to the sarcolemma. In the absence of dystrophin, muscle contraction leads to sarcolemma damage. This can be measured by the accumulation of Evans blue dye (EBD) in injured myofibers. AAV-6 AV.CMV.ΔR2-15/ΔR18-23/ΔC was delivered to the gastrocnemius muscle in 2-month-old adult mdx mice and EBD uptake assay was performed at 40 days later. Serial immunofluorescence staining with antibodies specific for the N-terminus, R16 and R17 revealed microgene expression (FIG. 9). R6-8 and C-terminus are deleted in the ΔR2-15/ΔR18-23/ΔC microgene. Antibodies specific for these regions did not yield positive staining. EBD was observed only in myofibers not transduced by AV.CMV.ΔR2-15/ΔR18-23/ΔC vector.

Figure 10A:
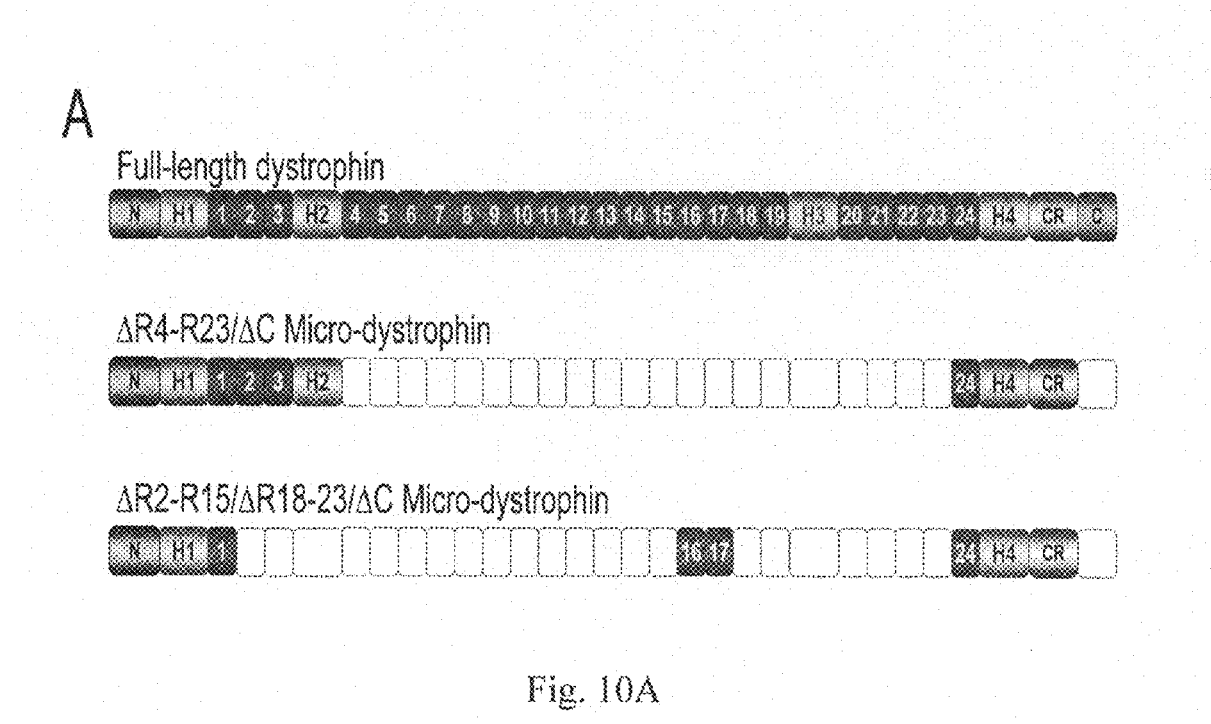
FIGS. 10A-10B show that the ΔR2-15/ΔR18-23/ΔC and the ΔR4-23/ΔC microgenes resulted in similar levels of muscle force improvement in mdx mice. AV.CMV.ΔR2-15/ΔR18-23/ΔC and AV.CMV.ΔR4-23/ΔC were packaged in AAV serotype-9 (AAV-9). AAV-9 vector was delivered to newborn male mdx mice via facial vein injection (1×10e12 vg particles/vector/mouse). Specific force of the extensor digitorium longus (EDL) muscle was measured at three months after AAV infection. Age and sex-matched BL10 and mdx mice were included as controls for muscle force measurement. Asterisk, the BL10 EDL muscle specific force was significantly higher than that of the other groups. Cross, the specific force from AAV infected mice was significantly higher than that of the mdx group but lower than that of the BL10 group. There was no statistical difference between AV.CMV.ΔR2-15/ΔR18-23/ΔC infected mice and AV.CMV.ΔR4-23/ΔC infected mice. Sample size, N=4 for BL10; N=5 for mdx; N=6 for AV.CMV.ΔR4-23/ΔC infected mdx mice; N=5 for AV.CMV.ΔR2-15/ΔR18-23/ΔC infected mdx mice.
Figure 10B:
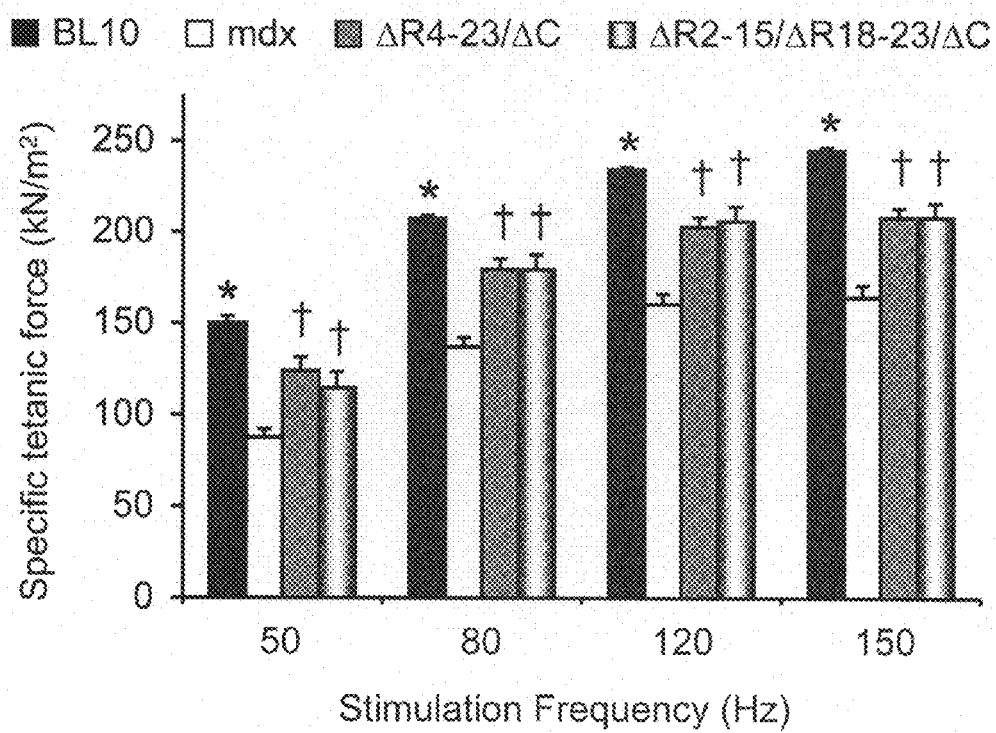
Figure 11A:
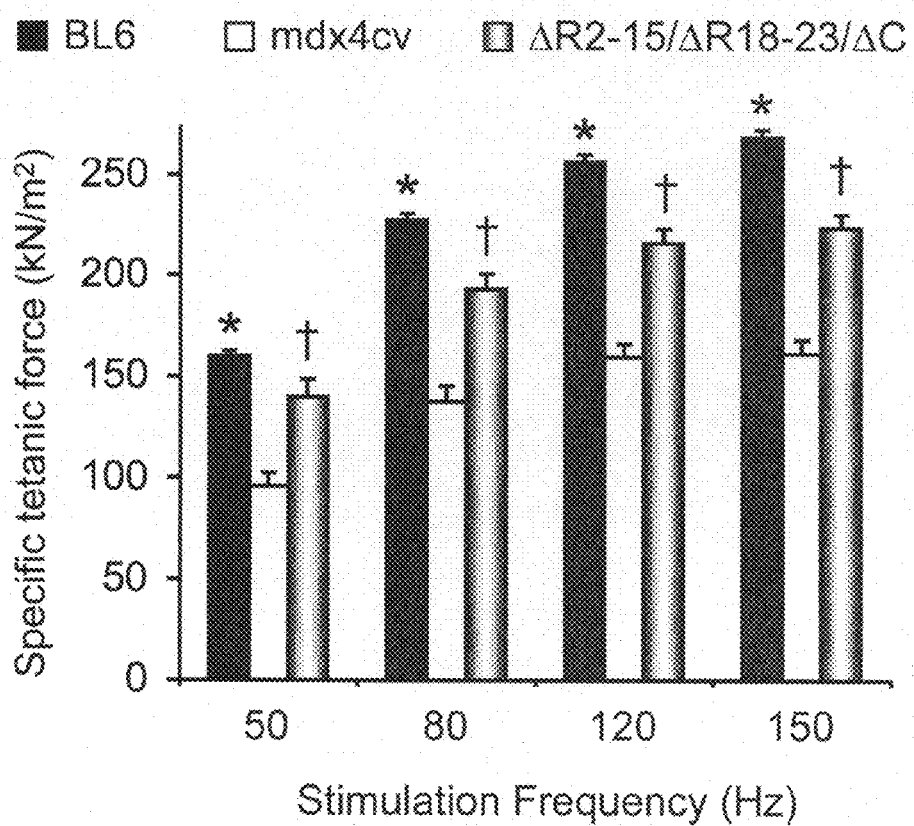
FIGS. 11A-11B show that systemic delivery of AAV-9 AV.CMV.ΔR2-15/ΔR18-23/ΔC in newborn mdx4cv mice improved skeletal muscle specific force and reduced the serum creatine kinase (CK) level. 1×10e12 vg particles AAV-9 AV.CMV.ΔR2-15/ΔR18-23/ΔC were delivered to newborn male mdx4cv mice via facial vein injection. Specific force of the extensor digitorium longus (EDL) muscle (FIG. 11A) and the serum creatine kinase level (FIG. 11B) were examined at three months after AAV infection. Age and sex-matched BL6 and mdx4cv mice were included as controls. Asterisk, the results from BL6 mice were significantly better than those of the other groups. Cross, the results from AAV infected mice were significantly better than those of the mdx4cv group but worse than those of the BL6 group. Sample size, N=7 for BL6; N=6 for mdx4cv; N=6 for AV.CMV.ΔR2-15/ΔR18-23/ΔC infected mdx4cv mice.
Figure 11B:
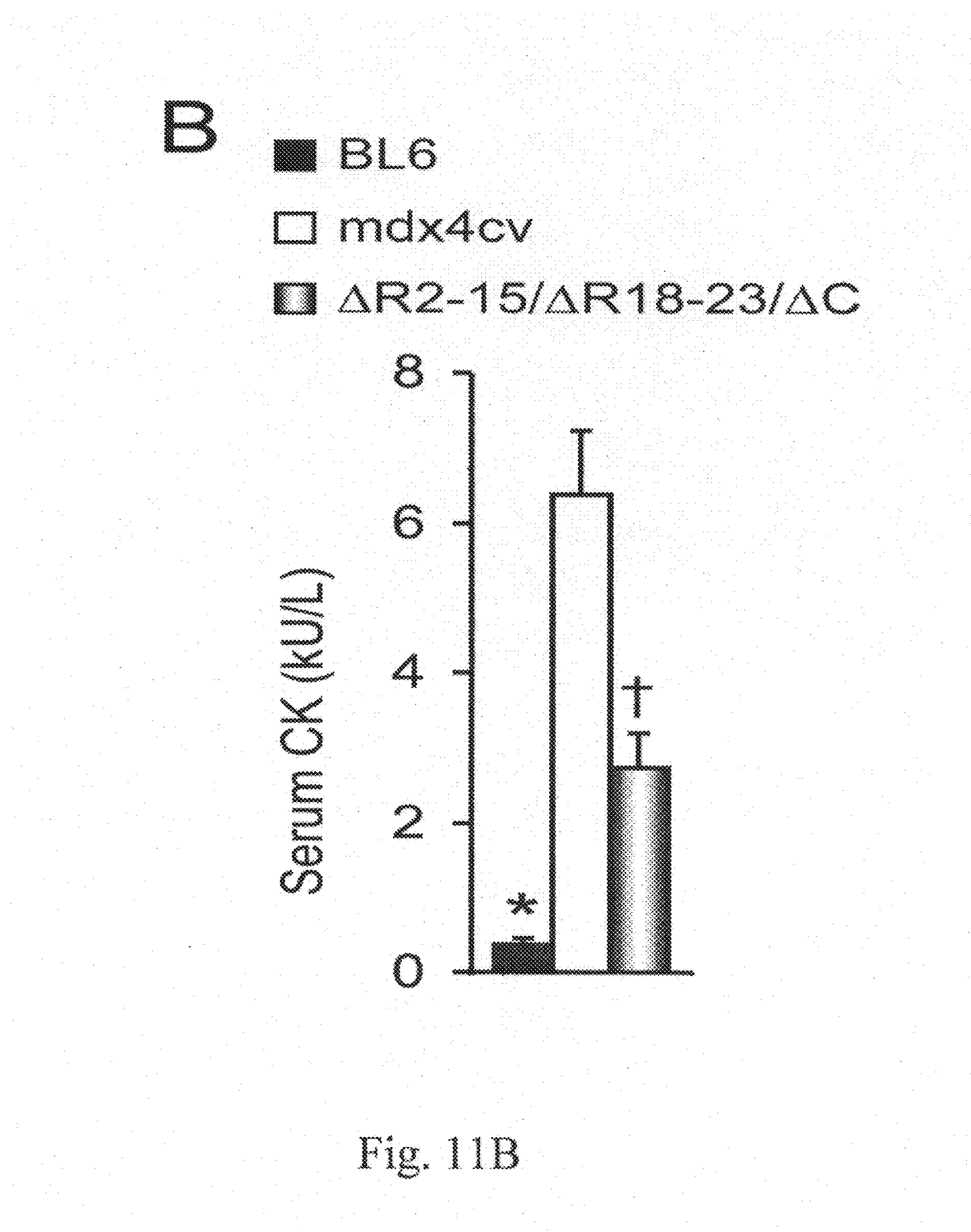

The R16-17 containing micro-dystrophin gene improves muscle force in mouse models of Duchenne muscular dystrophy (DMD). The ΔR4-23 microgene is one of the best-characterized microgenes in the literature (Abmayr et al., 2005; Gregorevic et al., 2006; Gregorevic et al., 2004; Harper et al., 2002; Liu et al., 2005; Yue et al., 2003; Yue et al., 2006). Experiments in mdx mice, utrophin/dystrophin double knockout mice and dystrophic dogs have yielded promising results. The extensor digitorium longus (EDL) muscle force was compared in mdx mice infected with either AV.CMV.ΔR4-23/ΔC or AV.CMV.ΔR2-15/ΔR18-23/ΔC. Despite the differences in the rod domain structure (FIG. 10A), both microgenes resulted in the same level of force improvement (FIG. 10B). An experiment was conducted to test whether the ΔR2-15/ΔR18-23/ΔC microgene could improve muscle force in mdx4cv mice. These mice were derived on the BL6 background and they carried a different mutation in the dystrophin gene. After systemic gene delivery in newborn mdx4cv mice, significant increase in the EDL muscle specific force was observed (FIG. 11A). Serum creatine kinase (CK) was elevated in DMD patients and in animal models of DMD. AAV therapy with the ΔR2-15/ΔR18-23/ΔC microgene significantly reduced the serum CK level in mdx4cv mice (FIG. 11B).

To further evaluate the therapeutic efficacy of the ΔR2-15/ΔR18-23/ΔC microgene, a more stringent test was performed in adult myoD/dystrophin double knockout (m-dko) mice (FIG. 12). Mdx mice displayed mild phenotype. This was partially due to robust muscle regeneration in mouse skeletal muscle. In m-dko mice, muscle regeneration was blocked by inactivating a skeletal muscle specific transcription factor myoD. M-dko mice displayed severe muscle disease similar to human patients (Duan, 2006; Megeney et al., 1996; Megeney et al., 1999). Systemic AAV-9 delivery was performed in 2-m-old male m-dko mice. At three months after AAV therapy, EDL muscle force was measured under single (twitch) and tetanic stimulation. Comparing with untreated mice, AV.CMV.ΔR2-15/ΔR18-23/ΔC infection significantly enhanced muscle force (FIGS. 12A and 12B). DMD muscle is especially sensitive to eccentric contraction induced injury. In untreated m-dko mice, eccentric contraction led to rapid reduction of the muscle force. AV.CMV.ΔR2-15/ΔR18-23/ΔC treatment significantly preserved muscle force following eccentric injury (FIG. 12C).

Figure 12A:
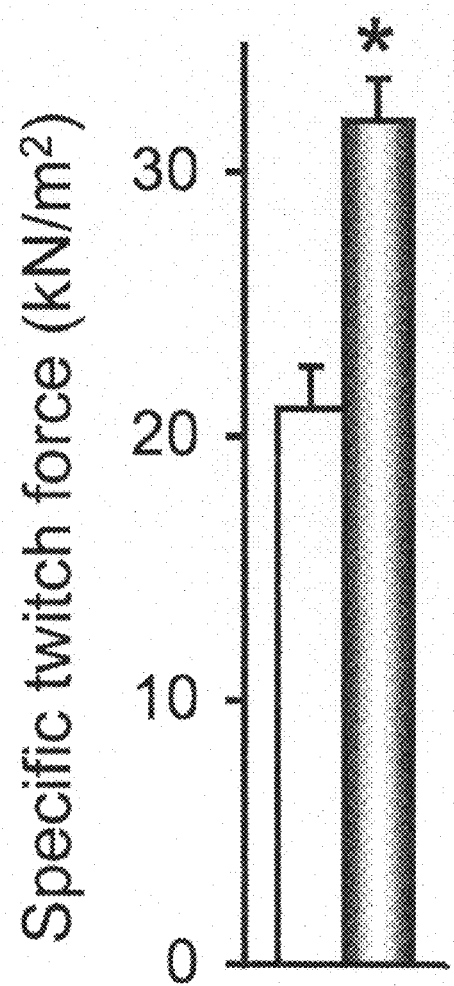
FIGS. 12A-12D show that systemic delivery of AAV-9 AV.CMV.ΔR2-15/ΔR18-23/ΔC in adult myoD/dystrophin double knockout mice (m-dko) improved skeletal muscle function and reduced the serum creatine kinase (CK) level. 5.5×10e12 vg particles of AAV-9 AV.CMV.ΔR2-15/ΔR18-23/ΔC were delivered to 2-m-old male m-dko mice via tail vein injection. The extensor digitorium longus (EDL) muscle function (FIGS. 12A to 12C) and the serum creatine kinase level (FIG. 12D) were examined at three months after AAV infection. Age and sex-matched uninfected littermate were included as controls.
Figure 12B:
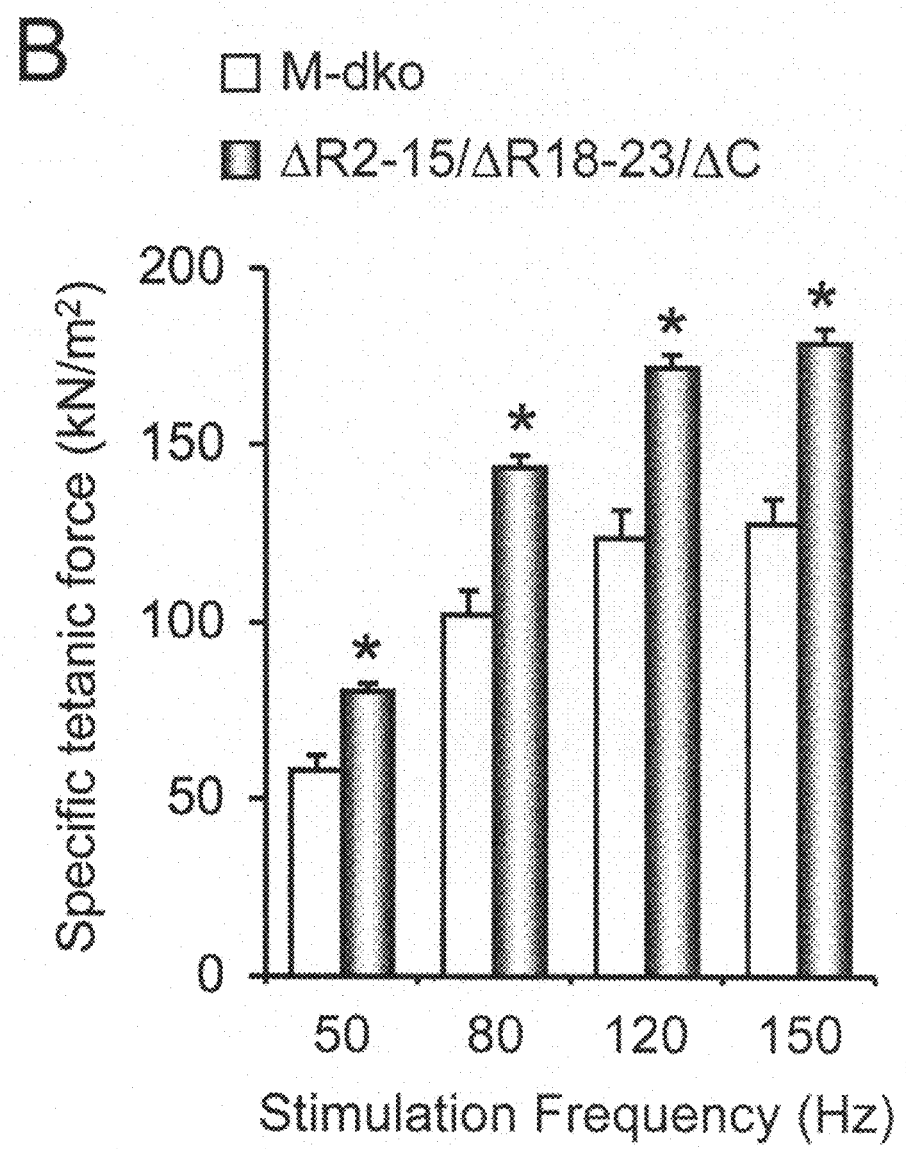
Figure 12C:
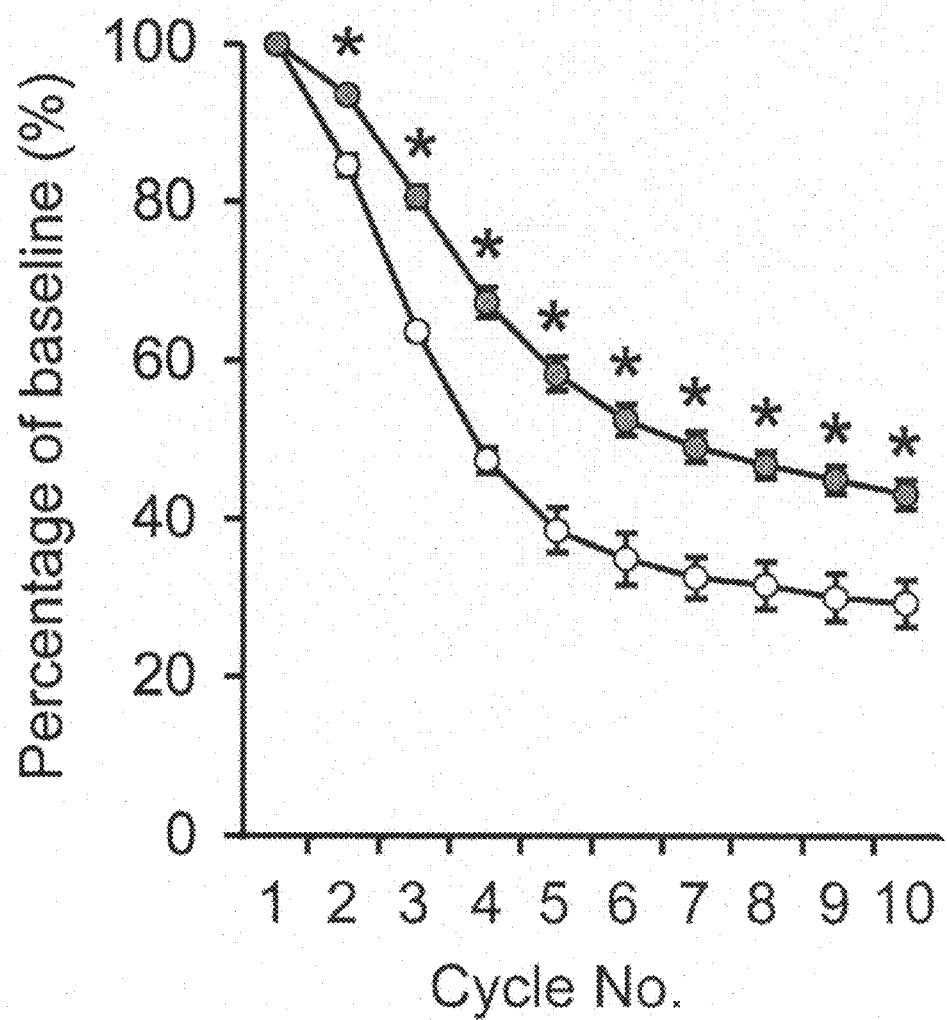
Figure 12D:
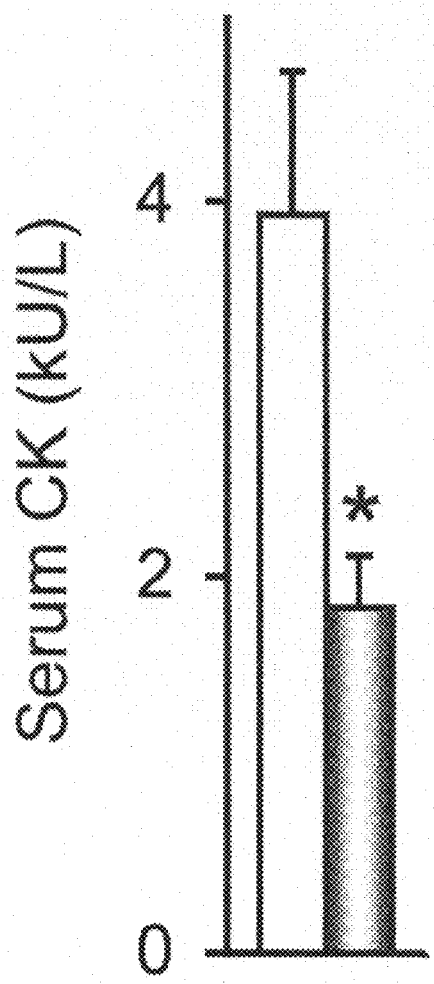

In addition to muscle force improvement, AAV therapy in adult m-dko mice also resulted in significant reduction in the serum CK level (FIG. 12D).

REFERENCES

Adams, M. E., Mueller, H. A., and Froehner, S. C. (2001). In vivo requirement of the alpha-syntrophin PDZ domain for the sarcolemmal localization of nNOS and aquaporin-4. J Cell Biol 155, 113-122.

Bachrach, E., Li, S., Perez, A. L., Schienda, J., Liadaki, K., Volinski, J., Flint, A., Chamberlain, J., and Kunkel, L. M. (2004). Systemic delivery of human microdystrophin to regenerating mouse dystrophic muscle by muscle progenitor cells. Proc Natl Acad Sci USA 101, 3581-3586.

Beesley, J. E. (1995). Histochemical methods for detecting nitric oxide synthase. Histochem J 27, 757-769.

Bostick, B., Ghosh, A., Yue, Y., Long, C., and Duan, D. (2007). Systemic AAV-9 transduction in mice is influenced by animal age but not by the route of administration. Gene Ther In-press (online publication Sep. 27, 2007. doi: 10.1038/sj.gt.3303029).

Bredt, D. S., Glatt, C. E., Hwang, P. M., Fotuhi, M., Dawson, T. M., and Snyder, S. H. (1991). Nitric oxide synthase protein and mRNA are discretely localized in neuronal populations of the mammalian CNS together with NADPH diaphorase. Neuron 7, 615-624.

Brenman, J. E., Chao, D. S., Gee, S. H., McGee, A. W., Craven, S. E., Santillano, D. R., Wu, Z., Huang, F., Xia, H., Peters, M. F., et al. (1996). Interaction of nitric oxide synthase with the postsynaptic density protein PSD-95 and alpha1-syntrophin mediated by PDZ domains. Cell 84, 757-767.

Brenman, J. E., Chao, D. S., xia, H., Aldape, K., and Bredt, D. S. (1995). Nitric oxide synthase complexed with dystrophin and absent from skeletal muscle sarcolemma in Duchenne muscular dystrophy. Cell 82, 743-752.

Chang, W. J., Iannaccone, S. T., Lau, K. S., Masters, B. S., McCabe, T. J., McMillan, K., Padre, R. C., Spencer, M. J., Tidball, J. G., and Stull, J. T. (1996). Neuronal nitric oxide synthase and dystrophin-deficient muscular dystrophy. Proc Natl Acad Sci USA 93, 9142-9147.

Chao, D. S., Gorospe, J. R., Brenman, J. E., Rafael, J. A., Peters, M. F., Froehner, S. C., Hoffman, E. P., Chamberlain, J. S., and Bredt, D. S. (1996). Selective loss of sarcolemmal nitric oxide synthase in Becker muscular dystrophy. J Exp Med 184, 609-618.

Crawford, G. E., Faulkner, J. A., Crosbie, R. H., Campbell, K. P., Froehner, S. C., and Chamberlain, J. S. (2000). Assembly of the dystrophin-associated protein complex does not require the dystrophin COOH-terminal domain. J Cell Biol 150, 1399-1410.

Dawson, T. M., Bredt, D. S., Fotuhi, M., Hwang, P. M., and Snyder, S. H. (1991). Nitric oxide synthase and neuronal NADPH diaphorase are identical in brain and peripheral tissues. Proc Natl Acad Sci USA 88, 7797-7801.

England, S. B., Nicholson, L. V., Johnson, M. A., Forrest, S. M., Love, D. R., Zubrzycka-Gaarn, E. E., Bulman, D. E., Harris, J. B., and Davies, K. E. (1990). Very mild muscular dystrophy associated with the deletion of 46% of dystrophin. Nature 343, 180-182.

Fabb, S. A., Wells, D. J., Serpente, P., and Dickson, G. (2002). Adeno-associated virus vector gene transfer and sarcolemmal expression of a 144 kDa micro-dystrophin effectively restores the dystrophin-associated protein complex and inhibits myofibre degeneration in nude/mdx mice. Hum Mol Genet. 11, 733-741.

Ferrer, A., Wells, K. E., and Wells, D. J. (2000). Immune responses to dystropin: implications for gene therapy of Duchenne muscular dystrophy. Gene Ther 7, 1439-1446.

Ghosh, A., Yue, Y., and Duan, D. (2006). Viral serotype and the transgene sequence influence overlapping adeno-associated viral (AAV) vector-mediated gene transfer in skeletal muscle. J Gene Med 8, 298-305.

Ghosh, A., Yue, Y., Long, C., Bostick, B., and Duan, D. (2007). Efficient Whole-body Transduction with Trans-splicing Adeno-associated Viral Vectors. Mol Ther 15, 750-755.

Gregorevic, P., Allen, J. M., Minami, E., Blankinship, M. J., Haraguchi, M., Meuse, L., Finn, E., Adams, M. E., Froehner, S. C., Murry, C. E., and Chamberlain, J. S. (2006). rAAV6-microdystrophin preserves muscle function and extends lifespan in severely dystrophic mice. Nat Med 12, 787-789.

Gregorevic, P., Blankinship, M. J., Allen, J. M., Crawford, R. W., Meuse, L., Miller, D. G., Russell, D. W., and Chamberlain, J. S. (2004). Systemic delivery of genes to striated muscles using adeno-associated viral vectors. Nat Med 10, 828-834.

Harper, S. Q., Hauser, M. A., DelloRusso, C., Duan, D., Crawford, R. W., Phelps, S. F., Harper, H. A., Robinson, A. S., Engelhardt, J. F., Brooks, S. V., and Chamberlain, J. S. (2002). Modular flexibility of dystrophin: implications for gene therapy of Duchenne muscular dystrophy. Nat Med 8, 253-261.

Hillier, B. J., Christopherson, K. S., Prehoda, K. E., Bredt, D. S., and Lim, W. A. (1999). Unexpected modes of PDZ domain scaffolding revealed by structure of nNOS-syntrophin complex. Science 284, 812-815.

Hope, B. T., Michael, G. J., Knigge, K. M., and Vincent, S. R. (1991). Neuronal NADPH diaphorase is a nitric oxide synthase. Proc Natl Acad Sci USA 88, 2811-2814.

Judge, L. M., Haraguchiln, M., and Chamberlain, J. S. (2006). Dissecting the signaling and mechanical functions of the dystrophin-glycoprotein complex. J Cell Sci 119, 1537-1546.

Kameya, S., Miyagoe, Y., Nonaka, I., Ikemoto, T., Endo, M., Hanaoka, K., Nabeshima, Y., and Takeda, S. (1999). alpha1-syntrophin gene disruption results in the absence of neuronal-type nitric-oxide synthase at the sarcolemma but does not induce muscle degeneration. J Biol Chem 274, 2193-2200.

Kerr, T. P., Sewry, C. A., Robb, S. A., and Roberts, R. G. (2001). Long mutant dystrophins and variable phenotypes: evasion of nonsense-mediated decay? Hum Genet. 109, 402-407.

Lai, Y., Yue, Y., Liu, M., and Duan, D. (2006). Synthetic intron improves transduction efficiency of the trans-splicing adeno-associated viral vectors. Hum Gene Ther 17, 1036-1042.

Lai, Y., Yue, Y., Liu, M., Ghosh, A., Engelhardt, J. F., Chamberlain, J. S., and Duan, D. (2005). Efficient in vivo gene expression by trans-splicing adeno-associated viral vectors. Nat Biotechnol 23, 1435-1439.

Li, S., Kimura, E., Ng, R., Fall, B. M., Meuse, L., Reyes, M., Faulkner, J. A., and Chamberlain, J. S. (2006). A highly functional mini-dystrophin/GFP fusion gene for cell and gene therapy studies of Duchenne muscular dystrophy. Hum Mol Genet. 15, 1610-1622.

Liu, M., Yue, Y., Harper, S. Q., Grange, R. W., Chamberlain, J. S., and Duan, D. (2005). Adeno-associated Virus-mediated Micro-dystrophin Expression Protects Young Mdx Muscle from Contraction-induced Injury. Mol Ther 11, 245-256.

Matsumoto, T., Nakane, M., Pollock, J. S., Kuk, J. E., and Forstermann, U. (1993). A correlation between soluble brain nitric oxide synthase and NADPH-diaphorase activity is only seen after exposure of the tissue to fixative. Neurosci Lett 155, 61-64.

McCabe, E. R., Towbin, J., Chamberlain, J., Baumbach, L., Witkowski, J., van Ommen, G. J., Koenig, M., Kunkel, L. M., and Seltzer, W. K. (1989). Complementary DNA probes for the Duchenne muscular dystrophy locus demonstrate a previously undetectable deletion in a patient with dystrophic myopathy, glycerol kinase deficiency, and congenital adrenal hypoplasia. J Clin Invest 83, 95-99.

Miyagoe-Suzuki, Y., and Takeda, S. I. (2001). Association of neuronal nitric oxide synthase (nNOS) with alpha1-syntrophin at the sarcolemma. Microsc Res Tech 55, 164-170.

Prior, T. W., Bartolo, C., Pearl, D. K., Papp, A. C., Snyder, P. J., Sedra, M. S., Burghes, A. H., and Mendell, J. R. (1995). Spectrum of small mutations in the dystrophin coding region. Am J Hum Genet. 57, 22-33.

Rando, T. A. (2001). Role of nitric oxide in the pathogenesis of muscular dystrophies: A "two hit" hypothesis of the cause of muscle necrosis. Microsc Res Tech 55, 223-235.

Rothe, F., Langnaese, K., and Wolf, G. (2005). New aspects of the location of neuronal nitric oxide synthase in the skeletal muscle: a light and electron microscopic study. Nitric Oxide 13, 21-35.

Sakamoto, M., Yuasa, K., Yoshimura, M., Yokota, T., Ikemoto, T., Suzuki, M., Dickson, G., Miyagoe-Suzuki, Y., and Takeda, S. (2002). Micro-dystrophin cDNA ameliorates dystrophic phenotypes when introduced into mdx mice as a transgene. Biochem Biophys Res Commun 293, 1265-1272.

Sampaolesi, M., Blot, S., D'Antona, G., Granger, N., Tonlorenzi, R., Innocenzi, A., Mognol, P., Thibaud, J. L., Galvez, B. G., Barthelemy, I., et al. (2006). Mesoangioblast stem cells ameliorate muscle function in dystrophic dogs. Nature 444, 574-579.

Sander, M., Chavoshan, B., Harris, S. A., Iannaccone, S. T., Stull, J. T., Thomas, G. D., and Victor, R. G. (2000). Functional muscle ischemia in neuronal nitric oxide synthase-deficient skeletal muscle of children with Duchenne muscular dystrophy. Proc Natl Acad Sci USA 97, 13818-13823.

Shiao, T., Fond, A., Deng, B., Wehling-Henricks, M., Adams, M. E., Froehner, S. C., and Tidball, J. G. (2004). Defects in neuromuscular junction structure in dystrophic muscle are corrected by expression of a NOS transgene in dystrophin-deficient muscles, but not in muscles lacking alpha- and beta1-syntrophins. Hum Mol Genet. 13, 1873-1884.

Spessert, R., and Claassen, M. (1998). Histochemical differentiation between nitric oxide synthase-related and -unrelated diaphorase activity in the rat olfactory bulb. Histochem J 30, 41-50.

Suminaga, R., Takeshima, Y., Wada, H., Yagi, M., and Matsuo, M. (2004). C-Terminal Truncated Dystrophin Identified in Skeletal Muscle of an Asymptomatic Boy with a Novel Nonsense Mutation of the Dystrophin Gene. Pediatr Res 56, 739-743.

Thomas, G. D., Sander, M., Lau, K. S., Huang, P. L., Stull, J. T., and Victor, R. G. (1998). Impaired metabolic modulation of alpha-adrenergic vasoconstriction in dystrophin-deficient skeletal muscle. Proc Natl Acad Sci USA 95, 15090-15095.

Tidball, J. G., and Wehling-Henricks, M. (2004). Expression of a NOS transgene in dystrophin-deficient muscle reduces muscle membrane damage without increasing the expression of membrane-associated cytoskeletal proteins. Mol Genet Metab 82, 312-320.

Tochio, H., Zhang, Q., Mandal, P., Li, M., and Zhang, M. (1999). Solution structure of the extended neuronal nitric oxide synthase PDZ domain complexed with an associated peptide. Nat Struct Biol 6, 417-421.

Torelli, S., Brown, S. C., Jimenez-Mallebrera, C., Feng, L., Muntoni, F., and Sewry, C. A. (2004). Absence of neuronal nitric oxide synthase (nNOS) as a pathological marker for the diagnosis of Becker muscular dystrophy with rod domain deletions. Neuropathol Appl Neurobiol 30, 540-545.

Tuffery, S., Lenk, U., Roberts, R. G., Coubes, C., Demaille, J., and Claustres, M. (1995). Protein truncation test: analysis of two novel point mutations at the carboxy-terminus of the human dystrophin gene associated with mental retardation. Hum Mutat 6, 126-135.

Wang, B., Li, J., and Xiao, X. (2000). Adeno-associated virus vector carrying human minidystrophin genes effectively ameliorates muscular dystrophy in mdx mouse model. Proc Natl Acad Sci USA 97, 13714-13719.

Warner, L. E., DelloRusso, C., Crawford, R. W., Rybakova, I. N., Patel, J. R., Ervasti, J. M., and Chamberlain, J. S. (2002). Expression of Dp260 in muscle tethers the actin cytoskeleton to the dystrophin-glycoprotein complex and partially prevents dystrophy. Hum Mol Genet. 11, 1095-1105.

Wehling, M., Spencer, M. J., and Tidball, J. G. (2001). A nitric oxide synthase transgene ameliorates muscular dystrophy in mdx mice. J Cell Biol 155, 123-132.

Wehling-Henricks, M., Jordan, M. C., Roos, K. P., Deng, B., and Tidball, J. G. (2005). Cardiomyopathy in dystrophin-deficient hearts is prevented by expression of a neuronal nitric oxide synthase transgene in the myocardium. Hum Mol Genet. 14, 1921-1933.

Wells, K. E., Torelli, S., Lu, Q., Brown, S. C., Partridge, T., Muntoni, F., and Wells, D. J. (2003). Relocalization of neuronal nitric oxide synthase (nNOS) as a marker for complete restoration of the dystrophin associated protein complex in skeletal muscle. Neuromuscul Disord 13, 21-31.

Yuasa, K., Miyagoe, Y., Yamamoto, K., Nabeshima, Y., Dickson, G., and Takeda, S. (1998). Effective restoration of dystrophin-associated proteins in vivo by adenovirus-mediated transfer of truncated dystrophin cDNAs. FEBS Lett 425, 329-336.

Yue, Y., Liu, M., and Duan, D. (2006). C-terminal truncated microdystrophin recruits dystrobrevin and syntrophin to the dystrophin-associated glycoprotein complex and reduces muscular dystrophy in symptomatic utrophin/dystrophin double knock-out mice. Mol Ther 14, 79-87.

Abmayr, S., Gregorevic, P., Allen, J. M., and Chamberlain, J. S. (2005). Phenotypic improvement of dystrophic muscles by rAAV/microdystrophin vectors is augmented by Igf1 codelivery. Mol Ther 12, 441-450.

Duan, D. (2006). Challenges and opportunities in dystrophin-deficient cardiomyopathy gene therapy. Hum Mol Genet. 15 Suppl 2, R253-261.

Gregorevic, P., Allen, J. M., Minami, E., Blankinship, M. J., Haraguchi, M., Meuse, L., Finn, E., Adams, M. E., Froehner, S. C., Murry, C. E., and Chamberlain, J. S. (2006). rAAV6-microdystrophin preserves muscle function and extends lifespan in severely dystrophic mice. Nat Med 12, 787-789.

Gregorevic, P., Blankinship, M. J., Allen, J. M., Crawford, R. W., Meuse, L., Miller, D. G., Russell, D. W., and Chamberlain, J. S. (2004). Systemic delivery of genes to striated muscles using adeno-associated viral vectors. Nat Med 10, 828-834.

Harper, S. Q., Hauser, M. A., DelloRusso, C., Duan, D., Crawford, R. W., Phelps, S. F., Harper, H. A., Robinson, A. S., Engelhardt, J. F., Brooks, S. V., and Chamberlain, J. S. (2002). Modular flexibility of dystrophin: implications for gene therapy of Duchenne muscular dystrophy. Nat Med 8, 253-261.

Liu, M., Yue, Y., Harper, S. Q., Grange, R. W., Chamberlain, J. S., and Duan, D. (2005). Adeno-associated virus-mediated micro-dystrophin expression protects young Mdx muscle from contraction-induced injury. Mol Ther 11, 245-256.

Megeney, L. A., Kablar, B., Garrett, K., Anderson, J. E., and Rudnicki, M. A. (1996). MyoD is required for myogenic stem cell function in adult skeletal muscle. Genes Dev 10, 1173-1183.

Megeney, L. A., Kablar, B., Perry, R. L., Ying, C., May, L., and Rudnicki, M. A. (1999). Severe cardiomyopathy in mice lacking dystrophin and MyoD. Proc Natl Acad Sci USA 96, 220-225.

Yue, Y., Li, Z., Harper, S. Q., Davisson, R. L., Chamberlain, J. S., and Duan, D. (2003). Microdystrophin Gene Therapy of Cardiomyopathy Restores Dystrophin-Glycoprotein Complex and Improves Sarcolemma Integrity in the Mdx Mouse Heart. Circulation 108, 1626-1632.

Yue, Y., Liu, M., and Duan, D. (2006). C-terminal truncated microdystrophin recruits dystrobrevin and syntrophin to the dystrophin-associated glycoprotein complex and reduces muscular dystrophy in symptomatic utrophin/dystrophin double knock-out mice. Mol Ther 14, 79-87.

```
SEQ ID NO: 1: Full-length human dystrophin protein sequence
MLWWEEVEDCYEREDVQKKTFTKWVNAQFSKFGKQHIENLFSDLQDGRRLLDLLEGLTGQ

KLPKEKGSTRVHALNNVNKALRVLQNNNVDLVNIGSTDTVDGNHKLTLGLIWNIILHWQV

KNVMKNIMAGLQQTNSEKILLSWVRQSTRNYPQVNVINFTTSWSDGLALNALIHSHRPDL

FDWNSVVCQQSATQRLEHAFNTARYQLGIEKLLDPEDVDTTYPDKKSILMYITSLFQVLP

QQVSIEAIQEVEMLPRPPKVTKEEHFQLHHQMHYSQQITVSLAQGYERTSSPKPRFKSYA

YTQAAYVTTSDPTRSPFPSQHLEAPEDKSFGSSLMESEVNLDRYQTALEEVLSWLLSAED

TLQAQGEISNDVEVVKDQFHTHEGYMMDLTAHQGRVGNILQLGSKLIGTGKLSEDEETEV

QEQMNLLNSRWECLRVASMEKQSNLHRVLMDLQNQKLKELNDWLTKTEERTRKMEEEPLG

PDLEDLKRQVQQHKVLQEDLEQEQVRVNSLTHMVVVVDESSGDHATAALEEQLKVLGDRW

ANICRWTEDRWVLLQDILLKWQRLTEEQCLFSAWLSEKEDAVNKIHTTGFKDQNEMLSSL

QKLAVLKADLEKKKQSMGKLYSLKQDLLSTLKNKSVTQKTEAWLDNFARCWDNLVQKLEK

STAQISQAVTTTQPSLTQTTVMETVTTVTTREQILVKHAQEELPPPPPQKKRQITVDSEI

RKRLDVDITELHSWITRSEAVLQSPEFAIFRKEGNFSDLKEKVNAIEREKAEKFRKLQDA

SRSAQALVEQMVNEGVNADSIKQASEQLNSRWIEFCQLLSERLNWLEYQNNIIAFYNQLQ

QLEQMTTTAENWLKIQPTTPSEPTAIKSQLKICKDEVNRLSGLQPQIERLKIQSIALKEK

GQGPMFLDADFVAFTNHFKQVFSDVQAREKELQTIFDTLPPMRYQETMSAIRTWVQQSET

KLSIPQLSVTDYEIMEQRLGELQALQSSLQEQQSGLYYLSTTVKEMSKKAPSEISRKYQS

EFEEIEGRWKKLSSQLVEHCQKLEEQMNKLRKIQNHIQTLKKWMAEVDVFLKEEWPALGD

SEILKKQLKQCRLLVSDIQTIQPSLNSVNEGGQKIKNEAEPEFASRLETELKELNTQWDH

MCQQVYARKEALKGGLEKTVSLQKDLSEMHEWMTQAEEEYLERDFEYKTPDELQKAVEEM

KRAKEEAQQKEAKVKLLTESVNSVIAQAPPVAQEALKKELETLTTNYQWLCTRLNGKCKT

LEEVWACWHELLSYLEKANKWLNEVEFKLKTTENTPGGAEEISEVLDSLENLMRHSEDNP

NQIRILAQTLTDGGVMDELINEELETFNSRWRELHEEAVRRQKLLEQSIQSAQETEKSLH

LIQESLTFIDKQLAAYIADKVDAAQMPQEAQKIQSDLTSHEISLEEMKKHNQGKEAAQRV

LSQIDVAQKKLQDVSMKFRLFQKPANFELRLQESKMILDEVKMHLPALETKSVEQEVVQS

QLNHCVNLYKSLSEVKSEVEMVIKTGRQIVQKKQTENPKELDERVTALKLHYNELGAKVT

ERKQQLEKCLKLSRKMRKEMNVLTEWLAATDMELTKRSAVEGMPSNLDSEVAWGKATQKE

IEKQKVHLKSITEVGEALKTVLGKKETLVEDKLSLLNSNWIAVTSRAEEWLNLLLEYQKH
```

METFDQNVDHITKWIIQADTLLDESEKKKPQQKEDVLKRLKAELNDIRPKVDSTRDQAAN

LMANRGDHCRKLVEPQISELNHRFAAISHRIKTGKASIPLKELEQFNSDIQKLLEPLEAE

IQQGVNLKEEDFNKDMNEDNEGTVKELLQRGDNLQQRITDERKREEIKIKQQLLQTKHNA

LKDLRSQRRKKALEISHQWYQYKRQADDLLKCLDDIEKKLASLPEPRDERKIKEIDRELQ

KKKEELNAVRRQAEGLSEDGAAMAVEPTQIQLSKRWREIESKFAQFRRLNFAQIHTVREE

TMMVMTEDMPLEISYVPSTYLTEITHVSQALLEVEQLLNAPDLCAKDFEDLFKQEESLKN

IKDSLQQSSGRIDIIHSKKTAALQSATPVERVKLQEALSQLDFQWEKVNKMYKDRQGRFD

RSVEKWRRFHYDIKIFNQWLTEAEQFLRKTQIPENWEHAKYKWYLKELQDGIGQRQTVVR

TLNATGEEIIQQSSKTDASILQEKLGSLNLRWQEVCKQLSDRKKRLEEQKNILSEFQRDL

NEFVLWLEEADNIASIPLEPGKEQQLKEKLEQVKLLVEELPLRQGILKQLNETGGPVLVS

APISPEEQDKLENXLKQTNLQWIKVSRALPEKQGEIEAQIKDLGQLEKKLEDLEEQLNHL

LLWLSPIRNQLEIYNQPNQEGPFDVQETEIAVQAKQPDVEEILSKGQHLYKEKPATQPVK

RKLEDLSSEWKAVNRLLQELRAKQPDLAPGLTTIGASPTQTVTLVTQPVVTKETAISKLE

MPSSLNLEVPALADFNRAJTELTDWLSLLDQVIKSQRVMVGDLEDINEMIIKQKATMQDL

EQRRPQLEELITAAQNLKNKTSNQEARTIITDRIERIQNQWDEVQEHLQNRRQQLNEMLK

DSTQWLEAKEEAEQVLGQARAKLESWKEGPYTVDAIQKKITETKQLAKDLRQWQTNVDVA

NDLALKLLRDYSADDTRKVHMITENINASWRSIHKRVSEREAALEETHRLLQQFPLDLEK

FLAWLTEAETTANVLQDATRKERLLEDSKGVKELMKQWQDLQGEIEAHTDVYHNLDENSQ

KILRSLEGSDDAVLLQRRLDNMMFKWSELRKKSLNIRSHLEASSDQWKRLHLSLQELLVW

LQLKDDELSRQAPIGGDFPAVQKQNDVHRAFKRELKTKEPVIMSTLETVRIFLTEQPLEG

LEKLYQEPRELPPEERAQNVTRLLRKQAEEVNTEWEKLNLHSADWQRKIDETLERLQELQ

EATDELDLKLRQAEVIKGSWQPVGDLLIDSLQDHLEKVKALRGEIAPLKENVSHVNDLAR

QLTTLGIQLSPYNLSTLEDLNTRWKLLQVAVEDRVRQLHEAHRDFGPASQHFLSTSVQGP

WERAISPNKVPYYINHETQTTCWDHPKMTELYQSLADLNNVRFSAYRTAMKLRRLQKALC

LDLLSLSAACDALDQHNLKQNDQPMDILQIINCLTTIYDRLEQEHNNLVNVPLCVDMCLN

WLLNVYDTGRTGRIRVLSFKTGIISLCKAHLEDKYRYLFKQVASSTGFCDQRRLGLLLHD

SIQIPRQLGEVASFGGSNIEPSVRSCFQFANNKPEIEAALFLDWMRLEPQSMVWLPVLHR

VAAAETAKHQAKCNICKECPIIGFRYRSLKHFNYDICQSCFFSGRVAKGHKMHYPMVEYC

TPTTSGEDVRDFAKVLKNKFRTKRYFAKHPRMGYLPVQTVLEGDNMETPVTLINFWPVDS

APASSPQLSHDDTHSRIEHYASRLAEMENSNGSYLNDSISPNESIDDEHLLIQHYCQSLN

QDSPLSQPRSPAQILISLESEERGELERILADLEEENRNLQAEYDRLKQQHEHKGLSPLP

SPPENMPTSPQSPRDAELIAEAKLLRQHKGRLEARMQILEDHNKQLESQHRLRQLLEQP

QAEAKVNGTTVSSPSTSLQRSDSSQPMLLRVVGSQTSDSMGEEDLLSPPQDTSTGLEEVM

EQLNNSFPSSRGRNTPGKPMREDTM*

SEQ ID NO: 2: Full-length dystrophin (The full-length gene
carries R16 and R17. It can restore nNOS)
ATGCTTTGGTGGGAAGAAGTAGAGGACTGTTATGAAAGAGAAGATGTTCAAAAGAAAACATT

CACAAAATGGGTAAATGCACAATTTTCTAAGTTTGGGAAGCAGCATATTGAGAACCTCTTCAG

TGACCTACAGGATGGGAGGCGCCTCCTAGACCTCCTCGAAGGCCTGACAGGGCAAAAACTGC

CAAAAGAAAAAGGATCCACAAGAGTTCATGCCCTGAACAATGTCAACAAGGCACTGCGGGTT

TTGCAGAACAATAATGTTGATTTAGTGAATATTGGAAGTACTGACATCGTAGATGGAAATCAT

-continued

```
AAACTGACTCTTGGTTTGATTTGGAATATAATCCTCCACTGGCAGGTCAAAAATGTAATGAAA
AATATCATGGCTGGATTGCAACAAACCAACAGTGAAAAGATTCTCCTGAGCTGGGTCCGACA
ATCAACTCGTAATTATCCACAGGTTAATGTAATCAACTTCACCACCAGCTGGTCTGATGGCCT
GGCTTTGAATGCTCTCATCCATAGTCATAGGCCAGACCTATTTGACTGGAATAGTGTGGTTTGC
CAGCAGTCAGCCACACAACGACTGGAACATGCATTCAACATCGCCAGATATCAATTAGGCAT
AGAGAAACTACTCGATCCTGAAGATGTTGATACCACCTATCCAGATAAGAAGTCCATCTTAAT
GTACATCACATCACTCTTCCAAGTTTTGCCTCAACAAGTGAGCATTGAAGCCATCCAGGAAGT
GGAAATGTTGCCAAGGCCACCTAAAGTGACTAAAGAAGAACATTTTCAGTTACATCATCAAAT
GCACTATTCTCAACAGATCACGGTCAGTCTAGCACAGGGATATGAGAGAACTTCTTCCCCTAA
GCCTCGATTCAAGAGCTATGCCTACACACAGGCTGCTTATGTCACCACCTCTGACCCTACACG
GAGCCCATTTCCTTCACAGCATTTGGAAGCTCCTGAAGACAAGTCATTTGGCAGTTCATTGAT
GGAGAGTGAAGTAAACCTGGACCGTTATCAAACAGCTTTAGAAGAAGTATTATCGTGGCTTCT
TTCTGCTGAGGACACATFFGCAAGCACAAGGAGAGATTCTAATGATGTGGAAGTGGTGAAAG
ACCAGTTTCATACTCATGAGGGGTACATGATGGATTTGACAGCCCATCAGGGCCGGGTTGGTA
ATATTCTACAATTGGGAAGTAAGCTGATTGGAACAGGAAAATTATCAGAAGATGAAGAAACT
GAAGTACAAGAGCAGATGAATCTCCTAAATTCAAGATGGGAATGCCTCAGGGTAGCTAGCAT
GGAAAAACAAAGCAATTTACATAGAGTTTTAATGGATCTCCAGAATCAGAAACTGAAAGAGT
TGAATGACTGGCTAACAAAAACAGAAGAAAGAACAAGGAAAATGGAGGAAGAGCCTCTTGG
ACCTGATCTTGAAGACCTAAAACGCCAAGTACAACAACATAAGGTGCTTCAAGAAGATCTAG
AACAAGAACAAGTCAGGGTCAATTTCTCTCACTCACATGGTGGTGGTAGTTGATGAATGTAGTG
GAGATCACGCAACTGCTGCTTTGGAAGAACAACTTAAGGTATTGGGAGATCGATGGGCAAAC
ATCTGTAGATGGACAGAAGACCGCTGGGTTCTTTTACAAGACATCCTTCTCAAATGGCAACGT
CTTACTGAAGAACAGTGCCTTTTTAGTGCATGGCTTTCAGAAAAAGAAGATGCAGTGAACAAG
ATTCACACAACTGGCTTTAAAGATCAAAATGAAATGTTATCAAGTCTTCAAAAACTGGCCGTT
TTAAAAGCGGATCTAGAAAAGAAAAAGCAATCCATGGGCAAACTGTATTCACTCAAACAAGA
TCTTCTTTCAACACTGAAGAATAAGTCAGTGACCCAGAAGACGGAAGCATGGCTGGATAACTT
TGCCCGGTGTTGGGATAATTTAGTCCAAAAACTTGAAAAGAGTACAGCACAGATTTCACAGGC
TGTCACCACCACTCAGCCATCACTAACACAGACAACTGTAATGGAAACAGTAACTACGGTGA
CCACAAGGGAACAGATCCTGGTAAAGCATGCTCAAGAGGAACTTCCACCACCACCTCCCCAA
AAGAAGAGGCAGATTACTGTGGATTCTGAAATTTAGGAAAAGGTTGGATGTTGATATAACTGA
ACTTCACAGCTGGATTACTCGCTCAGAAGCTGTGTTGCAGAGTCCTGAATTTGCAATCTTTCGG
AAGGAAGGCAACTTCTCAGACTTAAAAGAAAAAGTCAATGCCATAGAGCGAGAAAAAGCTG
AGAAGTTCAGAAAACTGCAAGATGCCAGCAGATCAGCTCAGGCCCTGGTGGAACAGATGGTG
AATGAGGGTGTTAATGCAGATAGCATCAAACAAGCCTCAGAACAACTGAACAGCCGGTGGAT
CGAATTCTGCCAGTTGCTAAGTGAGAGACTTAACTGGCTGGAGTATCAGAACAACATCATCGC
TTTCTATAATCAGCTACAACAATTGGAGCAGATGACAACTACTGCTGAAAACTGGTTGAAAAT
CCAACCCACCACCCCATCAGAGCCAACAGCAATTAAAAGTCAGTTAAAAATTTGTAAGGATG
AAGTCAACCGGCTATCAGGTCTTCAACCTCAAATTGAACGATTAAAAATTCAAAGCATAGCCC
TGAAAGAGAAAGGACAAGGACCCCATGTTCCTGGATGCAGACTTTGTGGCCTTTACAAATCATT
TTAAGCAAGTCTTTTCTGATGTGCAGGCCAGAGAGAAAGAGCTACAGACAATTTTTGACACTT
```

-continued

```
TGCCACCAATGCGCTATCAGGAGACCATGAGTGCCATCAGGACATGGGTCCAGCAGTCAGAA
ACCAAACTCTCCATAGCTCAACTTAGTGTCACCGACTATGAAATCATGGAGCAGAGACTCGGG
GAATTGCAGGCTTTACAAAGTTCTCTGCAAGAGCAACAAAGTGGCCTATACTATCTCAGCACC
ACTGTGAAAGAGATGTCGAAGAAAGCGCCCTCTGAAATTAGCCGGAAATATCAATCAGAATT
TGAAGAAATTGAGGGACGCTGGAAGAAGCTCTCCTCCCAGCTGGTTGAGCATTTGTCAAAAGC
TAGAGGAGCAAATGAATAAACTCCGAAAAATTCAGAATCACATACAAACCCTGAAGAAATGG
ATGGCTGAAGTTGATGTTTTTCTGAAGGAGGAATGGCCTGCCCTTGGGGATTCAGAAATTCTA
AAAAAGCAGCTGAAACAGTGCAGACTTTTAGTCAGTGATATTCAGACAATTCAGCCCAGTCTA
AACAGTGTCAATGAAGGTGGGCAGAAGATAAAGAATGAAGCAGAGCCAGAGTTTGCTTCGAG
ACTTGAGACAGAACTCAAAGAACTTAACACTCAGTGGGATCACATGTGGCAACAGGTCTATG
CCAGAAAGGAGGCCTTGAAGGGAGGTTTGGAGAAAACTGTAAGCCTCCAGAAAGATCTATCA
GAGATGCACGAATGGATGACACAAGCTGAAGAAGAGTATCTTGAGAGAGATTTTGAATATAA
AACTCCAGATGAATTACAGAAAGCAGTTGAAGAGATGAAGAGAGCTAAAGAAGAGGCCCAA
CAAAAAGAAGCGAAAGTGAAACTCCTTACTGAGTCTGTAAATAGTGTCATAGCTCAAGCTCC
ACCTGTAGCACAAGAGGCCTTAAAAAAGGAACTTGAAACTCTAACCACCAACTACCAGTGGC
TCTGCACTAGGCTGAATGGGAAATGCAAGACTTTGGAAGAAGTTTGGGCATGTTGGCATGAGT
TATTGTCATACTTGGAGAAAGCAAACAAGTGGCTAAATGAAGTAGAATTTAAACTTAAAACC
ACTGAAAACATTCCTGGCGGAGCTGAGGAAATCTCTGAGGTGCTAGATTCACTTGAAAATTTG
ATGCGACATTCAGAGGATAACCCAAATCAGATTCGCATATTGGCACAGACCCTAACAGATGG
CGGAGTCATGGATGAGCTAATCAATGAGGAACTTGAGACATTTAATTCTCGTTGGAGGGAACT
ACATGAAGAGGCTGTAAGGAGGCAAAAGTTGCTTGAACAGAGCATCCAGTCTGCCCAGGAGA
CTGAAAAATCCTTACACTTAATCCAGGAGTCCCTCACATTCATTGACAAGCAGTTGGCAGCTT
ATATTGCAGACAAGGTGGACGCAGCTCAAATGCCTCAGGAAGCCCAGAAAATCCAATCTGAT
TTGACAAGTCATGAGATCAGTTTAGAAGAAATGAAGAAACATAATCAGGGGAAGGAGGCTGC
CCAAAGAGTCCTGTCTCAGATTGATGTTGCACAGAAAAAATTACAAGATGTCTCCATGAAGTT
TCGATTATTCCAGAAACCAGCCAATTTGAGCTGCGTCTAGAAGAAAGTAAGATGATTTTAGA
TGAAGTGAAGATGCACTTGCCTGCATTGGAAACAAAGAGTGTGGAACAGGAAGTAGTACAGT
CACAGCTAAATCATTGTGTGAACTTGTATAAAAGTCTGAGTGAAGTGAAGTCTGAAGTGGAA
ATGGTGATAAAGACTGGACGTCAGATTGTACAGAAAAAGCAGACGGAAAATCCCAAAGAACT
TGATGAAAGAGTAACAGCTTTGAAATTGCATTATAATGAGCTGGGAGCAAAGGTAACAGAAA
GAAAGCAACAGTTGGAGAAATGCTTGAAATTGTCCCGTAAGATGCGAAAGGAAATGAATGTC
TTGACAGAATGGCTGGCAGCTACAGATATGGAATTGACAAAGAGATCAGCAGTTGAAGGAAT
GCCTAGTAATTTGGATTCTGAAGTTGCCTGGGGAAAGGCTACTCAAAAAGAGATTGAGAAAC
AGAAGGTGCACCTGAAGAGTATCACAGAGGTAGGAGAGGCCTTGAAAACAGTTTTGGGCAAG
AAGGAGACGTTGGTGGAAGATAAACTCAGTCTTCTGAATAGTAACTGGATAGCTGTCACCTCC
CGAGCAGAAGAGTGGTTAAATCTTTTGTTGGAATACCAGAAACACATGGAAACTTTTGACCAG
AATGTGGACCACATCACAAAGTGGATCATTCAGGCTGACACACTTTTGGATGAATCAGAGAA
AAAGAACCCCAGCAAAAAGAAGACGTGCTTAAGCGTTTAAAGGCAGAACTGAATGACATAC
GCCCAAAGGTGGACTCTACACGTGACCAAGCAGCAAACTTGATGGCAAACCGCGGTGACCAC
TGCAGGAAATTAGTAGAGCCCCAAATCTCAGAGCTCAACCATCGATTTGCAGCCATTTCACAC
```

-continued

```
AGAATTAAGACTGGAAAGGCCTCCATTCCTTTGAAGGAATGGAGCAGTTTAACTCAGATATA
CAAAAATTGCTTGAACCACTGGAGGCTGAAATTCAGCAGGGGTGAATCTGAAAGAGGAAGA
GTTCAATAAAGATATGAATGAAGACAATGAGGGTACTGTAAAAGAATTGTGCAAAGAGGAG
ACAACTTACAACAAAGAATCACAGATGAGAGAAAGAGAGAGGAAATAAAGATAAAACAGCA
GCTGTTACAGACAAAACATAATGCTCTCAAGGATTTGAGGTCTCAAAGAAGAAAAAAGGCTC
TAGAAATTTCTCATCAGTGGTATCAGTACAAGAGGCAGGCTGATGATCTCCTGAAATGCTTGG
ATGACATTGAAAAAAAATTAGCCAGCCTACCTGAGCCCAGAGATGAAAGGAAAATAAAGGA
AATTGATCGGGAATTGCAGAAGAAGAAAGAGGAGCTGAATGCAGTGCGTAGGCAAGCTGAG
GGCTTGTCTGAGGATGGGGCCGCAATGGCAGTGGAGCCAACTCAGATCCAGCTCAGCAAGCG
CTGGCGGGAAATTGAGAGCAAATTTGCTCAGTTTCGAAGACTCAACTTTGCACAAATTCACAC
TGTCCGTGAAGAAACGATGATGGTGATGACTGAAGACATGCCTTTGGAAATTTCTTATGTGCC
TTCTACTTATTTGACTGAAATCACTCATGTCTCACAAGCCCTATTAGAAGTGGAACAACTTCTC
AATGCTCCTGACCTCTGTGCTAAGGACTTTGAAGATCTCTTTAAGCAAGAGGAGTCTCTGAAG
AATATAAAGATAGTCTACAACAAAGCTCAGGTCGGATTGACATTATTCATAGCAAGAAGAC
AGCAGCATTGCAAAGTGCAACGCCTGTGGAAAGGGTGAAGCTACAGGAAGCTCTCTCCCAGC
TTGATTTCCAATGGGAAAAAGTTAACAAAATGTACAAGGACCGACAAGGGCGATTTGACAGA
TCTGTTGAGAAATGGCGGCGTTTTCATTATGATATAAAGATATTTAATCAGTGGCTAACAGAA
GCTGAACAGTTTCTCAGAAAGACACAAATTCCTGAGAATTGGGAACATGCTAAATACAAATG
GTATCTTAAGGAACTCCAGGATGGGATGGGCAGCGGCAAACTGTTGTCAGAACATTGAATGC
AACTGGGGAAGAAATAATTCAGCAATCCTCAAAAACAGATGGCAGTATTCTACAGGAAAAAT
TGGGAAGCCTGAATCTGCGGTGGCAGGAGGTCTGCAAACAGCTGTCAGACAGAAAAAAGAGG
CTAGAAGAACAAAAGAATATCTTGTCAGAATTTCAAAGAGATTTAAATGAATTTGTTTTATGG
TTGGAGGAAGCAGATAACATTGCTAGTATCCCACTTGAACCTGGAAAAGAGCAGCAACTAAA
AGAAAAGCTTGAGCAAGTCAAGTTACTGGTGGAAGAGTTGCCCCTGCGCCAGGGAATTCTCA
AACAATTAAATGAAACTGGAGGACCCGTGCTTGTAAGTGCTCCCATAAGCCCAGAAGAGCAA
GATAAACTTGAAAATAAGCTCAAGCAGACAAATCTCCAGTGGATAAAGGTTTCCAGAGCTTT
ACCTGAGAAACAAGGAGAAATTTGAAGCTCAAATAAAAGACCTTGGGCAGCTTGAAAAAAAG
CTTGAAGACCTTGAAGAGCAGTTAAATCATCTGCTGCTGTGGTATCTCCTATTAGGAATCAG
TTGGAAATTTATAACCAACCAAACCAAGAAGGACCATTTGACGTTCAGGAAACTGAAATAGC
AGTTCAAGCTAAACAACCGGATGTGGAAGAGATTTTGTCTAAAGGGCAGCATTTGTACAAGG
AAAAACCAGCCACTCAGCCAGTGAAGAGGAAGTTAGAAGATCTGAGCTCTGAGTGGAAGGCG
GTAAACCGTTTACTTCAAGAGCTGAGGGCAAAGCAGCCTGACCTAGCTCCTGGACTGACCACT
ATTGGAGCCTCTCCTACTCAGACTGTTACTCTGGTGACACAACCTGTGGTTACTAAGGAAACT
GCCATCTCCAAACTAGAAATGCCATCTTCCTTGATGTTGGAGGTACCTGCTCTGGCAGATTTCA
ACCGGGCTTGGACAGAACTTACCGACTGGCTTTCTCTGCTTGATCAAGTTATAAAATCACAGA
GGGTGATGGTGGGTGACCTTGAGGATATCAACGAGATGATCATCAAGCAGAAGGCAACAATG
CAGGATTTGGAACAGAGGCGTCCCCAGTTGGAAGAACTCATTACCGCTGCCCAAAATTTGAA
AAACAAGACCAGCAATCAAGAGGCTAGAACAATCATTACGGATCGAATTGAAAGAATTCAGA
ATCAGTGGGATGAAGTACAAGAACACCTTCAGAACCGGAGGCAACAGTTGAATGAAATGTTA
AAGGATTCAACACAATGGCTGGAAGCTAAGGAAGAAGCTGAGCAGGTCTTAGGACAGGCCAG
```

-continued

```
AGCCAAGCTTGAGTCATGGAAGGAGGGTCCCTATACAGTAGATGCAATCCAAAAGAAAATCA

CAGAAACCAAGCAGTTGGCCAAAGACCTCCGCCAGTGGCAGACAAATGTAGATGTGGCAAAT

GACTTGGCCCTGAAACTTCTCCGGGATTATTCTGCAGATGATACCAGAAAAGTCCACATGATA

ACAGAGAATATCAATGCCTCTTGGAGAAGCATTCATAAAAGGGTGAGTGAGCGAGAGGCTGC

TTTGGAAGAAACTCATAGATTACTGCAACAGTTCCCCCTGGACCTGGAAAAGTTTCTGCCTG

GCTTACAGAAGCTGAAACAACTGCCAATGTCCTACAGGATGCTACCCGTAAGGAAAGGCTCC

TAGAAGACTCCAAGGGAGTAAAAGAGCTGATGAAACAATGGCAAGACCTCCAAGGTGAAATT

GAAGCTCACACAGATGTTTATCACAACCTGGATGAAAACAGCCAAAAAATCCTGAGATCCCT

GGAAGGTTCCGATGATGCAGTCCTGTTACAAAGACGTTTGGATAACATGAACTTCAAGTGGAG

TGAACTTCGGAAAAAGTCTCTCAACATTAGGTCCCATTTGGAAGCCAGTTCTGACCAGTGGAA

GCGTCTGCACCTTTCTCTGCAGGAACTTCTGGTGTGGCTACAGCTGAAAGATGATGAATTAAG

CCGGCAGGCACCTATTTGGAGGCGACTTTCCAGCAGTTCAGAAGCAGAACGATGTACATAGGG

CCTTCAAGAGGGAATTGAAAACTAAAGAACCTGTAATCATGAGTACTCTTGAGACTGTACGA

ATATTTCTGACAGAGCAGCCTTTGGAAGGACTAGAGAAACTCTACCAGGAGCCCAGAGAGCT

GCCTCCTGAGGAGAGCCCAGAATGTCACTCGGCTTCTACGAAAGCAGGCTGAGGAGGTCA

ATACTGAGTGGGAAAAATTGAACCTGCACTCCGCTGACTGGCAGAGAAAAATAGATGAGACC

CTTGAAAGACTCCAGGAACTTCAAGAGGCCACGGATGAGCTGGACCTCAAGCTGCGCCAAGC

TGAGGTGATCAAGGGATCCTGGCAGCCCGTGGGCGATCTCCTCATTGACTCTCTCCAAGATCA

CCTCGAGAAAGTCAAGGCACTTCGAGGAGAAATTGCGCCTCTGAAAGAGAACGTGAGCCACG

TCAATGACCTTGCTCGCCAGCTTACCACTTTGGGCATTCAGCTCTCACCGTATAACCTCAGCAC

TCTGGAAGACCTGAACACCAGATGGAAGCTTCTGCAGGTGGCCGTCGAGGACCGAGTCAGGC

AGCTGCATGAAGCCCACAGGGACTTTGGTCCAGCATCTCAGCACTTTCTTTCCACGTCTGTCCA

GGGTCCCTGGGAGAGAGCCATCTCGCCAAACAAAGTGCCCTACTATATCAACCACGAGACTG

AAACAACTTGCTGGGACCATCCCAAAATGACAGAGCTCTACCAGTCTTTAGCTGACCTGAATA

ATGTCAGATTCTCAGCTTATAGGACTGCCATGAAACTCCGAAGACTGCAGAAGGCCCTTTGCT

TGGATCTCTTGAGCCTGTCAGCTGCATGTGATGCCTTGGACGAGCACAACCTCAAGCAAATG

ACCAGCCCATGGATATCCTGCAGATTATTAATTGTTTGACCACTATTTATGACCGCCTGGAGC

AAGAGCACAACAATTTGGTCAACGTCCCTCTCTGCGTGGATATGTGTCTGAACTGGCTGCTGA

ATGTTTATGATACGGGACGAACAGGGAGGATCCGTGTCCTGTCTTTTAAAACTGGCATCATTT

CCCTGTGTAAAGCACATTTGGAAGACAAGTACAGATACCTTTTCAAGCAAGTGGCAAGTTCAA

CAGGATTTTGTGACCAGCGCAGGCTGGGCCTCCTTCTGCATGATTCTATCCAAATTCCAAGAC

AGTTGGGTGAAGTTGCATCCTTTGGGGGCAGTAACATTGAGCCAAGTGTCCGGAGCTGCTTCC

AATTTGCTAATAATAAGCCAGAGATCGAAGCGGCCCTCTTCCTAGACTGGATGAGACTGGAAC

CCCAGTCCATGGTGTGGCTGCCCGTCCTGCACAGAGTGGCTGCTGCAGAAACTGCCAAGCATC

AGGCCAAATGTAACATCTGCAAAGAGTGTCCAATCATTTGGATTCAGGTACAGGAGTCTAAAG

CACTTTAATTATGACATCTGCCAAAGCTGCTTTTTTTCTGGTCGAGTTGCAAAAGGCCATAAAA

TGCACTATCCCATGGTGGAATATTGCACTCCGACTACATCAGGAGAAGATGTTCGAGACTTTG

CCAAGGTACTAAAAAACAAATTTCGAACCAAAAGGTATTTTGCGAAGCATCCCCGAATGGGC

TACCTGCCAGTGCAGACTGTCTTAGAGGGGGACAACATGGAAACTCCCGTTACTCTGATCAAC

TTCTGGCCAGTAGATTCTGCGCCTGCCTCGTCCCCTCAGCTTTCACACGATGATACTCATTCAC
```

-continued

GCATTGAACATTATGCTAGCAGGCTAGCAGAAATGGAAAACAGCAATGGATCTTATCTAAAT

GATAGCATCTCTCCTAATGAGAGCATAGATGATGAACATTTGTTAATCCAGCATTACTGCCAA

AGTTTGAACCAGGACTCCCCCCTGAGCCAGCCTCGTAGTCCTGCCCAGATCTTGATTCCTTAG

AGAGTGAGGAAAGAGGGGAGCTAGAGAGAATCCTAGCAGATCTTGAGGAAGAAAACAGGAA

TCTGCAAGGAGAATATGACCGTCTAAAGCAGCAGCACGAACATAAAGGCCTGTCCCCACTGC

CGTCCCCTCCTGAAATGATGCCCACCTGTCCCCAGAGTCCCCGGGATGCTGAGCTCATTGCTG

AGGCCAAGCTACTGCGTCAACACAAAGGCCGCCTGGAAGCCAGGATGCAAATCCTGGAAGAC

CACAATAAACAGCTGGAGTCACAGTTACACAGGCTAAGGCAGCTGCTGGAGCAACCCCAGGC

AGAGGCCAAAGTGAATGGCACAACGGTGTCCTCTCCTTCTACCTCTCTACAGAGGTCCGACAG

CAGTCAGCCTATGCTGCTCCGAGTGGTTGGCAGTCAAACTTCGGACTCCATGGGTGAGGAAGA

TCTTCTCAGTCCTCCCCAGGACACAAGCACAGGGTTAGAGGAGGTGATGGAGCAACTCAACA

ACTCCTTCCCTAGTTCAAGAGGAAGAAATACCCCTGGAAAGCCAATGAGAGAGGACACAATG

TAG

SEQ ID NO: 3: Δ17-48 (mini-dystrophin with 8.5 repeats and 3
hinges) (This minigene does not carry R16 or R17. It cannot
restore nNOS)
ATGCTTTGGTGGGAAGAAGTAGAGGACTGTTATGAAAGAGAAGATGTTCAAAAGAAAACATT

CACAAAATGGGTAAATGCACAATTTTCTAAGTTTGGGAAGCAGCATATTGAGAACCTCTTCAG

TGACCTACAGGATGGGAGGCGCCTCCTAGACCTCCTCGAAGGCCTGACAGGGCAAAAACTGC

CAAAAGAAAAGGATCCACAAGAGTTCATGCCCTGAACAATGTCAACAAGGCACTGCGGGTT

TTGCAGAACAATAATGTTGATTTAGTGAATATTGGAAGTACTGACATCGTAGATGGAAATCAT

AAACTGACTCTTGGTTTGATTTGGAATATAATCCTCCACTGGCAGGTCAAAAATGTAATGAAA

AATATCATGGCTGGATTGCAACAAACCAACAGTGAAAAGATTCTCCTGAGCTGGGTCCGACA

ATCAACTCGTAATTATCCACAGGTTAATGTAATCAACTTCACCACCAGCTGGTCTGATGGCCT

GGCTTTGAATGCTCTCATCCATAGTCATAGGCCAGACCTATTTGACTGGAATAGTGTGGTTTGG

CAGCAGTCAGCCACACAACGACTGGAACATGCATTCAACATCGCCAGATATCAATTAGGCAT

AGAGAAAGTACTCGATCCTGAAGATGTTGATACCACCTATCCAGATAAGAAGTCCATCTTAAT

GTACATCACATCACTCTTCCAAGTTTTGCCTCAACAAGTGAGCATTGAAGCCATCCAGGAAGT

GGAAATGTTGCCAAGGCCACCTAAAGTGACTAAAGAAGAACATTTTCAGTACATCATCAAAT

GCACTATTCTCAACAGATCACGGTCAGTCTAGCACAGGGATATGAGAGAACTTCTTCCCCTAA

GCCTCGATTCAAGAGCTATGCCTACACACAGGCTGCTTATGTCACCACCTCTGACCCTACACG

GAGCCCATTTCCTTCACAGCATTTGGAAGCTCCTGAAGACAAGTCATTTGGCAGTTCATTGAT

GGAGAGTGAAGTAAACCTGGACCGTTATCAAACAGCTTTAGAAGAAGTATTATCGTGGCTTCT

TTCTGCTGAGGACACATTGCAAGCACAAGGAGAGATTTCTAATGATGTGGAAGTGGTGAAAG

ACCAGTTTCATACTCATGAGGGGTACATGATGGATTTGACAGCCCATCAGGGCCGGGTTGGTA

ATATTCTACAATTGGGAAGTAAGCTGATTGGAACAGGAAAATTATCAGAAGATGAAGAAACT

GAAGTACAAGAGCAGATGAATCTCCTAAATTCAAGATGGGAATGCCTCAGGGTAGCTAGCAT

GGAAAAACAAAGCAATTTACATAGAGTTTTAATGGATCTCCAGAATCAGAAACTGAAAGAGT

TGAATGACTGGCTAACAAAAACAGAAGAAAGAACAAGGAAAATGGAGGAAGAGCCTCTTGG

ACCTGATCTTGAAGACCTAAAACGCCAAGTACAACAACATAAGGTGCTTCAAGAAGATCTAG

AACAAGAACAAGTCAGGGTCAATTCTCTCACTCACATGGTGGTGGTAGTTGATGAATCTAGTG

-continued

```
GAGATCACGCAACTGCTGCTTTGGAAGAACAAGTTTAAGGTATTGGGAGATCGATGGGCAAAC
ATCTGTAGATGGACAGAAGACCGCTGGGTTCTTTTACAAGACATCCTTCTCAAATGGCAACGT
CTTACTGAAGAACAGTGCCTTTTTAGTGCATGGCTTTCAGAAAAAGAAGATGCAGTGAACAAG
ATTCACACAACTGGCTTTAAAGATCAAATGAAATGTTATCAAGTCTTCAAAAACTGGCCGTT
TTAAAAGCGGATCTAGAAAAGAAAAAGCAATCCATGGGCAAACTGTATTCACTCAAACAAGA
TCTTCTTTCAACACTGAAGAATAAGTCAGTGACCCAGAAGACGGAAGCATGGCTGGATAACTT
TGCCCGGTGTTGGGATAATTTAGTCCAAAAACTTGAAAAGAGTACAGCACAGGAAACTGAAA
TAGCAGTTCAAGCTAAACAACCGGATGTGGAAGAGATTTTGTCTAAAGGGCAGCATTTGTACA
AGGAAAAACCAGCCACTCAGCCAGTGAAGAGGAAGTTAGAAGATCTGAGCTCTGAGTGGAAG
GCGGTAAACCGTTTACTTCAAGAGCTGAGGGCAAAGCAGCCTGACCTAGCTCCTGGACTGACC
ACTATTGGAGCCTCTCCTACTCAGACTGTTACTCTGGTGACACAACCTGTGGTTAGTAAGGAA
ACTGCCATCTCCAAACTAGAAATGCCATCTTCCTTGATGTTGGAGGTACCTGCTCTGGCAGATT
TCAACGGGCTTGGACAGAACTTACCGAGTGGCTTTCTCTGCTTGATCAAGTTATAAAATCAC
AGAGGGTGATGGTGGGTGACCTTGAGGATATCAACGAGATGATCATCAAGCAGAAGGCAACA
ATGCAGGATTTGGAACAGAGGCGTCCCCAGTTGGAAGAACTCATTACCGCTGCCCAAAATTTG
AAAAACAAGACCAGCAATCAAGAGGCTAGAACAATCATTACGGATCGAATTGAAAGAATTCA
GAATCAGTGGGATGAAGTACAAGAACACCTTCAGAACCGGAGGCAACAGTTGAATGAAATGT
TAAAGGATTCAACACAATGGCTGGAAGCTAAGGAAGAAGCTGAGCAGGTCTTAGGACAGGGC
AGAGCCAAGCTTGAGTCATGGAAGGAGGGTCCCTATACAGTAGATGCAATCCAAAAGAAAAT
CACAGAAACCAAGCAGTTGGCCAAAGACCTCCGCCAGTGGCAGACAAATGTAGATGTGGCAA
ATGACTTGGCCCTGAAACTTCTCCGGGATTATTCTGCAGATGATACCAGAAAAGTCCACATGA
TAACAGAGAATATCAATGCCTCTTGGAGAAGCATTCATAAAAGGGTGAGTGAGCGAGAGGCT
GCTTTGGAAGAAACTCATAGATTACTGCAACAGTTCCCCCTGGACCTGGAAAAGTTTCTTGCC
TGGCTTACAGAAGCTGAAACAACTGCCAATGTCCTACAGGATGCTACCCGTAAGGAAAGGCT
CCTAGAAGACTCCAAGGGAGTAAAAGAGCTGATGAAACAATGGCAAGACCTCCAAGGTGAA
ATTGAAGCTCACACAGATGTTTATCACAACCTGGATGAAAACAGCCAAAAAATCCTGAGATC
CCTGGAAGGTTCCGATGATGCAGTCCTGTTACAAAGACGTTTGGATAACATGAACTTCAAGTG
GAGTGAACTTCGGAAAAAGTCTCTCAACATTAGGTCCCATTTGGAAGCCAGTTCTGACCAGTG
GAAGCGTCTGCACCTTTCTCTGCAGGAACTTCTGGTGTGGCTACAGCTGAAAGATGATGAATT
AAGCCGGCAGGCACCTATTGGAGGCGACTTTCCAGCAGTTCAGAAGCAGAACGATGTACATA
GGGCCTTCAAGAGGGAATTGAAAACTAAAGAACCTGTAATCATGAGTACTCTTGAGACTGTA
CGAATATTTCTGACAGAGCAGCCTTTGGAAGGACTAGAGAAACTCTACCAGGAGCCCAGAGA
GCTGCCTCCTGAGGAGAGAGCCCAGAATGTCACTCGGCTTCTACGAAAGCAGGCTGAGGAGG
TCAATACTGAGTGGGAAAAATTGAACCTGCACTCCGCTGACTGGCAGAGAAAATAGATGAG
ACCCTTGAAAGACTCCAGGAACTTCAAGAGGCCACGGATGAGCTGGACCTCAAGCTGCGCCA
AGCTGAGGTGATCAAGGGATCCTGGCAGCCCGTGGGCGATCTCCTCATTGACTCTCTCCAAGA
TCACCTCGAGAAAGTCAAGGCACTTCGAGGAGAAATTGCGCCTCTGAAAGAACGTGAGCC
ACGTCAATGACCTTGCTCGCCAGCTTACCACTTTGGGCATTCAGCTCTCACCGTATAACCTCAG
CACTCTGGAAGACCTGAACACCAGATGGAAGCTTCTGCAGGTGGCCGTCGAGGACCGAGTCA
GGCAGCTGCATGAAGCCCACAGGGACTTTGGTCCAGCATCTCAGCACTTTCTTTCCACGTCTG
```

-continued

```
TCCAGGGTCGGTGGGAGAGAGCCATCTCGCCAAACAAAGTGCCCTACTATATCAACCACGAG

ACTCAAACAACTTGCTGGGACCATCCCAAAATGACAGAGCTCTACCAGTCTTTAGCTGACCTG

AATAATGTCAGATTCTCAGCTTATAGGACTGCCATGAAACTCCGAAGACTGCAGAAGGCCCTT

TGCTTGGATCTCTTGAGCCTGTCAGCTGCATGTGATGCCTTGGACCAGCACAACCTCAAGCAA

AATGACCAGCCCATGGATATCCTGCAGATTATTAATTGTTTGACCACTATTTATGACCGCCTGG

AGCAAGAGCACAACAATTTGGTCAACGTCCCTCTCTGCGTGGATATGTGTCTGAACTGGCTGC

TGAATGTTTATGATACGGGACGAACAGGGAGGATCCGTGTCCTGTCTTTTAAAACTGGCATCA

TTTCCCTGTGTAAAGCACATTTGGAAGACAAGTACAGATACCTTTTCAAGCAAGTGGCAAGTT

CAACAGGATTTTGTGACCAGCGCAGGCTGGGCCTCCTTCTGCATGATTCTATCCAAATTCCAA

GACAGTTGGGTGAAGTTGCATCCTTTGGGGGCAGTAACATTGAGCCAAGTGTCCGGAGCTGCT

TCCAATTTGCTAATAATAAGCCAGAGATCGAAGCGGCCCTCTTCCTAGACTGGATGAGACTGG

AACCCCAGTCCATGGTGTGGCTGCCCGTCCTGCACAGAGTGGCTGCTGCAGAAACTGCCAAGC

ATCAGGCCAAATGTAACATCTGCAAAGAGTGTCCAATCATTGGATTCAGGTACAGGAGTCTAA

AGCACTTTAATTATGACATCTGCCAAAGCTGCTTTTTTTCTGGTCGAGTTGCAAAAGGCCATAA

AATGCACTATCCCATGGTGGAATATTGCACTCCGACTACATCAGGAGAAGATGTTCGAGACTT

TGCCAAGGTACTAAAAAACAAATTTCGAACCAAAAGGTATTTTGCGAAGCATCCCCGAATGG

GCTACCTGCCAGTGCAGACTGTCTTAGAGGGGACAACATGGAAACTCCCGTTACTCTGATCA

ACTTCTGGCCAGTAGATTCTGCGCCTGCCTCGTCCCCTCAGCTTTCACACGATGATACTCATTC

ACGCATTGAACATTATGCTAGCAGGCTAGCAGAAATGGAAAACAGCAATGGATCTTATCTAA

ATGATAGCATCTCTCCTAATGAGAGCATAGATGATGAACATTTGTTAATCCAGCATTACTGCC

AAAGTTTGAACCAGGACTCCCCCCTGAGCCAGCCTCGTAGTCCTGCCCAGATCTTGATTTCCTT

AGAGAGTGAGGAAAGAGGGGAGCTAGAGAGAATCCTAGCAGATCTTGAGGAAGAAAACAGG

AATCTGCAAGCAGAATATGACCGTCTAAAGCAGCAGCACGAACATAAAGGCCTGTCCCCACT

GCCGTCCCTCCTGAAATGATGCCCACCTCTCCCCAGAGTCCCCGGGATGCTGAGCTCATTGC

TGAGGCCAAGCTACTGCGTCAACACAAAGGCCGCCTGGAAGCCAGGATGCAAATCCTGGAAG

ACCACAATAAACAGCTGGAGTCACAGTTACACAGGCTAAGGCAGGTGCTGGAGCAACCCCAG

GCAGAGGCCAAAGTGAATGGCACAACGGTGTCCTCTCCTTCTACCTCTCTACAGAGGTCCGAC

AGCAGTCAGCCTATGCTGCTCCGAGTGGTTGGCAGTCAAACTTCGGACTCCATGGGTGAGGAA

GATCTTCTCAGTCGTCCCCAGGACACAAGCACAGGGTTAGAGGAGGTGATGGAGCAACTCAA

CAACTCCTTTCCCTAGTTCAAGAGGAAGAAATACCCCTGGAAAGCCAATGAGAGAGGACACAA

TGTAG

SEQ ID NO: 4: ΔH2-R19 (mini-dystrophin with 8 repeats and 3
hinges) (This minigene does not carry R16 or R17. It cannot
restore nNOS)
ATGCTTGGTGGAAGAAGTAGAGGACTGTTATGAAAGAGAAGATGTTCAAAAGAAAACATT

CACAAAATGGGTAAATGCACAATTTTCTAAGTTTGGGAAGCAGCATATTGAGAACCTCTTCAG

TGACCTACAGGATGGGAGGCGCCTCCTAGACCTCCTCGAAGGCCTGACAGGGCAAAAACTGC

CAAAAGAAAAAGGATCCACAAGAGTTCATGCCCTGAACAATGTCAACAAGGCACTGCGGGTT

TTGCAGAACAATAATGTTGATTTAGTGAATATTGGAAGTACTGACATCGTAGATGGAAATCAT

AAACTGACTCTTGGTTTGATTTGGAATATAATCCTCCACTGGCAGGTCAAAAATGTAATGAAA

AATATCATGGCTGGATTGCAACAAACCAACAGTGAAAAGATTCTCCTGAGCTGGGTGCGACA

ATCAACTCGTAATTATCCACAGGTTAATGTAATCAACTTCACCACCAGCTGGTCTGATGGCCT
```

-continued

```
GGCTTTGAATGCTCTCATCCATAGTCATAGGCCAGACCTATTTGACTGGAATAGTGTGGTTTGC
CAGCAGTCAGCCACACAACGACTGGAACATGCATTCAACATCGCCAGATATCAATTAGGCAT
AGAGAAACTACTCGATCCTGAAGATGTTGATACCACCTATCCAGATAAGAAGTCCATCTTTAAT
GTACATCACATCACTCTTCCAAGTTTTGCCTCAACAAGTGAGCATTGAAGCCATCCAGGAAGT
GGAAATGTTGCCAAGGCCACCTAAAGTGACTAAAGAAGAACATTTTCAGTTACATCATCAAAT
GCACTATTCTCAACAGATCACGGTCAGTCTAGCACAGGGATATGAGAGAACTTCTTCCCCTAA
GCCTCGATTCAAGAGCTATGCCTACACACAGGCTGCTTATGTCACCCACCTCTGACCCTACACG
GAGCCCATTTCCTTCACAGCATTTGGAAGCTCCTGAAGACAAGTCATTTGGCAGTTCATTGAT
GGAGAGTGAAGTAAACCTGGACCGTTATCAAACAGCTTTAGAAGAAGTATTATCGTGGCTTCT
TTCTGCTGAGGACACATTGCAAGCACAAGGAGAGATTTCTAATGATGTGGAAGTGGTGAAAG
ACCAGTTTCATACTCATGAGGGGTACATGATGGATTTGACAGCCCATCAGGGCCGGGTTGGTA
ATATTCTACAATTGGGAAGTAAGCTGATTGGAACAGGAAAATTATCAGAAGATGAAGAAACT
GAAGTACAAGAGCAGATGAATCTCCTAAATTCAAGATGGGAATGCCTCAGGGTAGCTAGCAT
GGAAAAACAAAGCAATTTACATAGAGTTTTAATGGATCTCCAGAATCAGAAACTGAAAGAGT
TGAATGACTGGCTAACAAAAACAGAAGAAAGAACAAGGAAAATGGAGGAAGAGCCTCTTGG
ACCTGATCTTGAAGACCTAAAACGCCAAGTACAACAACATAAGGTGCTTCAAGAAGATCTAG
AACAAGAACAAGTCAGGGTCAATTCTCTCACTCACATGGTGGTGGTAGTTGATGAATCTAGTG
GAGATCACGCAACTGCTGCTTTGGAAGAACAACTTAAGGTATTGGGAGATCGATGGGCAAAC
ATCTGTAGATGGACAGAAGACCGCTGGGTTCTTTTACAAGACATCCTTCTCAAATGGGAACGT
CTTACTGAAGAACAGTGCCTTTTTAGTGCATGGCTTTCAGAAAAAGAAGATGCAGTGAACAAG
ATTCACACAACTGGCTTTAAAGATCAAAATGAAATGTTATCAAGTCTTCAAAAACTGGCCGTT
TTAAAAGCGGATCTAGAAAAGAAAAAGCAATCCATGGGCAAACTGTATTCACTCAAACAAGA
TCTTCTTTCAACACTGAAGAATAAGTCAGTGACCCAGAAGACGGAAGCATGGCTGGATAACTT
TGCCCGGTGTTGGGATAATTTAGTCCAAAAACTTGAAAAGAGTACAGCACAGATTTCACAGCA
GCCTGACCTAGCTCCTGGACTGACCACTATTGGAGCCTCTCCTACTCAGACTGTTACTCTGGTG
ACACAACCTGTGGTTACTAAGGAAACTGCCATCTCCAAACTAGAAATGCCATCTTCCTTGATG
TTGGAGGTACCTGCTCTGGCAGATTTCAACCGGGCTTGGACAGAACTTACCGACTGGCTTTCT
CTGCTTGATCAAGTTATAAAATCACAGAGGGTGATGGTGGGTGACCTTGAGGATATCAACGA
GATGATCATCAAGCAGAAGGCAACAATGCAGGATTTGGAACAGAGGCGTCCCCAGTTGGAAG
AACTCATTACCGCTGCCCAAAATTTGAAAAACAAGACCAGCAATCAAGAGGCTAGAACAATC
ATTACGGATCGAATTGAAAGAATTCAGAATCAGTGGGATGAAGTACAAGAACACCTTCAGAA
CCGGAGGCAACAGTTGAATGAAATGTTAAAGGATTCAACACAATGGCTGGAAGCTAAGGAAG
AAGCTGAGCAGGTCTTAGGACAGGCCAGAGCCAAGCTTGAGTCATGGAAGGAGGGTCCCTAT
ACAGTAGATGCAATCCAAAAGAAAATCACAGAAACCAAGCAGTTGGCCAAAGACCTCCGCGA
GTGGCAGACAAATGTAGATGTGGCAAATGACTTGGCCCTGAAACTTCTGCGGGATTATTCTGC
AGATGATACCAGAAAGTCCACATGATAACAGAGAATATCAATGCCTCTTGGAGAAGCATTC
ATAAAAGGGTGAGTGAGCGAGAGGCTGCTTTGGAAGAAACTCATAGATTACTGCAACAGTTC
CCCCTGGACCTGGAAAAGTTTCTTGCCTGGCTTACAGAAGCTGAAACAACTGCCAATGTCCTA
CAGGATGCTACCCGTAAGGAAAGGCTCCTAGAAGACTCCAAGGGAGTAAAAGAGCTGATGAA
ACAATGGCAAGACCTCCAAGGTGAAATTGAAGCTCACACAGATGTTTATGACAACCTGGATG
```

-continued

```
AAAACAGCCAAAAAATCCTGAGATCCCTGGAAGGTTCCGATGATGCAGTCCTGTTACAAAGA
CGTTTGGATAACATGAACTTCAAGTGGAGTGAACTTCGGAAAAAGTCTCTCAACATTAGGTCC
CATTTGGAAGCCAGTTCTGACCAGTGGAAGCGTCTGCACCTTTCTCTGCAGGAACTTCTGGTG
TGGCTACAGCTGAAAGATGATGAATTAAGCCGGCAGGCACCTATTGGAGGCGACTTTCCAGC
AGTTCAGAAGCAGAACGATGTACATAGGGCCTTCAAGAGGGAATTGAAAACTAAAGAACCTG
TAATCATGAGTACTCTTGAGACTGTACGAATATTTCTGACAGAGCAGCCTTTGGAAGGACTAG
AGAAACTCTACCAGGAGCCCAGAGAGCTGCCTCCTGAGGAGAGAGCCCAGAATGTCACTCGG
CTTCTACGAAAGCAGGCTGAGGAGGTCAATACTGAGTGGGAAAAATTGAACCTGCACTCCGC
TGACTGGCAGAGAAAAATAGATGAGACCCTTGAAAGACTCCAGGAACTTCAAGAGGCCACGG
ATGAGCTGGACCTCAAGCTGCGCCAAGCTGAGGTGATCAAGGGATCCTGGCAGCCCGTGGGC
GATCTCCTGATTGACTCTCTCCAAGATCACCTCGAGAAAGTCAAGGCACTTCGAGGAGAAATT
GCGCCTCTGAAAGAGAACGTGAGCGACGTCAATGACCTTGCTCGCCAGCTTACCACTTTGGGC
ATTCAGCTCTCACCGTATAACCTCAGCACTCTGGAAGACCTGAACACCAGATGGAAGCTTCTG
CAGGTGGCCGTCGAGGACCGAGTCAGGCAGCTGCATGAAGCCCACAGGGACTTTGGTCCAGC
ATCTCAGCACTTTCTTTCCACGTCTGTCCAGGGTCCCTGGGAGAGAGCCATCTCGCCAAACAA
AGTGCCCTACTATATCAACCACGAGACTCAAACAACTTGCTGGGACCATCCCAAAATGACAG
AGCTCTACCAGTCTTTAGCTGACCTGAATAATGTCAGATTCTCAGCTTATAGGACTGCCATGA
AACTCCGAAGACTGCAGAAGGCCCTTTGCTTGGATCTCTTGAGCCTGTCAGCTGCATGTGATG
CCTTGGACCAGCACAACCTCAAGCAAAATGACCAGCCCATGGATATCCTGCAGATTATTAATT
GTTTGACCACTATTTATGACCGCCTGGAGCAAGAGCACAACAATTTGGTCAACGTCCCTCTCT
GCGTGGATATGTGTCTGAACTGGCTGCTGAATGTTTATGATACGGGACGAACAGGGAGGATCC
GTGTCCTGTCTTTAAAAGTGGCATCATTTCCCTGTGTAAAGCACATTTGGAAGACAAGTACA
GATACCTTTTCAAGCAAGTGGCAAGTTCAACAGGATTTTGTGACCAGCGCAGGCTGGGCCTCC
TTCTGCATGATTCTATCCAAATCCAAGACAGTTGGGTGAAGTTGCATCCTTTGGGGGCAGTA
ACATTGAGCCAAGTGTCCGGAGCTGCTTCCAATTTGCTAATAATAAGCCAGAGATCGAAGCGG
CCCTCTTCCTAGACTGGATGAGACTGGAACCCCAGTCCATGGTGTGGCTGCCCGTCCTGCACA
GAGTGGCTGCTGGAGAAACTGCCAAGCATCAGGCCAAATGTAACATCTGCAAAGAGTGTCCA
ATCATTGGATTCAGGTACAGGAGTCTAAAGCACTTTAATTATGACATCTGCCAAAGCTGCTTT
TTTTCTGGTCGAGTTGCAAAAGGCCATAAAATGCACTATCCCATGGTGGAATATTGCACTCCG
ACTACATCAGGAGAAGATGTTCGAGACTTTGCCAAGGTACTAAAAAACAAATTTCGAACCAA
AAGGTATTTTGCGAAGCATCCCCGAATGGGCTACCTGCCAGTGCAGACTGTCTTAGAGGGGGA
CAACATGGAAACGCCTGCCTCGTCCCCTCAGCTTTCACACGATGATACTCATTCACGCATTGA
ACATTATGCTAGCAGGCTAGCAGAAATGGAAAACAGCAATGGATCTTATCTAAATGATAGCA
TCTCTCCTAATGAGAGCATAGATGATGAACATTTGTTAATCCAGCATTACTGCCAAAGTTTGA
ACCAGGACTCCCCCCTGAGCCAGCCTCGTAGTCCTGCCCAGATCTTGATTTCCTTAGAGAGTG
AGGAAAGAGGGGAGCTAGAGAGAATCCTAGCAGATCTTGAGGAAGAAAACAGGAATCTGCA
AGCAGAATATGACCGTCTAAAGCAGCAGCACGAACATAAAGGCCTGTCCCCACTGCCGTCCC
CTCCTGAAATGATGCCCACCTCTCCCCAGAGTCCCCGGGATGCTGAGCTCATTGCTGAGGCCA
AGCTACTGCGTCAACACAAAGGCCGCCTGGAAGCCAGGATGCAAATCCTGGAAGACCACAAT
AAACAGCTGGAGTCACAGTTACACAGGCTAAGGCAGCTGCTGGAGCAACCCCAGGCAGAGGC
```

-continued

CAAAGTGAATGGCACAACGGTGTCCTCTCCTTCTACCTCTCTACAGAGGTCCGACAGCAGTCA

GCCTATGCTGCTCCGAGTGGTTGGCAGTCAAACTTCGGACTCCATGGGTGAGGAAGATCTTCT

CAGTCCTCCCCAGGACACAAGCACAGGGTTAGAGGAGGTGATGGAGCAACTCAACAACTCCT

TCCCTAGTTGAAGAGGAAGAAATACCCCTGGAAAGCCAATGAGAGAGGACACAATGTAG

SEQ ID NO: 5: ΔH2-R17 (mini-dystrophin with 10 repeats and 3
hinges) (This minigene does not carry R16 or R17. It cannot
restore nNOS)
ATGCTTTGGTGGGAAGAAGTAGAGGACTGTTATGAAAGAGAAGATGTTCAAAAGAAAACATT

CACAAAATGGGTAAATGCACAATTTTCTAAGTTTGGGAAGCAGCATATTGAGAACCTCTTCAG

TGACCTACAGGATGGGAGGCGCCTCCTAGACCTCCTCGAAGGCCTGACAGGGCAAAAACTGC

CAAAAGAAAAAGGATCCACAAGAGTTCATGCCCTGAACAATGTCAACAAGGCACTGCGGGTT

TTGCAGAACAATAATGTTGATTTAGTGAATATTGGAAGTACTGACATCGTAGATGGAAATCAT

AAACTGACTCTTGGTTTGATTTGGAATATAATCCTCCACTGGCAGGTCAAAAATGTAATGAAA

AATATCATGGCTGGATTGCAACAAACCAACAGTGAAAAGATTCTCCTGAGCTGGGTCCGACA

ATCAACTCGTAATTATCCACAGGTTAATGTAATCAACTTCACCACCAGCTGGTCTGATGGCCT

GGCTTTGAATGCTCTCATCCATAGTCATAGGCCAGACCTATTTGACTGGAATAGTGTGGTTTGC

CAGCAGTCAGCCACACAACGACTGGAACATGCATTCAACATCGCCAGATATCAATTAGGCAT

AGAGAAACTACTCGATCCTGAAGATGTTGATACCACCTATCCAGATAAGAAGTCCATCTTAAT

GTACATCACATCACTCTTCCAAGTTTTGCCTCAACAAGTGAGCATTGAAGCCATCCAGGAAGT

GGAAATGTTGCCAAGGCCACCTAAAGTGACTAAAGAAGAACATTTTCAGTTACATCATCAAAT

GCACTATTCTCAACAGATCACGGTCAGTCTAGCACAGGGATATGAGAGAACTTCTTCCCCTAA

GCCTCGATTCAAGAGCTATGCCTACACACAGGCTGCTTATGTCACCACCTCTGACCCTACACG

GAGCCCATTTCCTTCACAGCATTTGGAAGCTCCTGAAGACAAGTCATTTGGCAGTTCATTGAT

GGAGAGTGAAGTAAACCTGGACCGTTATCAAACAGCTTTAGAAGAAGTATTATCGTGGCTTCT

TTCTGCTGAGGACACATTGCAAGCACAAGGAGAGATTTCTAATGATGTGGAAGTGGTGAAAG

ACCAGTTTCATACTCATGAGGGGTACATGATGGATTTGACAGCCCATCAGGGCCGGGTTGGTA

ATATTCTACAATTGGGAAGTAAGCTGATTGGAACAGGAAAATTATCAGAAGATGAAGAAACT

GAAGTACAAGAGCAGATGAATCTCCTAAATTCAAGATGGGAATGCCTCAGGGTAGCTAGCAT

GGAAAAACAAAGCAATTTACATAGAGTTTTAATGGATCTCCAGAATCAGAAACTGAAAGAGT

TGAATGACTGGCTAACAAAAACAGAAGAAAGAACAAGGAAAATGGAGGAAGAGCCTCTTGG

ACCTGATCTTGAAGACCTAAAACGCCAAGTACAACAACATAAGGTGCTTCAAGAAGATCTAG

AACAAGAACAAGTCAGGGTCAATTCTCTCACTCACATGGTGGTGGTAGTTGATGAATCTAGTG

GAGATCACGCAACTGCTGCTTTGGAAGAACAACTTAAGGTATTGGGAGATCGATGGGCAAAC

ATCTGTAGATGGACAGAAGACCGCTGGGTTCTTTTACAAGACATCCTTCTCAAATGGCAACGT

CTTACTGAAGAACAGTGCCTTTTTAGTGCATGGCTTTCAGAAAAAGAAGATGCAGTGAACAAG

ATTCACACAACTGGCTTTAAAGATCAAAATGAAATGTTATCAAGTCTTCAAAAACTGGCCGTT

TTAAAAGCGGATCTAGAAAAGAAAAAGCAATCCATGGGCAAACTGTATTCACTCAAACAAGA

TCTTCTTTCAACACTGAAGAATAAGTCAGTGACCCAGAAGACGGAAGCATGGCTGGATAACTT

TGCCCGGTGTTGGGATAATTTAGTCCAAAAACTTGAAAAGAGTACAGCACAGATTTCACAGCA

AAAGAATATCTTGTCAGAATTTCAAAGAGATTTAAATGAATTTGTTTTATGGTTGGAGGAAGC

AGATAACATTGCTAGTATCCCACTTGAACCTGGAAAAGAGCAGCAACTAAAAGAAAAGCTTG

-continued

```
AGCAAGTCAAGTTACTGGTGGAAGAGTTGCCCCTGCGCCAGGGAATTCTCAAACAATTAAAT
GAAACTGGAGGACCCGTGCTTGTAAGTGCTCCCATAAGCCCAGAAGAGCAAGATAAACTTGA
AAATAAGCTCAAGCAGACAAATCTCCAGTGGATAAAGGTTTCCAGAGCTTTACCTGAGAAAC
AAGGAGAAATTGAAGCTCAAATAAAAGACCTTGGGCAGCTTGAAAAAAAGCTTGAAGACCTT
GAAGAGCAGTTAAATCATCTGCTGCTGTGGTTATCTCGTATTAGGAATCAGTTGGAAATTTAT
AACCAACCAAACCAAGAAGGACCATTTGACGTTCAGGAAACTGAAATAGCAGTTCAAGCTAA
ACAACCGGATGTGGAAGAGATTTTGTCTAAAGGGCAGCATTTGTACAAGGAAAAACCAGCCA
CTGAGCCAGTGAAGAGGAAGTTAGAAGATCTGAGCTCTGAGTGGAAGGCGGTAAACCGTTTA
CTTCAAGAGCTGAGGGCAAAGCAGCCTGACCTAGCTCCTGGACTGACCACTATTGGAGCCTCT
CCTACTCAGACTGTTACTCTGGTGACACAACCTGTGGTTACTAAGGAAACTGCCATCTCCAAA
CTAGAAATGCCATCTTCCTTGATGTTGGAGGTACCTGCTCTGGCAGATTTCAACCGGGCTTGG
ACAGAACTTACCGACTGGCTTTCTCTGCTTGATCAAGTTATAAAATCACAGAGGGTGATGGTG
GGTGACCTTGAGGATATCAACGAGATGATCATCAAGCAGAAGGCAACAATGCAGGATTTGGA
ACAGAGGCGTCCCCAGTTGGAAGAACTCATTACCGCTGCCCAAAATTTGAAAAACAAGACCA
GCAATCAAGAGGCTAGAACAATCATTACGGATCGAATTGAAAGAATTCAGAATCAGTGGGAT
GAAGTACAAGAACACCTTCAGAACCGGAGGCAACAGTTGAATGAAATGTTAAAGGATTCAAC
ACAATGGCTGGAAGCTAAGGAAGAAGCTGAGCAGGTCTTAGGACAGGCCAGAGCCAAGCTTG
AGTCATGGAAGGAGGGTCCCTATACAGTAGATGCAATCCAAAAGAAAATCACAGAAACCAAG
CAGTTGGCCAAAGACCTCCGCCAGTGGCAGACAAATGTAGATGTGGCAAATGACTTGGCCCT
GAAACTTCTCCGGGATTATTCTGCAGATGATACCAGAAAAGTCCACATGATAACAGAGAATAT
CAATGCCTCTTGGAGAAGCATTCATAAAAGGGTGAGTGAGCGAGAGGCTGCTTTGGAAGAAA
CTCATAGATTACTGCAACAGTTCCCCCTGGACCTGGAAAAGTTTCTTGCCTGGCTTACAGAAG
CTGAAACAACTGCCAATGTCCTACAGGATGCTACCCGTAAGGAAAGGCTCCTAGAAGACTCC
AAGGGAGTAAAAGAGCTGATGAAACAATGGCAAGACCTCCAAGGTGAAATTGAAGCTCACAC
AGATGTTTATCACAACCTGGATGAAAACAGCCAAAAAATCCTGAGATCCCTGGAAGGTTCCG
ATGATGCAGTCCTGTTACAAAGACGTTTGGATAACATGAACTTCAAGTGGAGTGAACTTCGGA
AAAAGTCTCTCAACATTAGGTCCCATTTGGAAGCCAGTTCTGACCAGTGGAAGCGTCTGCACC
TTTCTCTGCAGGAACTTCTGGTGTGGCTAGAGCTGAAAGATGATGAATTAAGCCGGCAGGCAC
CTATTGGAGGCGACTTTCCAGCAGTTCAGAAGCAGAACGATGTACATAGGGCCTTCAAGAGG
GAATTGAAAACTAAAGAACCTGTAATCATGAGTACTCTTGAGACTGTACGAATATTTCTGACA
GAGCAGCCTTTGGAAGGACTAGAGAAACTCTACCAGGAGCCCAGAGAGCTGCCTCCTGAGGA
GAGAGCCCAGAATGTCACTCGGCTTCTACGAAAGCAGGCTGAGGAGGTCAATACTGAGTGGG
AAAAATTGAACCTGCACTCCGCTGACTGGCAGAGAAAAATAGATGAGACCCTTGAAAGACTC
CAGGAACTTCAAGAGGCCACGGATGAGCTGGACCTCAAGCTGCGCCAAGCTGAGGTGATCAA
GGGATCCTGGCAGCCGGTGGGCGATCTCCTCATTGACTCTCTCCAAGATCACCTCGAGAAAGT
CAAGGCACTTCGAGGAGAAATTGCGCCTCTGAAAGAAACGTGAGCCACGTCAATGACCTTG
CTCGCCAGCTTACCACTTTGGGCATTCAGCTCTCACCGTATAACCTCAGCACTCTGGAAGACCT
GAACACCAGATGGAAGCTTCTGCAGGTGGCCGTCGAGGACCGAGTCAGGCAGCTGCATGAAG
CCCACAGGGACTTTGGTCCAGCATCTCAGCACTTTCTTTCCACGTCTGTCCAGGGTCCCTGGGA
GAGAGCCATCTCGCCAAACAAAGTGCCCTACTATATCAACCACGAGACTCAAACAACTTGCTG
```

```
GGACCATCCCAAAATGACAGAGCTCTACCAGTCTTTAGCTGACCTGAATAATGTCAGATTCTC

AGCTTATAGGACTGCCATGAAACTCCGAAGACTGCAGAAGGCCCTTTGCTTGGATCTCTTGAG

CCTGTCAGCTGCATGTGATGCCTTGGACCAGCACAACCTCAAGCAAAATGACCAGCCCATGGA

TATCCTGCAGATTATTAATTGTTTGACCACTATTTATGACCGCCTGGAGCAAGAGCACAACAA

TTTGGTCAACGTCCCTCTCTGCGTGGATATGTGTCTGAACTGGCTGCTGAATGTTTATGATACG

GGACGAACAGGGAGGATCCGTGTCCTGTCTTTTAAAACTGGCATCATTTCCCTGTGTAAAGCA

CATTTGGAAGACAAGTACAGATACCTTTTCAAGCAAGTGGCAAGTTCAACAGGATTTTGTGAC

CAGCGCAGGCTGGGCCTCCTTCTGCATGATTCTATCCAAATTCCAAGACAGTTGGGTGAAGTT

GCATCCTTTGGGGGCAGTAACATTGAGCCAAGTGTCCGGAGCTGCTTCCAATTTGCTAATAAT

AAGCCAGAGATCGAAGCGGCCCTCTTCCTAGACTGGATGAGACTGGAACCCCAGTCCATGGT

GTGGCTGCCCGTCCTGCACAGAGTGGCTGCTGCAGAAACTGCCAAGCATCAGGCCAAATGTA

ACATCTGCAAAGAGTGTCCAATCATTGGATTCAGGTACAGGAGTCTAAAGCACTTTAATTATG

ACATCTGCCAAAGCTGCTTTTTTTCTGGTCGAGTTGCAAAAGGCCATAAAATGCACTATCCCA

TGGTGGAATATTGCACTCCGACTACATCAGGAGAAGATGTTCGAGACTTTGCCAAGGTACTAA

AAAACAAATTTCGAACCAAAAGGTATTTTGCGAAGCATCCCCGAATGGGCTACCTGCCAGTGC

AGACTGTCTTAGAGGGGGACAACATGGAAACGCCTGCCTCGTCCCCTCAGCTTTCACACGATG

ATACTCATTCACGCATTGAACATTATGCTAGCAGGCTAGCAGAAATGGAAAACAGCAATGGA

TCTTATCTAAATGATAGCATCTCTCCTAATGAGAGCATAGATGATGAACATTTGTTAATCCAG

CATTACTGCCAAAGTTTGAACCAGGACTCCCCCCTGAGCCAGCCTCGTAGTCCTGCCCAGATC

TTGATTTCCTTAGAGAGTGAGGAAAGAGGGGAGCTAGAGAGAATCCTAGCAGATCTTGAGGA

AGAAAACAGGAATCTGCAAGCAGAATATGACCGTCTAAAGCAGCAGCACGAACATAAAGGC

CTGTCCCCACTGCCGTCCCCTCCTGAAATGATGCCCACCTCTCCCCAGAGTCCCCGGGATGCTG

AGCTCATTGCTGAGGCCAAGCTACTGCGTCAACACAAAGGCCGCCTGGAAGCCAGGATGCAA

ATCCTGGAAGACCACAATAAACAGCTGGAGTCACAGTTACACAGGCTAAGGCAGCTGCTGGA

GCAACCCCAGGCAGAGGCCAAAGTGAATGGCACAACGGTGTCCTCTCCTTCTACCTCTCTACA

GAGGTCCGACAGCAGTCAGCCTATGCTGCTCCGAGTGGTTGGCAGTCAAACTTCGGACTCCAT

GGGTGAGGAAGATCTTCTCAGTCCTCCCCAGGACACAAGCACAGGGTTTAGAGGAGGTGATGG

AGCAACTCAACAACTCCTTCCCTAGTTCAAGAGGAAGAAATACCCCTGGAAAGCCAATGAGA

GAGGACACAATGTAG

SEQ ID NO: 6: ΔH2-R16 (mini-dystrophin with 11 repeats and 3
hinges) (This minigene carries R17 but not R16. It cannot
restore nNOS)
ATGGTTTGGTGGGAAGAAGTAGAGGACTGTTATGAAAGAAGATGTTCAAAAGAAAACATT

CACAAAATGGGTAAATGCACAATTTTCTAAGTTTGGGAAGCAGCATATTGAGAACCTCTTCAG

TGACCTACAGGATGGGAGGCGCCTCCTAGACCTCCTCGAAGGCCTGACAGGGCAAAAACTGC

CAAAAGAAAAGGATCCACAAGAGTTCATGCCCTGAACAATGTCAACAAGGCACTGCGGGTT

TTGCAGAACAATAATGTTGATTTAGTGAATATTGGAAGTACTGACATCGTAGATGGAAATCAT

AAACTGACTCTTGGTTTGATTTGGAATATAATCCTCCACTGGCAGGTCAAAAATGTAATGAAA

AATATCATGGCTGGATTGCAACAAACCAACAGTGAAAAGATTCTCCTGAGCTGGGTCCGACA

ATCAACTCGTAATTATCCACAGGTTAATGTAATCAACTTCACCACCAGCTGGTCTGATGGCCT

GGCTTTGAATGCTCTCATCCATAGTCATAGGCCAGACCTATTTGACTGGAATAGTGTGGTTTGC

CAGCAGTCAGCCACACAACGACTGGAACATGCATTCAACATCGCCAGATATCAATTAGGCAT
```

-continued

```
AGAGAAACTACTCGATCCTGAAGATGTTGATACCACCTATCCAGATAAGAAGTCCATCTTAAT

GTACATCACATCACTCTTCCAAGTTTTGCCTCAACAAGTGAGCATTGAAGCCATCCAGGAAGT

GGAAATGTTGCCAAGGCCACCTAAAGTGACTAAAGAAGAACATTTTCAGTTACATCATCAAAT

GCACTATTCTCAACAGATCACGGTCAGTCTAGCACAGGGATATGAGAGAACTTCTTCCCCTAA

GCCTCGATTCAAGAGCTATGCCTACACACAGGCTGCTTATGTCACCACCTCTGACCCTACACG

GAGCCCATTTCCTTCACAGCATTTGGAAGCTCCTGAAGACAAGTCATTTGGCAGTTCATTGAT

GGAGAGTGAAGTAAACCTGGACCGTTATCAAACAGCTTTAGAAGAAGTATTATCGTGGCTTCT

TTCTGCTGAGGACACATTGCAAGCACAAGGAGAGATTTCTAATGATGTGGAAGTGGTGAAAG

ACCAGTTTCATACTCATGAGGGGTACATGATGGATTTGACAGCCCATCAGGGCCGGGTTGGTA

ATATTCTACAATTGGGAAGTAAGCTGATTGGAACAGGAAAATTATCAGAAGATGAAGAAACT

GAAGTACAAGAGCAGATGAATCTCCTAAATTCAAGATGGGAATGCCTCAGGGTAGCTAGCAT

GGAAAAACAAAGCAATTTACATAGAGTTTTAATGGATCTCCAGAATCAGAAACTGAAAGAGT

TGAATGACTGGCTAACAAAAACAGAAGAAAGAACAAGGAAAATGGAGGAAGAGCCTCTTGG

ACCTGATCTTGAAGACCTAAAACGCCAAGTACAACAACATAAGGTGCTTCAAGAAGATCTAG

AACAAGAACAAGTCAGGGTCAATTCTCTCACTCACATGGTGGTGGTAGTTGATGAATCTAGTG

GAGATCACGCAACTGCTGCTTTGGAAGAACAACTTAAGGTATTGGGAGATCGATGGGCAAAC

ATCTGTAGATGGACAGAAGACCGCTGGGTTCTTTTACAAGACATCCTTCTCAAATGGCAACGT

CTTACTGAAGAACAGTGCCTTTTTAGTGCATGGCTTTCAGAAAAAGAAGATGCAGTGAACAAG

ATTCACACAACTGGCTTTAAAGATCAAAATGAAATGTTATCAAGTCTTCAAAAACTGGCCGTT

TTAAAAGCGGATCTAGAAAAGAAAAAGCAATCCATGGGCAAACTGTATTCACTCAAACAAGA

TCTTCTTCAACACTGAAGAATAAGTCAGTGACCCAGAAGACGGAAGCATGGCTGGATAACTT

TGCCCGGTGTTGGGATAATTTAGTCCAAAAACTTGAAAAGAGTACAGCACAGATTTCACAGTC

TGTTGAGAAATGGCGGCGTTTTCATTATGATATAAAGATATTTAATCAGTGGCTAACAGAAGC

TGAAGAGTTTCTCAGAAAGACACAAATTCCTGAGAATTGGGAACATGCTAAATACAAATGGT

ATCTTAAGGAACTCCAGGATGGCATTGGGCAGCGGCAAACTGTTGTCAGAACATTGAATGCA

ACTGGGGAAGAAATAATTCAGCAATCCTCAAAAACAGATGCCAGTATTCTACAGGAAAAATT

GGGAAGCCTGAATCTGCGGTGGCAGGAGGTCTGCAAACAGCTGTCAGACAGAAAAAAGAGG

CTAGAAGAACAAAAGAATATCTTGTCAGAATTTCAAAGAGATTTAAATGAATTTGTTTTATGG

TTGGAGGAAGCAGATAACATTGCTAGTATCCCACTTGAACCTGGAAAAGAGCAGCAACTAAA

AGAAAAGCTTGAGCAAGTCAAGTTACTGGTGGAAGAGTTGCCCCTGCGCCAGGGAATTCTCA

AACAATTAAATGAAACTGGAGGACCCGTGCTTGTAAGTGCTCCCATAAGCCCAGAAGAGCAA

GATAAACTTGAAAATAAGCTCAAGCAGACAAATCTCCAGTGGATAAAGGTTTCCAGAGCTTT

ACCTGAGAAACAAGGAGAAATTGAAGCTCAAATAAAAGACCTTGGGCAGCTTGAAAAAAAG

CTTGAAGACCTTGAAGAGCAGTTAAATCATCTGCTGCTGTGGTTATCTCCTATTAGGAATCAG

TTGGAAATTTATAACCAACCAAACCAAGAAGGACCATTTGACGTTCAGGAAACTGAAATAGC

AGTTCAAGCTAAACAACCGGATGTGGAAGAGATTTTGTCTAAAGGGCAGCATTTGTACAAGG

AAAAACCAGCCACTCAGCCAGTGAAGAGGAAGTTAGAAGATCTGAGCTCTGAGTGGAAGGCG

GTAAACCGTTTACTTCAAGAGCTGAGGGCAAAGCAGCCTGACCTAGCTCCTGGACTGACCACT

ATTGGAGCCTCTCCTACTCAGACTGTTACTCTGGTGACACAACCTGTGGTTACTAAGGAAACT

GCCATCTCCAAACTAGAAATGCCATCTTCCTTGATGTTGGAGGTACCTGCTCTGGCAGATTTCA
```

-continued

```
ACCGGGCTTGGACAGAACTTACCGACTGGCTTTCTCTGCTTGATCAAGTTATAAAATCACAGA

GGGTGATGGTGGGTGACCTTGAGGATATCAACGAGATGATCATCAAGCAGAAGGCAACAATG

CAGGATTTGGAACAGAGGCGTCCCCAGTTGGAAGAACTCATTACCGCTGCCCAAAATTTGAA

AAACAAGACCAGCAATCAAGAGGCTAGAACAATCATTACGGATCGAATTGAAAGAATTCAGA

ATCAGTGGGATGAAGTACAAGAACACCTTCAGAACCGGAGGCAACAGTTGAATGAAATGTTA

AAGGATTCAACACAATGGCTGGAAGCTAAGGAAGAAGCTGAGCAGGTCTTAGGACAGGCCAG

AGCCAAGCTTGAGTCATGGAAGGAGGGTCCCTATACAGTAGATGCAATCCAAAAGAAAATCA

CAGAAACCAAGCAGTTGGCCAAAGACCTCCGCCAGTGGCAGACAAATGTAGATGTGGCAAAT

GACTTGGCCCTGAAACTTCTCCGGGATTATTCTGCAGATGATACCAGAAAAGTCCACATGATA

ACAGAGAATATCAATGCCTCTTGGAGAAGCATTCATAAAAGGGTGAGTGAGCGAGAGGCTGC

TTTGGAAGAAACTCATAGATTACTGCAACAGTCCCCCTGGACCTGGAAAAGTTTCTTGCCTG

GCTTACAGAAGCTGAAACAACTGCCAATGTCCTACAGGATGCTACCCGTAAGGAAAGGCTCC

TAGAAGACTCCAAGGGAGTAAAAGAGCTGATGAAACAATGGCAAGACCTCCAAGGTGAAATT

GAAGCTCACACAGATGTTTATCACAACCTGGATGAAAACAGCCAAAAAATCCTGAGATCCGT

GGAAGGTTCCGATGATGCAGTCCTGTTACAAAGACGTTTGGATAACATGAACTTCAAGTGGAG

TGAACTTCGGAAAAAGTCTCTCAACATTAGGTCCCATTTGGAAGCCAGTTCTGACCAGTGGAA

GCGTCTGCACCTTTCTCTGCAGGAACTTCTGGTGTGGCTACAGCTGAAAGATGATGAATTAAG

CCGGCAGGCACCTATTGGAGGCGACTTTCCAGCAGTTCAGAAGCAGAACGATGTACATAGGG

CCTTCAAGAGGGAATTGAAAACTAAAGAACCTGTAATCATGAGTACTCTTGAGACTGTACGA

ATATTTCTGACAGAGCAGCCTTTGGAAGGACTAGAGAAACTCTACCAGGAGCCCAGAGAGCT

GCCTCCTGAGGAGAGAGCCCAGAATGTCACTCGGCTTCTACGAAAGCAGGCTGAGGAGGTCA

ATACTGAGTGGGAAAAATTGAACCTGCACTCCGCTGACTGGCAGAGAAAAATAGATGAGACC

CTTGAAAGACTCCAGGAACTTCAAGAGGCCACGGATGAGCTGGACCTCAAGCTGCGCCAAGC

TGAGGTGATCAAGGGATCCTGGCAGCCCGTGGGCGATCTCCTCATTGACTCTCTCCAAGATCA

CCTCGAGAAAGTCAAGGCACTTCGAGGAGAAATTTGCGCCTCTGAAAGAGAACGTGAGCCACG

TCAATGACCTTGCTCGCCAGCTTACCACTTTGGGCATTCAGCTCTCACCGTATAACCTCAGCAC

TCTGGAAGACCTGAACACCAGATGGAAGCTTCTGCAGGTGGCCGTCGAGGACCGAGTCAGGC

AGCTGCATGAAGCCCACAGGGACTTTGGTCCAGCATCTCAGCACTTTCTTTCCACGTCTGTCCA

GGGTCCCTGGGAGAGAGCCATCTCGCCAAACAAAGTGCCCTACTATATCAACCACGAGACTC

AAACAACTTGCTGGACCATCCCAAAATGACAGAGCTCTACCAGTCTTTAGCTGACCTGAATA

ATGTCAGATTCTCAGCTTATAGGACTGCCATGAAACTCCGAAGACTGCAGAAGGCCCTTTGCT

TGGATCTCTTGAGCCTGTCAGCTGCATGTGATGCCTTGGACCAGCACAACCTCAAGCAAATG

ACCAGCCCATGGATATCCTGCAGATTATTAATTGTTTGACCACTATTTATGACCGCCTGGAGC

AAGAGCACAACAATTTGGTCAACGTCCCTCTCTGCGTGGATATGTGTCTGAACTGGCTGCTGA

ATGTTTATGATACGGGACGAACAGGGAGGATCCGTGTCCTGTCTTTTAAAACTGGCATCATTT

CCCTGTGTAAAGCACATTTGGAAGACAAGTACAGATACCTTTTCAAGCAAGTGGCAAGTTCAA

CAGGATTTTGTGACCAGCGCAGGCTGGGCCTCCTTCTGCATGATTCTATCCAAATTCCAAGAC

AGTTGGGTGAAGTTGCATCCTTTGGGGGCAGTAACATTGAGCCAAGTGTCCGGAGCTGCTTCC

AATTTGCTAATAATAAGCCAGAGATCGAAGCGGCCCTCTTCCTAGACTGGATGAGACTGGAAC

CCCAGTCCATGGTGTGGCTGCCCGTCCTGCACAGAGTGGCTGCTGCAGAAACTGCCAAGCATC
```

-continued

AGGCCAAATGTAACATCTGCAAAGAGTGTCCAATCATTGGATTTCAGGTACAGGAGTCTAAAG

CACTTTAATTATGACATCTGCCAAAGCTGCTTTTTTTCTGGTCGAGTTGCAAAAGGCCATAAAA

TGCACTATCCCATGGTGGAATATTGCACTCCGACTACATCAGGAGAAGATGTTCGAGACTTTG

CCAAGGTACTAAAAAACAAATTTCGAACCAAAAGGTATTTTGCGAAGCATCCCCGAATGGGC

TACCTGCCAGTGCAGACTGTCTTAGAGGGGGACAACATGGAAACGCCTGCCTCGTCCCCTGAG

CTTTCACACGATGATACTCATTCACGCATTGAACATATGCTAGCAGGCTAGCAGAAATGGAA

AACAGCAATGGATCTTATCTAAATGATAGCATCTCTCCTAATGAGAGCATAGATGATGAACAT

TTTGTTAATCCAGCATTACTGCCAAAGTTTGAACCAGGACTCCCCCCTGAGCCAGCCTCGTAGT

CCTGCCCAGATCTTGATTTCCTTAGAGAGTGAGGAAAGAGGGGAGCTAGAGAGAATCCTAGC

AGATCTTGAGGAAGAAAACAGGAATCTGCAAGCAGAATATGACCGTCTAAAGCAGCAGCACG

AACATAAAGGCCTGTCCCCACTGCCGTCCCCTCCTGAAATGATGCCCACGTCTCCCCAGAGTC

CCCGGGATGCTGAGCTCATTGCTGAGGCCAAGCTACTGCGTCAACACAAAGGCCGCCTGGAA

GCCAGGATGCAAATCCTGGAAGACCACAATAAACAGCTGGAGTCACAGTTACACAGGCTAAG

GCAGCTGCTGGAGCAACCCCAGGCAGAGGCCAAAGTGAATGGCACAACGGTGTCCTCTCCTTT

CTACCTCTCTACAGAGGTCCGACAGCAGTCAGCCTATGCTGCTCCGAGTGGTTGGCAGTCAAA

CTTCGGACTCCATGGGTGAGGAAGATCTTCTCAGTCCTCCCCAGGACACAAGCACAGGGTTAG

AGGAGGTGATGGAGCAACTCAACAACTCCTTCCCTAGTTCAAGAGGAAGAAATACCCCTGGA

AAGCCAATGAGAGAGGACACAATGTAG

SEQ ID NO: 7: ΔH2-R15 (mini-dystrophin with 12 repeats and 3 hinges) (This minigene carries both R16 and R17. It can restore nNOS)
ATGCTTTGGTGGGAAGAAGTAGAGGACTGTTATGAAAGAAGATGTTCAAAAGAAAACATT

CACAAAATGGGTAAATGCACAATTTTCTAAGTTTGGGAAGCAGCATATTGAGAACCTCTTCAG

TGACCTACAGGATGGGAGGCGCCTCCTAGACCTCCTCGAAGGCCTGACAGGGCAAAAACTGC

CAAAAGAAAAAGGATCCACAAGAGTTCATGCCCTGAACAATGTCAACAAGGCACTGCGGGTT

TTGCAGAACAATAATGTTGATTTAGTGAATATTGGAAGTACTGACATCGTAGATGGAAATCAT

AAACTGACTGTTGGTTTGATTTGGAATATAATCCTCCACTGGCAGGTCAAAAATGTAATGAAA

AATATCATGGCTGGATTGCAACAAACCAACAGTGAAAAGATTCTCCTGAGCTGGGTCCGACA

ATCAACTCGTAATTATCCACAGGTTAATGTAATCAACTTCACCACCAGCTGGTCTGATGGCCT

GGCTTTGAATGCTCTCATCCATAGTCATAGGCCAGACCTATTTGACTGGAATAGTGTGGTTTGC

CAGCAGTCAGCCACACAACGACTGGAACATGCATTCAACATCGCCAGATATCAATTAGGCAT

AGAGAAACTACTCGATCCTGAAGATGTTGATACCACCTATCCAGATAAGAAGTCCATCTTAAT

GTACATCACATCACTCTTCCAAGTTTTGCCTCAACAAGTGAGCATTGAAGCCATCCAGGAAGT

GGAAATGTTGCCAAGGCCACCTAAAGTGACTAAAGAAGAACATTTTCAGTTACATCATCAAAT

GCACTATTCTCAACAGATCACGGTCAGTCTAGCACAGGGATATGAGAGAACTTCTTCCCCTAA

GCCTCGATTCAAGAGCTATGCCTACACACAGGCTGCTTATGTCACCACCTCTGACCCTACACG

GAGCCCATTTCCTTCACAGCATTTGGAAGCTCCTGAAGACAAGTCATTTGGCAGTTCATTGAT

GGAGAGTGAAGTAAACCTGGACCGTTATCAAACAGCTTTAGAAGAAGTATTATCGTGGCTTCT

TTCTGCTGAGGACACATTGCAAGCACAAGGAGAGATTTCTAATGATGTGGAAGTGGTGAAAG

ACCAGTTTCATACTCATGAGGGGTACATGATGGATTTGACAGCCCATCAGGGCCGGGTTGGTA

ATATTCTACAATTGGGAAGTAAGCTGATTGGAACAGGAAAATTATCAGAAGATGAAGAAACT

```
GAAGTACAAGAGCAGATGAATCTCCTAAATTCAAGATGGGAATGCCTCAGGGTAGCTAGCAT
GGAAAAACAAAGCAATTTACATAGAGTTTTAATGGATCTCCAGAATCAGAAACTGAAAGAGT
TGAATGACTGGCTAACAAAAACAGAAGAAAGAACAAGGAAAATGGAGGAAGAGCCTCTTGG
ACCTGATCTTGAAGACCTAAAACGCCAAGTACAACAACATAAGGTGCTTCAAGAAGATCTAG
AACAAGAACAAGTCAGGGTCAATTCTCTCACTCACATGGTGGTGGTAGTTGATGAATCTAGTG
GAGATCACGCAACTGCTGCTTTGGAAGAACAACTTAAGGTATTTGGGAGATCGATGGGCAAAC
ATCTGTAGATGGACAGAAGACCGCTGGGTTCTTTTACAAGACATCCTTCTCAAATGGCAACGT
CTTACTGAAGAACAGTGCCTTTTTAGTGCATGGCTTTCAGAAAAAGAAGATGCAGTGAACAAG
ATTCACACAACTGGCTTTAAAGATCAAAATGKAATGTTATCAAGTCTTCAAAAAGTGGCCGTT
TTAAAAGCGGATCTAGAAAAGAAAAAGCAATCCATGGGCAAACTGTATTCACTCAAACAAGA
TCTTCTTTCAACACTGAAGAATAAGTCAGTGACCCAGAAGACGGAAGCATGGCTGGATAACTT
TGCCCGGTGTTGGGATAATTTAGTCCAAAAACTTGAAAAGAGTACAGCACAGATTTCACAGG
AAATTTCTTATGTGCCTTCTACTTATTTGACTGAAATCACTCATGTCTCACAAGCCCTATTAGA
AGTGGAACAACTTCTCAATGCTCCTGACCTCTGTGCTAAGGACTTTGAAGATCTCTTTAAGCA
AGAGGAGTCTCTGAAGAATATAAAAGATAGTCTACAACAAAGCTCAGGTCGGATTGACATTA
TTCATAGCAAGAAGACAGCAGCATTGCAAAGTGCAACGCCTGTGGAAAGGGTGAAGCTACAG
GAAGCTCTCTCCCAGCTTGATTTCCAATGGGAAAAAGTTAACAAAATGTACAAGGACCGACA
AGGGCGATTTGACAGATCTGTTGAGAAATGGCGGCGTTTTCATTATGATATAAAGATATTTAA
TCAGTGGCTAACAGAAGCTGAACAGTTTCTCAGAAAGACACAAATTCCTGAGAATTGGGAAC
ATGCTAAATACAAATGGTATCTTAAGGAACTCCAGGATGGCATTGGGCAGCGGCAAACTGTT
GTCAGAACATTGAATGCAACTGGGGAAGAAATAATTCAGCAATCCTCAAAAACAGATGCCAG
TATTCTACAGGAAAAATTGGGAAGCCTGAATCTGCGGTGGCAGGAGGTCTGCAAACAGCTGT
CAGACAGAAAAAAGAGGCTAGAAGAACAAAAGAATATCTTGTCAGAATTTCAAAGAGATTTA
AATGAATTTGTTTTATGGTTGGAGGAAGCAGATAACATTGCTAGTATCCCACTTGAACCTGGA
AAAGAGCAGCAACTAAAAGAAAAGCTTGAGCAAGTCAAGTTACTGGTGGAAGAGTTGCCCCT
GCGCCAGGGAATTCTCAAACAATTAAATGAAACTGGAGGACCCGTGCTTGTAAGTGCTCCCAT
AAGCCCAGAAGAGCAAGATAAACTTGAAAATAAGCTCAAGCAGACAAATCTCCAGTGGATAA
AGGTTTCCAGAGCTTTACCTGAGAAACAAGGAGAAATTGAAGCTCAAATAAAAGACCTTGGG
CAGCTTGAAAAAAAGCTTGAAGACCTTGAAGAGCAGTTAAATCATCTGCTGCTGTGGTTATCT
CCTATTAGGAATCAGTTGGAAATTTATAACCAACCAAACCAAGAAGGACCATTTGACGTTCAG
GAAACTGAAATAGCAGTTCAAGCTAAACAACCGGATGTGGAAGAGATTTTGTCTAAAGGGCA
GCATTTGTACAAGGAAAAACCAGCCACTCAGCCAGTGAAGAGGAAGTTAGAAGATCTGAGCT
CTGAGTGGAAGGCGGTAAACCGTTTACTTCAAGAGCTGAGGGCAAAGCAGCCTGACCTAGCT
CCTGGACTGACCACTATTGGAGCCTCTCCTACTCAGACTGTTACTCTGGTGACACAACCTGTG
GTTACTAAGGAAACTGCCATCTCCAAACTAGAAATGCCATCTTCCTTGATGTTGGAGGTACCT
GCTCTGGCAGATTTCAACCGGGCTTGGACAGAACTTACCGACTGGCTTTCTCTGCTTGATCAA
GTTATAAAATCACAGAGGGTGATGGTGGGTGACCTTGAGGATATCAACGAGATGATCATCAA
GCAGAAGGCAACAATGCAGGATTTGGAACAGAGGCGTCCCCAGTTGGAAGAACTCATTACCG
CTGGCCAAAATTTGAAAAACAAGACCAGCAATCAAGAGGCTAGAACAATCATTACGGATCGA
ATTGAAAGAATTCAGAATCAGTGGGATGAAGTACAAGAACACCTTCAGAACCGGAGGCAACA
```

-continued

```
GTTGAATGAAATGTTAAAGGATTCAACACAATGGCTGGAAGCTAAGGAAGAAGCTGAGCAGG
TCTTAGGACAGGCCAGAGCCAAGCTTGAGTCATGGAAGGAGGGTCCCTATACAGTAGATGCA
ATCCAAAAGAAAATCACAGAAACCAAGCAGTTGGCCAAAGACCTCCGCCAGTGGCAGACAAA
TGTAGATGTGGCAAATGACTTGGCCCTGAAACTTCTCCGGGATTATTCTGCAGATGATACCAG
AAAAGTCCACATGATAACAGAGAATATCAATGCCTCTTGGAGAAGCATTCATAAAAGGGTGA
GTGAGCGAGAGGCTGCTTTGGAAGAAACTCATAGATTACTGCAACAGTTCCCCCTGGACCTGG
AAAAGTTTCTTGCCTGGCTTACAGAAGCTGAAACAACTGCCAATGTCCTACAGGATGCTACCC
GTAAGGAAAGGCTCCTAGAAGACTCCAAGGGAGTAAAAGAGCTGATGAAACAATGGCAAGA
CCTCCAAGGTGAAATTGAAGCTCACACAGATGTTTATCACAACCTGGATGAAAACAGCCAAA
AAATCCTGAGATCCCTGGAAGGTTCCGATGATGCAGTCCTGTTACAAAGACGTTTGGATAACA
TGAACTTCAAGTGGAGTGAACTTCGGAAAAAGTCTCTCAACATTAGGTCCCATTTGGAAGCCA
GTTCTGACCAGTGGAAGCGTCTGCACCTTTCTCTGCAGGAACTTCTGGTGTGGCTACAGCTGA
AAGATGATGAATTAAGCCGGCAGGCACCTATTGGAGGCGACTTTCCAGCAGTTCAGAAGCAG
AACGATGTACATAGGGCCTTCAAGAGGGAATTGAAAACTAAAGAACCTGTAATCATGAGTAC
TCTTGAGACTGTACGAATATTTCTGACAGAGCAGCCTTTGGAAGGACTAGAGAAACTCTACCA
GGAGCCCAGAGAGCTGCCTCCTGAGGAGAGAGCCCAGAATGTCACTCGGCTTCTACGAAAGC
AGGCTGAGGAGGTCAATACTGAGTGGGAAAAATTGAACCTGCACTCCGCTGACTGGCAGAGA
AAAATAGATGAGACCCTTGAAAGACTCCAGGAACTTCAAGAGGCCACGGATGAGCTGGACCT
CAAGCTGCGCGAAGCTGAGGTGATCAAGGGATCCTGGCAGCCCGTGGGCGATCTCCTCATTGA
CTCTCTCCAAGATCACCTCGAGAAAGTCAAGGCACTTCGAGGAGAAATTGCGCCTCTGAAAG
AGAACGTGAGCCACGTCAATGACCTTGCTCGCCAGCTTACCACTTTGGGCATTCAGCTCTCAC
CGTATAACCTCAGCACTCTGGAAGACCTGAACACCAGATGGAAGCTTCTGCAGGTGGCCGTCG
AGGACCGAGTCAGGCAGCTGCATGAAGCCCACAGGGACTTTGGTCCAGCATCTCAGCACTTTC
TTTCCACGTCTGTCCAGGGTCCCTGGGAGAGAGCCATCTCGCCAAACAAAGTGCCCTACTATA
TCAACCACGAGACTCAAACAACTTGCTGGGACCATCCCAAAATGACAGAGCTCTACCAGTCTT
TAGCTGACCTGAATAATGTCAGATTCTCAGCTTATAGGACTGCCATGAAACTCCGAAGACTGC
AGAAGGCCCTTTGCTTGGATCTCTTGAGCCTGTCAGCTGCATGTGATGCCTTGGACCAGCACA
ACCTCAAGCAAAATGACCAGCCCATGGATATCCTGCAGATTATTAATTGTTTGACCACTATTT
ATGACCGCCTGGAGCAAGAGCACAACAATTTGGTGAACGTGCCTCTCTGCGTGGATATGTGTC
TGAACTGGCTGGTGAATGTTTATGATACGGGACGAACAGGGAGGATCCGTGTCCTGTCTTTTA
AAACTGGCATCATTTCCCTGTGTAAAGCACATTTGGAAGACAAGTACAGATACCTTTTCAAGC
AAGTGGGAAGTTCAACAGGATTTTGTGACCAGCGCAGGCTGGGCCTCCTTCTGCATGATTCTA
TCCAAATTCCAAGACAGTTGGGTGAAGTTGCATCCTTTGGGGGCAGTAACATTGAGCCAAGTG
TCCGGAGCTGCTTCCAATTTGCTAATAATAAGCCAGAGATCGAAGCGGCCCTCTTCCTAGACT
GGATGAGACTGGAACCCCAGTCCATGGTGTGGCTGCCCGTCCTGCACAGAGTGGCTGCTGCAG
AAACTGCCAAGCATCAGGCCAAATGTAACATCTGCAAAGAGTGTCCAATCATTGGATTCAGGT
ACAGGAGTCTAAAGCACTTTAATTATGACATCTGCCAAAGCTGCTTTTTTTCTGGTCGAGTTGC
AAAAGGCCATAAAATGCACTATCCCATGGTGGAATATTGCACTCCGACTACATCAGGAGAAG
ATGTTCGAGACTTTGCCAAGGTACTAAAAAACAAATTTCGAACCAAAAGGTATTTTGCGAAGC
ATCCCCGAATGGGCTACCTGCCAGTGCAGACTGTCTTAGAGGGGGACAACATGGAAACGCCT
```

-continued

```
GCCTCGTCCCCTCAGCTTTCACAGGATGATACTCATTCACGCATTGAACATTATGCTAGCAGGC
TAGCAGAAATGGAAAACAGCAATGGATCTTTATCTAAATGATAGCATCTCTCCTAATGAGAGC
ATAGATGATGAACATTTGTTAATCCAGCATTACTGCCAAAGTTTGAACCAGGACTCCCCCCTG
AGCCAGCCTCGTAGTCCTGCCCAGATCTTGATTTCCTTAGAGAGTGAGGAAAGAGGGGAGCTA
GAGAGAATCCTAGCAGATCTTGAGGAAGAAAACAGGAATCTGCAAGCAGAATATGACCGTCT
AAAGCAGCAGCACGAACATAAAGGCCTGTCCCCACTGCCGTCCCCTCCTGAAATGATGCCCAC
CTCTCCCCAGAGTCCCCGGGATGCTGAGCTCATTGCTGAGGCCAAGCTACTGCGTCAACACAA
AGGCCGCCTGGAAGCCAGGATGCAAATCCTGGAAGACCACAATAAACAGCTGGAGTCACAGT
TACACAGGCTAAGGCAGCTGGTGGAGCAACCCCAGGCAGAGGCCAAAGTGAATGGCACAACG
GTGTCCTCTCCTTCTACCTCTCTACAGAGGTCCGACAGCAGTCAGCCTATGCTGCTCCGAGTGG
TTGGCAGTCAAACTTCGGACTCCATGGGTGAGGAAGATCTTCTCAGTCCTCCCCAGGACACAA
GCACAGGGTTAGAGGAGGTGATGGAGCAACTCAACAACTCCTTCCCTAGTTCAAGAGGAAGA
AATACCCCTGGAAAGCCAATGAGAGAGGACACAATGTAG
```

SEQ ID NO: 8: ΔH2-R15/ΔR18-19 (mini-dystrophin with 10 repeats and 3 hinges) (This minigene carries both R16 and R17. It can restore nNOS)

```
ATGCTTTGGTGGGAAGAAGTAGAGGACTGTTATGAAAGAGAAGATGTTCAAAAGAAAACATT
CACAAAATGGGTAAATGCACAATTTTCTAAGTTTGGGAAGCAGCATATTGAGAACCTCTTCAG
TGACCTACAGGATGGGAGGCGCCTCCTAGACCTCCTCGAAGGCCTGACAGGGCAAAAACTGC
CAAAAGAAAAAGGATCCACAAGAGTTCATGCCCTGAACAATGTCAACAAGGCACTGCGGGTT
TTGCAGAACAATAATGTTGATTTAGTGAATATTGGAAGTACTGACATCGTAGATGGAAATCAT
AAACTGACTCTTGGTTTGATTTGGAATATAATCCTCCACTGGCAGGTCAAAAATGTAATGAAA
AATATCATGGCTGGATTGCAACAAACCAACAGTGAAAAGATTCTCCTGAGCTGGGTCCGACA
ATCAACTCGTAATTATCCACAGGTTAATGTAATCAACTTCACCACCAGCTGGTCTGATGGCCT
GGCTTGAATGCTCTCATCCATAGTCATAGGCCAGACCTATTTGACTGGAATAGTGTGGTTTGC
CAGCAGTCAGCCACACAACGACTGGAACATGCATTCAACATCGCCAGATATCAATTAGGCAT
AGAGAAACTACTCGATCCTGAAGATGTTGATACCACCTATCCAGATAAGAAGTCCATCTTAAT
GTACATCACATCACTCTTCCAAGTTTTGCCTCAACAAGTGAGCATTGAAGCCATCCAGGAAGT
GGAAATGTTGCCAAGGCCACCTAAAGTGACTAAAGAAGAACATTTTCAGTTACATCATCAAAT
GCACTATTCTCAACAGATCACGGTCAGTCTAGCACAGGGATATGAGAGAACTTCTTCCCCTAA
GGCTCGATTCAAGAGCTATGCCTACACACAGGCTGCTTATGTCACCACCTCTGACCCTACACG
GAGCCCATTTCCTTCACAGCATTTGGAAGCTCCTGAAGACAAGTCATTTGGCAGTTCATTGAT
GGAGAGTGAAGTAAACCTGGACCGTTATCAAACAGCTTTAGAAGAAGTATTATCGTGGCTTCT
TTCTGCTGAGGACACATTGCAAGCACAAGGAGAGATTTCTAATGATGTGGAAGTGGTGAAAG
ACCAGTTTCATACTCATGAGGGGTACATGATGGATTTGACAGCCCATCAGGGCCGGGTTGGTA
ATATTCTACAATTGGGAAGTAAGCTGATTGGAACAGGAAAATTATCAGAAGATGAAGAAACT
GAAGTACAAGAGCAGATGAATCTCCTAAATTCAAGATGGAATGCCTCAGGGTAGCTAGCAT
GGAAAAACAAAGCAATTTACATAGAGTTTTAATGGATCTCCAGAATCAGAAACTGAAAGAGT
TGAATGACTGGCTAACAAAAACAGAAGAAGAACAAGGAAATGGAGGAAGAGCCTCTTGG
ACCTGATCTTGAAGACCTAAAACGCCAAGTACAACAACATAAGGTGCTTCAAGAAGATCTAG
AACAAGAACAAGTCAGGGTCAATTCTCTCACTCACATGGTGGTGGTAGTTGATGAATCTAGTG
GAGATCACGCAACTGCTGCTTTGGAAGAACAACTTAAGGTATTGGGAGATCGATGGGCAAAC
```

-continued

```
ATCTGTAGATGGACAGAAGACCGCTGGGTTCTTTTACAAGACATCCTTCTCAAATGGCAACGT
CTTACTGAAGAACAGTGCCTTTTTAGTGCATGGCTTTCAGAAAAAGAAGATGCAGTGAACAAG
ATTCACACAACTGGCTTTAAAGATCAAAATGAAATGTTATCAAGTCTTCAAAAACTGGCCGTT
TTAAAAGCGGATCTAGAAAAGAAAAAGCAATCCATGGGCAAACTGTATTCACTCAAACAAGA
TCTTCTTTCAACACTGAAGAATAAGTCAGTGACCCAGAAGACGGAAGCATGGCTGGATAACTT
TGCCCGGTGTTGGGATAATTTAGTCCAAAAACTTGAAAAGAGTACAGCACAGATTTCACAGG
AAATTTCTTATGTGCCTTCTACTTATTTGACTGAAATCACTCATGTCTCACAAGCCCTATTAGA
AGTGGAACAACTTCTCAATGCTCCTGACCTCTGTGCTAAGGACTTTGAAGATCTCTTTAAGCA
AGAGGAGTCTCTGAAGAATATAAAAGATAGTCTACAACAAAGCTCAGGTCGGATTGACATTA
TTCATAGCAAGAAGACAGCAGCATTGCAAAGTGCAACGCCTGTGGAAAGGGTGAAGCTACAG
GAAGCTCTCTCCCAGCTTGATTTCCAATGGGAAAAAGTTAACAAATGTACAAGGACCGACA
AGGGCGATTTGACAGATCTGTTGAGAAATGGCGGCGTTTTCATTATGATATAAAGATATTTAA
TCAGTGGCTAACAGAAGCTGAACAGTTTCTCAGAAAGACACAAATTCCTGAGAATTGGGAAC
ATGCTAAATACAAATGGTATCTTAAGGAACTCCAGGATGGCATTGGGCAGCGGCAAACTGTT
GTCAGAACATTGAATGCAACTGGGGAAGAAATAATTCAGCAATCCTCAAAAACAGATGCCAG
TATTCTACAGGAAAAATTGGGAAGCCTGAATCTGCGGTGGCAGGAGGTCTGCAAACAGCTGT
CAGACAGAAAAAGAGGCTAGAAGAACAGCCTGACCTAGCTCCTGGACTGACGACTATTGGA
GCCTCTCCTACTCAGACTGTTACTCTGGTGACACAACCTGTGGTTACTAAGGAAACTGCCATCT
CCAAACTAGAAATGCCATCTTCCTTGATGTTGGAGGTACCTGCTCTGGCAGATTTCAACCGGG
CTTGGACAGAACTTACCGACTGGCTTTCTGTGCTTGATCAAGTTATAAAATCACAGAGGGTGA
TGGTGGGTGACCTTGAGGATATCAACGAGATGATCATCAAGCAGAAGGCAACAATGCAGGAT
TTGGAACAGAGGCGTCCCCAGTTGGAAGAACTCATTACCGCTGCCCAAAATTTGAAAAACAA
GACCAGCAATCAAGAGGCTAGAACAATCATTACGGATCGAATTGAAAGAATTCAGAATCAGT
GGGATGAAGTACAAGAACACCTTCAGAACCGGAGGCAACAGTTGAATGAAATGTTAAAGGAT
TCAACACAATGGCTGGAAGCTAAGGAAGAAGCTGAGCAGGTCTTAGGACAGGCCAGAGCCAA
GCTTGAGTCATGGAAGGAGGGTCCCTATACAGTAGATGCAATCCAAAAGAAAATCACAGAAA
CCAAGGAGTTGGCCAAAGACCTCCGCCAGTGGCAGACAAATGTAGATGTGGCAAATGACTTG
GCCCTGAAACTTGTCCGGGATTATTCTGCAGATGATACCAGAAAAGTCCACATGATAACAGAG
AATATCAATGCCTCTTGGAGAAGCATTCATAAAAGGGTGAGTGAGCGAGAGGCTGCTTTGGA
AGAAACTCATAGATTACTGCAACAGTTCCCCCTGGACCTGGAAAAGTTTCTTGCCTGGCTTAC
AGAAGCTGAAACAACTGCCAATGTCCTACAGGATGCTACCCGTAAGGAAAGGCTCCTAGAAG
ACTCCAAGGGAGTAAAAGAGCTGATGAAACAATGGCAAGACCTCCAAGGTGAAATGAAGCT
CACACAGATGTTTATCACAACCTGGATGAAAACAGCCAAAAAATCCTGAGATCCCTGGAAGG
TTCCGATGATGCAGTCCTGTTACAAGACGTHTGGATAACATGAACTTCAAGTGGAGTGAACT
TCGGAAAAAGTCTCTCAACATTAGGTCCCATTTGGAAGCCAGTTCTGACCAGTGGAAGCGTCT
GCACCTTTCTCTGCAGGAACTTCTGGTGTGGCTACAGCTGAAAGATGATGAATTAAGCCGGCA
GGCACCTATTGGAGGCGACTTTCCAGCAGTTCAGAAGCAGAACGATGTACATAGGGCCTTCA
AGAGGGAATTGAAAACTAAAGAACCTGTAATCATGAGTACTCTTGAGACTGTACGAATATTTC
TGACAGAGCAGCCTTTGGAAGGACTAGAGAAACTCTACCAGGAGCCCAGAGAGCTGCCTCCT
GAGGAGAGAGCCCAGAATGTCACTCGGCTTCTACGAAAGCAGGCTGAGGAGGTCAATACTGA
```

-continued

```
GTGGGAAAAATTGAACCTGCACTCCGCTGACTGGCAGAGAAAAATAGATGAGACCCTTGAAA

GACTCCAGGAACTTCAAGAGGCCACGGATGAGCTGGACCTCAAGCTGCGCCAAGCTGAGGTG

ATCAAGGGATCCTGGCAGCCCGTGGGCGATCTCCTCATGACTCTCTCCAAGATCACCTCGAG

AAAGTCAAGGCACTTCGAGGAGAAATTGCGCCTCTGAAAGAGAACGTGAGCCACGTCAATGA

CCTTGCTCGCCAGCTTACCACTTTGGGCATTCAGCTCTCACCGTATAACCTCAGCACTCTGGAA

GACCTGAACACCAGATGGAAGCTTCTGCAGGTGGCCGTCGAGGACCGAGTCAGGCAGCTGCA

TGAAGCCCACAGGGACTTTGGTCCAGCATCTCAGCACTTTCTTTCCACGTCTGTCCAGGGTCCC

TGGGAGAGAGCCATCTCGCCAAACAAAGTGCCCTACTATATCAACCACGAGACTCAAACAAC

TTGCTGGGACCATCCCAAAATGACAGAGCTCTACCAGTCTTTAGCTGACCTGAATAATGTCAG

ATTCTCAGCTTATAGGACTGCCATGAAACTCCGAAGACTGCAGAAGGCCCTTTGCTTGGATCT

CTTGAGCCTGTCAGCTGCATGTGATGCCTTGGACCAGCACAACCTCAAGCAAATGACCAGCC

CATGGATATCCTGCAGATTATTAATTGTTTGACCACTATTTATGACCGCCTGGAGCAAGAGCA

CAACAATTTGGTCAACGTCCCTCTCTGCGTGGATATGTGTCTGAACTGGCTGCTGAATGTTTAT

GATACGGGACGAACAGGGAGGATCCGTGTCCTGTCTTTTAAAACTGGCATCATTTCCCTGTGT

AAAGCACATTTGGAAGACAAGTACAGATACCTTTTCAAGCAAGTGGCAAGTTCAACAGGATT

TTGTGACCAGCGCAGGCTGGGCCTCCTTCTGCATGATTCTATCCAAATTCCAAGACAGTTGGG

TGAAGTTGCATCCTTTGGGGGCAGTAACATTGAGCCAAGTGTCCGGAGCTGCTTCCAATTTGC

TAATAATAAGCCAGAGATCGAAGCGGCCCTCTTCCTAGACTGGATGAGACTGGAACCCCAGT

CCATGGTGTGGCTGCCCGTCCTGCACAGAGTGGCTGCTGCAGAAACTGCCAAGCATCAGGCCA

AATGTAACATCTGCAAAGAGTGTCCAATCATTGGATTCAGGTACAGGAGTCTAAAGCACTTTA

ATTATGACATCTGCCAAAGCTGCTTTTTTTCTGGTCGAGTTGCAAAAGGCCATAAAATGCACT

ATCCCATGGTGGAATATTGCACTCCGACTACATCAGGAGAAGATGTTCGAGACTTTGCCAAGG

TACTAAAAAACAAATTTCGAACCAAAAGGTATTTTGCGAAGCATCCCCGAATGGGCTACCTGC

CAGTGCAGACTGTCTTAGAGGGGACAACATGGAAACGCCTGCCTCGTCCCCTCAGCTTTCAC

ACGATGATACTCATTCACGCATTGAACATTATGCTAGCAGGCTAGCAGAAATGGAAAACAGC

AATGGATCTTATCTAAATGATAGCATCTCTCCTAATGAGAGCATAGATGATGAACATTTGTTA

ATCCAGCATTACTGCCAAAGTTTGAACCAGGACTCCCCCCTGAGCCAGCCTCGTAGTCCTGCC

CAGATCTTGATTTCCTTAGAGAGTGAGGAAAGAGGGGAGCTAGAGAGAATCCTAGCAGATCT

TGAGGAAGAAAACAGGAATCTGCAAGCAGAATATGACCGTCTAAAGCAGCAGCACGAACAT

AAAGGCCTGTCCCCACTGCCGTCCCCTCCTGAAATGATGCCCACCTCTCCCCAGAGTCCCCGG

GATGCTGAGCTCATTGCTGAGGCCAAGCTACTGCGTCAACACAAAGGCCGCGTGGAAGCCAG

GATGCAAATCCTGGAAGACCACAATAAACAGCTGGAGTCACAGTTACACAGGCTAAGGCAGC

TGCTGGAGCAACCCCAGGCAGAGGCCAAAGTGAATGGCACAACGGTGTCCTCTCCTTCTACCT

CTCTACAGAGGTCCGACAGCAGTCAGCCTATGCTGCTCCGAGTGGTTGGCAGTCAAACTTCGG

ACTCCATGGGTGAGGAAGATCTTCTCAGTCCTCCCCAGGACACAAGCACAGGGTTAGAGGAG

GTGATGGAGCAACTCAACAACTCCTTCCCTAGTTCAAGAGGAAGAAATACCCCTGGAAAGCC

AATGAGAGAGGACACAATGTAG
```

SEQ ID NO: 9: ΔH2-R15/Δ17-19 (mini-dystrophin with 9 repeats and 3 hinges) (This minigene carries R16 but not R17. It cannot restore nNOS)

ATGCTTTGGTGGGAAGAAGTAGAGGACTGTTATGAAAGAGAAGATGTTCAAAAGAAAACATT

CACAAAATGGGTAAATGCACAATTTTCTAAGTTTGGGAAGCAGCATATTGAGAACCTCTTCAG

TGACCTACAGGATGGGAGGCGCCTCCTAGACCTCCTCGAAGGCCTGACAGGGCAAAAACTGC

CAAAAGAAAAAGGATCCACAAGAGTTCATGCCCTGAAGAATGTCAACAAGGCACTGCGGGTT

TTGCAGAACAATAATGTTGATTTAGTGAATATTGGAAGTACTGAGATCGTAGATGGAAATCAT

AAACTGACTCTTGGTTTGATTTGGAATATAATCCTCCACTGGCAGGTCAAAAATGTAATGAAA

AATATCATGGCTGGATTGCAACAAACCAACAGTGAAAAGATTCTCCTGAGCTGGGTCCGACA

ATCAACTCGTAATTATCCACAGGTTAATGTAATCAACTTCACCACCAGCTGGTCTGATGGCCT

GGCTTTGAATGCTCTCATCCATAGTCATAGGCCAGACCTATTTGACTGGAATAGTGTGGTTTGC

CAGCAGTCAGCCACACAACGACTGGAACATGCATTCAACATCGCCAGATATCAATTAGGCAT

AGAGAAACTACTCGATCCTGAAGATGTTGATACCACCTATCCAGATAAGAAGTCCATCTTAAT

GTACATCACATCACTCTTCCAAGTTTTGCCTCAACAAGTGAGCATTGAAGCCATCCAGGAAGT

GGAAATGTTGCCAAGGCCACCTAAAGTGACTAAAGAAGAACATTTTCAGTTACATCATCAAAT

GCACTATTCTCAACAGATCACGGTCAGTCTAGCACAGGGATATGAGAGAACTTCTTCCCCTAA

GCCTCGATTCAAGAGCTATGCCTACACACAGGCTGCTTATGTCACCACCTCTGACCCTACACG

GAGCCCATTTCCTTCACAGCATTTGGAAGCTCCTGAAGACAAGTCATTTGGCAGTTCATTGAT

GGAGAGTGAAGTAAACCTGGACCGTTATCAAACAGCTTTAGAAGAAGTATTATCGTGGCTTCT

TTCTGCTGAGGACACATTGCAAGCACAAGGAGAGATTTCTAATGATGTGGAAGTGGTGAAAG

ACCAGTTTCATACTCATGAGGGGTACATGATGGATTTGACAGCCCATCAGGGCCGGGTTGGTA

ATATTCTACAATTGGGAAGTAAGCTGATTGGAACAGGAAAATTATCAGAAGATGAAGAAACT

GAAGTACAAGAGCAGATGAATCTCCTAAATTCAAGATGGGAATGCCTCAGGGTAGCTAGCAT

GGAAAAACAAAGCAATTTACATAGAGTTTTAATGGATCTCCAGAATCAGAAACTGAAAGAGT

TGAATGACTGGCTAACAAAAACAGAAGAAAGAACAAGGAAAATGGAGGAAGAGCCTCTTGG

ACCTGATCTTGAAGACCTAAAACGCCAAGTACAACAACATAAGGTGCTTCAAGAAGATCTAG

AACAAGAACAAGTCAGGGTCAATTCTCTCACTCACATGGTGGTGGTAGTTGATGAATCTAGTG

GAGATCACGCAACTGCTGCTTTGGAAGAACAACTTAAGGTATTGGGAGATCGATGGGCAAAC

ATCTGTAGATGGACAGAAGACCGCTGGGTTCTTTTACAAGACATCCTTCTCAAATGGCAACGT

CTTACTGAAGAACAGTGCCTTTTTAGTGCATGGCTTTCAGAAAAAGAAGATGCAGTGAACAAG

ATTCACACAACTGGCTTTAAAGATCAAAATGAAATGTTATCAAGTCTTCAAAAACTGGCCGTT

TTAAAAGCGGATCTAGAAAAGAAAAAGCAATCCATGGGCAAACTGTATTCACTCAAACAAGA

TCTTCTTTCAACACTGAAGAATAAGTCAGTGACCCAGAAGACGGAAGCATGGCTGGATAACTT

TGCCCGGTGTGGGATAATTTAGTCCAAAAACTTGAAAAGAGTACAGCACAGATTTCACAGG

AAATTCTTATGTGCCTTCTACTTATTTGACTGAAATCACTCATGTCTCACAAGCCCTATTAGA

AGTGGAACAACTTCTCAATGCTCCTGACCTCTGTGCTAAGGACTTTGAAGATCTCTTTAAGCA

AGAGGAGTCTCTGAAGAATATAAAAGATAGTCTACAACAAAGCTCAGGTCGGATTGACATTA

TTCATAGCAAGAAGACAGCAGCATTGCAAAGTGCAACGCCTGTGGAAAGGGTGAAGCTACAG

GAAGCTCTCTCCCAGCTTGATTTCCAATGGGAAAAAGTTAACAAAATGTACAAGGACCGACA

AGGGCGATTTGACAGACAGCCTGACCTAGCTCCTGGACTGACCACTATTGGAGCCTCTCCTAC

-continued

```
TCAGACTGTTACTCTGGTGACACAACCTGTGGTTACTAAGGAAACTGCCATCTCCAAACTAGA
AATGCCATCTTCCTTGATGTTGGAGGTACCTGCTCTGGCAGATTTCAACCGGGCTTGGACAGA
ACTTACCGACTGGCTTTCTCTGCTTGATCAAGTTATAAAATCACAGAGGGTGATGGTGGGTGA
CCTTGAGGATATCAACGAGATGATCATCAAGCAGAAGGCAACAATGCAGGATTTGGAACAGA
GGCGTCCCCAGTTGGAAGAACTCATTACCGCTGCCCAAAATTTGAAAAACAAGACCAGCAAT
CAAGAGGCTAGAACAATCATTACGGATCGAATTGAAAGAATTCAGAATCAGTGGGATGAAGT
ACAAGAACACCTTCAGAACCGGAGGCAACAGTTGAATGAAATGTTAAAGGATTCAACACAAT
GGCTGGAAGCTAAGGAAGAAGCTGAGCAGGTCTTAGGACAGGCCAGAGCCAAGCTTGAGTCA
TGGAAGGAGGGTCCCTATACAGTAGATGCAATCCAAAAGAAAATCACAGAAACCAAGCAGTT
GGCCAAAGACCTCCGCCAGTGGCAGACAAATGTAGATGTGGCAAATGACTTGGCCCTGAAAC
TTCTCCGGGATTATTCTGCAGATGATACCAGAAAAGTCCACATGATAACAGAGAATATCAATG
CCTCTTGGAGAAGCATTCATAAAAGGGTGAGTGAGCGAGAGGCTGCTTTGGAAGAAACTCAT
AGATTACTGCAACAGTTCCCCCTGGACCTGGAAAAGTTTCTTGCCTGGCTTACAGAAGCTGAA
ACAACTGCCAATGTCCTACAGGATGCTACCCGTAAGGAAAGGCTCCTAGAAGACTCCAAGGG
AGTAAAAGAGCTGATGAAACAATGGCAAGACCTCCAAGGTGAAATTGAAGCTCACACAGATG
TTTATCACAACCTGGATGAAAACAGCCAAAAAATCCTGAGATCCCTGGAAGGTTCCGATGATG
CAGTCCTGTTACAAAGACGTTTGGATAACATGAACTTCAAGTGGAGTGAACTTCGGAAAAAGT
CTCTCAACATTAGGTCCCATTTGGAAGCCAGTTCTGACCAGTGGAAGCGTCTGCACCTTTCTCT
GCAGGAACTTCTGGTGTGGCTACAGCTGAAAGATGATGAATTAAGCCGGCAGGCACCTATTG
GAGGCGACTTTCCAGCAGTTCAGAAGCAGAACGATGTACATAGGGCCTTCAAGAGGGAATTG
AAAACTAAAGAACCTGTAATCATGAGTACTCTGAGACTGTACGAATATTTCTGACAGAGCAG
CCTTTGGAAGGACTAGAGAAACTCTACCAGGAGCCCAGAGAGCTGCCTCCTGAGGAGAGAGC
CCAGAATGTCACTCGGCTTCTACGAAAGCAGGCTGAGGAGGTCAATACTGAGTGGGAAAAAT
TGAACCTGCACTCCGCTGACTGGCAGAGAAAAATAGATGAGACCCTTGAAAGACTCCAGGAA
CTTCAAGAGGCCACGGATGAGCTGGACCTCAAGCTGCGCCAAGCTGAGGTGATCAAGGGATC
CTGGCAGCCCGTGGGCGATCTCCTCATTGACTCTCTCCAAGATCACCTCGAGAAAGTCAAGGC
ACTTCGAGGAGAAATTGCGCCTCTGAAAGAGAACGTGAGCCACGTCAATGACCTTGCTCGCC
AGCTTACCACTTTGGGGATTCAGCTCTCACCGTATAACCTCAGCACTCTGGAAGACCTGAACA
CCAGATGGAAGCTTCTGCAGGTGGCCGTCGAGGACGGAGTCAGGCAGGTGCATGAAGCCCAC
AGGGACTTTGGTCCAGCATGTCAGCACTTTCTTTCCACGTCTGTCCAGGGTCCCTGGGAGAGA
GCCATCTCGCCAAACAAAGTGCCCTACTATATCAACCACGAGACTCAAACAACTTGCTGGGAC
CATCCCAAAATGACAGAGCTCTACCAGTCTTTAGCTGACCTGAATAATGTCAGATTCTCAGCT
TATAGGACTGCCATGAAACTCCGAAGACTGCAGAAGGCCCTTTGCTTGGATCTCTTGAGCCTG
TCAGCTGCATGTGATGCCTTGGACCAGCACAACCTCAAGCAAATGACCAGCCCATGGATATC
CTGCAGATTATTAATTGTTTGACCACTATTTATGACCGCCTGGAGCAAGAGCACAACAATTTG
GTCAACGTCCCTCTCTGCGTGGATATGTGTCTGAACTGGCTGCTGAATGTTTATGATACGGGA
CGAACAGGGAGGATCCGTGTCCTGTCTTTTAAAACTGGCATCATTTCCCTGTGTAAAGCACAT
TTGGAAGACAAGTACAGATACCTTTTCAAGCAAGTGGCAAGTTCAACAGGATTTTGTGACCAG
CGCAGGCTGGGCCTCCTTCTGCATGATTCTATCCAAATTCCAAGACAGTTGGGTGAAGTTGCA
TCCTTTGGGGGCAGTAACATTGAGCCAAGTGTCCGGAGCTGCTTCCAATTTGCTAATAATAAG
```

-continued

```
CCAGAGATCGAAGCGGCCCTCTTCCTAGACTGGATGAGACTGGAACCCCAGTCCATGGTGTGG

CTGCCCGTCCTGCACAGAGTGGCTGCTGCAGAAACTGCCAAGCATCAGGCCAAATGTAACATC

TGCAAAGAGTGTCCAATCATTGGATTCAGGTACAGGAGTCTAAAGCACTTTAATTATGACATC

TGCCAAAGCTGCTTTTTTTCTGGTCGAGTTGCAAAAGGCCATAAAATGCACTATCCCATGGTG

GAATATTGCACTCCGACTACATCAGGAGAAGATGTTCGAGACTTTGCCAAGGTACTAAAAAA

CAAATTTCGAAGCAAAAGGTATTTTGCGAAGCATCCCCGAATGGGCTACCTGCCAGTGCAGAC

TGTCTTAGAGGGGACAACATGGAAACGCCTGCCTCGTCCCCTCAGCTTTCACACGATGATAC

TCATTCACGCATTGAACATTATGCTAGCAGGCTAGCAGAAATGGAAAACAGCAATGGATCTTA

TCTAAATGATAGCATCTCTCCTAATGAGAGCATAGATGATGAACATTTGTTAATCCAGCATTA

CTGCCAAAGTTTGAACCAGGACTCCCCCCTGAGCCAGCCTCGTAGTCCTGCCCAGATCTTGAT

TTCCTTAGAGAGTGAGGAAGAGGGGAGCTAGAGAGAATCCTAGCAGATCTTGAGGAAGAAA

ACAGGAATCTGCAAGCAGAATATGACCGTCTAAAGCAGCAGCACGAACATAAAGGCCTGTCC

CCACTGCCGTCCCCTCCTGAAATGATGCCCACCTCTCCCCAGAGTCCCCGGGATGCTGAGCTC

ATTGCTGAGGCCAAGCTACTGCGTCAACACAAAGGCCGCCTGGAAGCCAGGATGCAAATCCT

GGAAGACCACAATAAACAGCTGGAGTCACAGTTACACAGGCTAAGGCAGCTGCTGGAGCAAC

CCCAGGCAGAGGCCAAAGTGAATGGCACAACGGTGTCCTCTCCTTCTACCTCTCTACAGAGGT

CCGACAGCAGTCAGCCTATGCTGCTCCGAGTGGTTGGCAGTCAAACTTCGGACTCCATGGGTG

AGGAAGATCTTCTCAGTCCTCCCCAGGACACAAGCACAGGGTTAGAGGAGGTGATGGAGCAA

CTCAACAACTCCTTCCCTAGTTGAAGAGGAAGAAATACCCCTGGAAAGCCAATGAGAGAGGA

CACAATGTAG

SEQ ID NO: 10: ΔH2-R15/ΔC (mini-dystrophin with 12 repeats and
3 hinges, no C-terminal domain) (This minigene carries both R16
and R17. It can restore nNOS)
ATGCTTTGGTGGGAAGAAGTAGAGGACTGTTATGAAAGAGAAGATGTTCAAAAGAAAACATT

CACAAAATGGGTAAATGCACAATTTTCTAAGTTTGGGAAGCAGCATATTGAGAACCTCTTCAG

TGACCTACAGGATGGGAGGCGCCTCCTAGACCTCCTCGAAGGCCTGACAGGGCAAAAACTGC

CAAAAGAAAAAGGATCCACAAGAGTTCATGCCCTGAACAATGTCAACAAGGCACTGCGGGTT

TTGCAGAACAATAATGTTGATTTAGTGAATATTGGAAGTACTGACATCGTAGATGGAAATCAT

AAACTGACTCTTGGTTTGATTTGGAATATAATCCTCCACTGGCAGGTCAAAAATGTAATGAAA

AATATGATGGCTGGATTGCAACAAACCAACAGTGAAAAGATTCTCCTGAGCTGGGTCCGACA

ATCAACTCGTAATTATCCACAGGTTAATGTAATCAACTTCACCACCAGCTGGTCTGATGGCCT

GGCTTTGAATGCTCTCATCCATAGTCATAGGCCAGACCTATTTGACTGGAATAGTGTGGTTTGC

CAGCAGTCAGCCACACAACGACTGGAACATGCATTCAACATCGCCAGATATCAATTAGGCAT

AGAGAAACTACTCGATCCTGAAGATGTTGATACCACCTATCCAGATAAGAAGTCCATCTTAAT

GTACATCACATCACTCTTCCAAGTTTTGCCTCAACAAGTGAGCATTGAAGCCATCCAGGAAGT

GGAAATGTTGCCAAGGCCACCTAAAGTGACTAAAGAAGAACATTTTCAGTTACATCATCAAAT

GCACTATTCTCAACAGATCACGGTCAGTCTAGCACAGGGATATGAGAGAACTTCTTCCCCTAA

GCCTCGATTCAAGAGCTATGCCTACACACAGGCTGCTTATGTCACCACCTCTGACCCTACACG

GAGCCCATTTCCTTCACAGCATTTGGAAGCTCCTGAAGACAAGTCATTTGGCAGTTCATTGAT

GGAGAGTGAAGTAAACCTGGACCGTTATCAAACAGCTTTAGAAGAAGTATTATCGTGGCTTCT

TTCTGCTGAGGACACATTGCAAGCACAAGGAGAGATTTCTAATGATGTGGAAGTGGTGAAAG

ACCAGTTTCATACTCATGAGGGGTACATGATGGATTTGACAGCCCATCAGGGCCGGGTTGGTA
```

-continued

```
ATATTCTACAATTGGGAAGTAAGCTGATTGGAACAGGAAAATTTATCAGAAGATGAAGAAACT
GAAGTACAAGAGCAGATGAATCTCCTAAATTCAAGATGGGAATGCCTCAGGGTAGCTAGCAT
GGAAAAACAAAGCAATTTACATAGAGTTTTAATGGATCTCCAGAATCAGAAACTGAAAGAGT
TGAATGACTGGCTAACAAAAACAGAAGAAAGAACAAGGAAAATGGAGGAAGAGCCTCTTGG
ACCTGATCTTGAAGACCTAAAACGCCAAGTACAACAACATAAGGTGCTTCAAGAAGATCTAG
AACAAGAACAAGTCAGGGTCAATTCTCTCACTCACATGGTGGTGGTAGTTGATGAATCTAGTG
GAGATCACGCAACTGCTGCTTTGGAAGAACAACTTAAGGTATTGGGAGATCGATGGGCAAAC
ATCTGTAGATGGACAGAAGACCGCTGGGTTCTTTTACAAGACATCCTTCTCAAATGGCAACGT
CTTACTGAAGAACAGTGCCTTTTTAGTGCATGGCTTTCAGAAAAAGAAGATGCAGTGAACAAG
ATTCACACAACTGGCTTTAAAGATCAAATGAAATGTTATCAAGTCTTCAAAAACTGGCCGTT
TTAAAAGCGGATCTAGAAAAGAAAAAGCAATCCATGGGCAAACTGTATTCACTCAAACAAGA
TCTTCTTTCAACACTGAAGAATAAGTCAGTGACCCAGAAGACGGAAGCATGGCTGGATAACTT
TGCCCGGTGTTGGGATAATTTAGTCCAAAAACTTGAAAAGAGTACAGCACAGATTTCACAGG
AAATTTCTTATGTGCCTTCTACTTATTTGACTGAAATCACTCATGTCTCACAAGCCCTATTAGA
AGTGGAACAACTTCTCAATGCTCCTGACCTCTGTGCTAAGGACTTTGAAGATCTCTTTAAGCA
AGAGGAGTCTCTGAAGAATATAAAAGATAGTCTACAACAAAGCTCAGGTCGGATTGACATTA
TTCATAGCAAGAAGACAGCAGCATTGCAAAGTGCAACGCCTGTGGAAAGGGTGAAGCTACAG
GAAGCTCTCTCCCAGCTTGATTTCCAATGGGAAAAAGTTAACAAAATGTACAAGGACGGACA
AGGGCGATTTGACAGATCTGTTGAGAAATGGCGGCGTTTTCATTATGATATAAAGATATTTAA
TCAGTGGCTAACAGAAGCTGAACAGTTTCTCAGAAAGACACAAATTCCTGAGAATTGGGAAC
ATGCTAAATACAAATGGTATCTTAAGGAACTCCAGGATGGCATTGGGCAGCGGCAAACTGTT
GTCAGAACATTGAATGCAACTGGGGAAGAAATAATTCAGCAATCCTCAAAAACAGATGCCAG
TATTCTACAGGAAAAATTGGGAAGCCTGAATCTGCGGTGGCAGGAGGTCTGCAAACAGCTGT
CAGACAGAAAAAGAGGCTAGAAGAACAAAAGAATATCTTGTCAGAATTTCAAAGAGATTTA
AATGAATTTGTTTTATGGTTGGAGGAAGCAGATAACATTGCTAGTATCCCACTTGAACCTGGA
AAAGAGCAGCAACTAAAAGAAAAGCTTGAGCAAGTCAAGTTACTGGTGGAAGAGTTGCCCCT
GCGCCAGGGAATTCTCAAACAATTAAATGAAACTGGAGGACCCGTGCTTGTAAGTGCTCCCAT
AAGCCCAGAAGAGCAAGATAAACTTGAAAATAAGCTCAAGCAGACAAATCTCCAGTGGATAA
AGGTTTCCAGAGCTTTACCTGAGAAACAAGGAGAAATTGAAGCTCAAATAAAAGACCTTGGG
CAGCTTGAAAAAAAGCTTGAAGACCTTGAAGAGCAGTTAAATCATCTGCTGCTGTGGTTATCT
CCTATTAGGAATCAGTTGGAAATTTATAACCAACCAAACCAAGAAGGACCATTTGACGTTCAG
GAAACTGAAATAGCAGTTCAAGCTAAACAACCGGATGTGGAAGAGATTTTGTCTAAAGGGCA
GCATTTGTACAAGGAAAAACCAGCCACTCAGCCAGTGAAGAGGAAGTTAGAAGATCTGAGCT
CTGAGTGGAAGGCGGTAAACCGTTTACTTCAAGAGCTGAGGGCAAAGCAGCCTGACCTAGCT
CCTGGACTGACCACTATTGGAGCCTCTCCTACTCAGACTGTTACTCTGGTGACACAACCTGTG
GTTACTAAGGAAACTGCCATCTCCAAACTAGAAATGCCATCTTCCTTGATGTTGGAGGTACCT
GCTCTGGCAGATTTCAACCGGGCTTGGACAGAACTTACCGACTGGCTTTCTCTGCTTGATCAA
GTTATAAAATCACAGAGGGTGATGGTGGGTGACCTTGAGGATATCAACGAGATGATCATCAA
GCAGAAGGCAACAATGCAGGATTTGGAACAGAGGCGTCCCCAGTTGGAAGAACTCATTACCG
CTGCCCAAAATTTGAAAAACAAGACCAGCAATCAAGAGGCTAGAACAATCATTACGGATCGA
```

-continued

```
ATTGAAAGAATTCAGAATCAGTGGGATGAAGTACAAGAACACCTTCAGAACCGGAGGCAACA

GTTGAATGAAATGTTAAAGGATTCAACACAATGGCTGGAAGCTAAGGAAGAAGCTGAGCAGG

TCTTAGGACAGGCCAGAGCCAAGCTTGAGTCATGGAAGGAGGGTCCCTATACAGTAGATGCA

ATCCAAAAGAAAATCACAGAAACCAAGCAGTTGGCCAAAGACCTCCGCCAGTGGCAGACAAA

TGTAGATGTGGCAAATGACTTGGCCCTGAAACTTCTCCGGGATTATTCTGCAGATGATACCAG

AAAAGTCCACATGATAACAGAGAATATCAATGCCTCTTGGAGAAGCATTCATAAAAGGGTGA

GTGAGCGAGAGGCTGCTTTGGAAGAAACTCATAGATTACTGCAACAGTTCCCCCTGGACCTGG

AAAAGTTTCTTGCCTGGCTTACAGAAGCTGAAACAACTGCCAATGTCCTACAGGATGCTACCC

GTAAGGAAAGGCTCCTAGAAGACTCCAAGGGAGTAAAAGAGCTGATGAAACAATGGCAAGA

CCTCCAAGGTGAAATTGAAGCTCACACAGATGTTTATCACAACCTGGATGAAAACAGCCAAA

AAATCCTGAGATCCCTGGAAGGTTCCGATGATGCAGTCCTGTTACAAAGACGTTTGGATAACA

TGAACTTCAAGTGGAGTGAACTTCGGAAAAAGTCTCTCAACATTAGGTCCCATTTGGAAGCCA

GTTCTGACCAGTGGAAGCGTCTGCACCTTTCTCTGCAGGAACTTCTGGTGTGGCTACAGCTGA

AAGATGATGAATTAAGCCGGCAGGCACCTATTGGAGGCGACTTTCCAGCAGTTCAGAAGCAG

AACGATGTACATAGGGCCTTCAAGAGGGAATTGAAAACTAAAGAACCTGTAATCATGAGTAC

TCTGAGACTGTACGAATATTTCTGACAGAGCAGCCTTTGGAAGGACTAGAGAAACTCTACCA

GGAGCCCAGAGAGCTGCCTCCTGAGGAGAGAGCCCAGAATGTCACTCGGCTTCTACGAAAGC

AGGCTGAGGAGGTCAATACTGAGTGGGAAAAATTGAACCTGCACTCCGCTGACTGGCAGAGA

AAAATAGATGAGACCCTTGAAAGACTCCAGGAACTTCAAGAGGCCACGGATGAGCTGGACCT

CAAGCTGCGCCAAGCTGAGGTGATCAAGGGATCCTGGCAGCCCGTGGGCGATCTCCTCATTGA

CTCTCTCCAAGATCACCTCGAGAAAGTCAAGGCACTTCGAGGAGAAATTGCGCCTCTGAAAG

AGAACGTGAGCCACGTCAATGACCTTGCTCGCCAGCTTACCACTTTGGGCATTCAGCTCTCAC

CGTATAACCTCAGCACTCTGGAAGACCTGAACACCAGATGGAAGCTTCTGCAGGTGGCCGTCG

AGGACCGAGTCAGGCAGCTGCATGAAGCCCACAGGGACTTTGGTCCAGCATCTCAGCACTTTC

TTTCCACGTCTGTCCAGGGTCCCTGGGAGAGAGCCATCTCGCCAAACAAAGTGCCCTACTATA

TCAACCACGAGACTCAAACAACTTGCTGGGACCATCCCAAAATGACAGAGCTCTACCAGTCTT

TAGCTGACCTGAATAATGTCAGATTCTCAGCTTATAGGACTGCCATGAAACTCCGAAGACTGC

AGAAGGCCCTTTGCTTGGATCTCTTGAGCCTGTCAGCTGCATGTGATGCCTTGGACCAGCACA

ACCTCAAGCAAAATGACCAGCCCATGGATATCCTGCAGATTATTAATTGTTTGACCACTATTT

ATGACCGCCTGGAGCAAGAGCACAACAATTTGGTCAACGTCCCTCTCTGCGTGGATATGTGTC

TGAACTGGCTGCTGAATGTTTATGATACGGGACGAACAGGGAGGATCCGTGTCCTGTCTTTTA

AAACTGGCATCATTTCCCTGTGTAAAGCACATTTGGAAGACAAGTACAGATACCTTTTCAAGC

AAGTGGCAAGTTCAACAGGATTTTGTGACCAGCGCAGGCTGGGCCTCCTTCTGCATGATTCTA

TCCAAATTCCAAGACAGTTGGGTGAAGTTGCATCCTTTGGGGGCAGTAACATTGAGCCAAGTG

TCCGGAGCTGCTTCCAATTTGCTAATAATAAGCCAGAGATCGAAGCGGCCCTCTTCCTAGACT

GGATGAGACTGGAACCCCAGTCCATGGTGTGGCTGCCCGTCCTGCACAGAGTGGCTGCTGCAG

AAACTGCCAAGCATCAGGCCAAATGTAACATCTGCAAAGAGTGTCCAATCATTGGATTCAGGT

ACAGGAGTCTAAAGCACTTTAATTATGACATCTGCCAAAGCTGCTTTTTTTCTGGTCGAGTTGC

AAAAGGCCATAAAATGCACTATCCCATGGTGGAATATTGCACTCCGACTACATCAGGAGAAG

ATGTTCGAGACTTTGCCAAGGTACTAAAAAACAAATTTCGAACCAAAAGGTATTTTGCGAAGC
```

-continued

ATCCCCGAATGGGCTACCTGCCAGTGCAGACTGTCTTAGAGGGGGACAACATGGAAACTGAC

ACAATGTAG

SEQ ID NO: 11: ΔR2-R15/ΔH3-R23/ΔC (micro-dystrophin with 6
repeats and 2 hinges, no C-terminal domain) (This microgene
carries both R16 and R17. It can restore nNOS)
ATGCTTTGGTGGGAAGAAGTAGAGGACTGTTATGAAAGAAGATGTTCAAAAGAAAACATT

CACAAAATGGGTAAATGCACAATTTTCTAAGTTTGGGAAGCAGCATATTGAGAACCTCTTCAG

TGACCTACAGGATGGGAGGCGCCTCCTAGACCTCCTCGAAGGCCTGACAGGGCAAAAACTGC

CAAAAGAAAAAGGATCCACAAGAGTTCATGCCCTGAACAATGTCAACAAGGCACTGCGGGTT

TTGCAGAACAATAATGTTGATTTAGTGAATATTGGAAGTACTGACATCGTAGATGGAAATCAT

AAACTGACTCTTGGTTTGATTTGGAATATAATCCTCCACTGGCAGGTCAAAAATGTAATGAAA

AATATCATGGCTGGATTGCAACAAACCAACAGTGAAAAGATTCTCCTGAGCTGGGTCCGACA

ATCAACTCGTAATTATCCAGAGGTTAATGTAATCAACTTCACCACCAGCTGGTCTGATGGCCT

GGCTTTGAATGCTCTCATCCATAGTCATAGGCCAGACCTATTTGACTGGAATAGTGTGGTTTGC

CAGCAGTCAGCCACACAACGACTGGAACATGCATTCAACATCGCCAGATATCAATTAGGCAT

AGAGAAACTACTCGATCCTGAAGATGTTGATACCACCTATCCAGATAAGAAGTCCATCTTAAT

GTACATCACATCACTCTTCCAAGTTTTGCCTCAACAAGTGAGCATTGAAGCCATCCAGGAAGT

GGAAATGTTGCCAAGGCCACCTAAAGTGACTAAAGAAGAACATTTTCAGTTACATCATCAAAT

GCACTATTCTCAACAGATCACGGTCAGTCTAGCACAGGGATATGAGAGAACTTCTTCCCCTAA

GCCTCGATTCAAGAGCTATGCCTACACACAGGCTGCTTATGTCACCACCTCTGACCCTACACG

GAGCCCATTTCCTTCACAGCATTTGGAAGCTCCTGAAGACAAGTCATTTGGCAGTTCATTGAT

GGAGAGTGAAGTAAACCTGGACCGTTATCAAACAGCTTTAGAAGAAGTATTATCGTGGCTTCT

TTCTGCTGAGGACACATTGCAAGCACAAGGAGAGATTTCTAATGATGTGGAAGTGGTGAAAG

ACCAGTTTCATACTCATGAGGGGTACATGATGGATTTGACAGCCCATCAGGGCCGGGTTGGTA

ATATTCTACAATTGGGAAGTAAGCTGATTGGAACAGGAAAATTATCAGAAGATGAAGAAACT

GAAGTACAAGAGCAGATGAATCTCCTAAATTCAAGATGGGAATGCCTCAGGGTAGCTAGCAT

GGAAAAACAAAGCAATTTACATAGAGAAATTTCTTATGTGCCTTCTACTTATTTGACTGAAAT

CACTCATGTCTCACAAGCCCTATTAGAAGTGGAACAACTTCTCAATGCTCCTGACCTCTGTGCT

AAGGACTTTGAAGATCTCTTTAAGCAAGAGGAGTCTCTGAAGAATATAAAAGATAGTCTACA

ACAAAGCTCAGGTCGGATTGACATTATTCATAGCAAGAAGACAGCAGCATTGCAAAGTGCAA

CGCCTGTGGAAAGGGTGAAGCTACAGGAAGCTCTCTCCCAGCTTGATTTCGAATGGGAAAAA

GTTAACAAAATGTACAAGGACCGACAAGGGCGATTTGACAGATCTGTTGAGAAATGGCGGCG

TTTTCATTATGATATAAAGATATTTAATCAGTGGCTAACAGAAGCTGAACAGTTTCTCAGAAA

GACACAAATTCCTGAGAATTGGGAACATGCTAAATACAAATGGTATCTTAAGGAACTCCAGG

ATGGCATTGGGCAGCGGCAAACTGTTGTCAGAACATTGAATGCAACTGGGGAAGAAATAATT

CAGCAATCCTCAAAAACAGATGCCAGTATTCTACAGGAAAAATTGGGAAGCCTGAATCTGCG

GTGGCAGGAGGTCTGCAAACAGCTGTCAGACAGAAAAAGAGGCTAGAAGAACAAAAGAAT

ATCTTGTCAGAATTTCAAAGAGATTTAAATGAATTTGTTTTATGGTTGGAGGAAGCAGATAAC

ATTGCTAGTATCCCACTTGAACCTGGAAAAGAGCAGCAACTAAAAGAAAAGCTTGAGCAAGT

CAAGTTACTGGTGGAAGAGTTGCCCCTGCGCCAGGGAATTCTCAAACAATTAAATGAAACTG

GAGGACCCGTGCTTGTAAGTGCTCCCATAAGCCCAGAAGAGCAAGATAAACTTGAAAATAAG

-continued

CTCAAGCAGACAAATCTCCAGTGGATAAAGGTTTCCAGAGCTTTACGTGAGAAAGAAGGAGA

AATTGAAGCTCAAATAAAAGACCTTGGGCAGCTTGAAAAAAAGCTTGAAGACCTTGAAGAGC

AGTTAAATCATCTGCTGCTGTGGTTATCTCCTATTAGGAATCAGTTGGAAATTTATAACCAACC

AAACCAAGAAGGACCATTTGACGTTCAGGAAACTGAAATAGCAGTCAAGCTAAACAACCGG

ATGTGGAAGAGATTTTGTCTAAAGGGCAGCATTTGTACAAGGAAAAACCAGCCACTCAGCCA

GTGAAGAGGAAGTTAGAAGATCTGAGCTCTGAGTGGAAGGCGGTAAACCGTTTACTTCAAGA

GCTGAGGGCAAAGACCCTTGAAAGACTCCAGGAACTTCAAGAGGCCACGGATGAGCTGGACC

TCAAGCTGCGCCAAGCTGAGGTGATCAAGGGATCCTGGCAGCCCGTGGGCGATCTCCTCATTG

ACTCTCTCCAAGATCACCTCGAGAAAGTCAAGGCACTTCGAGGAGAAATTGCGCCTCTGAAA

GAGAACGTGAGCCACGTCAATGACCTTGCTCGCCAGCTACCACTTTGGGCATTCAGCTCTCA

CCGTATAACCTCAGCACTCTGGAAGACCTGAACACCAGATGGAAGCTTCTGCAGGTGGCCGTC

GAGGACCGAGTCAGGCAGCTGCATGAAGCCCACAGGGACTTTGGTCCAGCATCTCAGCACTTT

CTTTCCACGTCTGTCCAGGGTCCCTGGGAGAGAGCCATCTCGCCAAACAAAGTGCCCTACTAT

ATCAACCACGAGACTCAAACAACTTGCTGGGACCATCCCAAAATGACAGAGCTCTACCAGTCT

TTAGCTGACCTGAATAATGTCAGATTCTCAGCTTATAGGACTGCCATGAAACTCCGAAGACTG

CAGAAGGCCCTTTGCTTGGATCTCTTGAGCCTGTCAGCTGCATGTGATGCCTTGGACCAGCAC

AACCTCAAGCAAATGACCAGCCCATGGATATCCTGCAGATTATTAATTGTTTGAGCACTATT

TATGACCGCCTGGAGCAAGAGCACAACAATTTGGTCAACGTCCCTCTCTGCGTGGATATGTGT

CTGAACTGGCTGCTGAATGTTTATGATACGGGACGAACAGGGAGGATCCGTGTCCTGTCTTTT

AAAACTGGCATCATTTCCCTGTGTAAAGCACATTTGGAAGACAAGTACAGATACCTTTTCAAG

CAAGTGGCAAGTTCAACAGGATTTTGTGACCAGCGCAGGCTGGGCCTCCTTCTGCATGATTCT

ATCCAAATTCCAAGACAGTTGGGTGAAGTTGCATCCTTTGGGGGCAGTAACATTGAGCCAAGT

GTCCGGAGCTGCTTCCAATTTGCTAATAATAAGCCAGAGATCGAAGCGGCCCTCTTCCTAGAC

TGGATGAGACTGGAACCCCAGTCCATGGTGTGGCTGCCCGTCCTGCACAGAGTGGCTGCTGCA

GAAACTGCCAAGCATCAGGCCAAATGTAACATCTGCAAAGAGTGTCCAATCATTGGATTCAG

GTACAGGAGTCTAAAGCACTTTAATTATGACATCTGCCAAAGCTGCTTTTTTTCTGGTCGAGTT

GCAAAAGGCCATAAAATGCACTATCCCATGGTGGAATATTGCACTCCGACTACATCAGGAGA

AGATGTTCGAGACTTTGCCAAGGTACTAAAAAACAAATTTCGAACCAAAAGGTATTTTGCGAA

GCATCCCCGAATGGGCTACCTGCCAGTGCAGACTGTCTTAGAGGGGGACAACATGGAAACTG

ACACAATGTAG

SEQ ID NO: 12: ΔR3-R15/ΔR18-23/ΔC (micro-dystrophin with 5
repeats and 2 hinges, no C-terminal domain) (This microgene
carries both R16 and R17. It can restore nNOS)
ATGCTTTGGTGGGAAGAAGTAGAGGACTGTTATGAAAGAAGATGTTCAAAAGAAAACATT

CACAAAATGGGTAAATGCACAATTTTCTAAGTTTGGGAAGCAGCATATTGAGAACCTCTTCAG

TGACCTACAGGATGGGAGGCGCCTCCTAGACCTCCTCGAAGGCCTGACAGGGCAAAAACTGC

CAAAAGAAAAGGATCCACAAGAGTTCATGCCCTGAACAATGTCAACAAGGCACTGCGGGTT

TTGCAGAACAATAATGTTGATTTAGTGAATATTGGAAGTACTGACATCGTAGATGGAAATCAT

AAACTGACTCTTGGTTTGATTTGGAATATAATCCTCCACTGGCAGGTCAAAAATGTAATGAAA

AATATCATGGCTGGATTGCAACAAACCAACAGTGAAAAGATTCTCCTGAGCTGGGTCCGACA

ATCAACTCGTAATTATCCACAGGTAATGTAATCAACTTCACCACCAGCTGGTCTGATGGCCT

GGCTTTGAATGCTCTCATCCATAGTCATAGGCCAGACCTATTTGACTGGAATAGTGTGGTTTGC

-continued

```
CAGCAGTCAGCCACACAACGACTGGAACATGCATTCAACATCGCCAGATATCAATTAGGCAT

AGAGAAACTACTCGATCCTGAAGATGTTGATACCACCTATCCAGATAAGAAGTCCATCTTAAT

GTACATCACATCACTCTTCCAAGTTTTGCCTCAACAAGTGAGCATTGAAGCCATCCAGGAAGT

GGAAATGTTGCCAAGGCCACCTAAAGTGACTAAAGAAGAACATTTTCAGTTACATCATCAAAT

GCACTATTCTCAACAGATCACGGTCAGTCTAGCACAGGGATATGAGAGAACTTCTTCCCCTAA

GCCTCGATTCAAGAGCTATGCCTACACACAGGCTGCTTATGTCACCACCTCTGACCCTACACG

GAGCCCATTTCCTTCACAGCATTTGGAAGCTCCTGAAGACAAGTCATTTGGCAGTTCATTGAT

GGAGAGTGAAGTAAACCTGGACCGTTATCAAACAGCTTTAGAAGAAGTATTATCGTGGCTTCT

TTCTGCTGAGGACACATTGCAAGCACAAGGAGAGATTTCTAATGATGTGGAAGTGGTGAAAG

ACCAGTTTCATACTCATGAGGGGTACATGATGGATTTGACAGCCCATCAGGGCCGGGTTGGTA

ATATTCTACAATTGGGAAGTAAGCTGATTGGAACAGGAAAATTATCAGAAGATGAAGAAACT

GAAGTACAAGAGCAGATGAATCTCCTAAATTCAAGATGGGAATGCCTCAGGGTAGCTAGCAT

GGAAAAACAAAGCAATTTACATAGAGTTTTAATGGATCTCCAGAATCAGAAACTGAAAGAGT

TGAATGACTGGCTAACAAAAACAGAAGAAAGAACAAGGAAAATGGAGGAAGAGCCTCTTGG

ACCTGATCTTGAAGACCTAAAACGCCAAGTACAACAACATAAGGTGCTTCAAGAAGATCTAG

AACAAGAACAAGTCAGGGTCAATTCTCTCACTCACATGGTGGTGGTAGTTGATGAATCTAGTG

GAGATCACGCAACTGCTGCTTTGGAAGAACAACTTAAGGTATTGGGAGATCGATGGGCAAAC

ATCTGTAGATGGACAGAAGACCGCTGGGTTCTTTTACAAGACGAAATTTCTTATGTGCCTTCT

ACTTATTTGACTGAAATCACTCATGTCTCACAAGCCCTATTAGAAGTGGAACAACTTCTCAAT

GCTCCTGACCTCTGTGCTAAGGACTTTGAAGATCTCTTTAAGCAAGAGGAGTCTCTGAAGAAT

ATAAAAGATAGTCTACAACAAAGCTCAGGTCGGATTGACATTATTCATAGCAAGAAGACAGC

AGCATTGCAAAGTGCAACGCCTGTGGAAAGGGTGAAGCTACAGGAAGCTCTCTCCCAGCTTG

ATTTCCAATGGGAAAAAGTTAACAAAATGTACAAGGACCGACAAGGGCGATTTGACAGATCT

GTTGAGAAATGGCGGCGTTTTCATTATGATATAAAGATATTTAATCAGTGGCTAACAGAAGCT

GAACAGTTTCTCAGAAAGACACAAATTCCTGAGAATTGGGAACATGCTAAATACAAATGGTA

TCTTAAGGAACTCCAGGATGGCATTGGGCAGCGGCAAACTGTTGTCAGAACATTGAATGCAA

CTGGGGAAGAAATAATTCAGCAATCCTCAAAAACAGATGCCAGTATTCTACAGGAAAAATTG

GGAAGCCTGAATCTGCGGTGGCAGGAGGTCTGCAAACAGCTGTCAGACAGAAAAAAGAGGCT

AGAAGAAACCCTTGAAAGACTCCAGGAACTTCAAGAGGCCACGGATGAGCTGGACCTCAAGC

TGCGCCAAGCTGAGGTGATCAAGGGATCCTGGCAGCCCGTGGGCGATCTCCTCATTGACTCTC

TCCAAGATCACCTCGAGAAAGTCAAGGCACTTCGAGGAGAAATTGCGCCTCTGAAAGAGAAC

GTGAGCCACGTCAATGACCTTGCTCGCCAGCTTACCACTTTGGGCATTCAGCTCTCACCGTATA

ACCTCAGCACTCTGGAAGACCTGAACACCAGATGGAAGCTTCTGCAGGTGGCCGTCGAGGAC

CGAGTCAGGCAGCTGCATGAAGCCCACAGGGACTTTGGTCCAGCATCTCAGCACTTTCTTTCC

ACGTCTGTCCAGGGTCCCTGGGAGAGAGCCATCTCGCCAAACAAAGTGCCCTACTATATCAAC

CACGAGACTCAAACAACTTGCTGGGACCATCCCAAAATGACAGAGCTCTACCAGTCTTTAGCT

GACCTGAATAATGTCAGATTCTCAGCTTATAGGACTGCCATGAAACTCCGAAGACTGCAGAAG

GCCCTTTGCTTGGATCTCTTGAGCCTGTCAGCTGCATGTGATGCCTTGGACCAGCACAACCTCA

AGCAAAATGACCAGCCCATGGATATCCTGCAGATTATTAATTGTTTGACCACTATTTATGACC

GCCTGGAGCAAGAGCACAACAATTTGGTCAACGTCCCTCTCTGCGTGGATATGTGTCTGAACT
```

-continued

```
GGCTGCTGAATGTTTATGATACGGGACGAACAGGGAGGATCCGTGTCCTGTCTTTTAAAACTG

GCATCATTTCCCTGTGTAAAGCACATTTGGAAGACAAGTACAGATACCTTTTCAAGCAAGTGG

CAAGTTCAACAGGATTTTGTGACCAGCGCAGGCTGGGCCTCCTTCTGCATGATTCTATCCAAA

TTCCAAGACAGTTGGGTGAAGTTGCATCCTTTGGGGGCAGTAACATTGAGCCAAGTGTCCGGA

GCTGCTTCCAATTTGCTAATAATAAGCCAGAGATCGAAGCGGCCCTCTTCCTAGACTGGATGA

GACTGGAACCCCAGTCCATGGTGTGGCTGCCCGTCCTGCACAGAGTGGCTGCTGCAGAAACTG

CCAAGCATCAGGCCAAATGTAACATCTGCAAAGAGTGTCCAATCATTGGATTCAGGTACAGG

AGTCTAAAGCACTTTAATTATGACATCTGCCAAAGCTGCTTTTTTTCTGGTCGAGTTGCAAAAG

GCCATAAAATGCACTATCCCATGGTGGAATATTGCACTCCGACTACATCAGGAGAAGATGTTC

GAGACTTTGCCAAGGTACTAAAAAACAAATTTCGAACCAAAAGGTATTTTGCGAAGCATCCCC

GAATGGGCTACCTGCCAGTGCAGACTGTCTTAGAGGGGACAACATGGAAACTGACACAATG

TAG
```

SEQ ID NO: 13: ΔR2-R15/ΔR18-23/ΔC (micro-dystrophin with 4
repeats and 2 hinges, no C-terminal domain) (This microgene
carries both R16 and R17. It can restore nNOS)

```
ATGCTTTGGTGGGAAGAAGTAGAGGACTGTTATGAAAGAGAAGATGTTCAAAAGAAAACATT

CACAAAATGGGTAAATGCACAATTTTCTAAGTTTGGGAAGCAGCATATTGAGAACCTCTTCAG

TGACCTACAGGATGGGAGGCGCCTCCTAGACCTCCTCGAAGGCCTGACAGGGCAAAAACTGC

CAAAAGAAAAAGGATCCACAAGAGTTCATGCCCTGAACAATGTCAACAAGGCACTGCGGGTT

TTGCAGAACAATAATGTTGATTTAGTGAATATTGGAAGTACTGACATCGTAGATGGAAATCAT

AAACTGACTCTTGGTTTGATTTGGAATATAATCCTCCACTGGCAGGTCAAAAATGTAATGAAA

AATATCATGGCTGGATTGCAACAAACCAACAGTGAAAAGATTCTCCTGAGCTGGGTCCGACA

ATCAACTCGTAATTATCCACAGGTTAATGTAATCAACTTCACCACCAGCTGGTCTGATGGCCT

GGCTTTGAATGCTCTCATCCATAGTCATAGGCCAGACCTATTTGACTGGAATAGTGTGGTTTGC

CAGCAGTCAGCCACACAACGACTGGAACATGCATTCAACATCGCCAGATATCAATTAGGCAT

AGAGAAACTACTCGATCCTGAAGATGTTGATACCACCTATCCAGATAAGAAGTCCATCTTAAT

GTACATCACATCACTCTTCCAAGTTTTGCCTCAACAAGTGAGCATTGAAGCCATCCAGGAAGT

GGAAATGTTGCCAAGGCCACCTAAAGTGACTAAAGAAGAACATTTTCAGTTACATCATCAAAT

GCACTATTCTCAACAGATCACGGTCAGTCTAGCACAGGGATATGAGAGAACTTCTTCCCCTAA

GCCTCGATTCAAGAGCTATGCCTACACACAGGCTGCTTATGTCACCACCTCTGACCCTACACG

GAGCCCATTTCCTTCACAGCATTTGGAAGCTCCTGAAGACAAGTCATTTGGCAGTTCATTGAT

GGAGAGTGAAGTAAACCTGGACCGTTATCAAACAGCTTTAGAAGAAGTATTATCGTGGCTTCT

TTCTGCTGAGGACACATTGCAAGCACAAGGAGAGATTTCTAATGATGTGGAAGTGGTGAAAG

ACCAGTTTCATACTCATGAGGGGTACATGATGGATTTGACAGCCCATCAGGGCCGGGTTGGTA

ATATTCTACAATTGGGAAGTAAGCTGATTGGAACAGGAAAATTATCAGAAGATGAAGAAACT

GAAGTACAAGAGCAGATGAATCTCCTAAATTCAAGATGGGAATGCCTCAGGGTAGCTAGCAT

GGAAAAACAAAGCAATTACATAGAGAAATTTCTTATGTGCCTTCTACTTATTTGACTGAAAT

CACTCATGTCTCACAAGCCCTATTAGAAGTGGAACAACTTCTCAATGCTCCTGACCTCTGTGCT

AAGGACTTTGAAGATCTCTTTAAGCAAGAGGAGTCTCTGAAGAATATAAAAGATAGTCTACA

ACAAAGCTCAGGTCGGATTGACATTATTCATAGCAAGAAGACAGCAGCATTGCAAAGTGCAA

CGCCTGTGGAAAGGGTGAAGCTACAGGAAGCTCTCTCCCAGCTTGATTTCCAATGGGAAAAA
```

-continued

```
GTTAACAAAATGTACAAGGACCGACAAGGGCGATTTGACAGATCTGTTGAGAAATGGCGGCG

TTTTCATTATGATATAAAGATATTTAATCAGTGGCTAACAGAAGCTGAACAGTTTCTCAGAAA

GACACAAATTCCTGAGAATTGGGAACATGCTAAATACAAATGGTATCTTAAGGAACTCCAGG

ATGGCATTGGGCAGCGGCAAACTGTTGTCAGAACATTGAATGCAACTGGGGAAGAAATAATT

CAGCAATCCTCAAAAACAGATGCCAGTATTCTACAGGAAAAATTGGGAAGCCTGAATCTGCG

GTGGCAGGAGGTCTGCAAACAGCTGTCAGACAGAAAAAAGAGGCTAGAAGAAACCCTTGAA

AGACTCCAGGAACTTCAAGAGGCCACGGATGAGCTGGACCTCAAGCTGCGCCAAGCTGAGGT

GATCAAGGGATCCTGGCAGCCCGTGGGCGATCTCCTCATTGACTCTCTCCAAGATCACCTCGA

GAAAGTCAAGGCACTTCGAGGAGAAATTGCGCCTCTGAAAGAGAACGTGAGCCACGTCAATG

ACCTTGCTCGCCAGCTTACCACTTTGGGCATTCAGCTCTCACCGTATAACCTCAGCACTCTGGA

AGACCTGAACACCAGATGGAAGCTTCTGCAGGTGGCCGTCGAGGACCGAGTCAGGCAGCTGC

ATGAAGCCCACAGGGACTTTGGTCCAGCATCTCAGCACTTTCTTTCCACGTCTGTCCAGGGTCC

CTGGGAGAGAGCCATCTCGCCAAACAAAGTGCCCTACTATATCAACCACGAGACTCAAACAA

CTTGCTGGGACGATCCCAAAATGACAGAGCTCTACCAGTCTTTAGCTGACCTGAATAATGTCA

GATTCTCAGCTTATAGGACTGCCATGAAACTCCGAAGACTGCAGAAGGCCCTTTGCTTGGATC

TCTTGAGCCTGTCAGCTGCATGTGATGCCTTGGACCAGCACAACCTCAAGCAAAATGACCAGC

CCATGGATATCCTGCAGATTATTAATTGTTTGACCACTATTTATGACCGCCTGGAGCAAGAGC

ACAACAATTTGGTCAACGTCCCTCTCTGCGTGGATATGTGTCTGAACTGGCTGCTGAATGTTTA

TGATACGGGACGAACAGGGAGGATCCGTGTCCTGTCTTTTAAAACTGGCATCATTTCCCTGTG

TAAAGCACATTTGGAAGACAAGTACAGATACCTTTTCAAGCAAGTGGCAAGTTCAACAGGAT

TTTGTGACCAGCGCAGGCTGGGCCTCCTTCTGCATGATTCTATCCAAATTCCAAGACAGTTGG

GTGAAGTTGCATCCTTTGGGGGCAGTAACATTGAGCCAAGTGTCCGGAGCTGCTTCCAATTTG

CTAATAATAAGCCAGAGATCGAAGCGGCCCTCTTCCTAGACTGGATGAGACTGGAACCCCAG

TCCATGGTGTGGCTGCCCGTCCTGCACAGAGTGGCTGCTGCAGAAACTGCCAAGCATCAGGCC

AAATGTAACATCTGCAAAGAGTGTCCAATCATTGGATTCAGGTACAGGAGTCTAAAGCACTTT

AATTATGACATCTGCCAAAGCTGCTTTTTTTCTGGTCGAGTTGCAAAAGGCCATAAAATGCAC

TATCCCATGGTGGAATATTGCACTCCGACTACATCAGGAGAAGATGTTCGAGACTTTGCCAAG

GTACTAAAAAACAAATTTCGAACCAAAAGGTATTTTGCGAAGCATCCCCGAATGGGCTACCTG

CCAGTGCAGACTGTCTTAGAGGGGGACAACATGGAAACTGACACAATGTAG
```

SEQ ID NO: 14: ΔR3-R15/ΔR17-23/ΔC (micro-dystrophin with 4 repeats and 2 hinges, no C-terminal domain) (This microgene carries R16 but not R17. It cannot restore nNOS)

```
ATGCTTTGGTGGGAAGAAGTAGAGGACTGTTATGAAAGAAGATGTTCAAAAGAAAACATT

CACAAAATGGGTAAATGCACAATTTTCTAAGTTTGGGAAGCAGCATATTGAGAACCTCTTCAG

TGACCTACAGGATGGGAGGCGCCTCCTAGACCTCCTCGAAGGCCTGACAGGGCAAAAACTGC

CAAAAGAAAAAGGATCCACAAGAGTTCATGCCCTGAACAATGTCAACAAGGCACTGCGGGTT

TTGCAGAACAATAATGTTGATTTAGTGAATATTGGAAGTACTGACATCGTAGATGGAAATCAT

AAACTGACTCTTGGTTTGATTTGGAATATAATCCTCCACTGGCAGGTCAAAAATGTAATGAAA

AATATCATGGCTGGATTGCAACAAACCAACAGTGAAAAGATT7CTCCTGAGCTGGGTCCGACA

ATCAACTCGTAATTATCCACAGGTTAATGTAATCAACTTCACCACCAGCTGGTCTGATGGCCT

GGCTTTGAATGCTCTCATCCATAGTCATAGGCCAGACCTATTTGACTGGAATAGTGTGGTTTGG

CAGCAGTCAGCCACACAACGACTGGAACATGCATTCAACATCGCCAGATATCAATTAGGCAT
```

-continued

```
AGAGAAACTACTCGATCCTGAAGATGTTGATACCACCTATCCAGATAAGAAGTCCATCTTAAT
GTACATCACATCACTCTTCCAAGTTTTGCCTCAACAAGTGAGCATGAAGCCATCCAGGAAGT
GGAAATGTTGCCAAGGCCACCTAAAGTGACTAAAGAAGAACATTTTCAGTTACATCATCAAAT
GCACTATTCTCAACAGATCACGGTCAGTCTAGCACAGGGATATGAGAGAACTTCTTCCCCTAA
GCCTCGATTCAAGAGCTATGCCTACACACAGGCTGCTTATGTCACCCACCTCTGACCCTACACG
GAGCGCATTTCCTTCACAGCATTTGGAAGCTCCTGAAGACAAGTCATTTGGCAGTTCATTGAT
GGAGAGTGAAGTAAACCTGGACCGTTATCAAACAGCTTTAGAAGAAGTATTATCGTGGCTTCT
TTCTGCTGAGGACACATTGCAAGCACAAGGAGAGATTTCTAATGATGTGGAAGTGGTGAAAG
ACCAGTTTCATACTCATGAGGGGTACATGATGGATTTGACAGCCCATCAGGGCCGGGTTGGTA
ATATTCTACAATTGGGAAGTAAGCTGATTGGAACAGGAAAATTATCAGAAGATGAAGAAACT
GAAGTACAAGAGCAGATGAATCTCCTAAATTCAAGATGGGAATGCCTCAGGGTAGCTAGCAT
GGAAAAACAAAGCAATTTACATAGAGTTTTAATGGATCTCCAGAATCAGAAACTGAAAGAGT
TGAATGACTGGCTAACAAAAACAGAAGAAAGAACAAGGAAAATGGAGGAAGAGCCTCTTGG
ACCTGATCTTGAAGACCTAAAACGCCAAGTACAACAACATAAGGTGCTTCAAGAAGATCTAG
AACAAGAACAAGTCAGGGTCAATTCTCTCACTCACATGGTGGTGGTAGTTGATGAATCTAGTG
GAGATCACGCAACTGCTGCTTTGGAAGAACAACTTAAGGTATTGGGAGATCGATGGGCAAAC
ATCTGTAGATGGACAGAAGACCGCTGGGTTCTTTTACAAGACGAAATTTCTTATGTGCCTTCT
ACTTATTTGACTGAAATCACTCATGTCTCACAAGCCCTATTAGAAGTGGAACAACTTCTCAAT
GCTCCTGACCTCTGTGCTAAGGACTTTGAAGATCTCTTTAAGCAAGAGGAGTCTCTGAAGAAT
ATAAAAGATAGTCTACAACAAAGCTCAGGTCGGATTGACATTATTCATAGCAAGAAGACAGC
AGCATTGCAAAGTGCAACGCCTGTGGAAAGGGTGAAGCTACAGGAAGCTCTCTCCCAGCTTG
ATTTCCAATGGGAAAAAGTTAACAAAATGTACAAGGACCGACAAGGGCGATTTGACAGAACC
CTTGAAAGACTCCAGGAACTTCAAGAGGCCACGGATGAGCTGGACCTCAAGCTGCGCCAAGC
TGAGGTGATCAAGGGATCCTGGCAGCCCGTGGGCGATCTCCTCATTGACTCTCTCCAAGATCA
CCTCGAGAAAGTCAAGGCACTTCGAGGAGAAATTGCGCCTCTGAAAGAGAACGTGAGCCACG
TCAATGACCTTGCTCGCCAGCTTACCACTTTGGGCATTCAGCTCTCACCGTATAACCTCAGCAC
TCTGGAAGACCTGAACACCAGATGGAAGCTTCTGCAGGTGGCCGTCGAGGACCGAGTCAGGC
AGCTGCATGAAGCCCACAGGGACTTTGGTCCAGCATCTCAGCACTTTCTTTCCACGTCTGTCCA
GGGTCCCTGGGAGAGAGCCATCTCGCCAAACAAAGTGCCCTACTATATCAACCACGAGACTC
AAACAACTTGCTGGGACCATCCCAAAATGACAGAGCTCTACCAGTCTTTAGCTGACCTGAATA
ATGTCAGATTCTCAGCTTATAGGACTGCCATGAAACTCCGAAGACTGCAGAAGGCCCTTTGCT
TGGATCTCTTGAGCCTGTCAGCTGCATGTGATGCCTTGGACCAGCACAACCTCAAGCAAATG
ACCAGCCCATGGATATCCTGCAGATTATTAATTGTTTGACCACTATTTATGACCGCCTGGAGC
AAGAGCACAACAATTTGGTCAACGTCCCTCTCTGCGTGGATATGTGTCTGAACTGGCTGCTGA
ATGTTTATGATACGGGACGAACAGGGAGGATCCGTGTCCTGTCTTTTAAAACTGGCATCATTT
CCCTGTGTAAAGCACATTTGGAAGACAAGTACAGATACCTTTTCAAGCAAGTGGCAAGTCAA
CAGGATTTTGTGACCAGCGCAGGCTGGGCCTCCTTCTGCATGATTCTATCCAAATTCCAAGAC
AGTTGGGTGAAGTTGCATCCTTTGGGGGCAGTAACATTGAGGCAAGTGTCCGGAGCTGCTTCC
AATTTGCTAATAATAAGCCAGAGATCGAAGCGGCCCTCTTCCTAGACTGGATGAGACTGGAAC
CCCAGTCCATGGTGTGGCTGCCCGTCCTGCACAGAGTGGCTGCTGCAGAAACTGCCAAGCATC
```

AGGCCAAATGTAACATCTGCAAAGAGTGTCCAATCATTGGATTCAGGTACAGGAGTCTAAAG

CACTTTAATTATGACATCTGCCAAAGCTGCTTTTTTTCTGGTCGAGTTGCAAAAGGCCATAAAA

TGCACTATCCCATGGTGGAATATTGCACTCCGACTACATCAGGAGAAGATGTTCGAGACTTTG

CCAAGGTACTAAAAAACAAATTTCGAACCAAAAGGTATTTTGCGAAGCATCCCCGAATGGGC

TACCTGCCAGTGCAGACTGTCTTAGAGGGGGACAACATGGAAACTGACACAATGTAG

SEQ ID NO: 15: AV.CMV.ΔR2-15/ΔR18-23/ΔC (This AAV vector contains
four repeats and two hinges. It carries both R16 and R17 and it
can restore nNOS)
CATTAATGAATCGGCCAACGCGCGGGGAGAGGCGGTTTGCGTATTGGGCGCTCTTCCGCTTCC

TCGCTCACTGACTCGCTGCGCTCGGTCGTTCGGCTGCGGCGAGCGGTATCAGCTCACTCAAAG

GCGGTAATACGGTTATCCACAGAATCAGGGGATAACGCAGGAAAGAACATGTGAGCAAAAG

GCCAGCAAAAGGCCAGGAACCGTAAAAAGGCCGCGTTGCTGGCGTTTTCCATAGGCTCCGC

CCCCCTGACGAGCATCACAAAAATCGACGCTCAAGTCAGAGGTGGCGAAACCCGACAGGACT

ATAAAGATACCAGGCGTTTCCCCCTGGAAGCTCCCTCGTGCGCTCTCCTGTTCCGACCCTGCCG

CTTACCGGATACCTGTCCGCCTTTCTCCCTTCGGGAAGCGTGGCGCTTTCTCATAGCTCACGCT

GTAGGTATCTCAGTTCGGTGTAGGTCGTTCGCTCCAAGCTGGGCTGTGTGCACGAACCCCCCG

TTCAGCCCGACCGCTGCGCCTTATCCGGTAACTATCGTCTTGAGTCCAACCCGGTAAGACACG

ACTTATCGCCACTGGCAGCAGCCACTGGTAACAGGATTAGCAGAGCGAGGTATGTAGGCGGT

GCTACAGAGTTCTTGAAGTGGTGGCCTAACTACGGCTACACTAGAAGGACAGTATTTGGTATC

TGCGCTCTGCTGAAGCCAGTTACCTTCGGAAAAAGAGTTGGTAGCTCTTGATCCGGCAAACAA

ACCACCGCTGGTAGCGGTGGTTTTTTTGTTTGCAAGCAGCAGATTACGCGCAGAAAAAAAGGA

TCTCAAGAAGATCCTTTGATCTTTTCTACGGGGTCTGACGCTCAGTGGAACGAAAACTCACGT

TAAGGGATTTTGGTCATGAGATTATCAAAAAGGATCTTCACCTAGATCCTTTTAAATTAAAAA

TGAAGTTTTAAATCAATCTAAAGTATATATGAGTAAACTTGGTCTGACAGTTACCAATGCTTA

ATCAGTGAGGCACCTATCTCAGCGATCTGTCTATTTCGTTCATCCATAGTTGCCTGACTCCCCG

TCGTGTAGATAACTACGATACGGGAGGGCTTACCATCTGGCCCCAGTGCTGCAATGATACCGC

GAGACCCACGCTGACCGGCTCCAGATTTATCAGCAATAAACCAGCCAGCCGGAAGGGCCGAG

CGCAGAAGTGGTCCTGCAAGTTTATCCGCCTCCATCCAGTGTATTAATTGTTGCCGGGAAGCT

AGAGTAAGTAGTTCGCCAGTTAATAGTTTGCGCAACGTTGTTGCCATTGCTACAGGCATCGTG

GTGTCAGGCTCGTCGTTTGGTATGGCTTCATTCAGCTCCGGTTCCCAACGATCAAGGCGAGTTA

CATGATCCCCCATGTTGTGCAAAAAAGCGGTTAGCTCCTTCGGTCCTCCGATCGTTGTCAGAA

GTAAGTTGGCCGCAGTGTTATCACTCATGGTTATGGCAGCACTGCATAATTCTCTTACTGTCAT

GCCATCCGTAAGATGCTTTTCTGTGACTGGTGAGTACTCAACCAAGTCATTCTGAGAATAGTG

TATGCGGCGACCGAGTTGCTCTTGCCCGGCGTCAATACGGGATAATACCGCGCCACATAGCAG

AACTTTAAAAGTGCTCATCATTGGAAAACGTTCTTCGGGGCGAAAACTCTCAAGGATCTTACC

GCTGTTGAGATCCAGTCGATGTAACCCACTCGTGCACCCAACTGATCTTCAGCATCTTTTACT

TTCACCAGCGTTTCTGGGTGAGCAAAAACAGGAAGGCAAAATGCCGCAAAAAAGGGAATAAG

GGCGACACGGAAATGTTGATACTCATACTCTTCCTTTTTCAATATTATTGAAGCATTTATCAG

GGTTATTGTCTCATGAGCGGATACATATTTGAATGTATTTAGAAAAATAAACAAATAGGGGTT

CCGCGCACATTTCCCCGAAAAGTGCCACCTGACGTCTAAGAAACCATTATTATCATGACATTA

ACCTATAAAAATAGGCGTATCACGAGGCCCTTTCGTCTCGCGCGTTTCGGTGATGACGGTGAA

-continued

```
AAGCTCTGACACATGCAGCTCCCGGAGACGGTCACAGCTTGTCTGTAAGCGGATGCCGGGAG
CAGACAAGCCCGTCAGGGCGCGTCAGCGGGTGTTGGCGGGTGTCGGGGCTGGCTTAACTATG
CGGCATCAGAGCAGATTGTACTGAGAGTGCACCATATGCGGTGTGAAATACCGCACAGATGC
GTAAGGAGAAAATACCGCATCAGGAATTCCAACATCCAATAAATCATACAGGCAAGGCAAAG
AATTAGCAAAATTAAGCAATAAAGCCTCAGAGCATAAAGCTAAATCGGTTGTACCAAAAACA
TTATGACCCTGTAATACTTTTGCGGGAGAAGCCTTTATTTCAACGCAAGGATAAAAATTTTTA
GAACCCTCATATATTTTAAATGCAATGCCTGAGTAATGTGTAGGTAAAGATTCAAACGGGTGA
GAAAGGCCGGAGACAGTCAAATCACCATCAATATGATATTCAACCGTTCTAGCTGATAAATTC
ATGCCGGAGAGGGTAGCTATTTTTGAGAGGTCTCTACAAAGGCTATCAGGTCATTGCCTGAGA
GTCTGGAGCAAACAAGAGAATCGATGAACGGTAATCGTAAAACTAGCATGTCAATCATATGT
ACCCCGGTTGATAATCAGAAAAGCCCCAAAAACAGGAAGATTGTATAAGCAAATATTTAAAT
TGTAAACGTTAATATTTTGTTAAAATTCGCGTTAAATTTTTGTAAATCAGCTCATTTTTTAACC
AATAGGCCGAAATCGGCAAAATCCCTTATAAATCAAAAGAATAGACCGAGATAGGGTTGAGT
GTTGTTCCAGTTTGGAACAAGAGTCCACTATTAAAGAACGTGGACTCCAACGTCAAAGGGCG
AAAAACCGTCTATCAGGGCGATGGCCCACTACGTGAACCATCACCCTAATCAAGTTTTTTGGG
GTCGAGGTGCCGTAAAGCACTAAATCGGAACCCTAAAGGGAGCCCCCGATTTAGAGCTTGAC
GGGGAAAGCCGGCGAACGTGGCGAGAAAGGAAGGGAAGAAAGCGAAAGGAGCGGGCGCTA
GGGCGCTGGCAAGTGTAGCGGTCACGCTGCGCGTAACCACCACACCCGCCGCGCTTAATGCG
CCGCTACAGGGCGCGTACTATGGTTGCTTTGACGAGCAGGTATAACGTGCTTTCCTCGTTAGA
ATCAGAGCGGGAGCTAAACAGGAGGCCGATTAAAGGGATTTTAGACAGGAACGGTACGCCAG
AATCCTGAGAAGTGTTTTTATAATCAGTGAGGCCACCGAGTAAAAGAGTCTGTCGATCACGCA
AATTAACCGTTGTCGCAATACTTCTTTGATTAGTAATAACATCACTTGCCTGAGTAGAAGAAC
TCAAACTATCGGCCTTGCTGGTAATATCCAGAACAATATTACCGCCAGCCATTGCAAGAGGAA
AAACGCTCATGGAAATACCTACATTTTGACGCTCAATCGTCTGGAATTCCATTCGCCATTCAG
GCTGCGCAACTGTTGGGAAGGGCGATCGGTGCGGGCCTCTTCGCTATTACGCCAGCTGGCGCG
CTCGCTCGCTCACTGAGGCCGCCCGGGCAAAGCCCGGGCGTCGGGCGACCTTTGGTCGCCCGG
CCTCAGTGAGCGAGCGAGCGCGCAGAGAGGGAGTGGCCAACTCCATCACTAGGGGTTCCTTG
TAGTTAATGATTAACCCGCCATGCTACTTATCTACGGCCGCGGTACCGCGTTACATAACTTAC
GGTAAATGGCCCGCCTGGCTGACCGCCCAACGACCCCCGCCCATTGACGTCAATAATGACGTA
TGTTCGCATAGTAACGCCAATAGGGACTTTCCATTGACGTCAATGGGTGGAGTATTTACGGTA
AACTGCCCACTTGGCAGTACATCAAGTGTATCATATGCCAAGTACGCCCCCTATTGACGTCAA
TGACGGTAAATGGCCCGCCTGGCATTATGCCCAGTACATGACCTTATGGGACTTTCCTACTTG
GCAGTACATCTACGTATTAGTCATCGCTATTACCATGGTGATGCGGTTTTGGCAGTACATCAAT
GGGCGTGGATAGCGGTTTGACTCACGGGGATTTCCAAGTCTCCACCCCATTGACGTCAATGGG
AGTTTGTTTTGGCACCAAAATCAACGGGACTTTCCAAAATGTCGTAACAACTCCGCCCCATTG
ACGCAAATGGGCGGTAGGCGTGTACGGTGGGAGGTCTATATAAGCAGAGCTCGTTTAGTGAA
CCGTCTAGACGCCGCGGTTTTTTTATCGCTGCCTTGATATACACTTTCCACCATGCTTTGGT
GGGAAGAAGTAGAGGACTGTTATGAAAGAGAAGATGTTCAAAAGAAAACATTCACAAAATG
GGTAAATGCACAATTTTCTAAGTTTGGGAAGCAGCATATTGAGAACCTCTTCAGTGACCTACA
GGATGGGAGGGGCCTCCTAGACCTCCTCGAAGGCCTGACAGGGCAAAAACTGCCAAAAGAAA
```

-continued

```
AAGGATCCACAAGAGTTCATGCCCTGAACAATGTCAACAAGGCACTGCGGGTTTTGCAGAAC
AATAATGTTGATTTAGTGAATATTGGAAGTACTGACATCGTAGATGGAAATCATAAACTGACT
CTTGGTTTGATTTGGAATATAATCCTCCACTGGCAGGTCAAAAATGTAATGAAAAATATCATG
GCTGGATTGCAACAAACCAACAGTGAAAAGATTCTCCTGAGCTGGGTCCGACAATCAACTCGT
AATTATCCACAGGTTAATGTAATCAACTTCACCACCAGCTGGTCTGATGGCCTGGCTTTGAAT
GCTCTCATCCATAGTCATAGGCCAGACCTATTTGACTGGAATAGTGTGGTTTGCCAGCAGTCA
GCCACACAACGACTGGAACATGCATTCAACATCGCCAGATATCAATTAGGCATAGAGAAACT
ACTCGATCCTGAAGATGTTGATACCACCTATCCAGATAAGAAGTCCATCTTAATGTACATCAC
ATCACTCTTCCAAGTTTTGCCTCAACAAGTGAGCATTGAAGCCATCCAGGAAGTGGAAATGTT
GCCAAGGCCACCTAAAGTGACTAAAGAAGAACATTTTCAGTTACATCATCAAATGCACTATTC
TCAACAGATCACGGTCAGTCTAGCACAGGGATATGAGAGAACTTCTTCCCCTAAGCCTCGATT
CAAGAGCTATGCCTACACACAGGCTGCTTATGTCACCACCTCTGACCCTACACGGAGCCCATT
TCCTTCACAGCATTTGGAAGCTCCTGAAGACAAGTCATTTGGCAGTTCATTGATGGAGAGTGA
AGTAAACCTGGACCGTTATCAAACAGCTTTAGAAGAAGTATTATCGTGGCTTCTTTCTGCTGA
GGACACATTGCAAGCACAAGGAGAGATTTCTAATGATGTGGAAGTGGTGAAAGACCAGTTTC
ATACTCATGAGGGGTACATGATGGATTTGACAGCGCATCAGGGCCGGGTTGGTAATATTCTAC
AATTGGGAAGTAAGCTGATTGGAACAGGAAAATTATCAGAAGATGAAGAAACTGAAGTACAA
GAGCAGATGAATCTCCTAAATTCAAGATGGGAATGCCTCAGGGTAGCTAGCATGGAAAAACA
AAGCAATTTACATAGAGAAATTTCTTATGTGCCTTCTACTTATTTGACTGAAATCACTCATGTC
TCACAAGCCCTATTAGAAGTGGAACAACTTCTCAATGCTCCTGACCTCTGTGCTAAGGACTTT
GAAGATCTCTTTAAGCAAGAGGAGTCTCTGAAGAATATAAAAGATAGTCTACAACAAAGCTC
AGGTCGGATTGACATTATTCATAGCAAGAAGACAGCAGCATTGCAAAGTGCAACGCCTGTGG
AAAGGGTGAAGCTACAGGAAGCTCTCTCCGAGCTTGATTTCCAATGGGAAAAAGTTAACAAA
ATGTACAAGGACCGACAAGGGCGATTTGACAGATCTGTTGAGAAATGGCGGCGTTTTCATTAT
GATATAAAGATATTTAATCAGTGGCTAACAGAAGCTGAACAGTTTCTCAGAAAGAGACAAAT
TCCTGAGAATTGGGAACATGCTAAATACAAATGGTATCTTAAGGAACTCCAGGATGGCATTGG
GCAGCGGCAAACTGTTGTCAGAACATTGAATGCAACTGGGGAAGAAATAATTCAGCAATCCT
CAAAAACAGATGCCAGTATTCTACAGGAAAAATTGGGAAGCCTGAATCTGCGGTGGCAGGAG
GTCTGCAAACAGCTGTCAGACAGAAAAAAGAGGCTAGAAGAAACCCTTGAAAGACTCCAGGA
ACTTCAAGAGGCCACGGATGAGGTGGACCTCAAGCTGCGCCAAGCTGAGGTGATCAAGGGAT
CCTGGCAGCCCGTGGGCGATCTCCTCATTGACTCTCTCCAAGATCACCTCGAGAAAGTCAAGG
CACTTCGAGGAGAAATTGCGCCTCTGAAAGAGAACGTGAGCCACGTCAATGACCTTGCTCGCC
AGCTTACCACTTTGGGCATTCAGCTCTCACCGTATAACCTCAGCACTCTGGAAGACCTGAACA
CCAGATGGAAGCTTCTGCAGGTGGCCGTCGAGGACCGAGTCAGGCAGCTGCATGAAGCCCAC
AGGGACTTTGGTCCAGCATCTCAGCACTTTCTTTCCACGTCTGTCCAGGGTCCCTGGGAGAGA
GCCATCTCGCCAAACAAAGTGCCCTACTATATCAACCACGAGACTCAAACAACTTGCTGGGAC
CATCCCAAAATGACAGAGCTCTACCAGTCTTTAGCTGACCTGAATAATGTCAGATTCTCAGCT
TATAGGACTGCCATGAAACTCCGAAGACTGCAGAAGGCCCTTTGCTTGGATCTCTTGAGCCTG
TCAGCTGCATGTGATGCCTTGGACCAGCACAACCTCAAGCAAAATGACCAGCCCATGGATATC
CTGCAGATTATTAATTGTTTGACCACTATTTATGACCGCCTGGAGCAAGAGCACAACAATTTG
```

```
GTCAACGTCCCTCTCTGCGTGGATATGTGTCTGAACTGGCTGCTGAATGTTTATGATACGGGA

CGAACAGGGAGGATCCGTGTCCTGTCTTTTAAAACTGGCATCATTTCCCTGTGTAAAGCACAT

TTGGAAGACAAGTACAGATACCTTTTCAAGCAAGTGGCAAGTTCAACAGGATTTTGTGACCAG

CGCAGGCTGGGCCTCCTTCTGCATGATTCTATCCAAATTCCAAGACAGTTGGGTGAAGTTGCA

TCCTTTGGGGGCAGTAACATTGAGCCAAGTGTCCGGAGCTGCTTCCAATTTGCTAATAATAAG

CCAGAGATCGAAGCGGCCCTCTTCCTAGACTGGATGAGACTGGAACCCCAGTCCATGGTGTGG

CTGCCCGTCCTGCACAGAGTGGCTGCTGCAGAAACTGCCAAGCATCAGGCCAAATGTAACATC

TGCAAAGAGTGTCCAATCATTGGATTCAGGTACAGGAGTCTAAAGCACTTTAATTATGACATC

TGCCAAAGCTGCTTTTTTTCTGGTCGAGTTGCAAAAGGCCATAAAATGCACTATCCCATGGTG

GAATATTGCACTCCGACTACATCAGGAGAAGATGTTCGAGACTTTGCCAAGGTACTAAAAAA

CAAATTTCGAACCAAAAGGTATTTTGCGAAGCATCCCCGAATGGGCTACCTGCCAGTGCAGAC

TGTCTTAGAGGGGGACAACATGGAAACTGACACAATGTAGGAAGTCTTTTCCACATGGCAGA

TGATTTGGGCAGAGCGATGGAGTCCTTAGTATCAGTCATGACAGATGAAGAAGGAGCAGAAT

AAATGTTTTACAACTCCTGATTCCCGCATGCGGCCGATCCAGACATGATAAGATACATTGATG

AGTTTGGACAAACCACAACTAGAATGCAGTGAAAAAAATGCTTTATTTGTGAAATTTGTGATG

CTATTGCTTTATTTGTAACCATTATAAGCTGCAATAAACAAGTTAACAACAACAATTGCATTC

ATTTTATGTTTCAGGTTCAGGGGGAGGTGTGGGAGGTTTTTTGCGGCCGTAGATAAGTAGCAT

GGCGGGTTAATCATTAACTACAAGGAACCCCTAGTGATGGAGTTGGCCACTCCCTCTCTGCGC

GCTCGCTCGCTCACTGAGGCCGGGCGACCAAAGGTCGCCCGACGCCCGGGCTTTGCCCGGGC

GGCCTCAGTGAGCGAGCGAGCGCGCAGCTGCTG

SEQ ID NO: 16: AV.CMV.ΔR3-15/ΔR18-23/ΔC (This AAV vector
contains five repeats and two hinges. It carries both R16 and
R17 and it can restore nNOS)
CATTAATGAATCGGCCAACGCGCGGGGAGAGGCGGTTTGCGTATTGGGCGCTCTTCCGCTTCC

TCGCTCACTGACTCGCTGCGCTCGGTCGTTCGGCTGCGGCGAGCGGTATCAGCTCACTCAAAG

GCGGTAATACGGTTATCCACAGAATCAGGGGATAACGCAGGAAAGAACATGTGAGCAAAAG

GCCAGCAAAAGGCCAGGAACCGTAAAAAGGCCGCGTTGCTGGCGTTTTTCCATAGGCTCCGC

CCCCCTGACGAGCATCACAAAAATCGACGCTCAAGTCAGAGGTGGCGAAACCCGACAGGACT

ATAAAGATACCAGGCGTTTCCCCCTGGAAGCTCCCTCGTGCGCTCTCCTGTTCCGACCCTGCCG

CTTACCGGATACCTGTCCGCCTTTCTCCCTTCGGGAAGCGTGGCGCTTTCTCATAGCTCACGCT

GTAGGTATCTCAGTTCGGTGTAGGTCGTTCGCTCCAAGCTGGGCTGTGTGCACGAACCCCCCG

TTCAGCCCGACCGCTGCGCCTTATCCGGTAACTATCGTCTTGAGTCCAACCCGGTAAGACACG

ACTTATCGCCACTGGCAGCAGCCACTGGTAACAGGATTAGCAGAGCGAGGTATGTAGGCGGT

GCTACAGAGTTCTTGAAGTGGTGGCCTAACTACGGCTACACTAGAAGGACAGTATTTGGTATC

TGCGCTCTGCTGAAGCCAGTTACCTTCGGAAAAAGAGTTGGTAGCTCTTGATCCGGCAAACAA

ACCACCGCTGGTAGCGGTGGTTTTTTTGTTTGCAAGCAGCAGATTACGCGCAGAAAAAAAGGA

TCTCAAGAAGATCCTTTGATCTTTTCTACGGGGTCTGACGCTCAGTGGAACGAAAACTCACGT

TAAGGGATTTTGGTCATGAGATTATCAAAAGGATCTTCACCTAGATCCTTTTAAATTAAAAA

TGAAGTTTTAAATCAATCTAAAGTATATATGAGTAAACTTGGTCTGACAGTTACCAATGCTTA

ATCAGTGAGGCACCTATCTGAGCGATCTGTCTATTTCGTTCATCCATAGTTGCCTGACTCCCCG

TCGTGTAGATAACTACGATACGGGAGGGCTTACCATCTGGCCCCAGTGCTGCAATGATACCGC

GAGACCCACGCTGACCGGCTCCAGATTTATCAGCAATAAACCAGCCAGCCGGAAGGGCCGAG
```

-continued

```
CGCAGAAGTGGTCCTGCAACTTTATCCGCCTCCATCCAGTCTATTAATTGTTGCCGGGAAGCT

AGAGTAAGTAGTTCGCCAGTTAATAGTTTGCGCAACGTTGTTGCCATTGCTACAGGCATCGTG

GTGTCACGCTCGTCGTTTGGTATGGCTTCATTCAGCTCCGGTTCCCAACGATCAAGGCGAGTTA

CATGATCCCCCATGTTGTGCAAAAAAGCGGTTAGCTCCTTCGGTCCTCCGATCGTTGTCAGAA

GTAAGTTGGCCGCAGTGTTATCACTCATGGTTATGGCAGCACTGCATAATTCTCTTACTGTCAT

GCCATCCGTAAGATGCTTTTCTGTGACTGGTGAGTACTCAACCAAGTCATTCTGAGAATAGTG

TATGCGGCGACCGAGTTGCTCTTGCCCGGCGTCAATAGGGGATAATACCGCGCCACATAGCAG

AACTTTAAAAGTGCTCATCATTGGAAAACGTTCTTCGGGGCGAAAACTCTCAAGGATCTTACC

GCTGTTGAGATCCAGTTCGATGTAACCCACTCGTGCACCCAACTGATCTTCAGCATCTTTTACT

TTCACCAGCGTTTCTGGGTGAGCAAAAACAGGAAGGCAAATGCCGCAAAAAAGGGAATAAG

GGCGACACGGAAATGTTGAATACTCATACTCTTCCTTTTTCAATATTATTGAAGCATTTATCAG

GGTTATTGTCTCATGAGCGGATACATATTTGAATGTATTTAGAAAAATAAACAAATAGGGGTT

CCGCGCACATTTCCCCGAAAAGTGCCACCTGACGTCTAAGAAACCATTATTATCATGACATTA

ACCTATAAAAATAGGCGTATCACGAGGCCCTTTCGTCTCGCGCGTTTCGGTGATGACGGTGAA

AACCTCTGACACATGCAGCTCCCGGAGACGGTCACAGCTTGTCTGTAAGCGGATGCCGGGAG

CAGACAAGCCCGTCAGGGCGCGTCAGCGGGTGTTGGCGGGTGTCGGGGCTGGCTTAACTATG

CGGCATCAGAGCAGATTGTACTGAGAGTGCACCATATGCGGTGTGAAATACCGCACAGATGC

GTAAGGAGAAAATACCGCATCAGGAATTCCAACATCCAATAAATCATACAGGCAAGGCAAAG

AATTAGCAAAATTAAGCAATAAAGCCTCAGAGCATAAAGCTAAATCGGTTGTACCAAAAACA

TTATGACCCTGTAATACTTTTGCGGGAGAAGCCTTTATTTCAACGCAAGGATAAAAATTTTTA

GAACCCTCATATATTTTAAATGCAATGCCTGAGTAATGTGTAGGTAAAGATTCAAACGGGTGA

GAAAGGCCGGAGACAGTCAAATCACCATCAATATGATATTCAACCGTTCTAGCTGATAAATTC

ATGCCGGAGAGGGTAGCTATTTTTGAGAGGTCTCTACAAAGGCTATCAGGTCATTGCCTGAGA

GTCTGGAGCAAACAAGAGAATCGATGAACGGTAATCGTAAAACTAGCATGTCAATCATATGT

ACCCCGGTTGATAATCAGAAAAGCCCCAAAAACAGGAAGATTGTATAAGCAAATATTTAAAT

TGTAAACGTTAATATTTTGTTAAAATTCGCGTTAAATTTTGTTAAATCAGCTCATTTTTTAACC

AATAGGCCGAAATCGGCAAAATCCCTTATAAATCAAAAGAATAGACCGAGATAGGGTTGAGT

GTTGTTCCAGTTTGGAACAAGAGTCCACTATTAAAGAACGTGGACTCCAACGTCAAAGGGCG

AAAAACCGTCTATCAGGGCGATGGCCCACTACGTGAACCATCACCCTAATCAAGTTTTTTGGG

GTCGAGGTGCCGTAAAGCACTAAATCGGAACCCTAAAGGGAGCCCCCGATTTAGAGCTTGAC

GGGGAAAGCCGGCGAACGTGGCGAGAAAGGAAGGGAAGAAAGCGAAAGGAGCGGGCGCTA

GGGCGCTGGCAAGTGTAGCGGTCACGCTGCGCGTAACCACCACACCCGCCGCGCTTAATGCG

CCGCTACAGGGCGCGTACTATGGTTGCTTTGACGAGCACGTATAACGTGCTTTCCTCGTTAGA

ATCAGAGCGGGAGCTAAACAGGAGGCCGATTAAAGGGATTTTAGACAGGAACGGTACGCCAG

AATCCTGAGAAGTGTTTTTATAATCAGTGAGGCCACCGAGTAAAAGAGTCTGTCCATCACGCA

AATTAACCGTTGTCGCAATACTTCTTGATTAGTAATAACATCACTTGCCTGAGTAGAAGAAC

TCAAACTATCGGCCTTGCTGGTAATATCCAGAACAATATTACCGCCAGCCATTGCAACAGGAA

AAACGCTCATGGAAATACCTACATTTTGACGCTCAATCGTCTGGAATTCCATTCGCCATTCAG

GCTGCGCAACTGTTGGGAAGGGCGATCGGTGCGGGCCTCTTCGCTATTACGCCAGCTGGCGCG

CTCGCTCGCTCACTGAGGCCGCCGGGGCAAAGCCCGGGCGTCGGGCGACCTTTGGTCGCCCGG
```

-continued

```
CCTCAGTGAGCGAGCGAGCGCGCAGAGAGGGAGTGGCCAACTCCATCACTAGGGGTTCCTTG

TAGTTAATGATTAACCCGCCATGCTACTTATCTACGGCCGCGGTACCACTCACGGGGATTTCC

AAGTCTCCACCCCATTGACGTCAATGGGAGTTTGTTTTGGCACCAAAATCAACGGGACTTTCC

AAAATGTCGTAATAACCCCGCCCCGTTGACGCAAATGGGCGGTAGGCGTGTACGGTGGGAGG

TCTATATAAGCAGAGCTCGTTTAGTGAACCGTCTCTAGACGCCGCGGTTTTTTTTATCGCTGC

CTTGATATACACTTTCCACCATGCTTTGGTGGGAAGAAGTAGAGGACTGTTATGAAAGAGAAG

ATGTTCAAAAGAAAACATTCACAAAATGGGTAAATGCACAATTTTCTAAGTTTGGGAAGCAG

CATATTGAGAACCTCTTCAGTGACCTACAGGATGGGAGGCGCCTCCTAGACCTCCTCGAAGGC

CTGACAGGGCAAAAACTGCCAAAAGAAAAAGGATCCACAAGAGTTCATGCCCTGAACAATGT

CAACAAGGCACTGCGGGTTTTGCAGAACAATAATGTTGATTTAGTGAATATTGGAAGTACTGA

CATCGTAGATGGAAATCATAAACTGACTCTTGGTTTGATTTGGAATATAATCCTCCACTGGCA

GGTCAAAAATGTAATGAAAAATATCATGGCTGGATTGCAACAAACCAACAGTGAAAAGATTC

TCCTGAGCTGGGTCCGACAATCAACTCGTAATTATCCACAGGTTAATGTAATCAACTTCACCA

CCAGCTGGTCTGATGGCCTGGCTTTGAATGCTCTCATCCATAGTCATAGGCCAGACCTATTTGA

CTGGAATAGTGTGGTTTGCCAGCAGTCAGCCACACAACGACTGGAACATGCATTCAACATCGC

CAGATATCAATTAGGCATAGAGAAACTACTCGATCCTGAAGATGTTGATACCACCTATCCAGA

TAAGAAGTCCATCTTAATGTACATCACATCACTCTTCCAAGTTTTGCCTCAACAAGTGAGCATT

GAAGCCATCCAGGAAGTGGAAATGTTGCCAAGGCCACCTAAAGTGACTAAAGAAGAACATTT

TCAGTTACATCATCAAATGCACTATTCTCAACAGATCACGGTCAGTCTAGCACAGGGATATGA

GAGAAGTTCTTCCCCTAAGCCTCGATTCAAGAGCTATGCCTACACACAGGCTGCTTATGTCAC

CACCTCTGACCCTACACGGAGCCCATTTCCTTCACAGCATTTGGAAGCTCCTGAAGACAAGTC

ATTTGGCAGTTCATTGATGGAGAGTGAAGTAAACCTGGACCGTTATCAAACAGCTTTAGAAGA

AGTATTATCGTGGCTTCTTTCTGCTGAGGACACATTGCAAGCACAAGGAGAGATTTCTAATGA

TGTGGAAGTGGTGAAAGACCAGTTTCATACTCATGAGGGGTACATGATGGATTTGACAGCCCA

TCAGGGCCGGGTTGGTAATATTCTACAATTGGGAAGTAAGCTGATTGGAACAGGAAAATTATC

AGAAGATGAAGAAACTGAAGTACAAGAGCAGATGAATCTCCTAAATTCAAGATGGGAATGCC

TCAGGGTAGCTAGCATGGAAAAACAAAGCAATTTACATAGAGTTTTAATGGATCTCCAGAATC

AGAAACTGAAAGAGTTGAATGACTGGCTAACAAAAACAGAAGAAAGAACAAGGAAAATGGA

GGAAGAGCCTCTTGGACCTGATCTTGAAGACCTAAAACGGCAAGTACAACAACATAAGGTGC

TTCAAGAAGATCTAGAACAAGAACAAGTCAGGGTCAATTCTCTCACTCACATGGTGGTGGTAG

TTGATGAATCTAGTGGAGATCACGCAACTGCTGCTTTGGAAGAACAACTTAAGGTATTGGGAG

ATCGATGGGCAAACATCTGTAGATGGACAGAAGACCGCTGGGTTCTTTTACAAGACGAAATTT

CTTATGTGCCTTCTACTTATTTGACTGAAATCACTCATGTCTCACAAGCCCTATTAGAAGTGGA

ACAACTTCTCAATGCTCCTGACCTCTGTGCTAAGGACTTTGAAGATCTCTTTAAGCAAGAGGA

GTCTCTGAAGAATATAAAAGATAGTCTACAACAAAGCTCAGGTCGGATTGACATTATTCATAG

CAAGAAGACAGCAGCATTGCAAAGTGCAACGCCTGTGGAAAGGGTGAAGCTACAGGAAGCTC

TCTCCCAGCTTGATTTCCAATGGGAAAAAGTTAACAAAATGTACAAGGACCGACAAGGGCGA

TTTGACAGATCTGTTGAGAAATGGCGGCGTTTTCATTATGATATAAAGATATTTAATCAGTGG

CTAACAGAAGCTGAACAGTTTCTCAGAAAGACACAAATTCCTGAGAATTGGGAACATGCTAA

ATACAAATGGTATCTTAAGGAACTCCAGGATGGCATTGGGCAGCGGCAAACTGTTGTCAGAA
```

-continued

```
CATTGAATGCAACTGGGGAAGAAATAATTCAGCAATCGTCAAAAACAGATGCCAGTATTCTA

CAGGAAAAATTGGGAAGCCTGAATCTGCGGTGGCAGGAGGTCTGCAAACAGCTGTCAGACAG

AAAAAAGAGGCTAGAAGAAACCCTTGAAAGACTCCAGGAACTTCAAGAGGCCACGGATGAG

CTGGACCTCAAGCTGCGCCAAGCTGAGGTGATCAAGGGATCCTGGCAGCCCGTGGGCGATCT

CCTCATTGACTCTCTCCAAGATCACCTCGAGAAAGTCAAGGCACTTCGAGGAGAAATTGCGCC

TCTGAAAGAGAACGTGAGCCACGTCAATGACCTTGCTCGCCAGCTTACCACTTTGGGCATTCA

GGTCTCACGGTATAACCTCAGCACTCTGGAAGACCTGAACACCAGATGGAAGCTTCTGCAGGT

GGCCGTCGAGGACCGAGTCAGGCAGCTGCATGAAGCCCACAGGGACTTTGGTCCAGCATCTC

AGCACTTTCTTTCCACGTCTGTCCAGGGTCCCTGGGAGAGAGCCATCTCGCCAAACAAAGTGC

CCTACTATATCAACCACGAGACTCAAACAACTTGCTGGGACCATCCCAAAATGACAGAGCTCT

ACCAGTCTTTAGCTGACCTGAATAATGTCAGATTCTCAGCTTATAGGACTGCCATGAAACTCC

GAAGACTGCAGAAGGCCCTTTGCTTGGATCTCTTGAGCCTGTCAGCTGCATGTGATGCCTTGG

ACCAGCACAACCTCAAGCAAAATGACCAGCCCATGGATATCCTGCAGATTATTAATTGTTTGA

CCACTATTTATGACCGCCTGGAGCAAGAGCACAACAATTTGGTCAACGTCCCTCTCTGCGTGG

ATATGTGTCTGAACTGGCTGCTGAATGTTTATGATACGGGACGAACAGGGAGGATCCGTGTCC

TGTCTTTTAAAACTGGCATCATTTCCCTGTGTAAAGCACATTTGGAAGACAAGTACAGATACC

TTTTCAAGCAAGTGGCAAGTTCAACAGGATTTTGTGACCAGCGCAGGCTGGGCCTCCTTCTGC

ATGATTCTATCCAAATTCCAAGACAGTTGGGTGAAGTTGCATCCTTTGGGGGCAGTAACATTG

AGCCAAGTGTCCGGAGCTGCTTCCAATTTGCTAATAATAAGCCAGAGATCGAAGCGGCCCTCT

TCCTAGACTGGATGAGACTGGAACCGCAGTCCATGGTGTGGCTGCCCGTCCTGCACAGAGTGG

CTGCTGCAGAAACTGCCAAGCATCAGGCCAAATGTAACATCTGCAAAGAGTGTCCAATCATTG

GATTCAGGTACAGGAGTCTAAAGCACTTTAATTATGACATCTGCCAAAGCTGCTTTTTTTCTGG

TCGAGTTGCAAAAGGCCATAAAATGCACTATCCCATGGTGGAATATTGCACTCCGACTACATC

AGGAGAAGATGTTCGAGACTTTGCCAAGGTACTAAAAAACAAATTTCGAACCAAAAGGTATT

TTGCGAAGCATCCCCGAATGGGCTACCTGCCAGTGCAGACTGTCTTAGAGGGGGACAACATG

GAAACTGACACAATGTAGGAAGTCTTTTCCACATGGCAGATGATTTGGGCAGAGCGATGGAG

TCCTTAGTATCAGTCATGACAGATGAAGAAGGAGCAGAATAAATGTTTTACAACTCCTGATTC

CCGCATGCGGCCGATCCAGACATGATAAGATACATTGATGAGTTTGGACAAACCACAACTAG

AATGCAGTGAAAAAAATGCTTTATTTGTGAAATTTGTGATGCTATTGCTTTATTTGTAACCATT

ATAAGCTGCAATAAACAAGTTAACAACAACAATTGCATTCATTTTATGTTTCAGGTTCAGGGG

GAGGTGTGGGAGGTTTTTTGCGGCCGTAGATAAGTAGCATGGCGGGTTAATCATTAACTACAA

GGAACCCCTAGTGATGGAGTTGGCCACTCCCTCTCTGCGCGCTCGGTCGCTCACTGAGGCCGG

GCGACCAAAGGTCGCCCGACGCCCGGGCTTTGCCCGGGCGGCCTCAGTGAGCGAGCGAGCGC

GCAGCTGCTG
```

Human dystrophin domain sequence
SEQ ID NO: 17: N-terminal domain
```
ATGCTTTGGTGGGAAGAAGTAGAGGACTGTTATGAAAGAGAAGATGTTCAAAAGAAAACATT

CACAAAATGGGTAAATGCACAATTTTCTAAGTTTGGGAAGCAGCATATTGAGAACCTCTTCAG

TGACCTACAGGATGGGAGGCGCCTCCTAGACCTCCTCGAAGGCCTGACAGGGCAAAAACTGC
```

-continued
```
CAAAAGAAAAAGGATCCACAAGAGTTCATGGCCTGAACAATGTCAACAAGGCACTGCGGGTT

TTGCAGAACAATAATGTTGATTTAGTGAATATTGGAAGTACTGACATCGTAGATGGAAATCAT

AAACTGACTCTTGGTTTGATTTGGAATATAATCCTCCACTGGCAGGTCAAAAATGTAATGAAA

AATATCATGGCTGGATTGCAACAAACCAACAGTGAAAAGATTCTCCTGAGCTGGGTCCGACA

ATCAACTCGTAATTATCCACAGGTTAATGTAATCAACTTCACCACCAGCTGGTCTGATGGCCT

GGCTTTGAATGCTCTCATCCATAGTCATAGGCCAGACCTATTTGACTGGAATAGTGTGGTTTGC

CAGCAGTCAGCCACACAACGACTGGAACATGCATTCAACATCGCCAGATATCAATTAGGCAT

AGAGAAACTACTCGATCCTGAAGATGTTGATACCACCTATCCAGATAAGAAGTCCATCTTAAT

GTACATCACATCACTCTTCCAAGTTTTGCCTCAACAAGTGAGCATTGAAGCCATCCAGGAAGT

GGAA

SEQ ID NO: 18: Hinge 1
ATGTTGCCAAGGCCACCTAAAGTGACTAAAGAAGAACATTTTCAGTTACATCATCAAATGCAC

TATTCTCAACAGATCACGGTCAGTCTAGCACAGGGATATGAGAGAACTTCTTCCCCTAAGCCT

CGATTCAAGAGCTATGCCTACACACAGGCTGCTTATGTCACCACCTCTGACCCTACACGGAGC

CCATTTCCTTCACAGCATTTGGAAGCTCCTGAAGACAAGTCATTTGGCAGTTCATTGATGGAG

SEQ ID NO: 19: Repeat 1
AGTGAAGTAAACCTGGACCGTTATCAAACAGCTTTAGAAGAAGTATTATCGTGGCTTCTTTCT

GCTGAGGACACATTGCAAGCACAAGGAGAGATTTCTAATGATGTGGAAGTGGTGAAAGACCA

GTTTCATACTCATGAGGGGTACATGATGGATTTGACAGCCCATCAGGGCCGGGTTGGTAATAT

TCTACAATTGGGAAGTAAGCTGATTGGAACAGGAAAATTATCAGAAGATGAAGAAACTGAAG

TACAAGAGCAGATGAATCTCCTAAATTCAAGATGGGAATGCCTCAGGGTAGCTAGCATGGAA

AAACAAAGCAATTTACATAGA

SEQ ID NO: 20: Repeat 2
GTTTTAATGGATCTCCAGAATCAGAAACTGAAAGAGTTGAATGACTGGCTAACAAAAACAGA

AGAAAGAACAAGGAAAATGGAGGAAGAGCCTCTTGGACCTGATCTTGAAGACCTAAAACGCC

AAGTACAACAACATAAGGTGCTTCAAGAAGATCTAGAACAAGAACAAGTCAGGGTCAATTCT

CTCACTCACATGGTGGTGGTAGTTGATGAATCTAGTGGAGATCACGCAACTGCTGCTTTGGAA

GAACAACTTAAGGTATTGGGAGATCGATGGGCAAACATCTGTAGATGGACAGAAGACCGCTG

GGTTCTTTTACAAGAC

SEQ ID NO: 21: Repeat 3
ATCCTTCTCAAATGGCAACGTCTTACTGAAGAACAGTGCCTTTTTAGTGCATGGCTTTCAGAA

AAAGAAGATGCAGTGAACAAGATTCACACAACTGGCTTTAAAGATCAAAATGAAATGTTATC

AAGTCTTCAAAAACTGGCCGTTTTAAAAGCGGATCTAGAAAAGAAAAAGCAATCCATGGGCA

AACTGTATTCACTCAAACAAGATCTTCTTTCAACACTGAAGAATAAGTCAGTGACCCAGAAGA

CGGAAGCATGGCTGGATAACTTTGCCCGGTGTTGGGATAATTTAGTCCAAAAACTTGAAAAGA

GTACAGCACAGATTTCACAG

SEQ ID NO: 22: Hinge 1
GCTGTCACCACCACTCAGCCATCACTAACACAGACAACTGTAATGGAAACAGTAACTACGGT

GACCACAAGGGAACAGATCCTGGTAAAGCATGCTCAAGAGGAACTTCCACCACCACCTCCCC

AAAAGAAGAGGCAGATTACTGTGGAT

SEQ ID NO: 23: Repeat 4
TCTGAAATTAGGAAAAGGTTGGATGTTGATATAACTGAACTTCACAGCTGGATTACTCGCTCA

GAAGCTGTGTTGCAGAGTCCTGAATTTGCAATCTTTCGGAAGGAAGGCAACTTCTCAGACTTA
```

-continued

AAAGAAAAAGTCAATGCCATAGAGCGAGAAAAAGCTGAGAAGTTCAGAAAACTGCAAGATG

CCAGCAGATCAGCTCAGGCCCTGGTGGAACAGATGGTGAATGAGGGTGTTAATGCAGATAGC

ATCAAACAAGCCT

SEQ ID NO: 24: Repeat 5
CAGAACAACTGAACAGCCGGTGGATCGAATTCTGCCAGTTGCTAAGTGAGAGACTTAACTGG

CTGGAGTATCAGAACAACATCATCGCTTTCTATAATCAGCTACAACAATTGGAGCAGATGACA

ACTACTGCTGAAAACTGGTTGAAAATCCAACCCACCACCCCATCAGAGCCAACAGCAATTAA

AAGTCAGTTAAAAATTTGTAAGGATGAAGTCAACCGGCTATCAGGTCTTCAACCTCAAATTGA

ACGATTAAAAATTCAAAGCATAGCCCTGAAAGAGAAAGGACAAGGACCCATGTTCCTGGATG

CAGACTTTGTGGCCTTTACAAATCATTTTAAGCAAGTCTTTTCTGATGTGCAGGCCAGAGAGA

AAGAGCTACAGACA

SEQ ID NO: 25: Repeat 6
ATTTTTGACACTTTGCCACCAATGCGCTATCAGGAGACCATGAGTGCCATCAGGACATGGGTC

CAGCAGTCAGAAACCAAACTCTCCATACCTCAACTTAGTGTCACCGACTATGAAATCATGGAG

CAGAGACTCGGGGAATTGCAGGCTTTACAAAGTTCTCTGCAAGAGCAACAAAGTGGCCTATA

CTATCTCAGCACCACTGTGAAAGAGATGTCGAAGAAAGCGCCCTCTGAAATTAGCCGGAAAT

ATCAATCAGAATTTGAAGAAATTGAGGGACGCTGGAAGAAGCTCTCCTCCCAGCTGGTTGAG

CATTGTCAAAAGCTAGAGGAG

SEQ ID NO: 26: Repeat 7
CAAATGAATAAACTCCGAAAAATTCAGAATCACATACAAACCCTGAAGAAATGGATGGCTGA

AGTTGATGTTTTTCTGAAGGAGGAATGGCCTGCCCTTGGGGATTCAGAAATTCTAAAAAAGCA

GCTGAAACAGTGCAGACTTTTAGTCAGTGATATTCAGACAATTCAGCCCAGTCTAAACAGTGT

CAATGAAGGTGGGCAGAAGATAAAGAATGAAGCAGAGCCAGAGTTTGCTTCGAGACTTGAGA

CAGAACTCAAAGAACTTAACACTCAGTGGGATCACATGTGCCAACAGGTCTATGCCAGAAAG

GAGGCCTTGAAGGGA

SEQ ID NO: 27: Repeat 8
GGTTTGGAGAAAACTGTAAGCCTCCAGAAAGATCTATCAGAGATGCACGAATGGATGACACA

AGCTGAAGAAGAGTATCTTGAGAGAGATTTTGAATATAAAACTCCAGATGAATTACAGAAAG

CAGTTGAAGAGATGAAGAGAGCTAAAGAAGAGGCCCAACAAAAGAAGCGAAAGTGAAACT

CCTTACTGAGTCTGTAAATAGTGTCATAGCTCAAGCTCCACCTGTAGCACAAGAGGCCTTAAA

AAAGGAACTTGAAACTCTAACCACCAACTACCAGTGGCTCTGCACTAGGCTGAATGGGAAAT

GCAAGACTTTGGAAGAA

SEQ ID NO: 28: Repeat 9
GTTTGGGCATGTTGGCATGAGTTATTGTCATACTTGGAGAAAGCAAACAAGTGGCTAAATGAA

GTAGAATTTAAACTTAAAACCACTGAAAACATTCCTGGCGGAGCTGAGGAAATCTCTGAGGT

GCTAGATTCACTTGAAAATTTGATGCGACATTCAGAGGATAACCCAAATCAGATTCGCATATT

GGCACAGACCCTAACAGATGGCGGAGTCATGGATGAGCTAATCAATGAGGAACTTGAGACAT

TTAATTCTCGTTGGAGGGAACTACATGAAGAGGCTGTAAGGAGGCAAAAGTTGCTTGAACAG

SEQ ID NO: 29: Repeat 10
AGCATCCAGTCTGCCCAGGAGACTGAAAAAATCCTTACACTTAATCCAGGAGTCCCTCACATTC

ATTGACAAGCAGTTGGCAGCTTATATTGCAGACAAGGTGGACGCAGCTCAAATGCCTCAGGA

-continued

AGCCCAGAAAATCCAATCTGATTTGACAAGTCATGAGATCAGTTTAGAAGAAATGAAGAAAC

ATAATCAGGGGAAGGAGGCTGCCCAAAGAGTCCTGTCTCAGATTGATGTTGCACAGAAAAAA

TTACAAGATGTCTCCATGAAGTTTCGATTATTCCAGAAA

SEQ ID NO: 30: Repeat 11
CCAGCCAATTTTGAGCTGCGTCTACAAGAAAGTAAGATGATTTTAGATGAAGTGAAGATGCAC

TTGCCTGCATTGGAAACAAAGAGTGTGGAACAGGAAGTAGTACAGTCACAGCTAAATCATTG

TGTGAACTTGTATAAAAGTCTGAGTGAAGTGAAGTCTGAAGTGGAAATGGTGATAAAGACTG

GACGTCAGATTGTACAGAAAAAGCAGACGGAAAATCCCAAAGAACTTGATGAAAGAGTAAC

AGCTTTGAAATTGCATTATAATGAGCTGGGAGCAAAGGTAACAGAAAGAAAGCAACAGTTGG

AGAAA

SEQ ID NO: 31: Repeat 12
TGCTTGAAATTGTCCCGTAAGATGCGAAAGGAAATGAATGTCTTGACAGAATGGCTGGCAGCT

ACAGATATGGAATTGACAAAGAGATCAGCAGTTGAAGGAATGCCTAGTAATTTGGATTCTGA

AGTTGCCTGGGGAAAGGCTACTCAAAAAGAGATTGAGAAACAGAAGGTGCACCTGAAGAGTA

TCACAGAGGTAGGAGAGGCCTTGAAAACAGTTTTGGGCAAGAAGGAGACGTTGGTGGAAGAT

AAACTCAGTCTTCTGAATAGTAACTGGATAGCTGTCACCTCCCGAGCAGAAGAGTGGTTAAAT

CTTTTGTTGGAA

SEQ ID NO: 32: Repeat 13
TACCAGAAACACATGGAAACTTTTGACCAGAATGTGGACCACATCACAAAGTGGATCATTCA

GGCTGACACACTTTTGGATGAATCAGAGAAAAAGAAACCCCAGCAAAAGAAGACGTGCTTA

AGCGTTTAAAGGCAGAACTGAATGACATACGCCCAAAGGTGGACTCTACACGTGACCAAGCA

GCAAACTTGATGGCAAACCGCGGTGACCACTGCAGGAAATTAGTAGAGCCCCAAATCTCAGA

GCTCAACCATCGATTTGCAGCCATTTCACACAGAATTAAGACTGGAAAGGCCTCCATT

SEQ ID NO: 33: Repeat 14
CCTTTGAAGGAATTGGAGCAGTTTAACTCAGATATACAAAAATTGCTTGAACCACTGGAGGCT

GAAATTCAGCAGGGGGTGAATCTGAAAGAGGAAGACTTCAATAAAGATATGAATGAAGACA

ATGAGGGTACTGTAAAAGAATTGTTGCAAAGAGGAGACAACTTACAACAAAGAATCACAGAT

GAGAGAAAGAGAGAGGAAATAAAGATAAAACAGCAGCTGTTACAGACAAAACATAATGCTC

TCAAGGATTTGAGGTCTCAAAGAAGAAAAAAGGCTCTAGAA

SEQ ID NO: 34: Repeat 15
ATTTCTCATCAGTGGTATCAGTACAAGAGGCAGGCTGATGATCTCCTGAAATGCTTGGATGAC

ATTGAAAAAAAATTAGCCAGCCTACCTGAGCCCAGAGATGAAAGGAAATAAAGGAAATTGA

TCGGGAATTGCAGAAGAAGAAAGAGGAGCTGAATGCAGTGCGTAGGCAAGCTGAGGGCTTGT

CTGAGGATGGGGCCGCAATGGCAGTGGAGCCAACTCAGATCCAGCTCAGCAAGCGCTGGCGG

GAAATTGAGAGCAAATTTGCTCAGTTTCGAAGACTCAACTTTGCACAA

SEQ ID NO: 35: Repeat 16
ATTCACACTGTCCGTGAAGAAACGATGATGGTGATGACTGAAGACATGCCTTTGGAAATTTCT

TATGTGCCTTCTACTTATTTGACTGAAATCACTCATGTCTCACAAGCCCTATTAGAAGTGGAAC

AACTTCTCAATGCTCCTGACCTCTGTGCTAAGGACTTTGAAGATCTCTTTAAGCAAGAGGAGT

CTCTGAAGAATATAAAAGATAGTCTACAACAAAGCTCAGGTCGGATTGACATTATTCATAGCA

AGAAGACAGCAGCATTGCAAAGTGCAACGCCTGTGGAAAGGGTGAAGCTACAGGAAGCTCTC

TCCCAGCTTGATTTCCAATGGGAAAAAGTTAACAAAATGTACAAGGACCGACAAGGGCGATT

TGACAGA

-continued

SEQ ID NO: 36: Repeat 17
TCTGTTGAGAAATGGCGGCGTTTTCATTATGATATAAAGATATTTAATCAGTGGCTAACAGAA

GCTGAACAGTTTCTCAGAAAGACACAAATTCCTGAGAATTGGGAACATGCTAAATACAAATG

GTATCTTAAGGAACTCCAGGATGGCATTGGGCAGCGGCAAACTGTTGTCAGAACATTGAATGC

AACTGGGGAAGAAATAATTCAGCAATCCTCAAAAACAGATGCCAGTATTCTACAGGAAAAT

TGGGAAGCCTGAATCTGCGGTGGCAGGAGGTCTGCAAACAGCTGTCAGACAGAAAAAGAGG

CTAGAAGAA

SEQ ID NO: 37: Repeat 18
CAAAAGAATATCTTGTCAGAATTTCAAAGAGATTTAAATGAATTTGTTTTATGGTTGGAGGAA

GCAGATAACATTGCTAGTATCCCACTTGAACCTGGAAAAGAGCAGCAACTAAAAGAAAAGCT

TGAGCAAGTCAAGTTACTGGTGGAAGAGTTGCCCCTGCGCCAGGGAATTCTCAAACAATTAA

ATGAAACTGGAGGACCCGTGCTTGTAAGTGCTCCCATAAGCCCAGAAGAGCAAGATAAACTT

GAAAATAAGCTCAAGCAGACAAATCTCCAGTGGATAAAGGTTTCCAGAGCTTTACCTGAGAA

ACAAGGAGAAATTGAAGCT

SEQ ID NO: 38: Repeat 19
CAAATAAAAGACCTTGGGCAGCTTGAAAAAAAGCTTGAAGACCTTGAAGAGCAGTTAAATCA

TCTGCTGCTGTGGTTATCTCCTATTAGGAATCAGTTGGAAATTTATAACCAACCAAACCAAGA

AGGACCATTTGACGTTCAGGAAACTGAAATAGCAGTTCAAGCTAAACAACCGGATGTGGAAG

AGATTTTGTCTAAAGGGCAGCATTTGTACAAGGAAAAACCAGCCACTCAGCCAGTGAAGAGG

AAGTTAGAAGATCTGAGCTCTGAGTGGAAGGCGGTAAACCGTTTACTTCAAGAGCTGAGGGC

AAAG

SEQ ID NO: 39: Hinge 3
CAGCCTGACCTAGCTCCTGGACTGACCACTATTGGAGCCTCTCCTACTCAGACTGTTACTCTGG

TGACACAACCTGTGGTTACTAAGGAAACTGCCATCTCCAAACTAGAAATGCCATCTTCCTTGA

TGTTGGAGGTACCT

SEQ ID NO: 40: Repeat 20
GCTCTGGCAGATTTCAACCGGGCTTGGACAGAACTTACCGACTGGCTTTCTCTGCTTGATCAA

GTTATAAAATCACAGAGGGTGATGGTGGGTGACCTTGAGGATATCAACGAGATGATCATCAA

GCAGAAGGCAACAATGCAGGATTTGGAACAGAGGCGTCCCCAGTTGGAAGAACTCATTACCG

CTGCCCAAAATTTGAAAAACAAGACCAGCAATCAAGAGGCTAGAACAATCATTACGGATCGA

ATTGAAAGAATTCAGAATCAGTGGGATGAAGTACAAGAACACCTTCAGAACCGGAGGCAACA

GTTGAATGAA

SEQ ID NO: 41: Repeat 21
ATGTTAAAGGATTCAACACAATGGCTGGAAGCTAAGGAAGAAGCTGAGCAGGTCTTAGGACA

GGCCAGAGCCAAGCTTGAGTCATGGAAGGAGGGTCCCTATACAGTAGATGCAATCCAAAAGA

AAATCACAGAAACCAAGCAGTTGGCCAAAGACCTCCGCCAGTGGCAGACAAATGTAGATGTG

GCAAATGACTTGGCCCTGAAACTTCTCCGGGATTATTCTGCAGATGATACCAGAAAAGTCCAC

ATGATAACAGAGAATATCAATGCCTCTTGGAGAAGCATTCATAAAAGGGTGAGTGAGCGAGA

GGCTGCTTTGGAAGAA

SEQ ID NO: 42: Repeat 22
ACTCATAGATTACTGCAACAGTTCCCCCTGGACCTGGAAAAGTTTCTTGCCTGGCTTACAGAA

GCTGAAACAACTGCCAATGTCCTACAGGATGCTACCCGTAAGGAAAGGCTCCTAGAAGACTC

CAAGGGAGTAAAAGAGCTGATGAAACAATGGCAAGACCTCCAAGGTGAAATTGAAGCTCACA

-continued

CAGATGTTTATCACAACCTGGATGAAAACAGCCAAAAAATCCTGAGATCCCTGGAAGGTTCC

GATGATGCAGTCCTGTTACAAAGACGTTTGGATAACATGAACTTCAAGTGGAGTGAACTTCGG

AAAAAGTCTCTCAACATTAGGTCCCATTTGGAAGCC

SEQ ID NO: 43: Repeat 23
AGTTCTGACCAGTGGAAGCGTCTGCACCTTTCTCTGCAGGAACTTCTGGTGTGGCTACAGCTG

AAAGATGATGAATTAAGCCGGCAGGCACCTATTGGAGGCGACTTTCCAGCAGTTCAGAAGCA

GAACGATGTACATAGGGCCTTCAAGAGGGAATTGAAAACTAAAGAACCTGTAATCATGAGTA

CTCTTGAGACTGTACGAATATTTCTGACAGAGCAGCCTTTGGAAGGACTAGAGAAACTCTACC

AGGAGCCCAGAGAGCTGCCTCCTGAGGAGAGCCCAGAATGTCACTCGGCTTCTACGAAAG

CAGGCTGAGGAGGTCAATACTGAGTGGGAAAAATTGAACCTGCACTCCGCTGACTGGCAGAG

AAAAATAGATGAG

SEQ ID NO: 44: Repeat 24
ACCCTTGAAAGACTCCAGGAACTTCAAGAGGCCACGGATGAGCTGGACCTCAAGCTGCGCCA

AGCTGAGGTGATCAAGGGATCCTGGCAGCCCGTGGGCGATCTCCTCATTGACTCTCTCCAAGA

TCACCTCGAGAAAGTCAAGGCACTTCGAGGAGAAATTGCGCCTCTGAAAGAACGTGAGCC

ACGTCAATGACCTTGCTCGCCAGCTTACCACTTTGGGCATTCAGCTCTCACCGTATAACCTCAG

CACTCTGGAAGACCTGAACACCAGATGGAAGCTTCTGCAGGTGGCCGTCGAGGACCGAGTCA

GGCAGCTGCATGAA

SEQ ID NO: 45: Hinge 4
GCCCACAGGGACTTTGGTCCAGCATCTCAGCACTTTCTTTCCACGTCTGTCCAGGGTCCCTGGG

AGAGAGCCATCTCGCCAAACAAAGTGCCCTACTATATCAACCACGAGACTCAAACAACTTGCT

GGGACCATCCCAAAATGACAGAGCTCTACCAGTCTTTAGCTGACCTGAATAATGTCAGATTCT

CAGCTTATAGGACTGCCATGAAACTC

SEQ ID NO: 46: Cysteine-rich domain
CGAAGACTGCAGAAGGCCCTTTGCTTGGATCTCTTGAGCCTGTCAGCTGCATGTGATGCCTTG

GACCAGCACAACCTCAAGCAAAATGACCAGCCCATGGATATCCTGCAGATTATTAATTGTTTG

ACCACTATTTATGACCGCCTGGAGCAAGAGCACAACAATTTGGTCAACGTCCCTCTCTGCGTG

GATATGTGTCTGAACTGGCTGCTGAATGTTTATGATACGGGACGAACAGGGAGGATCCGTGTC

CTGTCTTTTAAAACTGGCATCATTTCCCTGTGTAAAGCACATTTGGAAGACAAGTACAGATAC

CTTTTCAAGCAAGTGGCAAGTTCAACAGGATTTTGTGACCAGCGCAGGCTGGGCCTCCTTCTG

CATGATTCTATCCAAATTCCAAGACAGTTGGGTGAAGTTGCATCCTTTGGGGGCAGTAACATT

GAGCCAAGTGTCCGGAGCTGCTTCCAATTTGCTAATAATAAGCCAGAGATCGAAGCGGCCCTC

TTCCTAGACTGGATGAGACTGGAACCCCAGTCCATGGTGTGGCTGCCCGTCCTGCACAGAGTG

GCTGCTGCAGAAACTGCCAAGCATCAGGCCAAATGTAACATCTGCAAAGAGTGTCCAATCATT

GGATTCAGGTACAGGAGTCTAAAGCACTTTAATTATGACATCTGCCAAAGCTGCTTTTTTTCTG

GTCGAGTTGCAAAAGGCCATAAAATGCACTATCCCATGGTGGAATATTGCACTCCGACTACAT

CAGGAGAAGATGTTCGAGACTTTGCCAAGGTACTAAAAAACAAATTTCGAACCAAAAGGTAT

TTTGCGAAGCATCCCCGAATGGGCTACCTGCCAGTGCAGACTGTCTTAGAGGGGACAACATG

GAAACT

SEQ ID NO: 47: C-terminal domain
CCCGTTACTCTGATCAACTTCTGGCCAGTAGATTCTGCGCCTGCCTCGTCCCCTCAGCTTTCAC

ACGATGATACTCATTCACGCATTGAACATTATGCTAGCAGGCTAGCAGAAATGGAAAACAGC

AATGGATCTTATCTAAATGATAGCATCTCTCCTAATGAGAGCATAGATGATGAACATTTGTTA

-continued

ATCCAGCATTACTGCCAAAGTTTGAACCAGGACTCCCCCCTGAGCCAGCCTCGTAGTCCTGCC

CAGATCTTGATTTCCTTAGAGAGTGAGGAAAGAGGGGAGCTAGAGAGAATCCTAGCAGATCT

TGAGGAAGAAAACAGGAATCTGCAAGCAGAATATGACCGTCTAAAGCAGCAGCACGAACAT

AAAGGCCTGTCCCCACTGCCGTCCCCTCCTGAAATGATGCCCACCTCTCCCCAGAGTCCCCGG

GATGCTGAGCTCATTGCTGAGGCCAAGCTACTGCGTCAACACAAAGGCCGCCTGGAAGCCAG

GATGCAAATCCTGGAAGACCACAATAAACAGCTGGAGTCACAGTTACACAGGCTAAGGCAGC

TGCTGGAGCAACCCGAGGCAGAGGCCAAAGTGAATGGCACAACGGTGTCCTCTCCTTCTACCT

CTCTACAGAGGTCCGACAGCAGTCAGCCTATGCTGCTCCGAGTGGTTGGCAGTCAAACTTCGG

ACTCCATGGGTGAGGAAGATCTTCTCAGTCCTCCCCAGGACACAAGCACAGGGTTAGAGGAG

GTGATGGAGCAACTCAACAACTCCTTCCCTAGTTCAAGAGGAAGAAATACCCCTGGAAAGCC

AATGAGAGAGGACACAATGTAG

SEQ ID NO: 48: Full-length canine dystrophin DNA sequence
ATGCTTTGGTGGGAAGAAGTAGAGGACTGTTATGAAAGAGAAGATGTTCAAAAGAAAACATT

CACAAAATGGGTAAATGCACAGTTTTCTAAGTTTGGGAAGCAGCACATAGAGAACCTCTTCAG

TGACCTACAGGATGGGAGACGCCTCCTAGACCTTTTGGAAGGCCTGACAGGGCAAAAACTGC

CAAAAGAAAAAGGATCCACAAGAGTTCATGCCCTGAACAATGTCAACAAGGCACTGCGCGTC

TTGCAGAAAAATAATGTTGATTTAGTGAACATTGGAAGTACTGACATAGTAGATGGAAATCAC

AAACTGACTCTTGGTTTGATTTGGAATATAATCCTCCACTGGCAGGTCAAAAATGTAATGAAA

AATATCATGGCTGGATTGCAACAAACCAACAGTGAAAAGATTCTCCTGAGCTGGGTCCGACA

ATCAACTCGTAATTATCCACAGGTTAATGTCATTAACTTCACCACCAGCTGGTCTGATGGCCTG

GCTTTGAACGCTCTCATCCACAGTCATAGGCCAGACCTGTTTGATTGGAATAGTGTGGTTTGCC

AGCAGTCAGCCACACAACGCCTGGAACATGCATTCAACATTGCCAAATATCAATTAGGCATA

GAGAAACTGCTTGATCCTGAAGATGTTGCCACCACTTATCCAGATAAGAAGTCCATCTTAATG

TATATCACATCACTCTTCCAAGTTTTGCCTCAACAAGTGAGCATTGAAGCCATCCAGGAAGTG

GAAATGTTGCCAAGGCCATCTCAAGTTACTAGAGAAGAACATTTTCAGATACATCATCAAATG

CACTATTCTCAACAGATCACAGTCAGTCTAGCACAGGGATATGAACGAGCCCCTTCCTTTCCT

AAGCCTCGGTTCAAGAGCTATGCCTACACACAGGCTGCTTATGTCACCACTTCTGACCCCACA

CGGAGCCCACTTCCTTCACAGCATTTGGAAACTCCTGAAGACAAGTCATTTGGCCGGTCATTG

ACAGAGACCGAAGCAAACCTGGACAGTTATCAAACAGCTTTGGAAGAAGTACTCTCGTGGCT

TCTTTCAGCTGAGGATGCACTGCAAGCCCAAGGAGAGATTTCTAATGATGTCGAAGAAGTGA

AAGAACAATTTCATACTCATGAGGGATATATGATGGACTTGACATCCCATCAGGGACGGGTCG

GTAATGTTCTCCAACTGGGAAGTCAACTGATTGGAACAGGGAAATTATCAGAAGATGAAGAA

ACCGAAGTGCAGGAACAAATGAATCTCCTCAATTCAAGATGGGAATGCCTCAGGGTAGCTAG

CATGGAAAAACAAAGCAATTTACATAAAGTTCTAATGGATCTCCAGAATCAGCAACTGAAAG

AGTTAAATGACTGGCTAACCAAACAGAAGAGAGAACAAGGAAAATGGAGAAGGAGCCCCT

TGGACCTGATATTGAAGACCTAAAACGCCAAGTACAACAACATAAGGTGCTTCAAGAAGACT

TAGAACAGGAACAAGTCAGGGTCAATTCCCTCACTCATATGGTGGTGGTAGTCGATGAATCTA

GTGGAGACCATGCAACTGCTGCTTTGGAAGAACAACTTAAGGTACTGGGAGATCGATGGGCA

AACATCTGTAGGTGGACAGAAGATCGCTGGGTTCTTTTACAAGACATCCTCCTAAAATGGCAG

CGTTTTACTGAAGAACAGTGCCTTTTTAGTGCATGGCTTTCGGAGAAGGAAGATGCAGTGAAC

-continued

```
AAGATTCACACAACTGGCTTTAAGGATCAAAGTGAAGTGTTATCAAATCTTCAGAAACTGGCT
GTCTTAAAAACAGATCTGGAAAAGAAGAAGCAAACCATGGACAAACTCTGCTCACTCAACCA
AGACCTTCTTTCAGCGCTGAAAAACACAGTGGTAGCCCACAAGATGGAAGCATGGCTGGACA
ACTTTGCCCAGCGCTGGGATAATTTAGTCCAGAAACTTGAAAAAAGTTCAGCACAGATTTCAC
AGGCTGTCACCACCACTCAGCCATCACTAACACAGACAACTGTAATGGAAACAGTAACTATG
GTGACCACGAGGGAACACATCTTGGTAAAGCATGCCCAAGAGGAACTGCCACCACCACCCCC
TCAGAAGAAGAGGCAGATTATCGTGGATTCTGAAATTAGGAAAAGGTTGGATGTCGATATAA
CTGAACTTCACAGTTGGATTACTCGTTCAGAAGCTGTGTTGCAGAGTCCTGAATTTGCAATCTA
TCGGAAGGAAGGCAACTTCTCAGACCTTAAAGAAAAAGTCAATGCCATAGAGCGAGAAAAAG
CCGAGAAGTTCAGAAAACTGCAAGATGCCAGCAGATCAGCTCAGGCCCTGGTGGAACAGATG
GTGAATGAGGGTGTTAATGCTGACAGCATCAAACAAGCCTCCGAACAACTGAACAGCCGGTG
GATAGAGTTCTGCCAATTGCTAAGCGAGAGACTTAACTGGCTGGAGTATCAGAACAACATCAT
CACTTTCTATAATCAGCTACAACAATTGGAGCAGATGACAACTACTGCTGAAAACTGGTTGAA
AACCCAGCCTACCACCACATCAGAGCCAACAGCAATTAAAAGCCAGTTAAAAATTTGTAAGG
ATGAAATCAACCGACTGTCAGCTCTTCAGCCTCAAATCGAGCGATTAAAAATTCAAAGCATAG
CCCTGAAAGAGAAAGGACAAGGGCCAATGTTCCTGGATGCAGACTTTGTGGCCTTTACAAATC
ATTTTAACCAAGTCTTTGCTGATGTGCAGGCAAGAGAAAAAGAGCTACAAACAATTTTTGACA
GTTTGCCACCCATGCGCTATCAGGAGACTATGAGTACCATCCTGACATGGATCCAGCAGTCAG
AAACCAAACTCTCTATACCTCAGGTTACTGTCACTGAATATGACATCATGGAACAGAGACTCG
GAGAGCTACAGGCTTTACAAAGCTCTCTGCAAGAGCAACAAAATGGCCTAAACTATCTCAGC
ACCACTGTGAAAGAGATGTCAAAGAAAGCACCACTGTCTGATATTAGTCGGAAATATCAATC
AGAATTTGAAGAGATTGAGGGACGTTGGAAGAAGCTGTCTTCCCAGCTGGTTGAACATTGTCA
AAAGTTGGAGGAGCAAATGGCTAAACTTCGAAAAATTCAGAATCACATAAAAACTCTGAAGA
AATGGATCACTGAAGTCGATGTTTTCCTGAAGGAGGAATGGCCTGCCCTTGGGGATTCAGAAA
TTCTGAAAAGACAGCTGAAACAGTGCAGGCTTTTAGTCAATGACATTCAGACCATCCAGCCTA
GTCTCAACAGTGTCAATGAAGGGGCTCAGAAGATGAAGAATGAAGCAGAACCAGAGTTTGCT
GGCAGACTTGAGACAGAGCTCCGAGAACTTAACACCCAGTGGGATTACATGTGCCGCCAGGT
CTATGCCAGGAAGGAAGCCTTAAAAGGAGGTTTTGGATAAAACTGTAAGTCTTCAGAAAGATC
TGTCAGAGATGCATGAGTGGATGACACAAGCTGAAGAAGAATACCTAGAGAGAGATTTCGAA
TACAAGACCCCTGATGAATTACAGACAGCAGTTGAAGAGATGAAGAGAGCTAAAGAAGAGG
CCCAGCAAAAAGAAGCAAAAGTGAAACTCCTAACCGAGTCCGTCAATAGTGTCATAGCTCAG
GCTCCACCTGCAGCACAAGAGGCCTTAAAAAAGGAACTTGACACTCTCACCACCAACTACCA
GTGGCTCTGCACCAGGCTCAATGGCAAATGCAAGACCTTGGAAGAAGTTTGGGCGTGCTGGC
ATGAGTTATTGTCCTACTTGGAGAAGGCAAACAAGTGGCTAAGTGAAGTAGAAGTCAAGCTT
AAAACCACTGAAAATATTTCTGGGGGAGCTGAGGAAATCGCCGAGGTGCTTGATTCGCTTGA
AAATTTGATGCAACATTCAGAGGATAACCCGAATCAGATTCGCATATTGGCACAGACCTTGAC
AGATGGTGGAGTCATGGATGAACTGATCAATGAGGAGCTTGAGACATTTAATTCTCGTTGGAG
AGAACTCCATGAAGAGGCTGTGAGGAGGCAAAAGTTGCTTGAGCAGAGTATCCAGTCGGCCC
AGGAGATAGAAAAATCCTTGCACTTAATTCAGGAGTCCCTCTCTTCCATTGACAAGCAGTTGG
CAGCTTATATTGCTGACAAAGTGGATGCAGCTCAGATGCCTCAGGAAGCCCAGAAAATCCAA
```

-continued

```
TCAGATTTGACAAGTCATGAGATCAGTTTAGAAGAAATGAAGAAACATAACCAGGGAAAGGA
GACTGCCCAAAGGGTACTATCCCAAATTGATGTGGCACAGAAAAAATTGCAGGATGTTTCCAT
GAAGTTTCGATTATTCCAGAAGCCAGCCAATTTTGAGCAGCGCCTACAAGAAAGTAAAATGAT
TTTAGATGAAGTGAAGATGCATTTACCTGCGTTGGAAACAAAGAGTGTGGAACAGGAAGTAG
TACAGTCACAGTTAAATCATTGTGTGAACTTGTATAAAAGTCTGAGTGAAGTGAAGTCTGAAG
TGGAAATGGTAATAAAAACTGGACGTCAGATTGTACAGAAGAAGCAGACGGAAAACCCGAA
AGAGCTTGATGAAGAGTTACAGCTTTGAAATTGCATTATAATGAGCTGGGAGCAAAGGTGA
CAGAAAGAAAGCAACAGTTGGAAAAATGCTTGAAATTGTCCCGTAAGATGCGAAAGGAAATG
AATGCCCTGACAGAATGGCTGGCAGCTACAGATATGGAACTGACAAAGAGATCGGCAGTTGA
AGGAATGCCTAGTAATTTGGATTCTGAAGTTGCCTGGGGAAAGGCTACTCAGAAAGAGATTG
AGAAACAGAAGGTTCACCTAAAGAGTGTCACAGAGGTAGGAGAGGCCTTGAAAACGGTTTTG
GGCAAGAAGGAAATGTTGGTGGAAGATAAACTGAGTCTTCTGAATAGTAACTGGATAGCCGT
CACTTCCCGAGCAGAAGAGTGGTTAAACCTTTTATTGGAATACCAGAAACACATGGAAACTTT
TGACCAGAATGTGGATTACATCACAAACTGGATCATTCAGGCTGATGCACTTTTGGATGAATC
TGAGAAAAAGAAACCTCAGCAAAAAGAAGACATACTTAAGCGTTTAAAGGCTGAAATGAATG
ACATACGTCCAAAGGTGGATTCTACACGTGACCAAGCAGCAAACCTGATGGCAAACCGCGGC
GACCACTGCAGGAAAGTAGTAGAGCCCAAAATCTCAGAGCTCAACCATCGATTTGCAGCCAT
TTCTCACAGAATTAAGACTGGAAAGGCCTCCATTCCTTTGAAGGAATTGGAGCAGTTTAACTC
AGATATACAAAAATTGCTTGAACCACTGGAGGCTGAAATTCAGCAGGGGTGAATCTGAAAG
AGGAAGACTTCAATAAAGATATGAGTGAAGACAATGAGGGTACTGTAAAAGAATTGTTGCAA
AGAGGAGACAACTTACAACAAAGAATCACAGATGAGAGAAAGCGAGAGGAAATAAAGATAA
AACAACAGCTGTTACAGACAAAACATAATGCTCTCAAGGATTTGAGGTCTCAAAGAAGAAAA
AAGGCTCTAGAAATTTCTCACCAGTGGTATCAGTACAAGAGGCAGGCTGATGATCTCCTGAAA
TGCTTGGATGACATTGAAAAAAAATTAGCCAGCCTACCTGAACCCAGAGATGAAAGGAAAAT
AAAGGAAATTGATCGTGAATTGCAGAAGAAGAAAGAGGAGCTGAATGCAGTGCGTAGGCAA
GCTGAGGGCTTGTCTGAGGATGGGGCCGCAATGGCAGTGGAGCCAACTCAGATCCAGCTCAG
CAAGCGCTGGCGGGAAATTGAGAGCAAATTTGCTCAGTTTCGAAGACTCAACTTTGCACAAAT
TCACACTGTCCATGAAGAGTCAGTGGTGGCGATGACTGAAGACATGCCTTTGGAAATTTCTTA
TGTGCCTTCTACTTACCTGACTGAGATCACTCATGTCTCACAAGCCCTATCAGAAGTGGAAGA
GCTTCTTAATGCTCCCGACCTTTGTGCTCAAGATTTTGAAGATCTCTTTAAACAAGAGGAATCC
TTGAAGAACATAAAAGACAGCCTGCAACAAATCTCAGGTCGGATTGACATCATTCACAATAA
AAAGACAGCAGCATTGCACAGTGCCACTCCTGCAGAAAGGGCAAAGCTCCAGGAAGCTCTCT
CACGGCTTGATTTCCAATGGGAAAGAGTTAACAATATGTACAAGGACCGACAAGGGAGATTT
GACAGATCTGTGGAAAAATGGCGGCGGTTTCATTATGATATGAAGATACTTAATCAATGGCTA
ACAGAAGCTGAACAGTTTCTCAAAAAGACACAAATTCCTGAGAATTGGGAACATGCCAAATA
CAAATGGTATCTTAAGGAACTCCAGGATGGCATTGGACAGCGGCAAAGTGTTGTCAGGGTATT
GAATGCAACTGGGGAAGAAATAATTCAACAGTCCTCAAAAACAGATGCCAGTATTCTCCAAG
AAAAACTGGGAAGCCTGAATCTGCGGTGGCAGGAGGTCTGCAAACAGCTGGCAGAAAGAAA
AAAGAGGCTAGAGGAACAGAAGAATATCTTGTCAGAATTTCAAAGAGATGTAAATGAATTTG
TTTTATGGTTGGAAGAAGCGGATAACGTTGCTAATATTCCACTTGAACCTGGAAATGAGCAGC
```

-continued

```
AGCTAAAAGAAAAACTTGAACAAGTCAAGTTACTGGCAGAAGAGTTGCCCCTGCGCCAGGGA
ATTCTAAAACAATTAAATGAAACTGGAGGAACAGTGCTTGTAAGTGCTCCCCTAAGCCCAGA
AGAGCAAGATAAACTTGAAAATAAGCTCAAGCAGACAAATCTTCAGTGGATAAAGGTTTCTA
GAAATCTGCCTGAGAAGCAAGAAGAAATTGAGGCACACGTAAAAGACCTTGGACAGCTGGAA
GAGCAGTTAAATCATCTGCTTCTATGGCTGTCTCCTATTAGGAATCAGTTGGAAATTTACAATC
AGCCAAATCAAACAGGACCATTTGACATCAAGGAAATTGAAGTAGCAGTTCAAGCTAAACAG
CCGGATGTGGAAGGGATTTTGTCTAAAGGGCAGCATTTGTACAAGGAAAAACCAGCCACTCA
GCCAGCGAAGAGAAAGCTGGAAGATCTCAGCTCTGATTGGAAGGTGGTAACTCAGTTGCTTC
AAGAGCTGCGGGCAAAGCAACCTGGCCCAGCTCCTGGACTGACCACTGTCAGAGCCCCTCCC
AGTCAGACTGTTACTCTGGTGACACAACCCGCGGTTACCAAGGAAACTGCCATCTCCAAACTA
GAAATGCCATCTTCATTGCTGTTGGAGGTACCTGCACTGGCAGATTTCAACCGAGCTTGGACA
GAACTTACCGACTGGCTGTCTCTGCTTGATCGAGTTATAAAATCACAGAGGGTGATGGTGGGT
GATCTTGAAGACATTAACGAGATGATCATCAAGCAGAAGGCAACGCTGCAGGATTTGGAACA
GAGGCGCCCCCAGTTGGAAGAACTCATTACCGCTGCCCAGAATTTGAAAAACAAGACCAGCA
ATCAAGAGGCTAGAACAATCATTACTGATCGAATTGAAAGAATTCAGAGTCAGTGGGATGAA
GTACAGGAACATCTTCAGAACCGGAGGCTACAGTTGACTGAAATGTTAAAGGATTCCACACA
ATGGCTGGAAGCTAAAGAGGAGGCTGAGCAGGTGTTGGGGCAGGCCAGAGCCAAGCTTGAGT
CATGGAAGGAGGCTCCCTACACAGTAGATGCAATCCAAAAGAAAATCACAGAAACCAAGCAG
TTGGCCAAAGACCTCCGCCAGTGGCAGATAAATGTAGATGTTGCAAATGATTTGGCACTGAAA
CTTCTCCGAGATTATTCTGCAGATGATACCAGAAAAGTACACATGATAACAGAGAACATCAAT
GCCTCTTGGGCAAGCATCCATAAAAGATTGAGTGAGCGAGAGGCTGCTCTGGAAGAAACCCA
CAGATTACTGCAACAGTTCCCCTTGGACCTGGAGAAGTTCCTTGCCTGGCTTACAGAAGCCGA
AACAACTGCCAACGTCCTGCAGGATGCCACCCATAAGGAAAGGCTTCTAGAAGATTCCAAGG
GAGTAAGAGAGCTGATGAAACAATGGCAAGACCTCCAAGGAGAAATCGAAGCTCACACAGA
TATCTATCACAACCTGGACGAAAATGGCCAAAAAGTCCTGAGATCCCTGGAAGGTTCTGACG
ATGCAGCCTTGTTGCAAAGACGTTTGGATAACATGAACTTCAAGTGGAGCGAACTTCGGAAA
AAGTCTCTCAACATTAGGTCTCACTTGGAAGCCAGTTCTGACCAGTGGAAGCGTCTGCACCTT
TCTCTTCAGGAACTTCTGGTATGGCTCCAGCTGAAAGATGATGAGTTAAGCCGGCAGGCACCC
ATTGGAGGAGACTTTCCAGCGGTGCAGAAGCAGAATGATGTACACAGGGCCTTCAAGAGGGA
ATTGAAAACGAAAGAACCTGTAATCATGAGTACTCTTGAGACTGTACGAATATTTCTGACAGA
GCAGCCTTTAGAAGGACTAGAGAAACTCTACCAGGAGCCCAGAGAGCTGCCTCCTGAAGAGA
GAGCCCAGAATGTCACACGGCTCCTACGAAAGCAAGCTGAGGAGGTCAACACTCAGTGGGAA
AAACTGAACGTGCACTCTGCAGACTGGCAGAGAAAAATAGACGAGGCCCTCGAAAGACTCCA
GGAGCTTCAGGAAGCAACAGATGAGCTGGATCTCAAACTACGTCAGGCAGAGGTGATCAAAG
GATCCTGGCAGCCTGTGGGTGACCTCCTCATTGACTCTCTCCAAGATCACCTCGAAAAAGTCA
AGGCGCTTCGAGGAGAAATTACACCTCTGAAAGAGAATGTCAGCTACGTCAATGACCTTGCTC
GCCAACTCACTACGTTGGGCATTCAGCTGTCACCATATAACCTCAACACTCTGGAAGACCTGA
ACACCAGATGGAAGCTTCTGCAGGTGGCCATTGAGGACCGCATCAGGCAGCTGCATGAAGCG
CACAGGGACTTTGGACCAGCCTCCCAGCACTTCCTTTCCACTTCTGTCCAGGGTCCCTGGGAG
AGAGCCATCTCACCAAACAAAGTGCCCTACTATATCAACCACGAGACCCAAACAACTTGCTG
```

-continued

```
GGACCATCCCAAAATGACAGAGCTCTACCAGTCTTTAGCTGACCTGAATAATGTCAGGTTCTC
AGCTTACAGGACTGCCATGAAACTCCGAAGACTGCAGAAGGCCCTTTGCTTGGATCTCTTGAG
CCTATCGGCTGCATGCGATGCCTTGGACCAGCACAACCTCAAGCAAAATGACCAGCCCATGG
ATATCCTGCAGGTCATTAACTGTCTGACCACTATTTATGATCGCCTAGAGCAAGAGCACAACA
ATCTGGTCAACGTCCCTCTCTGCGTGGATATGTGTCTCAATTGGCTGCTGAATGTTTATGACAC
GGGACGAACGGGGAGGATCCGGGTCCTGTCTTTTAAAACTGGCATCATTTCTCTGTGTAAAGC
CCATTTGGAAGACAAGTACAGATACCTCTTCAAGCAAGTGGCAAGTTCGACAGGATTTTGTGA
CCAGCGCAGGCTGGGCCTCCTCCTGCATGACTCTATCCAGATCCCAAGACAGTTGGGTGAAGT
CGCATCGTTCGGGGGCAGTAACATTGAGCCGAGTGTCAGGAGCTGCTTCCAGTTTGCTAATAA
TAAGCCTGAGATCGAAGCGGCCCTCTTCCTAGACTGGATGCGCCTGGAGCCCCAGTCCATGGT
GTGGCTGCCTGTCCTGCACCGAGTGGCTGCCGCGGAAACTGCCAAGCACCAGGCCAAGTGCA
ACATCTGCAAGGAGTGTCCCATCATCGGATTCAGGTACAGGAGTCTAAAGCACTTTAATTATG
ACATCTGGCAAAGTTGCTTTTTTTCTGGTCGAGTTGCAAAAGGCCATAAAATGCACTATCCCAT
GGTGGAATACTGCACTCCGACTACATCGGGAGAAGATGTCCGTGACTTTGCCAAGGTACTAAA
AAACAAATTTCGAACCAAAAGGTATTTTGCGAAGCATCCCCGAATGGGCTACCTGCCAGTGCA
GACTGTCTTAGAGGGGACAACATGGAAACTCCTGTCACTCTGATCAACTTCTGGCCGGTAGA
TTCTGCGCCTGCCTCGTCCCCTCAGCTTTCACACGATGATACTCATTCACGCATTGAGCATTAT
GCTAGCAGGCTAAAAAAAATGGAAAACAGCAATGGATCTTATCTAAATGATAGCATCTCTCCT
AATGAGAGCATAGATGATGAACATTTGTTAATCCAGCATTACTGGCGAAGTTTGAACCAGGA
ATCCCCCCTGAGCCAGCCTCGTAGTCCTGCCCAGATCTTGATTTCCTTAGAGAGTGAGGAAAG
AGGGGAGCTAGAGAGAATCCTAGCAGATCTTGAGGGGAGAAACAGAAATCTGCAAGCAGAG
TATGATCGTCTAAAGCAGCAGCATGAACACAAAGGCCTGTCCCCACTGCCATCCCCTCCTGAA
ATGATGCCTACTTCTCCCCAAAGTCCCCGGGATGCTGAGCTCATCGCTGAGGCCAAGCTGCTG
CGTCAACACAAAGGCCGCCTGGAAGCCAGGATGCAAATCCTTGAAGACCATAACAAACAACT
GGAATCCCAGTTACACAGGCTCAGGCAGCTGCTGGAGCAACCCCAGGCAGAGGCCAAGGTGA
ATGGTACAACGGTGTCTTCTCCTTCTACCTCTCTTCAGAGGTCAGATAGCAGTCAGCCTATGCT
GCTCCGGGTGGTCGGCAGTCAGACTTCAGAATCCATGGGCGAGGAAGACCTGCTCAGCCCTCC
CCAGGACACAAGCACAGGGTTAGAGGAAGTGATGGAGCAGCTCAACCACTCCTTCCCTAGTT
CCAGAGGAAGAAATACCCCTGGGAAGCCAATGAGAGAGGACACAATGTAG
```

SEQ ID NO: 49: Full-length canine dystrophin protein sequence

```
MLWWEEVEDCYEREDVQKKTFTKWVNAQFSKFGKQHIENLFSDLQDGRRLLDLLEGLTGQ
KLPKEKGSTRVHALNNVNKALRVLQKNNVDLVNIGSTDIVDGNHKLTLGLIWNIILHWQV
KNVMKNIMAGLQQTNSEKILLSWVRQSTRNYPQVNVINFTTSWSDGLALNALIHSHRPDL
FDWNSVVCQQSATQRLEHAFNIAKYQLGIEKLLDPEDVATTYPDKKSILMYITSLFQVLP
QQVSIEAIQEVEMLPRPSQVTREEHFQIHHQMHYSQQITVSLAQGYERAPSFPKPRFKSY
AYTQAAYVTTSDPTRSPLPSQHLETPEDKSFGRSLTETEANLDSYQTALEEVLSWLLSAE
DALQAQGEISNDVEEVKEQFHTHEGYMMDLTSHQGRVGNVLQLGSQLIGTGKLSEDEETE
VQEQMNLLNSRWECLRVASMEKQSNLHKVLMDLQNQQLKELNDWLTKTEERTRKMEKEPL
GPDIEDLKRQVQQHKVLQEDLEQEQVRVNSLTHMVVVVDESSGDHATAALEEQLKVLGDR
WANICRWTEDRWVLLQDILLKWQRFTEEQCLFSAWLSEKEDAVNKIHTTGFKDQSEVLSN
LQKLAVLKTDLEKKKQTMDKLCSLNQDLLSALKNTVVAHKMEAWLDNFAQRWDNLVQKLE
```

-continued

```
KSSAQISQAVTTTQPSLTQTTVMETVTMVTTREHILVKHAQEELPPPPPQKKRQIIVDSE

IRKRLDVDITELHSWITRSEAVLQSPEFAIYRKEGNFSDLKEKVNAIEREKAEKFRKLQD

ASRSAQALVEQMVNEGVNADSIKQASEQLNSRWIEFCQLLSERLNWLEYQNNIITFYNQL

QQLEQMTTTAENWLKTQPTTTSEPTAIKSQLKICKDEINRLSALQPQIERLKIQSIALKE

KGQGPMFLDADFVAFTNHFNQVFADVQAREKELQTIFDSLPPMRYQETMSTILTWIQQSE

TKLSIPQVTVTEYDIMEQRLGELQALQSSLQEQQNGLNYLSTTVKEMSKKAPLSDISRKY

QSEFEEIEGRWKKLSSQLVEHCQKLEEQMAKLRKIQNHIKTLKKWITEVDVFLKEEWPAL

GDSEILKRQLKQCRLLVNDIQTIQPSLNSVNEGAQKMKNEAEPEFAGRLETELRELNTQW

DYMCRQVYARKEALKGGLDKTVSLQKDLSEMHEWMTQAEEEYLERDFEYKTPDELQTAVE

EMKRAKEEAQQKEAKVKLLTESVNSVIAQAPPAAQEALKKELDTLTTNYQWLCTRLNGKC

KTLEEVWACWHELLSYLEKANKWLSEVEVKLKTTENISGGAEEIAEVLDSLENLMQHSED

NPNQIRILAQTLTDGGVMDELINEELETFNSRWRELHEEAVRRQKLLEQSIQSAQEIEKS

LHLIQESLSSIDKQLAAYIADKVDAAQMPQEAQKIQSDLTSHEISLEEMKKHNQGKETAQ

RVLSQIDVAQKKLQDVSMKFRLFQKPANFEQRLQESKMILDEVKMHLPALETKSVEQEVV

QSQLNHCVNLYKSLSEVKSEVEMVIKTGRQIVQKKQTENPKELDERVTALKLHYNELGAK

VTERKQQLEKCLKLSRKMRKEMNALTEWLAATDMELTKRSAVEGMPSNLDSEVAWGKATQ

KEIEKQKVHLKSVTEVGEALKTVLGKKEMLVEDKLSLLNSNWIAVTSRAEEWLNLLLEYQ

KHMETFDQNVDYITNWIIQADALLDESEKKKPQQKEDILKRLKAEMNDIRPKVDSTRDQA

ANLMANRGDHCRKVVEPKISELNHRFAAISHRIKTGKASIPLKELEQFNSDIQKLLEPLE

AEIQQGVNLKEEDFNKDMSEDNEGTVKELLQRGDNLQQRITDERKREEIKIKQQLLQTKH

NALKDLRSQRRKKALEISHQWYQYKRQADDLLKCLDDIEKKLASLPEPRDERKIKEIDRE

LQKKEELNAVRRQAEGLSEDGAAMAVEPTQIQLSKRWREIESKFAQFRRLNFAQIHTVH

EESVVAMTEDMPLEISYVPSTYLTEITHVSQALSEVEELLNAPDLCAQDFEDLFKQEESL

KNIKDSLQQISGRIDIIHNKKTAALHSATPAERAKLQEALSRLDFQWERVNNMYKDRQGR

FDRSVEKWRRFHYDMKILNQWLTEAEQFLKKTQIPENWEHAKYKWYLKELQDGIGQRQSV

VRVLNATGEEIIQQSSKTDASILQEKLGSLNLRWQEVCKQLAERKKRLEEQKNILSEFQR

DVNEFVLWLEEADNVANIPLEPGNEQQLKEKLEQVKLLAEELPLRQGILKQLNETGGTVL

VSAPLSPEEQDKLENKLKQTNLQWIKVSRNLPEKQEEIEAHVKDLGQLEEQLNHLLLWLS

PIRNQLEIYNQPNQTGPFDIKEIEVAVQAKQPDVEGILSKGQHLYKEKPATQPAKRKLED

LSSDWKVVTQLLQELRAKQPGPAPGLTTVRAPPSQTVTLVTQPAVTKETAISKLEMPSSL

LLEVPALADFNRAWTELTDWLSLLDRVIKSQRVMVGDLEDINEMIIKQKATLQDLEQRRP

QLEELITAAQNLKNKTSNQEARTIITDRIERIQSQWDEVQEHLQNRRLQLTEMLKDSTQW

LEAKEEAEQVLGQARAKLESWKEAPYTVDAIQKKITETKQLAKDLRQWQINVDVANDLAL

KLLRDYSADDTRKVHMITENINASWASIHKRLSEREAALEETHRLLQQFPLDLEKFLAWL

TEAETTANVLQDATHKERLLEDSKGVRELMKQWQDLQGEIEAHTDIYHNLDENGQKVLRS

LEGSDDAALLQRRLDNMNFKWSELRKKSLNIRSHLEASSDQWKRLHLSLQELLVWLQLKD

DELSRQAPIGGDFPAVQKQNDVHRAFKRELKTKEPVIMSTLETVRIFLTEQPLEGLEKLY

QEPRELPPEERAQNVTRLLRKQAEEVNTQWEKLNVHSADWQRKIDEALERLQELQEATDE

LDLKLRQAEVIKGSWQPVGDLLIDSLQDHLEKVKALRGEITPLKENVSYVNDLARQLTTL

GIQLSPYNLNTLEDLNTRWKLLQVAIEDRIRQLHEAHRDFGPASQHFLSTSVQGPWERAI
```

```
SPNKVPYYINHETQTTCWDHPKMTELYQSLADLNNVRFSAYRTAMKLRRLQKAICLDLLS

LSAACDALDQHNLKQNDQPNDILQVINCLTTIYDRLEQEHNNLVNVPLCVDMCLNWLLNV

YDTGRTGRIRVLSFKTGIISLCKAHLEDKYRYLFKQVASSTGFCDQRRLGLLLHDSIQIP

RQLGEVASFGGSNIEPSVRSCFQFANNKPEIEAALFLDWMRLEPQSMVWLPVLHRVAAAE

TAKHQAKCNICKECPIIGFRYRSLKHFNYDICQSCFFSGRVAKGHKMHYPMVEYCTPTTS

GEDVRDFAKVLKNKFRTKRYFAKHPRMGYLPVQTVLEGDNMETPVTLINFWPVDSAPASS

PQLSHDDTHSRIEHYASRLKKMENSNGSYLNDSISPNESIDDEHLLIQHYWRSLNQESPL

SQPRSPAQILISLESEERGELERILADLEGRNRNLQAEYDRLKQQHEHKGLSPLPSPPEM

MPTSPQSPRDAELIAEAKLLRQHKGRLEARMQILEDHNKQLESQLHRLRQLLEQPQAEAK

VNGTTVSSPSTSLQRSDSSQPMLLRVVGSQTSESMGEEDLLSPPQDTSTGLEEVMEQLNH

SFPSSRGRNTPGKPMREDTM*

Full-length human dystrophin protein domain structure (total 3685 aa)
SEQ ID NO: 50: N-terminal domain (from 1 aa to 252 aa; total 252 aa)
MLWWEEVEDCYEREDVQKKTFTKWVNAQFSKFGKQHIENLFSDLQDGRRLLDLLEGLTGQKLPKEKGSTRV

HALNNVNKALRVLQNNNVDLVNIGSTDIVDGNHKLTLGLIWNIILHWQVKVMKNIMAGLQQTNSEKILLSW

VRQSTRNYPQVNVINFTTSWSDGLALNALIHSHRPDLFDWNSVVCQQSATQRLEHAFNIARYQLGIEKLLD

PEDVDTTYPDKKSILMYITSLFQVLPQQVSIEAIQEVE

SEQ ID NO: 51: Mid-rod domain (from 253 aa to 3112 aa; total 2860 aa)
MLPRPPKVTKEEHFQLHHQMHYSQQITVSLAQGYERTSSPKPRFKSYAYTQAAYVTTSDPTRSPFPSQHLE

APEDKSFGSSLMESEVNLDRYQTALEEVLSWLLSAEDTLQAQGEISNDVEVVKDQFHTHEGYMMDLTAHQG

RVGNILQLGSKLIGTKLSEDEETEVQEQMNLLNSRWECLRVASMEKQSNLHRVLMDLQNQKLKELNDWLT

KTEERTRKMEEEPLGPDLEDLKRQVQQHKVLQEDLEQEQVRVNSLTHMVVVVDESSGDHATAALEEQLKVL

GDRWANICRWTEDRWVLLQDILLKWQRLTEEQCLFSAWLSEKEDAVNKIHTTGFKDQNEMLSSLQKLAVLK

ADLEKKKQSMGKLYSLKQDLLSTLKNKSVTQKTEAWLDNFARCWDNLVQKLEKSTAQISQAVTTTQPSLTQ

TTVMETVTTVTTREQILVKHAQEELPPPPPQKKRQITVDSEIRKRLDVDITELHSWITRSEAVLQSPEFAI

FRKEGNFSDLKEKVNAIEREKAEKFRKLQDASRSAQALVEQMVNEGVNADSIKQASEQLNSRWIEFCQLLS

ERLNWLEYQNNIIAFYNQLQQLEQMTTTAENWLKIQPTTPSEPTAIKSQLKICKDEVNRLSGLQPQIERLK

IQSIALKEKGQGPMFLDADFVAFTNHFKQVFSDVQAREKELQTIFDTLPPMRYQETMSAIRTWVQQSETKL

SIPQLSVTDYEIMEQRLGELQALQSSLQEQQSGLYYLSTTVKEMSKKAPSEISRKYQSEFEEIEGRWKKLS

SQLVEHCQKLEEQMNKLRKIQNHIQTLKKWMAEVDVFLKEEWPALGDSEILKKQLKQCRLLVSDIQTIQPS

LNSVNEGGQKIKNEAEPEFASRLETELKELNTQWDHMCQQVYARKEALKGGLEKTVSLQKDLSEMHEWMTQ

AEEEYLERDFEYKTPDELQKAVEEMKRAKEEAQQKEAKVKLLTESVNSVIAQAPPVAQEALKKELETLTTN

YQWLCTRLNGKCKTLEEVWACWHELLSYLEKANKWLNEVEFKLKTTENIPGGAEEISEVLDSLENLMRHSE

DNPNQIRILAQTLTDGGVMDELINEELETFNSRWRELHEEAVRRQKLLEQSIQSAQETEKSLHLIQESLTF

IDKQLAAYIADKVDAAQMPQEAQKIQSDLTSHEISLEEMKKHNQGKEAAQRVLSQIDVAQKKLQDVSMKFR

LFQKPANFELRLQESKMILDEVKMHLPALETKSVEQEVVQSQLNHCVNLYKSLSEVKSEVEMVIKTGRQIV

QKKQTENPKELDERVTALKLHYNELGAKVTERKQQLEKCLKLSRKMRKEMNVLTEWLAATDMELTKRSAVE

GMPSNLDSEVAWGKATQKEIEKQKVHLKSITEVGEALKTVLGKKETLVEDKLSLLNSNWIAVTSRAEEWLN

LLLEYQKHMETFDQNVDHITKWIIQADTLLDESEKKKPQQKEDVLKRLKAELNDIRPKVDSTRDQAANLMA

NRGDHCRKLVEPQISELNHRFAAISHRIKTGKASIPLKELEQFNSDIQKLLEPLEAEIQQGVNLKEEDFNK
```

-continued

DMNEDNEGTVKELLQRGDNLQQRITDERKREEIKIKQQLLQTKHNALKDLRSQRRKKALEISHQWYQYKRQ

ADDLLKCLDDIEKKLASLPEPRDERKIKEIDRELQKKEELNAVRRQAEGLSEDGAAMAVEPTQIQLSKRW

REIESKFAQFRRLNFAQIHTVREETMMVMTEDMPLEISYVPSTYLTEITHVSQALLEVEQLLNAPDLCAKD

FEDLFKQEESLKNIKDSLQQSSGRIDIIHSKKTAALQSATPVERVKLQEALSQLDFQWEKVNKMYKDRQGR

FDRSVEKWRRFHYDIKIFNQWLTEAEQFLRKTQIPENWEHAKYKWYLKELQDGIGQRQTVVRTLNATGEEI

IQQSSKTDASILQEKLGSLNLRWQEVCKQLSDRKKRLEEQKNILSEFQRDLNEFVLWLEEADNIASIPLEP

GKEQQLKEKLEQVKLLVEELPLRQGILKQLNETGGPVLVSAPISPEEQDKLENKLKQTNLQWIKVSRALPE

KQGEIEAQIKDLGQLEKKLEDLEEQLNHLLLWLSPIRNQLEIYNQPNQEGPFDVQETEIAVQAKQPDVEEI

LSKGQHLYKEKPATQPVKRKLEDLSSEWKAVNRLLQELRAKQPDLAPGLTTIGASPTQTVTLVTQPVVTKE

TAISKLEMPSSLMLEVPALADFNRAWTELTDWLSLLDQVIKSQRVMVGDLEDINEMIIKQKATMQDLEQRR

PQLEELITAAQNLKNKTSNQEARTIITDRIERIQNQWDEVQEHLQNRRQQLNEMLKDSTQWLEAKEEAEQV

LGQARAKLESWKEGPYTVDAIQKKITETKQLAKDLRQWQTNVDVANDLALKLLRDYSADDTRKVHMITENI

NASWRSIHKRVSEREAALEETHRLLQQFPLDLEKFLAWLTEAETTANVLQDATRKERLLEDSKGVKELMKQ

WQDLQGEIEAHTDVYHNLDENSQKILRSLEGSDDAVLLQRRLDNMNFKWSELRKKSLNIRSHLEASSDQWK

RLHLSLQELLVWLQLKDDELSRQAPIGGDFPAVQKQNDVHRAFKRELKTKEPVIMSTLETVRIFLTEQPLE

GLEKLYQEPRELPPEERAQNVTRLLRKQAEEVNTEWEKLNLHSADWQRKIDETLERLQELQEATDELDLKL

RQAEVIKGSWQPVGDLLIDSLQDHLEKVKALRGEIAPLKENVSHVNDLARQLTTLGIQLSPYNLSTLEDLN

TRWKLLQVAVEDRVRQLHEAHRDFGPASQHFLSTSVQGPWERAISPNKVPYYINHETQTTCWDHPKMTELY

QSLADLNNVRFSAYRTAMKL

SEQ ID NO: 52: Cysteine-rich domain (from 3113 aa to 3408 aa; total
296 aa, cysteine residues are bolded)
RRLQKALCLDLLSLSAACDALDQHNLKQNDQPMDILQIINCLTTIYDRLEQEHNNLVNVPLCVDMCLNWLL

NVYDTGRTGRIRVLSFKTGIISLCKAHLEDKYRYLFKQVASSTGFCDQRRLGLLLHDSIQIPRQLGEVASF

GGSNIEPSVRSCFQFANNKPEIEAALFLDWMRLEPQSMVWLPVLHRVAAAETAKHQAKCNICKECPIIGFR

YRSLKHFNYDICQSCFFSGRVAKGHKMHYPMVEYCTPTTSGEDVRDFAKVLKNKFRTKRYFAKHPRMGYLP

VQTVLEGDNMET

SEQ ID NO: 53: C-terminal domain (from 3409 aa to 3695 aa; total 277 aa)
PVTLINFWPVDSAPASSPQLSHDDTHSRIEHYASRLAEMENSNGSYLNDSISPNESIDDEHLLIQHYCQSL

NQDSPLSQPRSPAQILISLESEERGELERILADLEEENRNLQAEYDRLKQQHEHKGLSPLPSPPEMMPTSP

QSPRDAELIAEAKLLRQHKGRLEARMQILEDHNKQLESQLHRLRQLLEQPQAEAKVNGTTVSSPSTSLQRS

DSSQPMLLRVVGSQTSDSMGEEDLLSPPQDTSTGLEEVMEQLNNSFPSSRGRNTPGKPMREDTM*

---

What is claimed is:

1. An isolated synthetic nucleic acid molecule comprising a synthetic mini-dystrophin or micro-dystrophin gene encoding a synthetic, non-full-length, dystrophin protein that is able to restore nNOS to the sarcolemma, wherein the non-full-length dystrophin protein comprises, from the N terminus to the C terminus:
   (1) the N-terminal domain of the dystrophin protein or a modified N-terminal domain of the dystrophin protein,
   (2) at least two repeats of the mid-rod domain of the dystrophin protein, wherein said at least two repeats comprise R16 and R17,
   (3) at least 2 hinge regions of the dystrophin protein, whereas said at least two hinge regions comprise H1 and H4, and
   (4) the cysteine-rich domain of the dystrophin protein;
   wherein the mini- or micro-dystrophin gene is between 5 kb to about 8 kb in length or less than 5 kb in length, respectively.

2. The isolated nucleic acid molecule of claim 1, wherein the at least two repeats of the mid-rod domain of the dystrophin protein are selected from the group consisting of (1) R1, R16, R17 and R24, (2) R1-R2, R16, R17 and R24, (3) R1, R16-R19 and 24, (4) R1-R3, R16, R17 and R20-R24, and (5) R1-R3 and R16-R24.

3. The isolated nucleic acid molecule of claim 1, wherein at least 2 hinge regions of the dystrophin protein comprise H1, H3 and H4.

4. The isolated nucleic acid molecule of claim 1, wherein the sequence is selected from the group consisting of SEQ ID NOs: 7-8 and 10-13.

5. The isolated nucleic acid molecule of claim 1 further comprising a sequence encoding the C-terminal domain of the dystrophin protein.

6. A single recombinant adeno-associated virus (AAV) vector comprising the nucleic acid molecule of claim 1, wherein said nucleic acid molecule is operably linked to an expression cassette and viral inverted terminal repeats (ITR).

7. A dual recombinant AAV vector system, comprising two AAV vectors, wherein one of the two AAV vectors comprises a part of the nucleic acid molecule of claim 1, and the other vector comprise the remaining part of said nucleic acid molecule, and wherein said two vectors further comprise sequences that permit recombination with each other to produce said nucleic acid in full length.

8. A pharmaceutical composition comprising one or more of the AAV vector of claim 6 or 7 and a pharmaceutically acceptable carrier.

* * * * *